United States Patent
Chen et al.

(10) Patent No.: US 9,783,539 B2
(45) Date of Patent: Oct. 10, 2017

(54) INDOLOQUINOLONE COMPOUNDS AS ANAPLASTIC LYMPHOMA KINASE (ALK) INHIBITORS

(71) Applicant: Jiangsu Ascentage Biomed Development Inc., Taizhou, Jiansu (CN)

(72) Inventors: Jianyong Chen, Ann Arbor, MI (US); Yunlong Zhou, Jiangsu (CN); Shaomeng Wang, Superior Township, MI (US); Ming Guo, Jiangsu (CN); Dajun Yang, Jiangsu (CN); Lingling Jiao, Jiangsu (CN); Yu Jing, Jiangsu (CN); Xu Qian, Jiangsu (CN); Liu Liu, Ann Arbor, MI (US); Longchuan Bai, Ann Arbor, MI (US); Chao-Yie Yang, Ann Arbor, MI (US); Donna McEachern, Ann Arbor, MI (US)

(73) Assignee: Jiangsu Ascentage Biomed Development Inc., Taizhou, Jiangsu (CN)

( * ) Notice: Subject to any disclaimer, the term of this patent is extended or adjusted under 35 U.S.C. 154(b) by 0 days.

(21) Appl. No.: 15/121,847

(22) PCT Filed: Feb. 27, 2014

(86) PCT No.: PCT/CN2014/072650
§ 371 (c)(1),
(2) Date: Aug. 26, 2016

(87) PCT Pub. No.: WO2015/127629
PCT Pub. Date: Sep. 3, 2015

(65) Prior Publication Data
US 2017/0066761 A1  Mar. 9, 2017

(51) Int. Cl.
*A61K 31/5377* (2006.01)
*C07D 413/14* (2006.01)
*C07D 471/04* (2006.01)

(52) U.S. Cl.
CPC ................. *C07D 471/04* (2013.01)

(58) Field of Classification Search
CPC ............ A61K 31/5375; A61K 31/4745; C07D 413/14; C07D 471/04
USPC .................. 514/232.8, 285; 544/125; 546/70
See application file for complete search history.

(56) References Cited

FOREIGN PATENT DOCUMENTS

| DE | 2113343 A1 | 9/1972 |
|---|---|---|
| JP | 2013-107869 A | 6/2013 |

OTHER PUBLICATIONS

Chen, Y-L. et al.: Synthesis and anticancer evaluation of certain indolo{2,3-b}quinoline derivatives. Biorg.& Medic. Chem., vol. 12, pp. 6539-6546, 2004.*
Sayed, I.E. et al.: Synthesis and Antiplasmodial activity of Aminoalkylamino-substituted Neocryptolepine derivatives. J. Med. Chem., vol. 52, pp. 2979-2988, 2009.*
Lu, W-J. et al.: In vitro antiproliferative activity of 11-aminoalkylamino-substituted 5H-indolo[2,3-b]quinolines; improving activity of neocryptolepines by installation of ester substituent. Med. Chem. Res., vol. 22, pp. 4492-4504, 2013.*
Chen, J. et al., "LDK378: A promising anaplastic lymphoma kinase (ALK) inhibitor," *J. Med. Chem.*, 2013, 56 (14), 5673-5674.
Chen, Y. et al., "Synthesis and anticancer evaluation of certain indolo[2,3-b]quinoline derivatives," *Bioorganic & Medicinal Chemistry*, 2004, 12 (24), 6539-6546.
Hallberg, B., et al., "Mechanistic insight into ALK receptor tyrosine kinase in human cancer biology, " *Nature Reviews Cancer*, 2013, 13, pp. 685-700.
International Search Report issued in International Application No. PCT/CN2014/072650 filed on Feb. 27, 2014, and mailed from the State Intellectual Property Office of the People's Republic of China on Dec. 2, 2014.
Kinoshita, K., et al., "9-Substituted 6,6-dimethyl-11-oxo-6, 11-dihydro-5h-benzo[b]carbazoles as highly selective and potent anaplastic lymphoma kinase inhibitors," *J. Med. Chem.*, 2011, 54, 6286-6294.
Kinoshita, K., et al., "Design and synthesis of a highly selective, orally active and potent anaplastic lymphoma kinase inhibitor (CH5424802)," *Bioorganic & Medicinal Chemistry*, 2012, 20 (3), 1271-1280.
Lu, W., et al., "In vitro anti proliferative activity of 11-aminoalkylaminosubstituted 5H-indolo[2,3-b]quinolines; improving activity of neocryptolepines by installation of ester substituent," *Med. Chem. Res.*, 2013, 22, 4492-4504.
Bergman, J. et al., "Studies of the reactions between indole-2,3-diones (isatins) and 2-aminobenzylamine", Tetrahedron, 2003, 59 (7), pp. 1033-1048.
Mei, Z. et al., "Synthesis and in vitro antimalarial testing of neocryptolepines: SAR study for improved activity by introduction and modifications of side chains at C2 and C11 on indolo[2,3-b]quinolines", Journal of Medicinal Chemistry, 2013, 56 (4), pp. 1431-1442.
Sayed, I.E. et al., "Neocryptolepine analogues containing substituted side-chains at: synthesis and antischistosomicidal activity", Medicinal Chemistry Research, 2012, 21 (12), pp. 4219-4229.
Voute, N. et al., "Studies on the Claisen rearrangements in the indolo[2,3-b]quinoline system", Organic & Biomolecular Chemistry, 2010, 8 (2), pp. 442-450.
Wang, L. et al., "Synthesis and in vitro antiproliferative activity of new 11-aminoalkylamino-substituted 5-and 6-indolo[2,3-]quinolines; structureactivity relationships of neocryptolepines and 6-methyl congeners", Bioorganic & Medicinal Chemistry, 2012, 20 (15), pp. 4820-4829.

* cited by examiner

*Primary Examiner* — Charanjit Aulakh
(74) *Attorney, Agent, or Firm* — Finnegan, Henderson, Farabow, Garrett & Dunner LLP

(57) ABSTRACT

Disclosed herein are certain indoloquinolone compounds, methods of preparation thereof, pharmaceutical compositions thereof, and uses thereof, such as their uses as ALK inhibitors.

20 Claims, No Drawings

INDOLOQUINOLONE COMPOUNDS AS ANAPLASTIC LYMPHOMA KINASE (ALK) INHIBITORS

FIELD OF THE INVENTION

The invention is in the field of medicinal chemistry. In particular, the invention relates to novel indoloquinolone compounds capable of inhibiting the kinase activity of anaplastic lymphoma kinase (ALK). This invention also relates to pharmaceutical compositions comprising such compounds and to the use of such compounds in treatment of diseases modulated by ALK such as cancer and neurological disorders such as depression. Thus, compounds of the invention are useful in treating patients with cancers expressing modified ALK or cancers related to ALK expression.

BACKGROUND OF THE INVENTION

Anaplastic lymphoma kinase (ALK) is a receptor tyrosine kinase (RTK) belonging to the insulin receptor superfamily. ALK fusion genes have been identified in anaplastic large cell lymphomas (ALCL; Morris, S. W. eta al., Science 263: 1281 (1994)), inflammatory myofibroblastic tumor (IMT; Griffin, C. A. et al., *Cancer Res.* 59: 2776 (1999)), squamous cell carcinoma (SCC; Jazii, F. R. et al, *World J. Gastroenterol.* 12: 7104 (2006)), diffuse large B-cell lymphoma (DLBCL; Gascoyne, R. D. et al., *Blood* 102: 2568 (2003)), and non-small-cell lung cancer (NSCLC; Soda, M. et al., *Nature* 448: 561 (2007)).

Among ALK fusion genes identified to date, nucleophosmin (NPM) is the most common partner in ALCL (Morris, S. W. eta al., Science 263: 1281 (1994)) while echinoderm microtubule-associated protein-like-4 (EML4) is the main partner in NSCLC. NPM-ALK fusion is detected in about 75% of all ALK-positive ALCL patients and is implicated in the pathogenesis of ALCL (Li, R. et al., Med. Res. Rev. 28: 372 (2008)). EML4-ALK fusion in NSCLC was the first fusion gene found to be oncogenic in solid tumor (Mano H. et al., Cancer Sci. 99: 2349 (2008)) and was detected in approximately 5% of NSCLC patients (Koivenen, J. P. et al., Clin. Cancer Res. 14: 4275 (2008)). Moreover, genetic amplification and overexpression of ALK have been discovered to cause childhood neuroblastoma (Osajima-Hakomori, Y. et al., Am. J. Pathol. 167:213 (2005)). ALK fusion genes are oncogenic drivers in a small percentage of blood and solid tumors. ALK inhibitors are being pursued as a new class of therapy for the treatment of human cancers harboring a rearrangement of the ALK gene (ALK-positive tumors).

Crizotinib was the first ALK inhibitor approved by the US Food and Drug Administration (FDA) in 2011 for the treatment of ALK-positive NSCLC patients. Although crizitinib is very effective in the initial stage of the treatment, acquired drug resistance caused by mutations of ALK has been identified in patients treated with crizotinib. Therefore, there is a clear need for new ALK inhibitors (second generation of ALK inhibitors), which inhibit not only wild-type ALK but also ALK mutations that are resistant to crizotinib.

Although several such second-generation ALK inhibitors, including CH5424802 (Sakamoto H, et al., Cancer Cell. 19:679 (2011)), LDK378 (Marsilje T. H, J Med Chem. 56:5675 (2013)), AP26113 (Katayama, R., Proc Natl Acad Sci USA. 108:7535 (2011)) are currently in clinical trials, it would be desirable to have additional such ALK inhibitors for the treatment of human cancers harboring ALK fusion genes.

Researchers have also discovered that a number of cancers, such as brain and lung cancers, implicate c-ros oncogene 1 (ROS1) protein. (Acquaviva J. et al., BBA-Rev. Cancer. 1795:37 (2009)). ROS1 protein is a close relative of ALK. Similar to ALK, inhibition of ROS1 provides potential treatment for diseases, such as lung and brain cancers, which are treatable by inhibition of ROS1.

The present invention provides a new class of compounds that may inhibit not only wild-type ALK but also mutated ALK and ROS1.

SUMMARY OF THE INVENTION

Disclosed herein are certain indoloquinolone compounds as ALK inhibitors.

Specifically, disclosed herein is at least one compound of formula (I), and/or at least one pharmaceutically acceptable salt thereof:

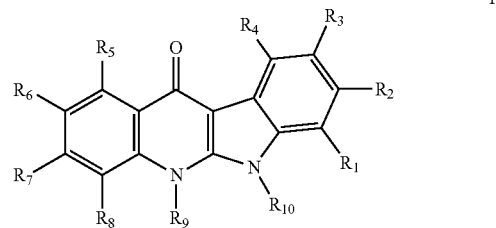

wherein $R_1$, $R_2$, $R_3$, $R_4$, $R_5$, $R_6$, $R_7$, and $R_8$ are independently selected from hydrogen, alkyl, alkynyl, alkenyl, alkoxy, halo, hydroxyl, —CN, —COOR$^b$, —CONR$^b$R$^c$, —NR$^b$R$^c$, —NO$_2$, —O— cycloalkyl, —O-heterocyclyl, —O-aryl, —O-heteroaryl, cycloalkyl, heterocyclyl, aryl, and heteroaryl, etc., wherein $R_9$ and $R_{10}$ are independently selected from hydrogen, alkyl, cycloalkyl, heterocyclyl, aryl, and heteroaryl, etc., wherein the above alkyl, alkynyl, alkenyl, alkoxy, cycloalkyl, heterocyclyl, aryl, and heteroaryl are each optionally substituted with at least one group, such as one, two, three, or four groups, independently selected from R$^a$, R$^a$ is selected from alkyl, alkoxy, halo, hydroxyl, —CN, alkenyl, alkynyl, cycloalkyl, heterocyclyl, aryl, heteroaryl, —COOR$^b$, —CONR$^b$R$^c$, —NR$^b$R$^c$, and oxo, wherein each of the alkyl, alkoxy, alkenyl, alkynyl, cycloalkyl, heterocyclyl, aryl, heteroaryl group is optionally substituted with at least one group, such as one, two, three or four groups, independently selected from alkyl, hydroxyl, alkoxy, halo, —COOR$^b$, —CONR$^b$R$^c$, and —NR$^b$R$^c$, R$^b$ and R$^c$ are each independently selected from hydrogen, alkyl, alkenyl, cycloalkyl, heterocyclyl, aryl, and heteroaryl.

Further disclosed herein is a pharmaceutical composition, comprising at least one compound of formula (I) and/or at least one pharmaceutically acceptable salt thereof and at least one pharmaceutically acceptable carrier.

Also disclosed herein is a method of treating in a subject a disease responsive to inhibition of ALK and/or inhibition of ROS 1. This method of treating the disease comprises administering to the subject in need thereof an effective amount of at least one compound of formula (I) and/or at least one pharmaceutically acceptable salt thereof.

Also disclosed herein is a method of treating in a subject a cancer responsive to inhibition of ALK and/or inhibition of ROS 1. This method of treating such cancer comprises administering to the subject in need thereof an effective amount of at least one compound of formula (I) and/or at least one pharmaceutically acceptable salt thereof.

Also disclosed herein is a use of at least one compound of formula (I) and/or at least one pharmaceutically acceptable salt thereof in preparation of a medication for treating cancer responsive to inhibition of ALK.

Also disclosed herein is a medicine or pharmaceutical composition for treating cancer responsive to inhibition of ALK, which comprises at least one compound of formula (I) and/or at least one pharmaceutically acceptable salt thereof and at least one pharmaceutically acceptable carrier.

Cancers as disclosed herein include, for example, lung cancer, pancreatic cancer, skin cancer, bone cancer, head and neck cancer, uterine cancer, ovarian cancer, rectal cancer, breast cancer, colorectal cancer, stomach cancer, colon cancer, acute or chronic leukemia, adenocarcinoma, lymphoma, melanoma, prostate cancer, bladder cancer, kidney cancer, brain tumor, Hodgkin's Disease, neoplasms of the central nervous system (CNS), primary CNS lymphoma, mesothelioma, small intestine cancer, and esophagus cancer.

In some embodiments, the cancer is lung cancer, such as non-small cell lung cancer. In some embodiments, the cancer is brain cancer.

In some embodiments, the cancer is chosen from lung adenocarcinoma, cholangiocarcinoma, ovarian cancer, gastric adenocarcinoma, colorectal cancer, inflammatory myofibroblastic tumor, angiosarcoma, and epitheloid hemangioendothelioma.

As used herein, the following words, phrases and symbols are generally intended to have the meanings as set forth below, except to the extent that the context in which they are used indicates otherwise. The following abbreviations and terms have the indicated meanings throughout.

A dash ("-") that is not between two letters or symbols is used to indicate a point of attachment for a substituent. For example, —CONH$_2$ is attached through the carbon atom.

The term "alkyl" herein refers to a hydrocarbon group selected from linear and branched saturated hydrocarbon groups comprising from 1 to 18, such as from 1 to 12, further such as from 1 to 10, even further such as from 1 to 6, carbon atoms.

The term "alkoxy" herein refers to a straight or branched alkyl group comprising from 1 to 10 carbon atoms attached through an oxygen bridge such as methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, and the like. In some embodiments, alkoxy groups comprise from 1 to 6 carbon atoms attached through the oxygen bridge.

The term "alkenyl" herein refers to a hydrocarbon group selected from linear and branched hydrocarbon groups, comprising at least one C=C double bond and from 2 to 18, such as from 2 to 6, carbon atoms. Examples of the alkenyl group may be selected from ethenyl or vinyl (—CH=CH$_2$), prop-1-enyl (—CH=CHCH$_3$), prop-2-enyl (—CH$_2$CH=CH$_2$), 2-methylprop-1-enyl, buta-1-enyl, buta-2-enyl, buta-3-enyl, buta-1,3-dienyl, 2-methylbuta-1,3-diene, hex-1-enyl, hex-2-enyl, hex-3-enyl, hex-4-enyl, and hexa-1,3-dienyl groups. The point of attachment can be on the unsaturated carbon or saturated carbon.

The term "alkynyl" herein refers to a hydrocarbon group selected from linear and branched hydrocarbon groups, comprising at least one C≡C triple bond and from 2 to 18, such as from 2 to 6, carbon atoms. Examples of the alkynyl group include ethynyl (—C≡CH), 1-propynyl (—C≡CCH$_3$), 2-propynyl (propargyl, —CH$_2$C≡CH), 1-butynyl, 2-butynyl, and 3-butynyl groups. The point of attachment can be on the unsaturated carbon or saturated carbon.

The term "cycloalkyl" herein refers to a hydrocarbon group selected from saturated and partially unsaturated cyclic hydrocarbon groups, comprising monocyclic and polycyclic (e.g., bicyclic and tricyclic) groups. For example, the cycloalkyl group may comprise from 3 to 12, such as from 3 to 8, further such as from 3 to 6, from 3 to 5, or from 3 to 4, carbon atoms. Even further for example, the cycloalkyl group may be selected from monocyclic group comprising from 3 to 12, such as from 3 to 8, or from 3 to 6, carbon atoms. Examples of the monocyclic cycloalkyl group include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, and cyclododecyl groups. Examples of the bicyclic cycloalkyl groups include those comprising from 7 to 12 ring atoms arranged as a bicycle ring selected from [4,4], [4,5], [5,5], [5,6] and [6,6] ring systems, or as a bridged bicyclic ring selected from bicyclo[2.2.1]heptane, bicyclo[2.2.2]octane, and bicyclo[3.2.2]nonane, etc. The ring may be saturated or have at least one double bond (i.e. partially unsaturated), but is not fully conjugated, and is not aromatic, as aromatic is defined herein. The cycloalkyl may be substituted with, for example, oxo and/or other hetero atoms.

The term "aryl" herein refers to a group selected from:

5- and 6-membered carbocyclic aromatic rings, for example, phenyl;

bicyclic ring systems such as 7 to 12 membered bicyclic ring systems wherein at least one ring is carbocyclic and aromatic, selected, for example, from naphthalene, indane, and 1,2,3,4-tetrahydroquinoline; and tricyclic ring systems such as 10 to 15 membered tricyclic ring systems, wherein at least one ring is carbocyclic and aromatic, for example, fluorene.

In some embodiments, the aryl group is selected from 5 and 6-membered carbocyclic aromatic rings fused to a 5- to 7-membered cycloalkyl or heterocyclic ring optionally comprising at least one heteroatom selected from N, O, and S, provided that the point of attachment is at the carbocyclic aromatic ring when the carbocyclic aromatic ring is fused with a heterocyclic ring, and the point of attachment can be at the carbocyclic aromatic ring or at the cycloalkyl group when the carbocyclic aromatic ring is fused with a cycloalkyl group. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Aryl, however, does not encompass or overlap in any way with heteroaryl, separately defined below. Hence, if one or more carbocyclic aromatic rings are fused with a heterocyclic aromatic ring, the resulting ring system is heteroaryl, not aryl, as defined herein.

The term "halo" herein refers to F, Cl, Br or I.

The term "heteroaryl" herein refers to a group selected from:
- 5- to 7-membered aromatic, monocyclic rings comprising at least one heteroatom, for example, from 1 to 4, or, in some embodiments, from 1 to 3, heteroatoms, selected from N, O, and S, with the remaining ring atoms being carbon;
- 8- to 12-membered bicyclic rings comprising at least one heteroatom, for example, from 1 to 4, or, in some embodiments, from 1 to 3, or, in other embodiments, 1 or 2, heteroatoms, selected from N, O, and S, with the remaining ring atoms being carbon and wherein at least one ring is aromatic and at least one heteroatom is present in the aromatic ring, and with the point of attachment being on any ring; and
- 11- to 14-membered tricyclic rings comprising at least one heteroatom, for example, from 1 to 4, or in some embodiments, from 1 to 3, or, in other embodiments, 1 or 2, heteroatoms, selected from N, O, and S, with the remaining ring atoms being carbon and wherein at least one ring is aromatic and at least one heteroatom is present in an aromatic ring, and with the point of attachment being on any ring.

In some embodiments, the heteroaryl group includes a 5- to 7-membered heterocyclic aromatic ring fused to a 5- to 7-membered cycloalkyl ring. For such fused, bicyclic heteroaryl ring systems wherein only one of the rings comprises at least one heteroatom, the point of attachment may be at the heteroaromatic ring or at the cycloalkyl ring.

When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1.

Examples of the heteroaryl group include, but are not limited to, (as numbered from the linkage position assigned priority)pyridyl (such as 2-pyridyl, 3-pyridyl, or 4-pyridyl), cinnolinyl, pyrazinyl, 2,4-pyrimidinyl, 3,5-pyrimidinyl, 2,4-imidazolyl, imidazopyridinyl, isoxazolyl, oxazolyl, thiazolyl, isothiazolyl, thiadiazolyl, tetrazolyl, thienyl, triazinyl, benzothienyl, furyl, benzofuryl, benzoimidazolyl, indolyl, isoindolyl, indolinyl, phthalazinyl, pyrazinyl, pyridazinyl, pyrrolyl, triazolyl, quinolinyl, isoquinolinyl, pyrazolyl, pyrrolopyridinyl (such as 1H-pyrrolo[2,3-b]pyridin-5-yl), pyrazolopyridinyl (such as 1H-pyrazolo[3,4-b]pyridin-5-yl), benzoxazolyl (such as benzo[d]oxazol-6-yl), pteridinyl, purinyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, furazanyl, benzofurazanyl, benzothiophenyl, benzothiazolyl, benzoxazolyl, quinazolinyl, quinoxalinyl, naphthyridinyl, furopyridinyl, benzothiazolyl (such as benzo[d]thiazol-6-yl), indazolyl (such as 1H-indazol-5-yl) and 5,6,7,8-tetrahydroisoquinoline.

The term "heterocyclyl" herein refers to a ring selected from 4- to 12-membered monocyclic, bicyclic and tricyclic, saturated and partially unsaturated rings comprising at least one carbon atoms in addition to at least one heteroatom, such as from 1-4 heteroatoms, further such as from 1-3, or further such as 1 or 2 heteroatoms, selected from oxygen, sulfur, and nitrogen. "Heterocyclyl" herein also refers to a 5- to 7-membered saturated or partially unsaturated carbocyclic ring comprising at least one heteroatom selected from N, O, and S (heterocyclic ring) fused with 5-, 6-, and/or 7-membered cycloalkyl, heterocyclic or carbocyclic aromatic ring, provided that the point of attachment is at the heterocyclic ring when the heterocyclic ring is fused with a carbocyclic aromatic ring, and that the point of attachment can be at the cycloalkyl or heterocyclic ring when the heterocylic ring is fused with cycloalkyl. "Heterocyclyl" herein also refers to an aliphatic spirocyclic ring comprising at least one heteroatom selected from N, O, and S. The rings may be saturated or have at least one double bond (i.e. partially unsaturated). The heterocyclyl may be substituted with, for example, oxo. The point of the attachment may be carbon or heteroatom. A heterocyclyl is not a heteroaryl as defined herein.

Examples of the heterocycle include, but not limited to, (as numbered from the linkage position assigned priority) 1-pyrrolidinyl, 2-pyrrolidinyl, 2,4-imidazolidinyl, 2,3-pyrazolidinyl, 1-piperidinyl, 2-piperidinyl, 3-piperidinyl, 4-piperidinyl, 2,5-piperazinyl, pyranyl, 2-morpholinyl, 3-morpholinyl, oxiranyl, aziridinyl, thiiranyl, azetidinyl, oxetanyl, thietanyl, 1,2-dithietanyl, 1,3-dithietanyl, dihydropyridinyl, tetrahydropyridinyl, thiomorpholinyl, thioxanyl, piperazinyl, homopiperazinyl, homopiperidinyl, azepanyl, oxepanyl, thiepanyl, 1,4-oxathianyl, 1,4-dioxepanyl, 1,4-oxathiepanyl, 1,4-oxaazepanyl, 1,4-dithiepanyl, 1,4-thiazepanyl and 1,4-diazepane 1,4-dithianyl, 1,4-azathianyl, oxazepinyl, diazepinyl, thiazepinyl, dihydrothienyl, dihydropyranyl, dihydrofuranyl, tetrahydropyranyl, tetrahydrothienyl, tetrahydropyranyl, tetrahydrothiopyranyl, 1-pyrrolinyl, 2-pyrrolinyl, 3-pyrrolinyl, indolinyl, 2H-pyranyl, 4H-pyranyl, 1,4-dioxanyl, 1,3-dioxolanyl, pyrazolinyl, pyrazolidinyl, dithianyl, dithiolanyl, pyrazolidinylimidazolinyl, pyrimidinonyl, 1,1-dioxo-thiomorpholinyl, 3-azabicyco[3.1.0]hexanyl, 3-azabicyclo[4.1.0]heptanyl and azabicyclo[2.2.2]hexanyl. Substituted heterocycles also include ring systems substituted with one or more oxo moieties, such as piperidinyl N-oxide, morpholinyl-N-oxide, 1-oxo-1-thiomorpholinyl and 1,1-dioxo-1-thiomorpholinyl.

Compounds disclosed herein may contain an asymmetric center and may thus exist as enantiomers. Where the compounds disclosed herein possess two or more asymmetric centers, they may additionally exist as diastereomers. Enantiomers and diastereomers fall within the broader class of stereoisomers. All such possible stereoisomers as substantially pure resolved enantiomers, racemic mixtures thereof, as well as mixtures of diastereomers are intended to be included. All stereoisomers of the compounds disclosed herein and/or pharmaceutically acceptable salts thereof are intended to be included. Unless specifically mentioned otherwise, reference to one isomer applies to any of the possible isomers. Whenever the isomeric composition is unspecified, all possible isomers are included. OK When the compounds disclosed herein contain olefinic double bonds, unless specified otherwise, such double bonds are meant to include both E and Z geometric isomers.

By "optional" or "optionally" is meant that the subsequently described event or circumstance may or may not occur, and that the description includes instances where the event or circumstance occurs and instances in which it does not. For example, "alkyl optionally substituted with X" encompasses both "alkyl" and "alkyl substituted with X". It will be understood by those skilled in the art, with respect to any group containing one or more substituents, that such groups are not intended to introduce any substitution or substitution patterns that are sterically impractical, synthetically non-feasible and/or inherently unstable.

In some embodiments, "substituted with one or more groups" refers to two hydrogens on the designated atom or group being independently replaced with two selections from the indicated group of substituents. In some embodiments, "substituted with one or more groups" refers to three hydrogens on the designated atom or group being independently replaced with three selections from the indicated group of substituents. In some embodiments, "substituted with one or more groups" refers to four hydrogens on the designated atom or group being independently replaced with four selections from the indicated group of substituents.

"Pharmaceutically acceptable salts" include, but are not limited to, salts with inorganic acids, selected, for example, from hydrochlorates, phosphates, diphosphates, hydrobromates, sulfates, sulfinates, and nitrates; as well as salts with organic acids, selected, for example, from malates, maleates, fumarates, tartrates, succinates, citrates, lactates, methanesulfonates, p-toluenesulfonates, 2-hydroxyethylsulfonates, benzoates, salicylates, stearates, alkanoates such as acetate, and salts with HOOC—(CH$_2$)n-COOH, wherein n is selected from 0 to 4. Similarly, examples of pharmaceutically acceptable cations include, but are not limited to, sodium, potassium, calcium, aluminum, lithium, and ammonium.

In addition, if a compound disclosed herein is obtained as an acid addition salt, the free base can be obtained by basifying a solution of the acid salt. Conversely, if the product is a free base, an addition salt, such as a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used without undue experimentation to prepare non-toxic pharmaceutically acceptable addition salts.

"Treating," "treat," or "treatment" or "alleviation" refers to administering at least one compound and/or at least one stereoisomer thereof, if any, and/or at least one pharmaceutically acceptable salt thereof disclosed herein to a subject in recognized need thereof that has, for example, cancer.

The term "effective amount" refers to an amount of at least one compound and/or at least one stereoisomer thereof, if any, and/or at least one pharmaceutically acceptable salt thereof disclosed herein effective to "treat," as defined above, a disease or disorder in a subject.

Disclosed herein is at least one compound of formula (I), and/or at least one pharmaceutically acceptable salt thereof:

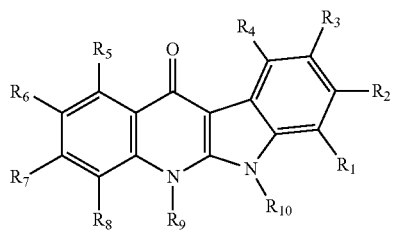

I wherein $R_1$, $R_2$, $R_3$, $R_4$, $R_5$, $R_6$, $R_7$, and $R_8$ are independently selected from hydrogen, alkyl, alkynyl, alkenyl, alkoxy, halo, hydroxyl, —CN, —COOR$^b$, —CONR$^b$R$^c$, —NR$^b$R$^c$, —NO$_2$, —O-cycloalkyl, —O-heterocyclyl, —O-aryl, —O-heteroaryl, cycloalkyl, heterocyclyl, aryl, and heteroaryl, wherein $R_9$ and $R_{10}$ are independently selected from hydrogen, alkyl, cycloalkyl, heterocyclyl, aryl, and heteroaryl, wherein the above alkyl, alkynyl, alkenyl, alkoxy, cycloalkyl, heterocyclyl, aryl, and heteroaryl are each optionally substituted with at least one group, such as one, two, three, or four groups, independently selected from R$^a$, R$^a$ is selected from alkyl, alkoxy, halo, hydroxyl, —CN, alkenyl, alkynyl, cycloalkyl, heterocyclyl, aryl, heteroaryl, —COOR$^b$, —CONR$^b$R$^c$, —NR$^b$R$^c$, and oxo, wherein each of the alkyl, alkoxy, alkenyl, alkynyl, cycloalkyl, heterocyclyl, aryl, heteroaryl is optionally substituted with at least one group, such as one, two, three or four groups, independently selected from alkyl, hydroxyl, alkoxy, halo, —COOR$^b$, —CONR$^b$R$^c$, and —NR$^b$R$^c$, R$^b$ and R$^c$ are each independently selected from hydrogen, alkyl, alkenyl, cycloalkyl, heterocyclyl, aryl, and heteroaryl.

In some embodiments, $R_1$, $R_2$, $R_3$, $R_4$, $R_5$, $R_6$, and $R_8$ in formula (I) are independently selected from hydrogen, alkyl, alkynyl, alkenyl, alkoxy, halo, hydroxyl, and —CN, wherein the alkyl, alkynyl, alkenyl, alkoxy, and cycloalkyl are each optionally substituted with at least one group, such as one, two, three, or four groups, independently selected from R$^a$. In some embodiments, $R_2$ in formula (I) is —CN. In some embodiments, $R_3$ in formula (I) is hydrogen or —CN. In some embodiments, $R_6$ in formula (I) is selected from hydrogen, alkyl, alkynyl, alkenyl, alkoxy, and cycloalkyl, wherein the alkyl, alkynyl, alkenyl, alkoxy, and cycloalkyl are unsubstituted. In some embodiments, $R_1$, $R_4$, and $R_5$ are hydrogen. In some embodiments, $R_8$ is hydrogen or halo, such as fluoro.

In some embodiments, $R_7$ in formula (I) is selected from cycloalkyl, heterocycyl, aryl and heteroaryl, wherein the cycloalkyl, heterocycyl, aryl and heteroaryl are each optionally substituted with at least one group, such as one, two, three, or four groups, independently selected from R$^a$. In some embodiments, $R_7$ in formula (I) is heterocycyl optionally substituted with at least one group, such as one, two, three, or four groups, independently selected from R$^a$. In some embodiments, $R_7$ in formula (I) is heterocyclyl optionally substituted with at least one group, such as one, two, three, or four groups, independently selected from alkyl, cycloalkyl and heterocyclyl, wherein each of the alkyl, cycloalkyl and heterocyclyl is optionally substituted with at least one group, such as one, two, three or four groups, independently selected from alkyl, hydroxyl, and alkoxy.

In some embodiments, $R_7$ in formula (I) is selected from piperidinyl, piperazinyl, and morpholinyl optionally substituted with at least one group, such as one, two, three, or four groups, independently selected from alkyl (such as methyl, ethyl, or iso-propyl), cycloalkyl and heterocyclyl (such as piperidiny, piperazinyl, or morpholinyl), wherein each of the alkyl, cycloalkly, and heterocyclyl is optionally substituted by hydroxyl.

In some embodiments, $R_9$ in formula (I) is selected from hydrogen, alkyl, and cycloalkyl, wherein each of the alkyl and cycloalkyl is optionally substituted with at least one group, such as one, two, three, or four groups, independently selected from R$^a$. In some embodiments, $R_9$ in formula (I) is selected from alkyl and cycloalkyl, wherein each of the alkyl and cycloalkyl is optionally substituted with at least one group, such as one, two, three, or four groups, independently selected from alkyl, halo, and hydroxyl.

In some embodiments, the at least one compound of formula (I), and/or at least one pharmaceutically acceptable salt thereof, is selected from compounds of formula (II):

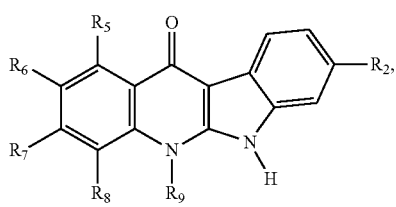

II wherein $R_2$, $R_5$, $R_6$, $R_7$, $R_8$, and $R_9$ are the same as those defined in formula (I) above.

In some embodiments, $R_2$, $R_5$, $R_6$, and $R_8$ in formula (II) are independently selected from hydrogen, alkyl, alkynyl, alkenyl, alkoxy, halo, hydroxyl, and —CN, wherein the alkyl, alkynyl, alkenyl, alkoxy, and cycloalkyl are each optionally substituted with at least one group, such as one, two, three, or four groups, independently selected from $R^a$. In some embodiments, $R_2$ in formula (II) is —CN. In some embodiments, $R_5$ is hydrogen. In some embodiments, $R_6$ in formula (II) is selected from hydrogen, alkyl, alkynyl, alkenyl, alkoxy, halo, hydroxyl, and —CN, wherein the alkyl, alkynyl, alkenyl, alkoxy, and cycloalkyl are unsubstituted. In some embodiment, $R_8$ in formula (II) is hydrogen or halo, such as fluoro.

In some embodiments, $R_7$ in formula (II) is selected from cycloalkly, heterocycyl, aryl and heteroaryl, wherein the cycloalkly, heterocycyl, aryl and heteroaryl are each optionally substituted with at least one group, such as one, two, three, or four groups, independently selected from $R^a$. In some embodiments, $R_7$ in formula (II) is heterocycyl optionally substituted with at least one group, such as one, two, three, or four groups, independently selected from $R^a$. In some embodiments, $R_7$ in formula (II) is heterocyclyl optionally substituted with at least one group, such as one, two, three, or four groups, independently selected from alkyl, cycloalkyl and heterocyclyl, wherein each of the alkyl, cycloalkyl and heterocyclyl is optionally substituted with at least one group, such as one, two, three or four groups, independently selected from alkyl, hydroxyl, and alkoxy.

In some embodiments, $R_7$ in formula (II) is selected from piperidinyl, piperazinyl, and morpholinyl optionally substituted with at least one group, such as one, two, three, or four groups, independently selected from alkyl (such as methyl, ethyl, or iso-propyl), cycloalkly and heterocyclyl (such as piperidiny, piperazinyl, or morpholinyl), wherein each of the alkyl, cycloalkly, and heterocyclyl is optionally substituted by hydroxyl.

In some embodiments, $R_9$ in formula (II) is selected from hydrogen, alkyl, and cycloalkyl, wherein each of the alyl and cycloalkyl is optionally substituted with at least one group, such as one, two, three, or four groups, independently selected from $R^a$. In some embodiments, $R_9$ in formula (II) is selected from alkyl and cycloalkyl, wherein each of the alkyl and cycloalkyl is optionally substituted with at least one group, such as one, two, three, or four groups, independently selected from alkyl, halo, and hydroxyl.

In some embodiments, at least one compound of formula (I), and/or at least one pharmaceutically acceptable salt thereof, is selected from compounds of formula (III):

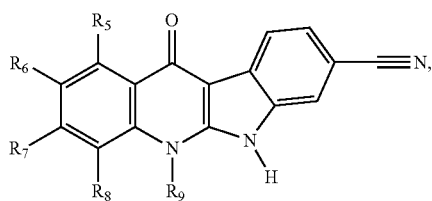

wherein $R_5$, $R_6$, $R_7$, $R_8$, and $R_9$ are the same as those defined in formula (I) above.

In some embodiments, $R_5$, $R_6$, and $R_8$ in formula (III) are independently selected from hydrogen, alkyl, alkynyl, alkenyl, alkoxy, halo, hydroxyl, and —CN, wherein the alkyl, alkynyl, alkenyl, alkoxy, and cycloalkyl are each optionally substituted with at least one group, such as one, two, three, or four groups, independently selected from $R^a$. In some embodiments, $R_5$ is hydrogen. In some embodiments, $R_6$ in formula (III) is selected from hydrogen, alkyl, alkynyl, alkenyl, alkoxy, halo, hydroxyl, and —CN, wherein the alkyl, alkynyl, alkenyl, alkoxy, and cycloalkyl are unsubstituted. In some embodiments, $R_8$ in formula (III) is hydrogen or halo, such as fluoro.

In some embodiments, $R_7$ in formula (III) is selected from cycloalkly, heterocycyl, aryl and heteroaryl, wherein the cycloalkly, heterocycyl, aryl and heteroaryl are each optionally substituted with at least one group, such as one, two, three, or four groups, independently selected from $R^a$. In some embodiments, $R_7$ in formula (III) is heterocycyl optionally substituted with at least one group, such as one, two, three, or four groups, independently selected from $R^a$. In some embodiments, $R_7$ in formula (III) is heterocyclyl optionally substituted with at least one group, such as one, two, three, or four groups, independently selected from alkyl, cycloalkyl and heterocyclyl, wherein each of the alkyl, cycloalkyl and heterocyclyl is optionally substituted with at least one group, such as one, two, three or four groups, independently selected from alkyl, hydroxyl, and alkoxy.

In some embodiments, $R_7$ in formula (III) is selected from piperidinyl, piperazinyl, and morpholinyl optionally substituted with at least one group, such as one, two, three, or four groups, independently selected from alkyl (such as methyl, ethyl, or iso-propyl), cycloalkly and heterocyclyl (such as piperidinyl, piperazinyl, or morpholinyl), wherein each of the alkyl, cycloalkly, and heterocyclyl is optionally substituted by hydroxyl.

In some embodiments, $R_9$ in formula (III) is selected from hydrogen, alkyl, and cycloalkyl, wherein each of the alyl and cycloalkyl is optionally substituted with at least one group, such as one, two, three, or four groups, independently selected from $R^a$. In some embodiments, $R_9$ in formula (III) is selected from alkyl and cycloalkyl, wherein each of the alkyl and cycloalkyl is optionally substituted with at least one group, such as one, two, three, or four groups, independently selected from alkyl, halo, and hydroxyl.

In some embodiments, the at least one compound of formula (I), and/or at least one pharmaceutically acceptable salt thereof, is selected from compounds of formula (IV):

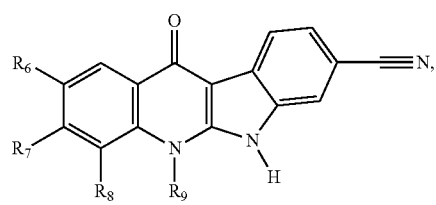

wherein $R_6$, $R_7$, $R_8$, and $R_9$ are the same as those defined in formula (I) above.

In some embodiments, $R_6$ and $R_8$ in formula (IV) are independently selected from hydrogen, alkyl, alkynyl, alkenyl, alkoxy, halo, hydroxyl, and —CN, wherein the alkyl, alkynyl, alkenyl, alkoxy, and cycloalkyl are each optionally substituted with at least one group, such as one, two, three, or four groups, independently selected from $R^a$. In some embodiments, $R_6$ in formula (IV) is selected from hydrogen, alkyl, alkynyl, alkenyl, alkoxy, halo, hydroxyl, and —CN, wherein the alkyl, alkynyl, alkenyl, alkoxy, and cycloalkyl are unsubstituted. In some embodiment, $R_8$ in formula (IV) is hydrogen or halo, such as fluoro.

In some embodiments, $R_7$ in formula (IV) is selected from cycloalkly, heterocycyl, aryl and heteroaryl, wherein the cycloalkly, heterocycyl, aryl and heteroaryl are each optionally substituted with at least one group, such as one, two, three, or four groups, independently selected from $R^a$. In some embodiments, $R_7$ in formula (IV) is heterocycyl optionally substituted with at least one group, such as one, two, three, or four groups, independently selected from $R^a$. In some embodiments, $R_7$ in formula (IV) is heterocyclyl optionally substituted with at least one group, such as one, two, three, or four groups, independently selected from alkyl, cycloalkyl and heterocyclyl, wherein each of the alkyl, cycloalkyl and heterocyclyl is optionally substituted with at least one group, such as one, two, three or four groups, independently selected from alkyl, hydroxyl, and alkoxy.

In some embodiments, $R_7$ in formula (IV) is selected from piperidinyl, piperazinyl, and morpholinyl optionally substituted with at least one group, such as one, two, three, or four groups, independently selected from alkyl (such as methyl, ethyl, or iso-propyl), cycloalkly and heterocyclyl (such as piperidiny, piperazinyl, or morpholinyl), wherein each of the alkyl, cycloalkly, and heterocyclyl is optionally substituted by hydroxyl.

In some embodiments, $R_9$ in formula (IV) is selected from hydrogen, alkyl, and cycloalkyl, wherein each of the alyl and cycloalkyl is optionally substituted with at least one group, such as one, two, three, or four groups, independently selected from $R^a$. In some embodiments, $R_9$ in formula (IV) is selected from alkyl and cycloalkyl, wherein each of the alkyl and cycloalkyl is optionally substituted with at least one group, such as one, two, three, or four groups, independently selected from alkyl, halo, and hydroxyl.

In some embodiments, the at least one compound of formula (I), and/or at least one pharmaceutically acceptable salt thereof, is selected from compounds of formula (V):

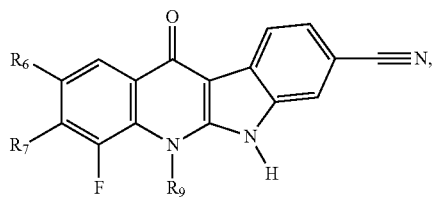

wherein $R_6$, $R_7$, and $R_9$ are the same as those defined in formula (I) above.

In some embodiments, $R_6$ in formula (V) are independently selected from hydrogen, alkyl, alkynyl, alkenyl, alkoxy, halo, hydroxyl, and —CN, wherein the alkyl, alkynyl, alkenyl, alkoxy, and cycloalkyl are each optionally substituted with at least one group, such as one, two, three, or four groups, independently selected from $R^a$. In some embodiments, $R_6$ in formula (V) is selected from hydrogen, alkyl, alkynyl, alkenyl, alkoxy, halo, hydroxyl, and —CN, wherein the alkyl, alkynyl, alkenyl, alkoxy, and cycloalkyl are unsubstituted.

In some embodiments, $R_7$ in formula (V) is selected from cycloalkly, heterocycyl, aryl and heteroaryl, wherein the cycloalkly, heterocycyl, aryl and heteroaryl are each optionally substituted with at least one group, such as one, two, three, or four groups, independently selected from $R^a$. In some embodiments, $R_7$ in formula (V) is heterocycyl optionally substituted with at least one group, such as one, two, three, or four groups, independently selected from $R^a$. In some embodiments, $R_7$ in formula (V) is heterocyclyl optionally substituted with at least one group, such as one, two, three, or four groups, independently selected from alkyl, cycloalkyl and heterocyclyl, wherein each of the alkyl, cycloalkyl and heterocyclyl is optionally substituted with at least one group, such as one, two, three or four groups, independently selected from alkyl, hydroxyl, and alkoxy.

In some embodiments, $R_7$ in formula (V) is selected from piperidinyl, piperazinyl, and morpholinyl optionally substituted with at least one group, such as one, two, three, or four groups, independently selected from alkyl (such as methyl, ethyl, or iso-propyl), cycloalkly and heterocyclyl (such as piperidiny, piperazinyl, or morpholinyl), wherein each of the alkyl, cycloalkly, and heterocyclyl is optionally substituted by hydroxyl.

In some embodiments, $R_9$ in formula (V) is selected from hydrogen, alkyl, and cycloalkyl, wherein each of the alyl and cycloalkyl is optionally substituted with at least one group, such as one, two, three, or four groups, independently selected from $R^a$. In some embodiments, $R_9$ in formula (V) is selected from alkyl and cycloalkyl, wherein each of the alkyl and cycloalkyl is optionally substituted with at least one group, such as one, two, three, or four groups, independently selected from alkyl, halo, and hydroxyl.

In some embodiments, $R_9$ is methyl, ethyl, propyl, iso-propyl, cyclopropanyl, cyclobutyl, cyclopentyl, cyclohexyl, butyl, 2-butyl, 2-pentyl, 3-pentyl, and 2,2-dimethyl-propyl optionally substituted with at least one group selected from halo (such as fluoro) and hydroxyl.

Also disclosed herein is at least one compound selected from the following compounds, and/or at least one pharmaceutically acceptable salt thereof:

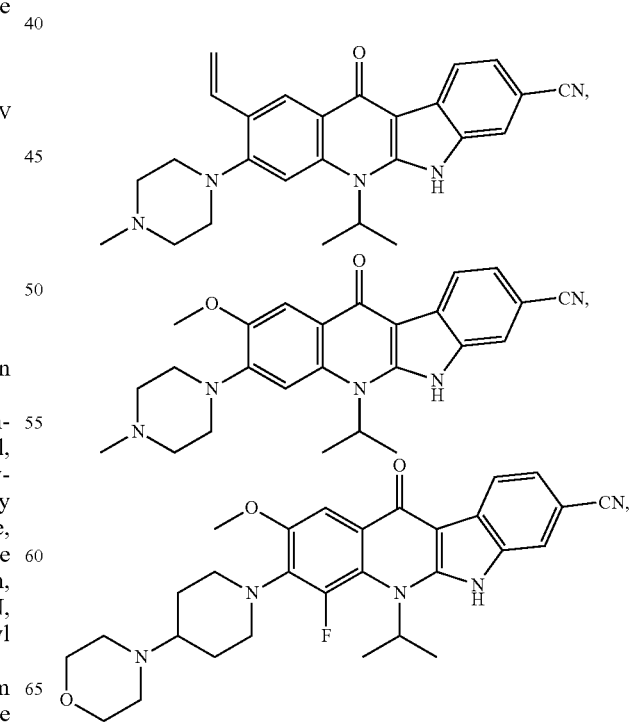

-continued
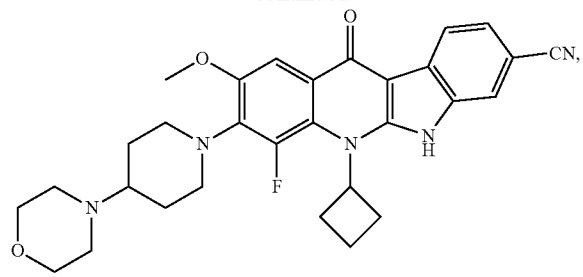
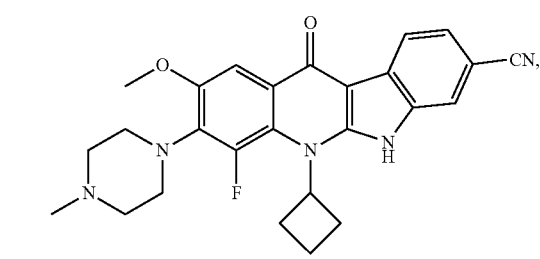
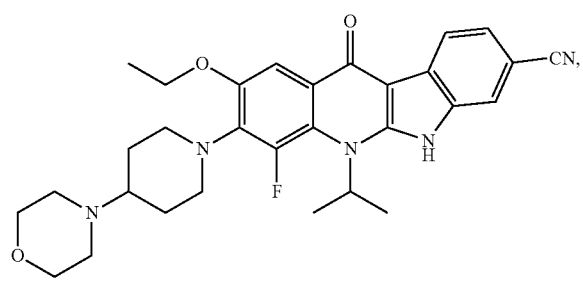
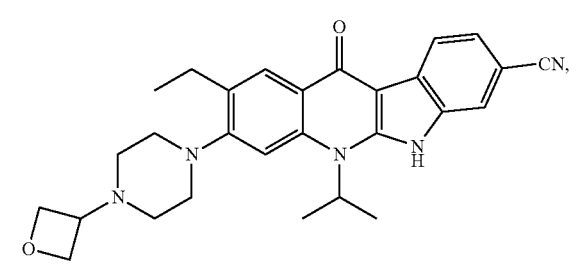
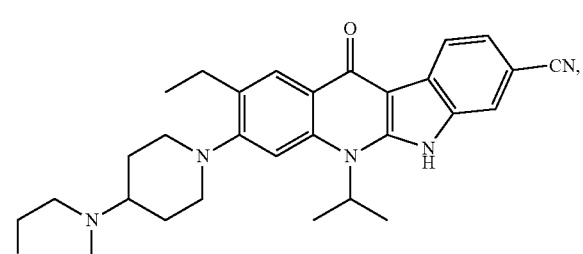
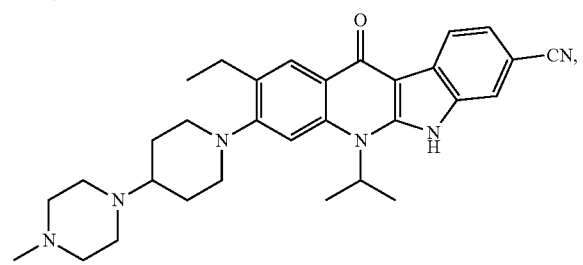
-continued
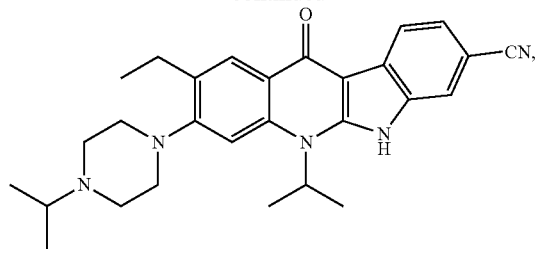
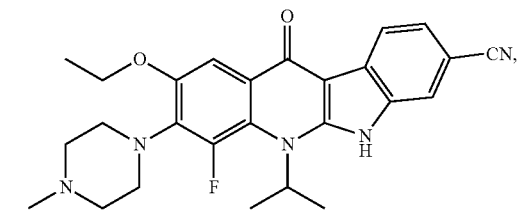
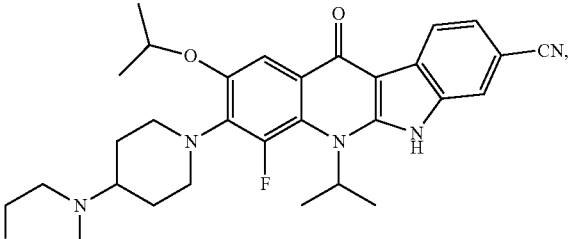
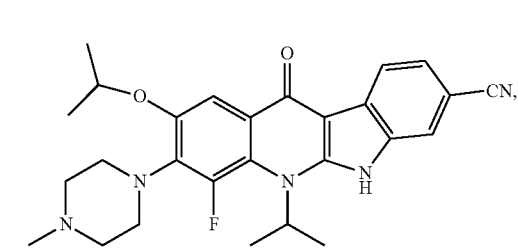
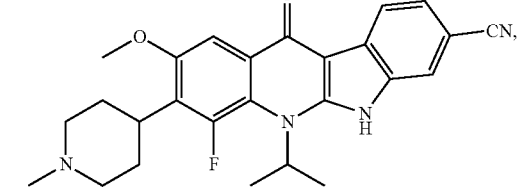
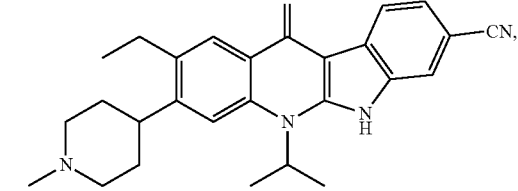
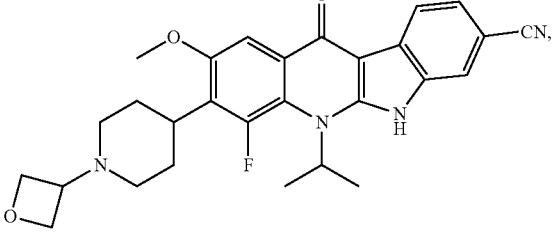

15
-continued
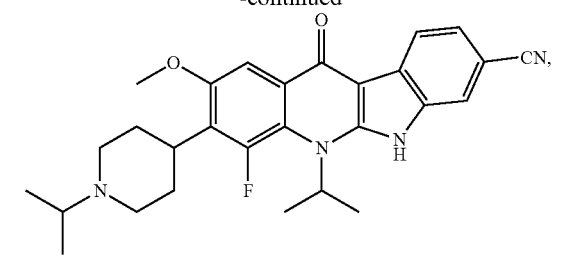
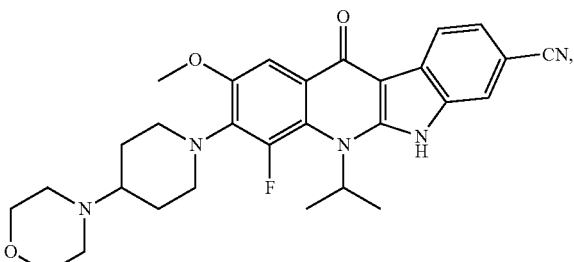
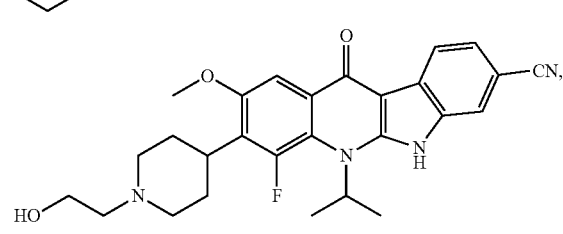
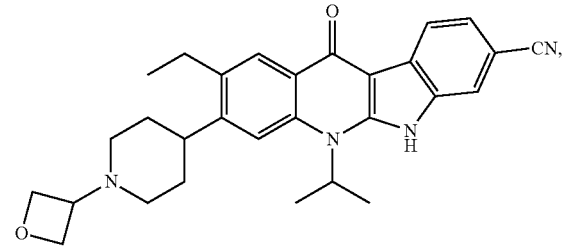
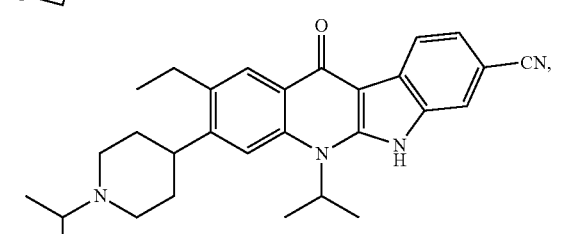
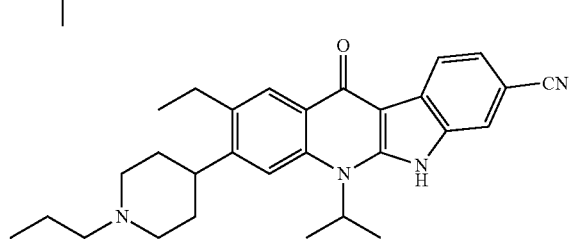
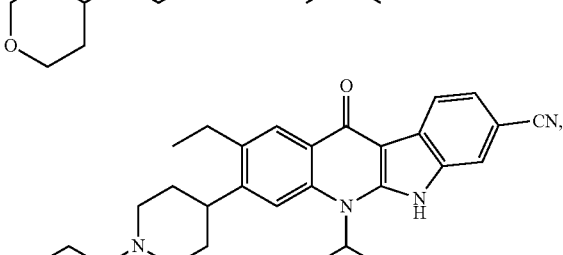
16
-continued
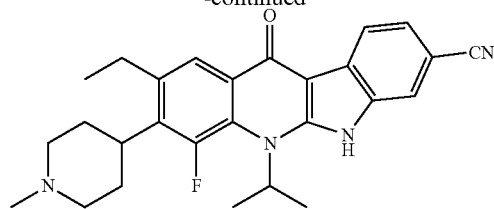
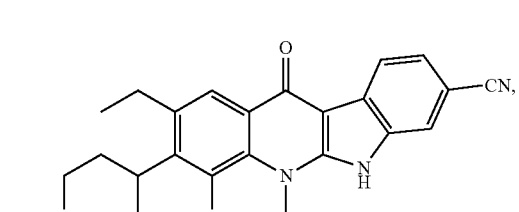
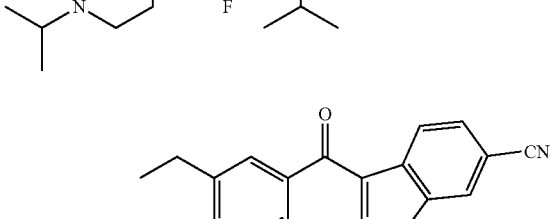
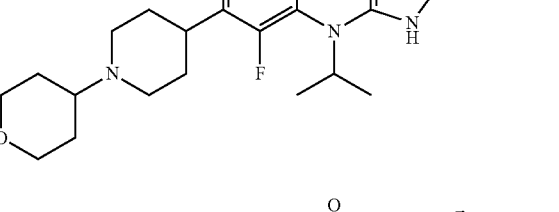
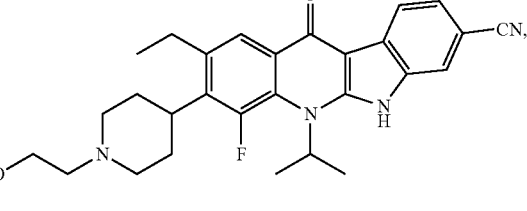
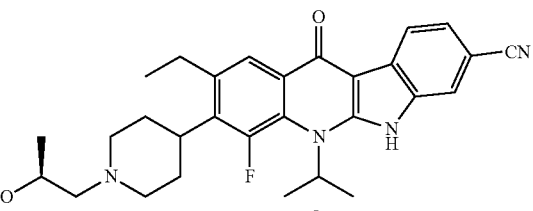
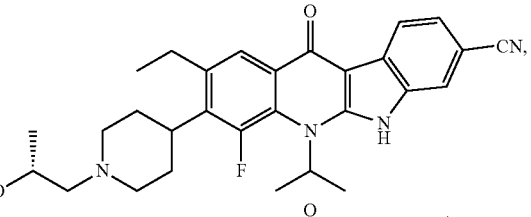
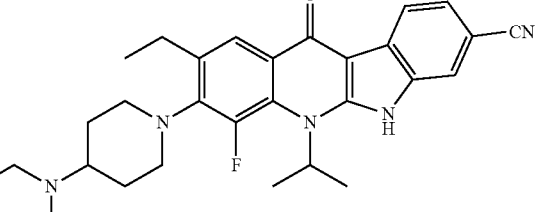

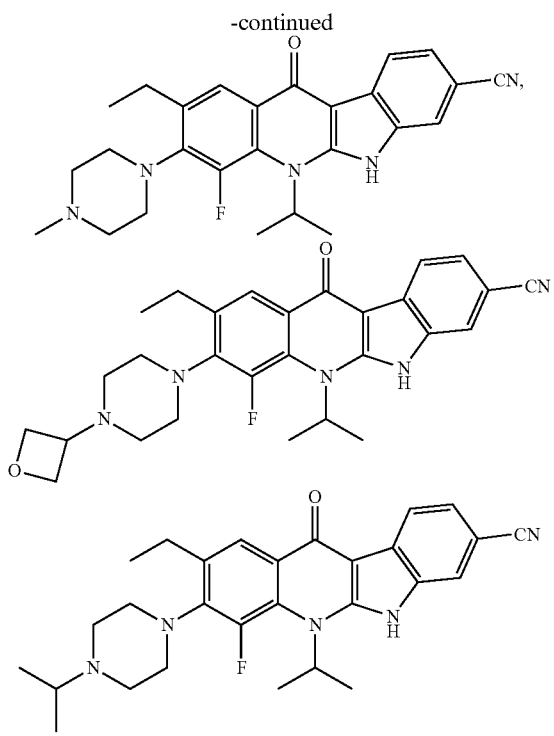

Also disclosed herein is a method of treating a disease, such as cancer, which is responsive to inhibition of ALK, comprising administering to a subject, such as a mammal or human, in need of treating for the disease, such as cancer, an effective amount of at least one compound of formula (I) (such as formulae (II), (III), (IV) and (V)), and/or at least one pharmaceutically acceptable salt thereof.

Also disclosed herein is a pharmaceutical composition, comprising at least one compound of formula (I) (such as formulae (II), (III), (IV) and (V)) and/or at least one pharmaceutically acceptable salt thereof, and at least one pharmaceutically acceptable carrier.

The pharmaceutical composition comprising at least one compound of formula (I) (such as formulae (II), (III), (IV) and (V)) and/or at least one pharmaceutically acceptable salt thereof, and at least one pharmaceutically acceptable carrier, can be administered in various known manners, such as orally, topically, rectally, parenterally, by inhalation spray, or via an implanted reservoir, although the most suitable route in any given case will depend on the particular host, and nature and severity of the conditions for which the active ingredient is being administered. The term "parenteral" as used herein includes subcutaneous, intracutaneous, intravenous, intramuscular, intraarticular, intraarterial, intrasynovial, intrasternal, intrathecal, intralesional and intracranial injection or infusion techniques. The compositions disclosed herein may be conveniently presented in unit dosage form and prepared by any of the methods well known in the art.

The at least one compound of formula (I) (such as formulae (II), (III), (IV) and (V)) and/or at least one pharmaceutically acceptable salt thereof can be administered orally in solid dosage forms, such as capsules, tablets, troches, dragées, granules and powders, or in liquid dosage forms, such as elixirs, syrups, emulsions, dispersions, and suspensions. The at least one compound of formula (I) (such as formulae (II), (III), (IV) and (V)) and/or at least one pharmaceutically acceptable salt thereof can also be administered parenterally, in sterile liquid dosage forms, such as dispersions, suspensions or solutions. Other dosages forms that can also be used to administer the at least one compound of formula (I) (such as formulae (II), (III), (IV) and (V)) and/or at least one pharmaceutically acceptable salt thereof include ointment, cream, drops, transdermal patch or powder for topical administration, an ophthalmic solution or suspension formation, i.e., eye drops, for ocular administration, an aerosol spray or powder composition for inhalation or intranasal administration, or a cream, ointment, spray or suppository for rectal or vaginal administration.

Gelatin capsules containing the at least one compound of formula (I) (such as formulae (II), (III), (IV) and (V)) and/or at least one pharmaceutically acceptable salt thereof and powdered carriers, such as lactose, starch, cellulose derivatives, phosphate sodium, magnesium stearate, stearic acid, sodium stearyl fumarate and the like, can also be used. Similar diluents can be used to make compressed tablets. Both tablets and capsules can be manufactured as sustained release products to provide for continuous release of medication over a period of time. Compressed tablets can be sugar coated or film coated to mask any unpleasant taste and protect the tablet from the atmosphere, or enteric coated for selective disintegration in the gastrointestinal tract.

Liquid dosage forms for oral administration can further comprise at least one agent selected from coloring and flavoring agents to increase patient acceptance.

In general, water, suitable oil, saline, aqueous dextrose (glucose), and related sugar solutions and glycols such as propylene glycol or polyethylene glycols, and solubilizing agents such as cyclodextrins and polysorbate 80, can be examples of suitable carriers for parenteral solutions. Solutions for parenteral administration may comprise a water soluble salt of the at least one compound disclosed herein, at least one suitable stabilizing agent, and if necessary, at least one buffer substance. Antioxidizing agents such as sodium bisulfate, sodium sulfite, or ascorbic acid, either alone or combined, can be examples of suitable stabilizing agents. Citric acid and its salts and sodium EDTA can also be used as examples of suitable stabilizing agents. In addition, parenteral solutions can further comprise at least one preservative, selected, for example, from benzalkonium chloride, methyl- and propylparaben, and chlorobutanol.

A pharmaceutically acceptable carrier is, for example, selected from carriers that are compatible with active ingredients of the pharmaceutical composition (and in some embodiments, capable of stabilizing the active ingredients) and not deleterious to the subject to be treated. For example, solubilizing agents, such as cyclodextrins (which can form specific, more soluble complexes with the at least one compound and/or at least one pharmaceutically acceptable salt disclosed herein), can be utilized as pharmaceutical excipients for delivery of the active ingredients. Examples of other carriers include colloidal silicon dioxide, magnesium stearate, cellulose, sodium lauryl sulfate, and pigments such as D&C Yellow #10. Suitable pharmaceutically acceptable carriers are disclosed in *Remington's Pharmaceutical Sciences*, A. Osol, a standard reference text in the art.

The at least one compound of formula (I) (such as formulae (II), (III), (IV) and (V)) and/or at least one pharmaceutically acceptable salt thereof can further be examined for efficacy in treating cancer by in vivo assays. For example, the at least one compound and/or the at least one pharmaceutically acceptable salt thereof can be administered to an animal (e.g., a mouse model) having cancer and its therapeutic effects can be accessed. Positive results in one or more of such tests are sufficient to increase the scientific storehouse of knowledge and hence sufficient to demonstrate practical utility of the compounds and/or salts tested. Based on the results, an appropriate dosage range and administration route for animals, such as humans, can also be determined.

For administration by inhalation, the at least one compound of formula (I) (such as formulae (II), (III), (IV) and (V)) and/or at least one pharmaceutically acceptable salt thereof may be conveniently delivered in the form of an aerosol spray presentation from pressurized packs or nebulisers. The at least one compound of formula (I) (such as formulae (II), (III), (IV) and (V)) and/or at least one pharmaceutically acceptable salt thereof may also be delivered as powders, which may be formulated and the powder composition may be inhaled with the aid of an insufflation powder inhaler device. One exemplary delivery system for inhalation can be a metered dose inhalation (MDI) aerosol, which may be formulated as a suspension or solution of at least one compound of formula (I) (such as formulae (II), (III), (IV) and (V)) and/or at least one pharmaceutically acceptable salt thereof in at least one suitable propellant, selected, for example, from fluorocarbons and hydrocarbons.

For ocular administration, an ophthalmic preparation may be formulated with an appropriate weight percentage of a solution or suspension or gel of the at least one compound of formula (I) (such as formulae (II), (III), (IV) and (V)) and/or at least one pharmaceutically acceptable salt in an appropriate ophthalmic vehicle, such that the at least one compound of formula (I) (such as formulae (II), (III), (IV) and (V)) and/or at least one pharmaceutically acceptable salt is maintained in contact with the ocular surface for a sufficient time period to allow the compound to penetrate the corneal and internal regions of the eye.

Useful pharmaceutical dosage-forms for administration of the at least one compound of formula (I) (such as formulae (II), (III), (IV) and (V)) and/or at least one pharmaceutically acceptable salt thereof include, but are not limited to, hard and soft capsules, such as HPMC capsules, tablets, parenteral injectables, and oral suspensions.

The dosage administered will be dependent on factors, such as the age, health and weight of the recipient, the extent of disease, type of concurrent treatment, if any, frequency of treatment, and the nature of the effect desired. In general, a daily dosage of the active ingredient can vary, for example, from 0.1 to 2000 milligrams per day. For example, 10-500 milligrams once or multiple times per day may be effective to obtain the desired results.

In some embodiments, the at least one compound of formula (I) (such as formulae (II), (III), (IV) and (V)) and/or at least one pharmaceutically acceptable salt can be present in an amount of 1, 5, 10, 15, 25, 50, 75, 100, 125, 150, 200, 250, 300, 400 and 500 mg in a capsule.

In some embodiments, a large number of unit capsules can be prepared by filling standard two-piece hard gelatin capsules each with, for example, 100 milligrams of the at least one compound of formula (I) (such as formulae (II), (III), (IV) and (V)) and/or at least one pharmaceutically acceptable salt thereof in powder, 150 milligrams of lactose, 50 milligrams of cellulose, and 6 milligrams magnesium stearate.

In some embodiments, a mixture of the at least one compound of formula (I) (such as formulae (II), (III), (IV) and (V)) and/or at least one pharmaceutically acceptable salt thereof and a digestible oil such as soybean oil, cottonseed oil or olive oil can be prepared and injected by means of a positive displacement pump into liquid-filled hard capsules containing 5, 10, 20 or 50 milligrams of the active ingredient.

In some embodiments, the at least one compound of formula (I) (such as formulae (II), (III), (IV) and (V)) and/or at least one pharmaceutically acceptable salt can be present in an amount of 1, 5, 10, 15, 25, 50, 75, 100, 125, 150, 200, 250, 300, 400 and 500 mg in a tablet.

In some embodiments, a large number of tablets can be prepared by conventional procedures so that the dosage unit comprises, for example, 100 milligrams of the at least one compound of formula (I) (such as formulae (II), (III), (IV) and (V)) and/or at least one pharmaceutically acceptable salt thereof, 0.2 milligrams of colloidal silicon dioxide, 5 milligrams of magnesium stearate, 275 milligrams of microcrystalline cellulose, 11 milligrams of starch, 10 milligrams of crospovidone, and 98.8 milligrams of lactose. Appropriate coatings may, for example, be applied to increase palatability or delay absorption.

In some embodiments, a parenteral composition suitable for administration by injection can be prepared by stirring 0.5% by weight of the at least one compound of formula (I) (such as formulae (II), (III), (IV) and (V)) and/or at least one pharmaceutically acceptable salt thereof in 20% by volume propylene glycol (PEG), such as PEG 400. The solution is made to the expected volume with water for injection and sterilized.

In some embodiment, an aqueous suspension can be prepared for oral administration. For example, each 5 milliliters of an aqueous suspension comprising 100 milligrams of finely divided at least one compound of formula (I) (such as formulae (II), (III), (IV) and (V)) and/or at least one pharmaceutically acceptable salt thereof, 100 milligrams of sodium carboxymethyl cellulose, 5 milligrams of sodium benzoate, 1.0 grams of sorbitol solution, U.S.P., and 0.025 milliliters of vanillin can be used.

The same dosage forms can generally be used when the at least one compound of formula (I) (such as formulae (II), (III), (IV) and (V)) and/or at least one pharmaceutically acceptable salt thereof are administered stepwise or in conjunction with at least one other therapeutic agent. When drugs are administered in physical combination, the dosage form and administration route should be selected depending on the compatibility of the combined drugs. Thus, the term "co-administration" is understood to include the administration of at least two agents concomitantly or sequentially, or alternatively as a fixed dose combination of the at least two active components.

The at least one compound of formula (I) (such as formulae (II), (III), (IV) and (V)) and/or at least one pharmaceutically acceptable salt thereof can be administered as the sole active ingredient or in combination with at least one second active ingredient, selected, for example, from other active ingredients known to be useful for treating the target cancers in a patient.

The compounds of the invention can be prepared using the general synthetic routes shown below in Scheme 1, Scheme 2, and Scheme 3 and described more fully in the examples.

The at least one compound of formula (I) can be prepared by following Scheme 1 as illustrated below:

Scheme 1

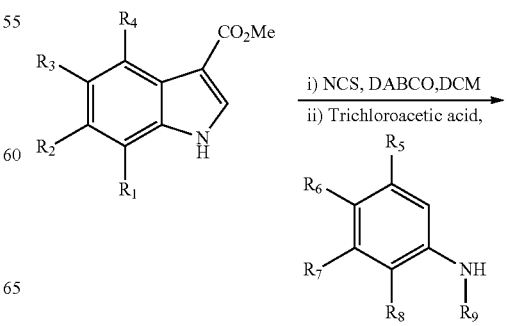

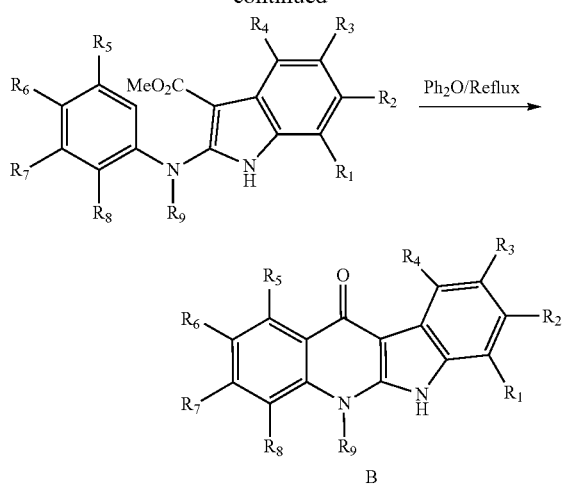

The mixture of methyl ester substituted indole (1.0 equiv.) and DABCO (0.55 equiv.) in $CH_2Cl_2$ was cooled in an ice-water bath. To that cooled mixture was added NCS (1.1 equiv.). After the mixture was stirred under ice-water bath for 2 hours, N-substituted aniline (1.1 equiv.) and Trichloroacetic acid (0.25 equiv.) in $CH_2Cl_2$ were added. The ice-water bath was removed, and the reaction temperature was allowed to warm up to room temperature. After the reaction mixture was stirred for 2 to 3 hours at room temperature, $CH_2Cl_2$ (50 ml), water (50 ml), saturated aqueous $NaHCO_3$ (50 ml), and brine (50 ml) were added to the reaction mixture. $CH_2Cl_2$ layer was separated and concentrated in vacuo. The residue was purified on silica gel column to afford A as an oil or foam. The yield ranged from 50% to 80%.

The suspension of A in $Ph_2O$ was stirred vigorously and refluxed at approximately 280° C. for 1 to 3 hours until the reaction was complete. The reaction mixture was cooled down to room temperature, after which the reaction mixture was filtered. Hexane was used to wash the solid on the filter to remove $Ph_2O$. Compound B was obtained as grey or brown colored powder. The yield ranged from 20% to 50%.

One of ordinary skill in the art can recognize that the desired substituents for variables $R_1$-$R_9$ can be obtained through transformations before, after, or simultaneously when the cyclization in $Ph_2O$ occurs. For example, when $R_7$ is, for example, fluoro, the replacement of fluoro with a nucleophile (such as optionally substituted piperazine or piperidine) can be accomplished after cyclization, as illustrated below:

Scheme 1-1

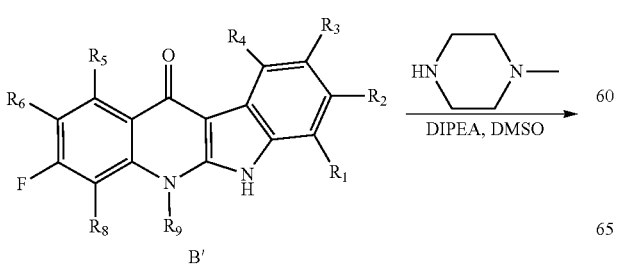

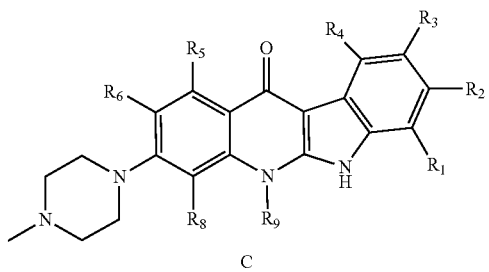

The mixture of compound B' (60 mg), DIPEA (0.5 ml), 1-Methylpiperazine (0.5 ml) and DMSO (2 ml) was heated to 120 to 140° C. After stirred at 120-140° C. for 2-7 days, the mixture was filtered and the filtrate was purified by preparative HPLC. The collected portions were dried on lyophilizer to afford compound C as a powder. The yield ranged from 10% to 50%.

The following schemes further exemplified the preparation of indoloquinolone compounds of formula (I) (such as formulae (II), (III), (IV), or (V)):

Scheme 1-2

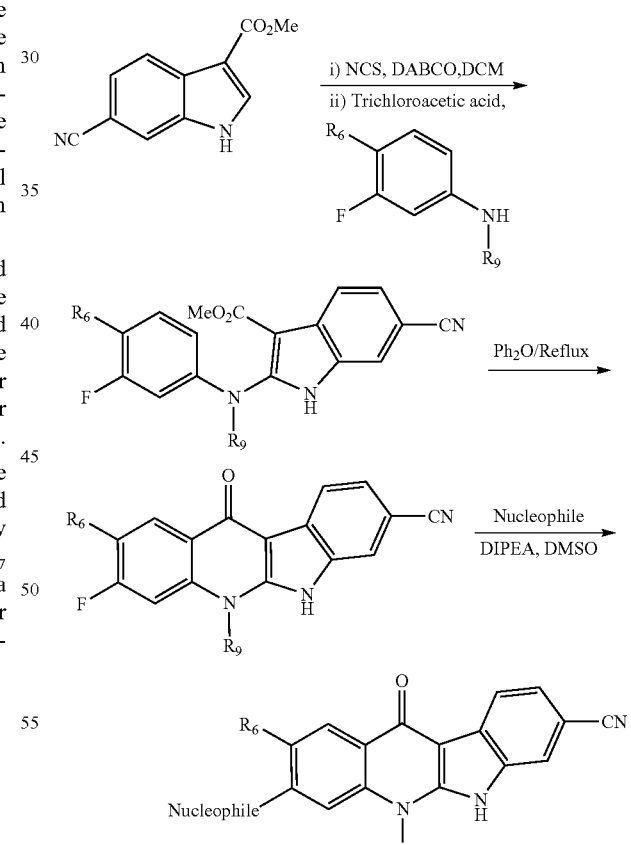

When $R_6$ is bromo or iodo, $R_6$ in Scheme 1-1 can be transformed into other groups, such as alkenyl, alkynyl, aryl or heteroaryl group, under, for example, Suzuki type reaction conditions, wherein the alkenyl can be further reduced to alkyl, as illustrated below:

Scheme 1-3
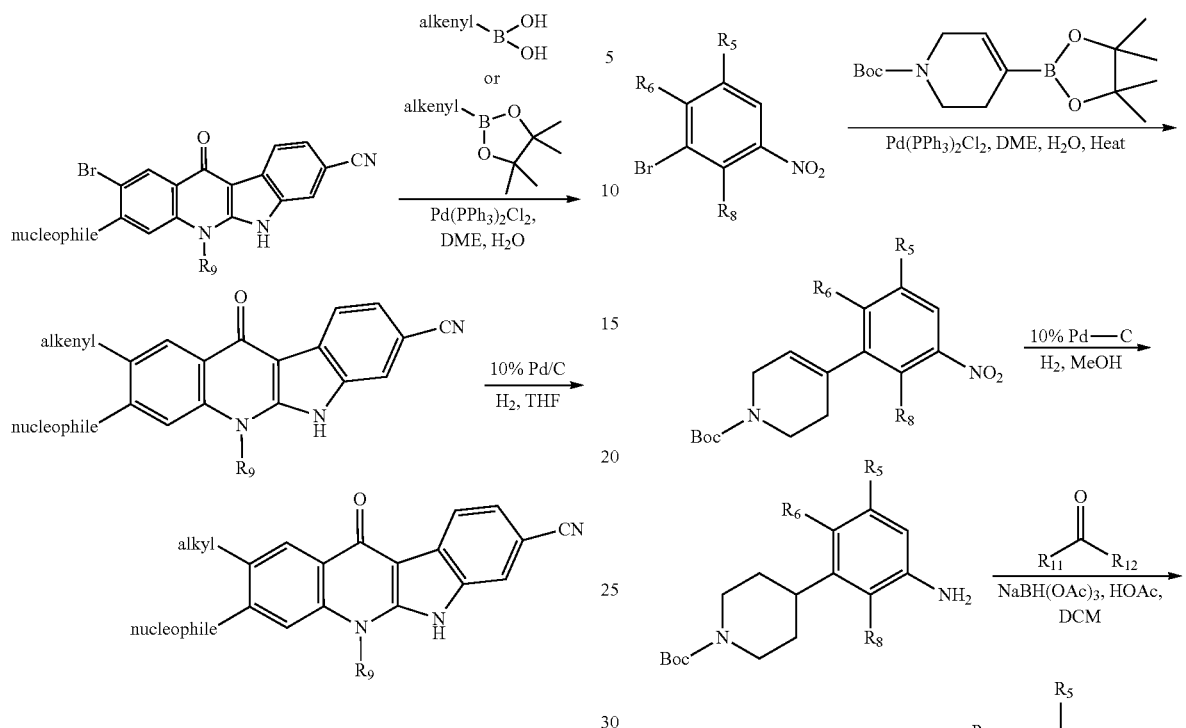
Scheme 1-4
When R$_7$ is bromo or iodo, R$_7$ in Scheme 1-1 can be transformed into other groups, such as alkenyl, alkynyl, aryl or heteroaryl group, under, for example, Suzuki type reaction conditions, wherein the alkenyl can be further reduced to alkyl, as illustrated below:
Scheme 1-5
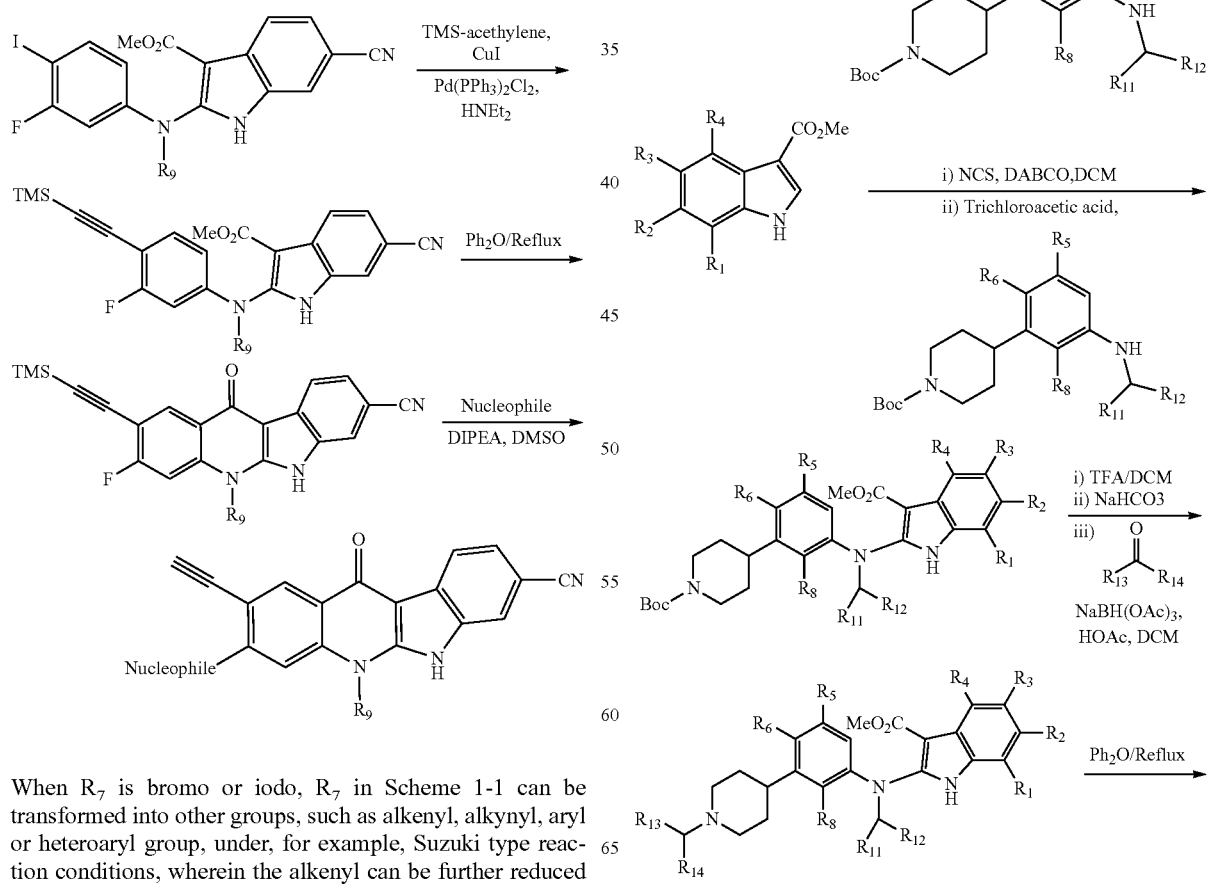

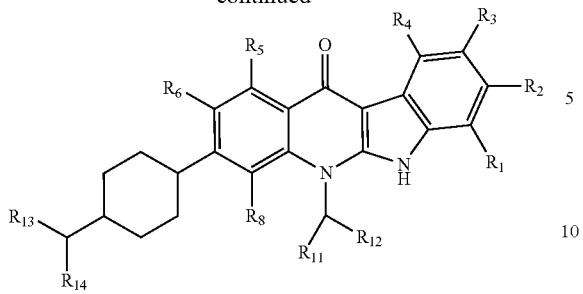

The following scheme illustrates another general synthetic route to prepare N-substituted anilines, which involves Schiff base formation and subsequent reduction:

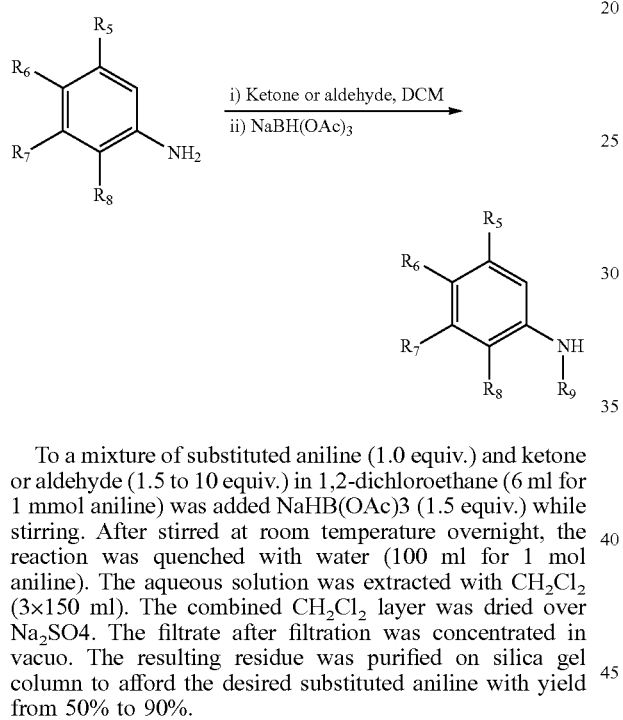

To a mixture of substituted aniline (1.0 equiv.) and ketone or aldehyde (1.5 to 10 equiv.) in 1,2-dichloroethane (6 ml for 1 mmol aniline) was added NaHB(OAc)3 (1.5 equiv.) while stirring. After stirred at room temperature overnight, the reaction was quenched with water (100 ml for 1 mol aniline). The aqueous solution was extracted with $CH_2Cl_2$ (3×150 ml). The combined $CH_2Cl_2$ layer was dried over $Na_2SO4$. The filtrate after filtration was concentrated in vacuo. The resulting residue was purified on silica gel column to afford the desired substituted aniline with yield from 50% to 90%.

In some embodiments, $R_7$ can be fluoro. In some embodiments, $R_5$ and $R_8$ are hydrogen. In some embodiments, the ketone can be cyclic ketone.

Modification of the above Scheme can be used to synthesize numerous compounds of the invention as will be apparent to those skilled in the art.

The invention is further described by reference to the following examples, which are intended to exemplify the claimed invention but not to limit it in any way.

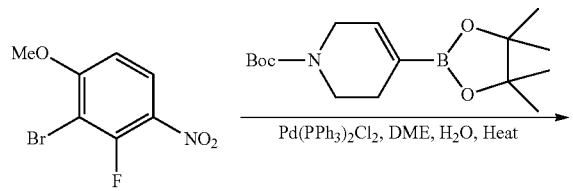

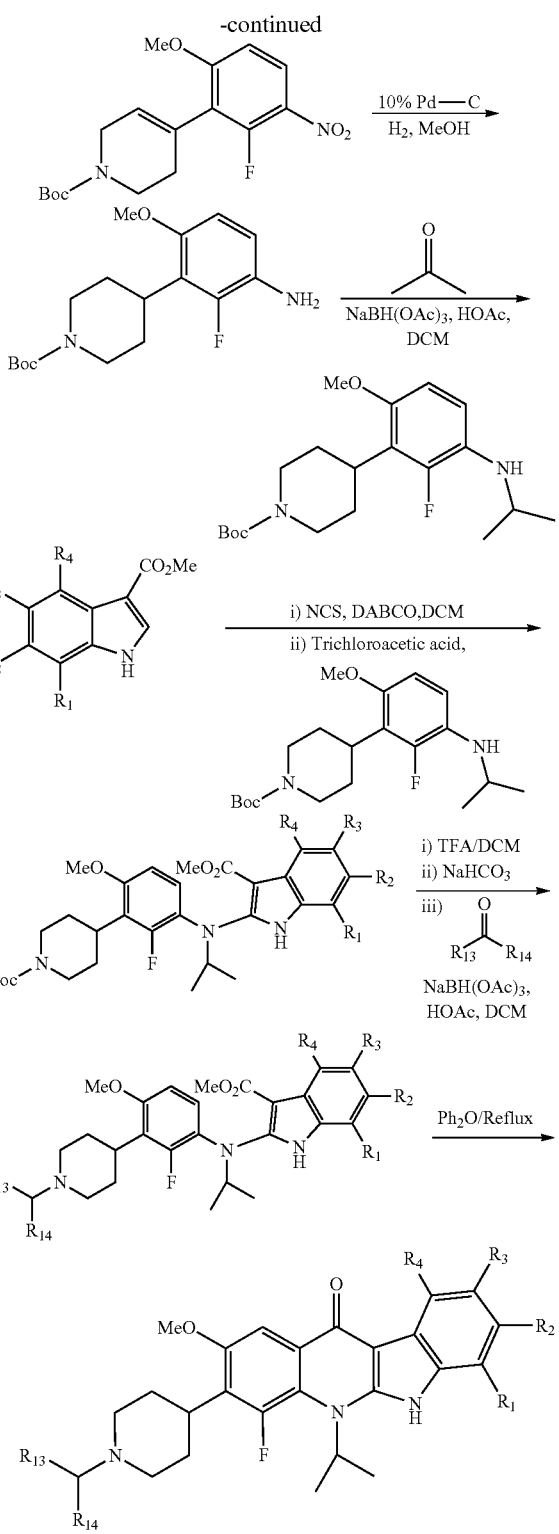

EXAMPLES

The examples below are intended to be purely exemplary and should not be considered to be limiting in any way. Efforts have been made to ensure accuracy with respect to numbers used (for example, amounts, temperature, etc.), but some experimental errors and deviations should be accounted for. Unless indicated otherwise, temperature is in degrees Centigrade. Reagents were purchased from commercial suppliers such as Sigma-Aldrich, Alfa Aesar, or TCI, and were used without further purification unless otherwise indicated.

Unless otherwise indicated, the reactions set forth below were performed under a positive pressure of nitrogen or argon or with a drying tube in anhydrous solvents; the reaction flasks were fitted with rubber septa for the introduction of substrates and reagents via syringe; and glassware was oven dried and/or heat dried.

Unless otherwise indicated, column chromatography purification was conducted on a Biotage system (Manufacturer: Dyax Corporation) having a silica gel column or on a silica SepPak cartridge (Waters), or was conducted on a Teledyne IscoCombiflash purification system using self-packed or prepacked silica gel cartridges.

$^1$H NMR spectra were recorded on a Varian instrument operating at 400 MHz. $^1$H-NMR spectra were obtained using CDCl$_3$, CD$_2$Cl$_2$, CD$_3$OD, D$_2$O, d$_6$-DMSO, d$_6$-acetone or (CD$_3$)$_2$CO as solvent and tetramethylsilane (0.00 ppm) or residual solvent (CDCl$_3$: 7.25 ppm; CD$_3$OD: 3.31 ppm; D$_2$O: 4.79 ppm; d$_6$-DMSO: 2.50 ppm; d$_6$-acetone: 2.05; (CD$_3$)$_2$CO: 2.05) as the reference standard. When peak multiplicities are reported, the following abbreviations are used: s (singlet), d (doublet), t (triplet), q (quartet), qn (quintuplet), sx (sextuplet), m (multiplet), br (broadened), dd (doublet of doublets), dt (doublet of triplets). Coupling constants, when given, are reported in Hertz (Hz). All compound names except the reagents were generated by ChemDraw.

In the following examples, the abbreviations below are used:

DMSO Dimethyl sulfoxide
DIPEA Diisopropylethylamine
DCM Dichloromethane
MeOH Methanol
Hex n-Hexane
EA Ethyl acetate
THF Tetrahydrogenfuran
EtOAc Ethyl acetate
DABCO 1,4-Diazo[2.2.2]bicyclooctane
DME Dimethoxyethane
TFA Trifluoroacetic acid Example 1 (ALK-18)

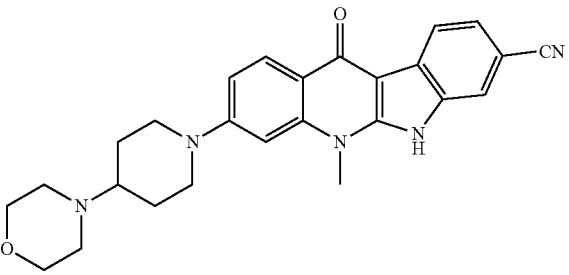 [SMILES: Cn1c2cc(N3CCC(N4CCOCC4)CC3)ccc2c(=O)c2c3ccc(C#N)cc3[nH]c21]

5-Methyl-3-(4-morpholinopiperidin-1-yl)-11-oxo-6,11-dihydro-5H-indolo[2,3-b]quinoline-8-carbonitrile

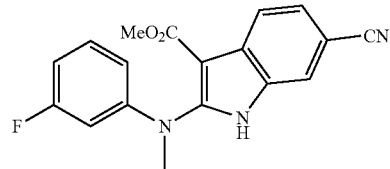 [SMILES: COC(=O)c1c(N(C)c2cccc(F)c2)[nH]c2cc(C#N)ccc12]

Step A: Methyl 6-cyano-2-((3-fluorophenyl)(methyl)amino)-1H-indole-3-carboxylate DABCO (62 mg, 0.55 mmol) was added to a solution of Methyl 6-cyano-1H-indole-3-carboxylate (200 mg, 1 mmol) in DCM (20 mL) and the mixture was cooled to 0° C. N-Chlorosuccinimide (147 mg, 1.1 mmol) was then added and the reaction was stirred at 0° C. for 2 hr. A solution of 3-Fluoro-N-methylaniline (125 mg, 1 mmol) and Trichloroacetic acid (41 mg, 0.25 mmol) in DCM (5 mL) was added dropwise and the reaction was stirred for 2 hr at room temperature. The reaction was quenched by adding water and the mixture was extracted with DCM. Solvent was removed under vacuum and the residue was purified by silica gel chromatography (Hex:EA=4:1) to afford Methyl 6-cyano-2-((3-fluorophenyl)(methyl)amino)-1H-indole-3-carboxylate (220 mg, 68% yield). $^1$H NMR (400 MHz, CDCl$_3$) δ ppm 8.26 (s, 1H), 8.03 (d, J=8.6 Hz, 1H), 7.46 (d, J=1.8 Hz, 1H), 7.39 (dd, J=8.6, 1.8 Hz, 1H), 7.21-7.18 (m, 1H), 6.66-6.49 (m, 3H), 3.85 (s, 3H), 3.43 (s, 3H).

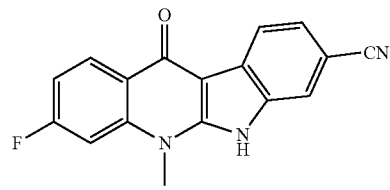 [SMILES: Cn1c2cc(F)ccc2c(=O)c2c3ccc(C#N)cc3[nH]c21]

Step B: 3-Fluoro-5-methyl-11-oxo-6,11-dihydro-5H-indolo[2,3-b]quinoline-8-carbonitrile Methyl 6-cyano-2-((3-fluorophenyl)(methyl)amino)-1H-indole-3-carboxylate (220 mg, 0.68 mmol) was dissolved in Diphenyl ether (10 mL) and the solution was refluxed for 1 hr. The mixture was cooled to RT. Hexane (20 mL) was added and the precipitate was collected by filtration. The precipitate was purified by silica gel chromatography (Hex:EA=2:1) to afford 3-Fluoro-5-methyl-11-oxo-6,11-dihydro-5H-indolo[2,3-b]quinoline-8-carbonitrile (178 mg, 90% yield). MS m/z=292 [M+H].

Step C: 5-Methyl-3-(4-morpholinopiperidin-1-yl)-11-oxo-6,11-dihydro-5H-indolo[2,3-b]quinoline-8-carbonitrile 4-Morpholinopiperidine (262 mg, 1.56 mmol) and DIPEA (0.5 ml) were added to a solution of 3-Fluoro-5-methyl-11-oxo-6,11-dihydro-5H-indolo[2,3-b]quinoline-8-carbonitrile (150 mg, 0.52 mmol) in DMSO (2 ml) and the mixture was heated to 120 to 140° C. for 3 days. The reaction mixture was cooled to RT and purified by preparative HPLC to afford 5-Methyl-3-(4-morpholinopiperidin-1-yl)-11-oxo-6,11-dihydro-5H-indolo[2,3-b]quinoline-8-carbonitrile (70 mg, 31% yield). $^1$H NMR (300 MHz, CD$_3$OD) δ ppm 8.30 (d, J=7.0 Hz, 1H), 8.28 (d, J=8.0 Hz, 1H), 7.58 (s, 1H), 7.52 (d, J=8.0 Hz, 1H), 7.12 (d, J=7.0 Hz, 1H), 6.84 (s, 1H), 4.37-4.10 (m, 4H), 4.00-3.72 (m, 2H), 3.89 (s, 3H), 3.70-3.20 (m, 5H), 3.18-3.00 (m, 2H), 2.40-2.26 (m, 2H), 1.97-1.86 (m, 2H).

Example 2 (ALK-20)

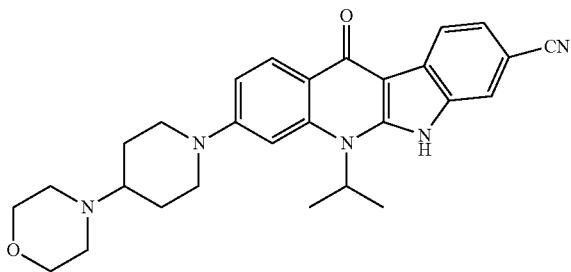 [SMILES: CC(C)n1c2cc(N3CCC(N4CCOCC4)CC3)ccc2c(=O)c2c3ccc(C#N)cc3[nH]c21]

5-isoPropyl-3-(4-morpholinopiperidin-1-yl)-11-oxo-6,11-dihydro-5H-indolo[2,3-b]quinoline-8-carbonitrile

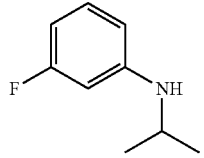

Step A: 3-Fluoro-N-isopropylaniline

Acetone (11.6 g, 200 mmol), Acetic acid (1.8 g, 30 mmol), and Sodium triacetoxyborohydride (6.36 g, 30 mmol) were added to a solution of 3-Fluoroaniline (2.22 g, 20 mmol) in DCM (120 mL) and the mixture was stirred at RT for 12 hr. Water was added to quench the reaction and the mixture was extracted with DCM. The solvent was removed under and the residue was purified by silica gel chromatography to afford 3-Fluoro-N-isopropylaniline (2.6 g, 85% yield). $^1$H NMR (400 MHz, CDCl$_3$) δ ppm 7.15-7.08 (m, 1H), 6.45-6.27 (m, 3H), 3.65-3.60 (m, 2H), 1.25 (d, J=6.2 Hz, 6H).

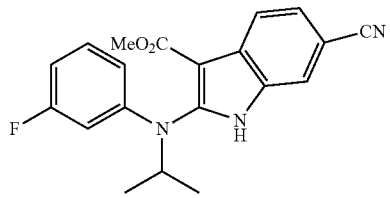 [SMILES: COC(=O)c1c(N(c2cccc(F)c2)C(C)C)[nH]c2cc(C#N)ccc12]

Step B: Methyl 6-cyano-2-((3-fluorophenyl)(isopropyl)amino)-1H-indole-3-carboxylate DABCO (62 mg, 0.55 mmol) was added to a solution of Methyl 6-cyano-1H-indole-3-carboxylate (200 mg, 1 mmol) in DCM (20 mL) and the mixture was cooled to 0° C. N-Chlorosuccinimide (147 mg, 1.1 mmol) was then added and the reaction was stirred at 0° C. for 2 hr. A solution of 3-Fluoro-N-isopropylaniline (153 mg, 1 mmol) and Trichloroacetic acid (41 mg, 0.25 mmol) in DCM (5 mL) was added dropwise and the reaction was stirred for 2 hr at room temperature. The reaction was quenched by adding water and the mixture was extracted with DCM. Solvent was removed under vacuum and the residue was purified by silica gel chromatography (Hex:EA=4:1) to afford Methyl 6-cyano-2-((3-fluorophenyl)(isopropyl)amino)-1H-indole-3-carboxylate (265 mg, 75% yield). $^1$H NMR (400 MHz, CDCl$_3$) δ ppm 8.39 (s, 1H), 8.23 (d, J=8.4 Hz, 1H), 7.64-7.59 (m, 1H), 7.50 (dd, J=8.4, 1.5 Hz, 1H), 7.24-7.22 (m, 1H), 6.74-6.64 (m, 1H), 6.60-6.56 (m, 2H), 4.56-4.49 (m, 1H), 3.81 (s, 3H), 1.32 (d, J=6.6 Hz, 6H).

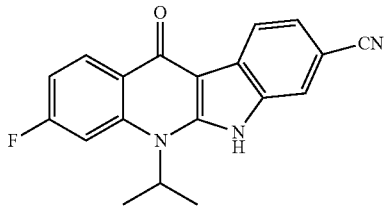 [SMILES: CC(C)n1c2cc(F)ccc2c(=O)c2c3ccc(C#N)cc3[nH]c21]

Step C: 3-Fluoro-5-isopropyl-11-oxo-6,11-dihydro-5H-indolo[2,3-b]quinoline-8-carbonitrile Methyl 6-cyano-2-((3-fluorophenyl)(isopropyl)amino)-1H-indole-3-carboxylate (265 mg, 0.75 mmol) was dissolved in Diphenyl ether (10 mL) and the solution was refluxed for 1 hr. The mixture was cooled to RT. Hexane (20 mL) was added and the precipitate was collected by filtration. The precipitate was purified by silica gel chromatography (Hex:EA=2:1) to afford 3-Fluoro-5-isopropyl-11-oxo-6,11-dihydro-5H-indolo[2,3-b]quinoline-8-carbonitrile (190 mg, 79% yield). $^1$H NMR (400 MHz, DMSO-d$_6$) δ ppm 12.24 (s, 1H), 8.45 (dd, J=8.8, 7.1 Hz, 1H), 8.32 (dd, J=7.9, 2.7 Hz, 1H), 8.05-7.84 (m, 2H), 7.66-7.64 (m, 1H), 7.34-7.25 (m, 1H), 5.35-5.32 (m, 1H), 1.75 (d, J=7.1 Hz, 6H).

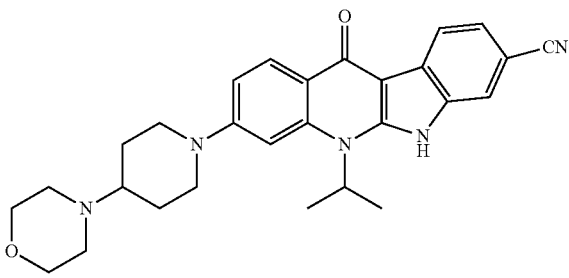 [SMILES: CC(C)n1c2cc(N3CCC(N4CCOCC4)CC3)ccc2c(=O)c2c3ccc(C#N)cc3[nH]c21]

Step D: 5-isoPropyl-3-(4-morpholinopiperidin-1-yl)-11-oxo-6,11-dihydro-5H-indolo[2,3-b]quinoline-8-carbonitrile 4-Morpholinopiperidine (262 mg, 1.56 mmol) and DIPEA (0.5 ml) were added to a solution of 3-Fluoro-5-isopropyl-11-oxo-6,11-dihydro-5H-indolo[2,3-b]quinoline-8-carbonitrile (190 mg, 0.59 mmol) in DMSO (2 ml) and the mixture was heated to 120 to 140° C. for 3 days. The reaction mixture was cooled to RT and purified by preparative HPLC to afford 5-isoPropyl-3-(4-morpholinopiperidin-1-yl)-11-oxo-6,11-dihydro-5H-indolo[2,3-b]quinoline-8-carbonitrile (75 mg, 27% yield). ¹H NMR (300 MHz, CD₃OD) δ ppm 8.39 (d, J=8.0 Hz, 1H), 8.38 (d, J=8.9 Hz, 1H), 7.82 (s, 1H), 7.56 (dd, J=8.0, 1.3 Hz, 1H), 7.30-7.15 (m, 2H), 5.45-5.32 (m, 1H), 4.38-4.10 (m, 4H), 3.90-3.72 (m, 2H), 3.70-3.20 (m, 5H), 3.18-3.00 (m, 2H), 2.40-2.30 (m, 2H), 1.97-1.80 (m, 2H), 1.87 (d, J=7.1 Hz, 6H).

Example 3 (ALK-21)

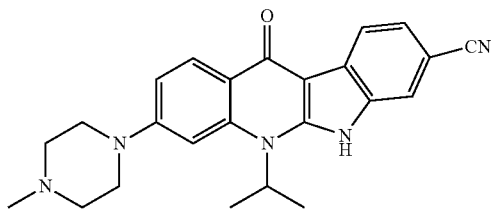 [SMILES: CC(C)n1c2cc(N3CCN(C)CC3)ccc2c(=O)c2c3ccc(C#N)cc3[nH]c21]

5-isoPropyl-3-(4-methylpiperazin-1-yl)-11-oxo-6,11-dihydro-5H-indolo[2,3-b]quinoline-8-carbonitrile 1-Methylpiperazine (0.5 mL) and DIPEA (0.5 ml) were added to a solution of 3-Fluoro-5-isopropyl-11-oxo-6,11-dihydro-5H-indolo[2,3-b]quinoline-8-carbonitrile (190 mg, 0.59 mmol) in DMSO (2 ml) and the mixture was heated to 120 to 140° C. for 3 days. The reaction mixture was cooled to RT and purified by preparative HPLC to afford 5-isoPropyl-3-(4-methylpiperazin-1-yl)-11-oxo-6,11-dihydro-5H-indolo[2,3-b]quinoline-8-carbonitrile (48 mg, 20% yield). ¹H NMR (300 MHz, CD₃OD) δ ppm 8.42 (d, J=8.1 Hz, 1H), 8.39 (d, J=9.2 Hz, 1H), 7.81 (d, J=1.3 Hz, 1H), 7.55 (dd, J=8.1, 1.3 Hz, 1H), 7.28 (d, J=1.8 Hz, 1H), 7.21 (dd, J=9.2, 1.8 Hz, 1H), 5.50-5.30 (m, 1H), 4.36-4.10 (m, 2H), 3.80-3.60 (m, 2H), 3.55-3.20 (m, 4H), 3.04 (s, 3H), 1.87 (d, J=7.1 Hz, 6H).

Example 4 (ALK-22)

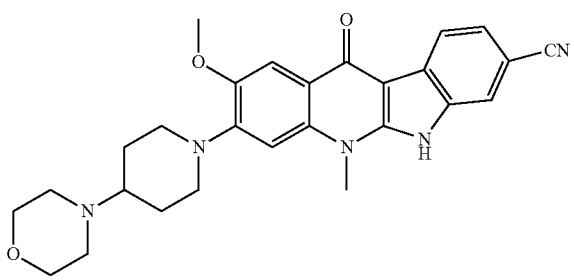 [SMILES: COc1cc2c(=O)c3c4ccc(C#N)cc4[nH]c3n(C)c2cc1N1CCC(N2CCOCC2)CC1]

2-Methoxy-5-methyl-3-(4-morpholinopiperidin-1-yl)-11-oxo-6,11-dihydro-5H-indolo[2,3-b]quinoline-8-carbonitrile

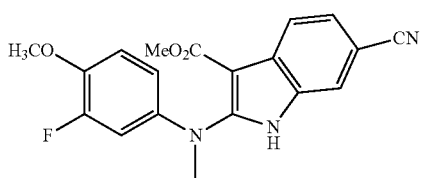

Step A: Methyl 6-cyano-2-((3-fluoro-4-methoxyphenyl)(methyl)amino)-1H-indole-3-carboxylate DABCO (62 mg, 0.55 mmol) was added to a solution of Methyl 6-cyano-1H-indole-3-carboxylate (200 mg, 1 mmol) in DCM (20 mL) and the mixture was cooled to 0° C. N-Chlorosuccinimide (147 mg, 1.1 mmol) was then added and the reaction was stirred at 0° C. for 2 hr. A solution of 3-Fluoro-4-methoxy-N-methylaniline (155 mg, 1 mmol) and Trichloroacetic acid (41 mg, 0.25 mmol) in DCM (5 mL) was added dropwise and the reaction was stirred for 2 hr at room temperature. The reaction was quenched by adding water and the mixture was extracted with DCM. Solvent was removed under vacuum and the residue was purified by silica gel chromatography (Hex:EA=4:1) to afford Methyl 6-cyano-2-((3-fluoro-4-methoxyphenyl)(methyl)amino)-1H-indole-3-carboxylate (220 mg, 62% yield). ¹H NMR (400 MHz, CDCl₃) δ ppm 8.14 (s, 1H), 7.85 (d, J=8.1 Hz, 1H), 7.44 (dd, J=8.1, 1.4 Hz, 1H), 7.40 (d, J=1.4 Hz, 1H), 7.17-7.06 (m, 3H), 3.98 (s, 3H), 3.96 (s, 3H), 1.57 (s, 3H).

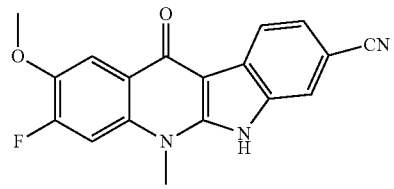 [SMILES: COc1cc2c(=O)c3c4ccc(C#N)cc4[nH]c3n(C)c2cc1F]

Step B: 3-Fluoro-2-methoxy-5-methyl-11-oxo-6,11-dihydro-5H-indolo[2,3-b]quinoline-8-carbonitrile Methyl 6-cyano-2-((3-fluoro-4-methoxyphenyl)(methyl)amino)-1H-indole-3-carboxylate (220 mg, 0.62 mmol) was dissolved in Diphenyl ether (10 mL) and the solution was refluxed for 1 hr. The mixture was cooled to RT. Hexane (20 mL) was added and the precipitate was collected by filtration. The precipitate was purified by silica gel chromatography (Hex:EA=2:1) to afford 3-Fluoro-2-methoxy-5-methyl-11-oxo-6,11-dihydro-5H-indolo[2,3-b]quinoline-8-carbonitrile (140 mg, 70% yield). MS m/z: 322 [M+H].

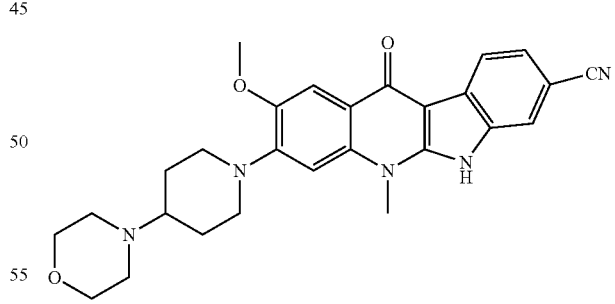

Step C: 2-Methoxy-5-methyl-3-(4-morpholinopiperidin-1-yl)-11-oxo-6,11-dihydro-5H-indolo[2,3-b]quinoline-8-carbonitrile 4-Morpholinopiperidine (262 mg, 1.56 mmol) and DIPEA (0.5 ml) were added to a solution of 3-Fluoro-2-methoxy-5-methyl-11-oxo-6,11-dihydro-5H-indolo[2,3-b]quinoline-8-carbonitrile (140 mg, 0.44 mmol) in DMSO (2 ml) and the mixture was heated to 120 to 140° C. for 3 days.

The reaction mixture was cooled to RT and purified by preparative HPLC to afford 2-Methoxy-5-methyl-3-(4-morpholinopiperidin-1-yl)-11-oxo-6,11-dihydro-5H-indolo[2,3-b]quinoline-8-carbonitrile (55 mg, 27% yield). $^1$H NMR (300 MHz, CD$_3$OD) δ ppm 8.28 (d, J=8.4 Hz, 1H), 7.81 (s, 1H), 7.52 (s, 1H), 7.48 (d, J=8.4 Hz, 1H), 6.94 (s, 1H), 4.27-3.70 (m, 6H), 4.05 (s, 3H), 3.89 (s, 3H), 3.66-3.23 (m, 5H), 2.92-2.80 (m, 2H), 2.40-2.30 (m, 2H), 2.20-2.00 (m, 2H).

Example 5 (ALK-23)

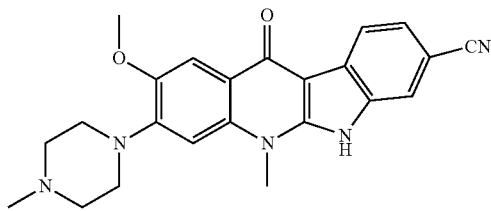 [SMILES: COc1cc2c(=O)c3c4ccc(C#N)cc4[nH]c3n(C)c2cc1N1CCN(C)CC1]

2-Methoxy-5-methyl-3-(4-methylpiperazin-1-yl)-11-oxo-6,11-dihydro-5H-indolo[2,3-b]quinoline-8-carbonitrile 1-Methylpiperazine (0.5 mL) and DIPEA (0.5 ml) were added to a solution of 3-Fluoro-2-methoxy-5-methyl-11-oxo-6,11-dihydro-5H-indolo[2,3-b]quinoline-8-carbonitrile (140 mg, 0.44 mmol) in DMSO (2 ml) and the mixture was heated to 120 to 140° C. for 3 days. The reaction mixture was cooled to RT and purified by preparative HPLC to afford 2-Methoxy-5-methyl-3-(4-methylpiperazin-1-yl)-11-oxo-6,11-dihydro-5H-indolo[2,3-b]quinoline-8-carbonitrile (58 mg, 33% yield). $^1$H NMR (300 MHz, CD$_3$OD) δ ppm 8.24 (d, J=8.3 Hz, 1H), 7.82 (s, 1H), 7.50-7.40 (m, 2H), 6.96 (s, 1H), 4.05 (s, 3H), 4.03-3.90 (m, 2H), 3.89 (s, 3H), 3.80-3.65 (m, 2H), 3.55-3.40 (m, 2H), 3.26-3.14 (m, 2H), 3.05 (s, 3H).

Example 6 (ALK-24)

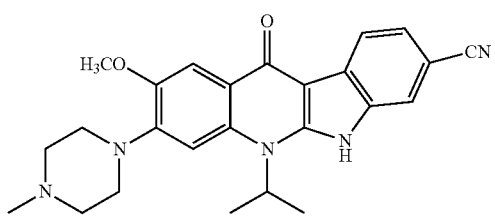 [SMILES: COc1cc2c(=O)c3c4ccc(C#N)cc4[nH]c3n(C(C)C)c2cc1N1CCN(C)CC1]

5-isoPropyl-2-methoxy-3-(4-methylpiperazin-1-yl)-11-oxo-6,11-dihydro-5H-indolo[2,3-b]quinoline-8-carbonitrile

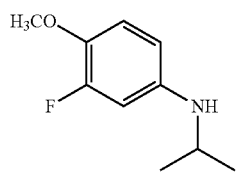

Step A: 3-Fluoro-N-isopropyl-4-methoxyaniline

Acetone (11.6 g, 200 mmol), Acetic acid (1.8 g, 30 mmol), and Sodium triacetoxyborohydride (6.36 g, 30 mmol) were added to a solution of 3-Fluoro-4-methoxyaniline (2.82 g, 20 mmol) in DCM (120 mL) and the mixture was stirred at RT for 12 hr. Water was added to quench the reaction and the mixture was extracted with DCM. The solvent was removed under and the residue was purified by silica gel chromatography to afford 3-Fluoro-N-isopropyl-4-methoxyaniline (2.90 g, 79% yield). $^1$H NMR (400 MHz, CDCl$_3$) δ ppm 6.84 (dd, J=9.5, 8.7 Hz, 1H), 6.41 (dd, J=13.5, 2.7 Hz, 1H), 6.33-6.27 (m, 1H), 3.83 (s, 3H), 3.54-3.52 (m, 1H), 3.28 (s, 1H), 1.21 (d, J=6.3 Hz, 6H).

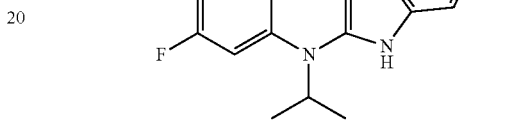

Step B: Methyl 6-cyano-2-((3-fluoro-4-methoxyphenyl)(isopropyl)amino)-1H-indole-3-carboxylate DABCO (62 mg, 0.55 mmol) was added to a solution of Methyl 6-cyano-1H-indole-3-carboxylate (200 mg, 1 mmol) in DCM (20 mL) and the mixture was cooled to 0° C. N-Chlorosuccinimide (147 mg, 1.1 mmol) was then added and the reaction was stirred at 0° C. for 2 hr. A solution of 3-Fluoro-N-isopropyl-4-methoxyaniline (183 mg, 1 mmol) and Trichloroacetic acid (41 mg, 0.25 mmol) in DCM (5 mL) was added dropwise and the reaction was stirred for 2 hr at room temperature. The reaction was quenched by adding water and the mixture was extracted with DCM. Solvent was removed under vacuum and the residue was purified by silica gel chromatography (Hex:EA=4:1) to afford Methyl 6-cyano-2-((3-fluoro-4-methoxyphenyl)(isopropyl)amino)-1H-indole-3-carboxylate (250 mg, 66% yield). $^1$H NMR (400 MHz, CDCl$_3$) δ ppm 8.08-8.06 (m, 2H), 7.45-7.36 (m, 2H), 7.05-6.87 (m, 3H), 4.88-4.80 (m, 1H), 3.92 (s, 3H), 3.88 (s, 3H), 1.26 (d, J=6.6 Hz, 6H).

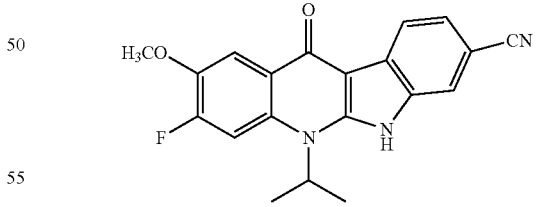

Step C: 3-Fluoro-5-isopropyl-2-methoxy-11-oxo-6,11-dihydro-5H-indolo[2,3-b]quinoline-8-carbonitrile Methyl 6-cyano-2-((3-fluoro-4-methoxyphenyl)(isopropyl)amino)-1H-indole-3-carboxylate (250 mg, 0.66 mmol) was dissolved in Diphenyl ether (10 mL) and the solution was refluxed for 1 hr. The mixture was cooled to RT. Hexane (20 mL) was added and the precipitate was collected by filtration. The precipitate was purified by silica gel chromatography (Hex:EA=2:1) to afford 3-Fluoro-5-isopropyl-2-methoxy-11-oxo-6,11-dihydro-5H-indolo[2,3-b]quinoline-8-carbonitrile (175 mg, 76% yield). $^1$H NMR (400 MHz, DMSO-$d_6$) δ 12.15 (s, 1H), 8.32 (d, J=8.0 Hz, 1H), 8.04-7.94 (m, 2H), 7.90 (d, J=1.3 Hz, 1H), 7.63 (dd, J=8.0, 1.3 Hz, 1H), 5.35-5.27 (m, 1H), 3.98 (s, 3H), 1.73 (d, J=6.9 Hz, 6H).

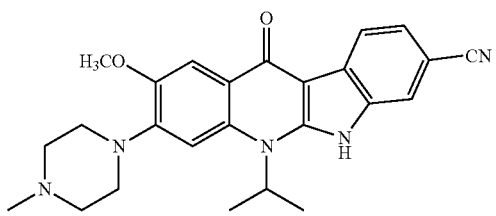 [SMILES: COc1cc2c(=O)c3c4ccc(C#N)cc4[nH]c3n(C(C)C)c2cc1N1CCN(C)CC1]

Step D: 5-isoPropyl-2-methoxy-3-(4-methylpiperazin-1-yl)-11-oxo-6,11-dihydro-5H-indolo[2,3-b]quinoline-8-carbonitrile 1-Methylpiperazine (0.5 mL) and DIPEA (0.5 ml) were added to a solution of 3-Fluoro-5-isopropyl-2-methoxy-11-oxo-6,11-dihydro-5H-indolo[2,3-b]quinoline-8-carbonitrile (175 mg, 0.50 mmol) in DMSO (2 ml) and the mixture was heated to 120 to 140° C. for 3 days. The reaction mixture was cooled to RT and purified by preparative HPLC to afford 5-isoPropyl-2-methoxy-3-(4-methylpiperazin-1-yl)-11-oxo-6,11-dihydro-5H-indolo[2,3-b]quinoline-8-carbonitrile (56 mg, 26% yield). $^1$H NMR (300 MHz, CD$_3$OD) δ ppm 8.42 (d, J=8.1 Hz, 1H), 8.00 (s, 1H), 7.82 (s, 1H), 7.57 (d, J=8.1 Hz, 1H), 7.36 (s, 1H), 5.44-5.35 (m, 1H), 4.05 (s, 3H), 4.02-3.92 (m, 2H), 3.70-3.63 (m, 2H), 3.50-3.18 (m, 4H), 3.05 (s, 3H), 1.88 (d, J=7.1 Hz, 6H).

Example 7 (ALK-25)

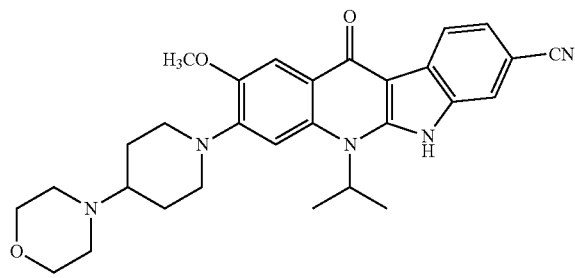 [SMILES: COc1cc2c(=O)c3c4ccc(C#N)cc4[nH]c3n(C(C)C)c2cc1N1CCC(N2CCOCC2)CC1]

5-isoPropyl-2-methoxy-3-(4-morpholinopiperidin-1-yl)-11-oxo-6,11-dihydro-5H-indolo[2,3-b]quinoline-8-carbonitrile 4-Morpholinopiperidine (252 mg, 1.5 mmol) and DIPEA (0.5 ml) were added to a solution of 3-Fluoro-5-isopropyl-2-methoxy-11-oxo-6,11-dihydro-5H-indolo[2,3-b]quinoline-8-carbonitrile (175 mg, 0.50 mmol) in DMSO (2 ml) and the mixture was heated to 120 to 140° C. for 3 days. The reaction mixture was cooled to RT and purified by preparative HPLC to afford 5-isoPropyl-2-methoxy-3-(4-methylpiperazin-1-yl)-11-oxo-6,11-dihydro-5H-indolo[2,3-b]quinoline-8-carbonitrile (72 mg, 29% yield). $^1$H NMR (400 MHz, DMSO-$d_6$) δ ppm 12.18 (s, 1H), 9.87 (s, 1H), 8.31 (d, J=8.1 Hz, 1H), 7.89 (d, J=1.4 Hz, 1H), 7.81 (s, 1H), 7.61 (dd, J=8.1, 1.4 Hz, 1H), 7.21 (s, 1H), 5.35-5.25 (m, 1H), 4.10-4.02 (m, 2H), 3.94 (s, 3H), 3.83-3.79 (m, 2H), 3.75-3.70 (m, 2H), 3.57-3.52 (m, 2H), 3.47-3.36 (m, 1H), 3.22-3.18 (m, 2H), 2.80-2.75 (m, 2H), 2.24-2.23 (m, 2H), 1.86-1.82 (m, 2H), 1.76 (d, J=6.8 Hz, 6H).

Example 8 (ALK-34)

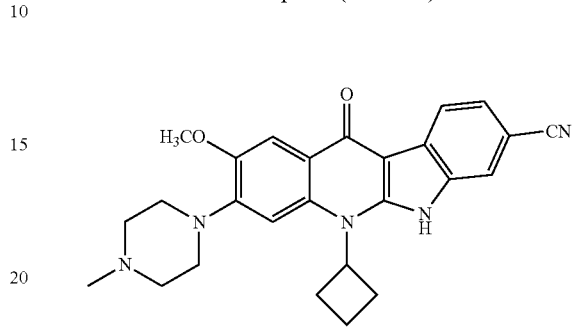

5-Cyclobutyl-2-methoxy-3-(4-methylpiperazin-1-yl)-11-oxo-6,11-dihydro-5H-indolo[2,3-b]quinoline-8-carbonitrile

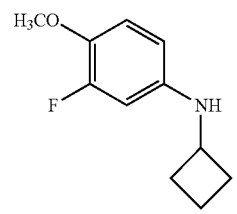 [SMILES: COc1ccc(NC2CCC2)cc1F]

Step A: N-Cyclobutyl-3-fluoro-4-methoxyaniline

Cyclobutanone (14.0 g, 200 mmol), Acetic acid (1.8 g, 30 mmol), and Sodium triacetoxyborohydride (6.36 g, 30 mmol) were added to a solution of 3-Fluoro-4-methoxyaniline (2.82 g, 20 mmol) in DCM (120 mL) and the mixture was stirred at RT for 12 hr. Water was added to quench the reaction and the mixture was extracted with DCM. The solvent was removed under and the residue was purified by silica gel chromatography to afford N-Cyclobutyl-3-fluoro-4-methoxyaniline (2.4 g, 61% yield). $^1$H NMR (300 MHz, CDCl$_3$) δ ppm 6.81 (t, J=9.1 Hz, 1H), 6.40-6.19 (m, 2H), 3.82 (s, 3H), 3.79-3.77 (m, 1H), 3.65 (s, 1H), 2.50-2.30 (m, 2H), 1.80-1.78 (m, 4H).

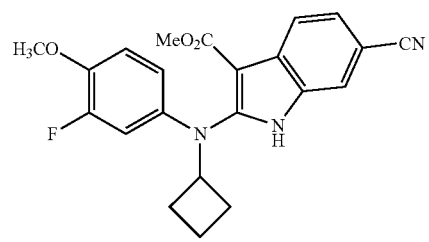 [SMILES: COC(=O)c1c(N(c2ccc(OC)c(F)c2)C2CCC2)[nH]c2cc(C#N)ccc12]

Step B: Methyl 6-cyano-2-(cyclobutyl(3-fluoro-4-methoxyphenyl)amino)-1H-indole-3-carboxylate DABCO (62 mg, 0.55 mmol) was added to a solution of Methyl 6-cyano-1H-indole-3-carboxylate (200 mg, 1 mmol) in DCM (20 mL) and the mixture was cooled to 0° C. N-Chlorosuccinimide (147 mg, 1.1 mmol) was then added and the reaction was stirred at 0° C. for 2 hr. A solution of N-Cyclobutyl-3-fluoro-4-methoxyaniline (195 mg, 1 mmol) and Trichloroacetic acid (41 mg, 0.25 mmol) in DCM (5 mL) was added dropwise and the reaction was stirred for 2 hr at room temperature. The reaction was quenched by adding water and the mixture was extracted with DCM. Solvent was removed under vacuum and the residue was purified by silica gel chromatography (Hex:EA=4:1) to afford Methyl 6-cyano-2-(cyclobutyl(3-fluoro-4-methoxyphenyl)amino)-1H-indole-3-carboxylate (245 mg, 62% yield). $^1$H NMR (400 MHz, CDCl$_3$) δ ppm 8.62 (s, 1H), 8.17 (d, J=8.4 Hz, 1H), 7.55 (d, J=1.5 Hz, 1H), 7.47 (dd, J=8.4, 1.5 Hz, 1H), 6.89 (t, J=9.1 Hz, 1H), 6.64 (dd, J=12.9, 2.8 Hz, 1H), 6.60-6.51 (m, 1H), 4.55-4.43 (m, 1H), 3.86 (s, 3H), 3.81 (s, 3H), 2.40-2.28 (m, 2H), 2.00-1.90 (m, 2H), 1.77-1.63 (m, 2H).

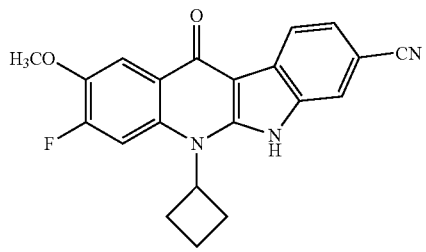 [SMILES: COc1cc2c(=O)c3c4ccc(C#N)cc4[nH]c3n(C3CCC3)c2cc1F]

Step C: 5-Cyclobutyl-3-fluoro-2-methoxy-11-oxo-6,11-dihydro-5H-indolo[2,3-b]quinoline-8-carbonitrile Methyl 6-cyano-2-(cyclobutyl(3-fluoro-4-methoxyphenyl)amino)-1H-indole-3-carboxylate (245 mg, 0.66 mmol) was dissolved in Diphenyl ether (10 mL) and the solution was refluxed for 1 hr. The mixture was cooled to RT. Hexane (20 mL) was added and the precipitate was collected by filtration. The precipitate was purified by silica gel chromatography (Hex:EA=2:1) to afford 5-Cyclobutyl-3-fluoro-2-methoxy-11-oxo-6,11-dihydro-5H-indolo[2,3-b]quinoline-8-carbonitrile (155 mg, 65% yield). MS m/z=362 [M+H].

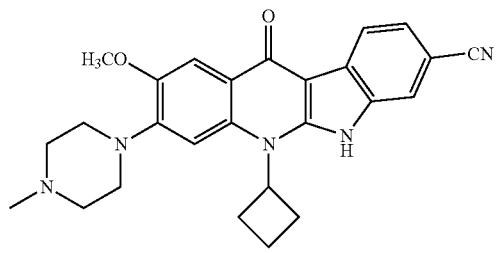 [SMILES: COc1cc2c(=O)c3c4ccc(C#N)cc4[nH]c3n(C3CCC3)c2cc1N1CCN(C)CC1]

Step D: 5-Cyclobutyl-2-methoxy-3-(4-methylpiperazin-1-yl)-11-oxo-6,11-dihydro-5H-indolo[2,3-b]quinoline-8-carbonitrile 1-Methylpiperazine (0.5 mL) and DIPEA (0.5 ml) were added to a solution of 5-Cyclobutyl-3-fluoro-2-methoxy-11-oxo-6,11-dihydro-5H-indolo[2,3-b]quinoline-8-carbonitrile (155 mg, 0.50 mmol) in DMSO (2 ml) and the mixture was heated to 120 to 140° C. for 3 days. The reaction mixture was cooled to RT and purified by Preparative HPLC to afford 5-Cyclobutyl-2-methoxy-3-(4-methylpiperazin-1-yl)-11-oxo-6,11-dihydro-5H-indolo[2,3-b]quinoline-8-carbonitrile (43 mg, 20% yield). $^1$H NMR (300 MHz, CD$_3$OD) δ ppm 8.39 (d, J=8.1 Hz, 1H), 7.94 (s, 1H), 7.79 (s, 1H), 7.55 (d, J=8.1 Hz, 1H), 7.14 (s, 1H), 5.31-5.25 (m, 1H), 4.03 (s, 3H), 3.95-3.91 (m, 2H), 3.69-3.65 (m, 2H), 3.45-3.37 (m, 2H), 3.19-3.14 (m, 2H), 3.07-2.99 (m, 5H), 2.68-2.53 (m, 2H), 2.04-2.02 (m, 2H).

Example 9 (ALK-35)

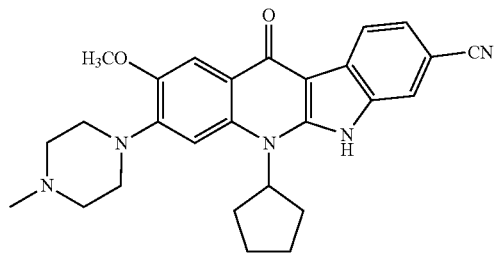 [SMILES: COc1cc2c(=O)c3c4ccc(C#N)cc4[nH]c3n(C3CCCC3)c2cc1N1CCN(C)CC1]

5-Cyclopentyl-2-methoxy-3-(4-methylpiperazin-1-yl)-11-oxo-6,11-dihydro-5H-indolo[2,3-b]quinoline-8-carbonitrile

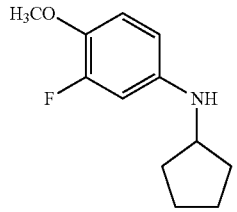 [SMILES: COc1ccc(NC2CCCC2)cc1F]

Step A: N-Cyclopentyl-3-fluoro-4-methoxyaniline

Cyclopentanone (16.8 g, 200 mmol), Acetic acid (1.8 g, 30 mmol), and Sodium triacetoxyborohydride (6.36 g, 30 mmol) were added to a solution of 3-Fluoro-4-methoxyaniline (2.82 g, 20 mmol) in DCM (120 mL) and the mixture was stirred at RT for 12 hr. Water was added to quench the reaction and the mixture was extracted with DCM. The solvent was removed under and the residue was purified by silica gel chromatography to afford N-Cyclopentyl-3-fluoro-4-methoxyaniline (2.0 g, 48% yield). MS m/z=210 [M+H].

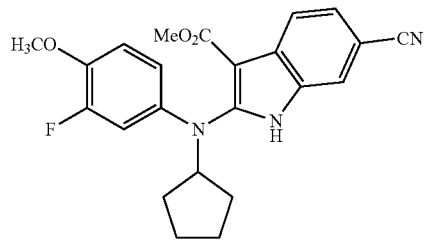 [SMILES: COC(=O)c1c(N(c2ccc(OC)c(F)c2)C2CCCC2)[nH]c2cc(C#N)ccc12]

Step B: Methyl 6-cyano-2-(cyclopentyl(3-fluoro-4-methoxyphenyl)amino)-1H-indole-3-carboxylate DABCO (62 mg, 0.55 mmol) was added to a solution of Methyl 6-cyano-1H-indole-3-carboxylate (200 mg, 1 mmol) in DCM (20 mL) and the mixture was cooled to 0° C. N-Chlorosuccinimide (147 mg, 1.1 mmol) was then added and the reaction was stirred at 0° C. for 2 hr. A solution of N-Cyclopentyl-3-fluoro-4-methoxyaniline (209 mg, 1 mmol) and Trichloroacetic acid (41 mg, 0.25 mmol) in DCM (5 mL) was added dropwise and the reaction was stirred for 2 hr at room temperature. The reaction was quenched by adding water and the mixture was extracted with DCM. Solvent was removed under vacuum and the residue was purified by silica gel chromatography (Hex:EA=4:1) to afford Methyl 6-cyano-2-(cyclopentyl(3-fluoro-4-methoxyphenyl)amino)-1H-indole-3-carboxylate (280 mg, 69% yield). $^1$H NMR (400 MHz, CDCl$_3$) δ ppm 8.55 (s, 1H), 8.13 (d, J=8.3 Hz, 1H), 7.50 (d, J=1.4 Hz, 1H), 7.44 (dd, J=8.3, 1.4 Hz, 1H), 6.92 (t, J=9.1 Hz, 1H), 6.79 (dd, J=12.7, 2.7 Hz, 1H), 6.75-6.71 (m, 1H), 4.61-4.52 (m, 1H), 3.87 (s, 3H), 3.83 (s, 3H), 2.09-1.98 (m, 2H), 1.66-1.62 (m, 4H), 1.59-1.47 (m, 2H).

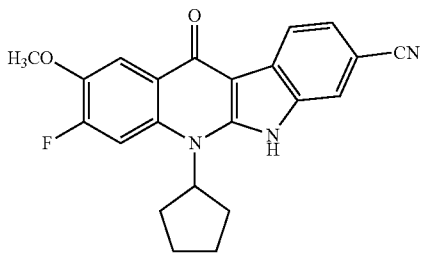 [SMILES: COc1cc2c(=O)c3c4ccc(C#N)cc4[nH]c3n(C3CCCC3)c2cc1F]

Step C: 5-Cyclopentyl-3-fluoro-2-methoxy-11-oxo-6,11-dihydro-5H-indolo[2,3-b]quinoline-8-carbonitrile Methyl 6-cyano-2-(cyclopentyl(3-fluoro-4-methoxyphenyl)amino)-1H-indole-3-carboxylate (280 mg, 0.69 mmol) was dissolved in Diphenyl ether (10 mL) and the solution was refluxed for 1 hr. The mixture was cooled to RT. Hexane (20 mL) was added and the precipitate was collected by filtration. The precipitate was purified by silica gel chromatography (Hex:EA=2:1) to afford 5-Cyclopentyl-3-fluoro-2-methoxy-11-oxo-6,11-dihydro-5H-indolo[2,3-b]quinoline-8-carbonitrile (130 mg, 50% yield). MS m/z=376 [M+H].

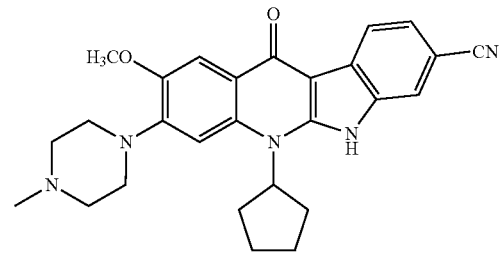 [SMILES: COc1cc2c(=O)c3c4ccc(C#N)cc4[nH]c3n(C3CCCC3)c2cc1N1CCN(C)CC1]

Step D: 5-Cyclopentyl-2-methoxy-3-(4-methylpiperazin-1-yl)-11-oxo-6,11-dihydro-5H-indolo[2,3-b]quinoline-8-carbonitrile 1-Methylpiperazine (0.5 mL) and DIPEA (0.5 ml) were added to a solution of 5-Cyclopentyl-3-fluoro-2-methoxy-11-oxo-6,11-dihydro-5H-indolo[2,3-b]quinoline-8-carbonitrile (130 mg, 0.35 mmol) in DMSO (2 ml) and the mixture was heated to 120 to 140° C. for 3 days. The reaction mixture was cooled to RT and purified by preparative HPLC to afford 5-Cyclopentyl-2-methoxy-3-(4-methylpiperazin-1-yl)-11-oxo-6,11-dihydro-5H-indolo[2,3-b]quinoline-8-carbonitrile (51 mg, 32% yield). $^1$H NMR (300 MHz, CD$_3$OD) δ ppm 8.29 (d, J=8.1 Hz, 1H), 7.94 (s, 1H), 7.65 (d, J=1.3 Hz, 1H), 7.45 (dd, J=8.1, 1.3 Hz, 1H), 7.08 (s, 1H), 5.40-5.28 (m, 1H), 4.03 (s, 3H), 3.96-3.94 (m, 2H), 3.71-3.67 (m, 2H), 3.51-3.18 (m, 4H), 3.03 (s, 3H), 2.54-2.47 (m, 2H), 2.41-2.13 (m, 4H), 2.10-1.89 (m, 2H).

Example 10 (ALK-36)

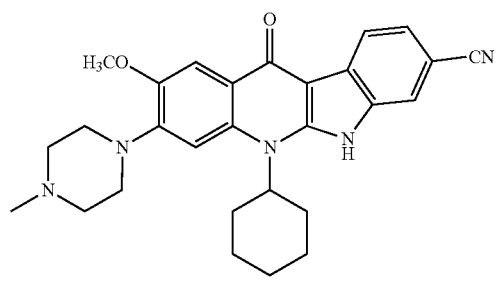 [SMILES: COc1cc2c(=O)c3c4ccc(C#N)cc4[nH]c3n(C3CCCCC3)c2cc1N1CCN(C)CC1]

5-Cyclohexyl-2-methoxy-3-(4-methylpiperazin-1-yl)-11-oxo-6,11-dihydro-5H-indolo[2,3-b]quinoline-8-carbonitrile

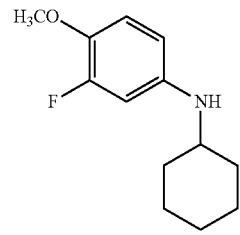 [SMILES: COc1ccc(NC2CCCCC2)cc1F]

Step A: N-Cyclohexyl-3-fluoro-4-methoxyaniline

Cyclohexanone (19.62 g, 200 mmol), Acetic acid (1.8 g, 30 mmol), and Sodium triacetoxyborohydride (6.36 g, 30 mmol) were added to a solution of 3-Fluoro-4-methoxyaniline (2.82 g, 20 mmol) in DCM (120 mL) and the mixture was stirred at RT for 12 hr. Water was added to quench the reaction and the mixture was extracted with DCM. The solvent was removed under and the residue was purified by silica gel chromatography to afford N-Cyclohexyl-3-fluoro-4-methoxyaniline (2.8 g, 63% yield). MS m/z=224 [M+H].

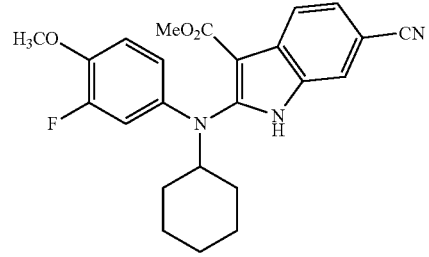 [SMILES: COC(=O)c1c(N(c2ccc(OC)c(F)c2)C2CCCCC2)[nH]c2cc(C#N)ccc12]

Step B: Methyl 6-cyano-2-(cyclohexyl(3-fluoro-4-methoxyphenyl)amino)-1H-indole-3-carboxylate DABCO (62 mg, 0.55 mmol) was added to a solution of methyl 6-cyano-1H-indole-3-carboxylate (200 mg, 1 mmol) in DCM (20 mL) and the mixture was cooled to 0° C. N-Chlorosuccinimide (147 mg, 1.1 mmol) was then added and the reaction was stirred at 0° C. for 2 hr. A solution of N-Cyclohexyl-3-fluoro-4-methoxyaniline (223 mg, 1 mmol) and Trichloroacetic acid (41 mg, 0.25 mmol) in DCM (5 mL) was added dropwise and the reaction was stirred for 2 hr at room temperature. The reaction was quenched by adding water and the mixture was extracted with DCM. Solvent was removed under vacuum and the residue was purified by silica gel chromatography (Hex:EA=4:1) to afford Methyl 6-cyano-2-(cyclohexyl(3-fluoro-4-methoxyphenyl)amino)-1H-indole-3-carboxylate (240 mg, 57% yield). $^1$H NMR (400 MHz, CDCl$_3$) δ ppm 8.06 (d, J=8.3 Hz, 1H), 8.02 (s, 1H), 7.45-7.37 (m, 2H), 7.04-6.82 (m, 3H), 4.37-4.26 (m, 1H), 3.92 (s, 3H), 3.88 (s, 3H), 2.10-2.06 (m, 2H), 1.85-1.62 (m, 2H), 1.67-1.63 (m, 2H), 1.47-1.35 (m, 2H), 1.30-1.27 (m, 2H).

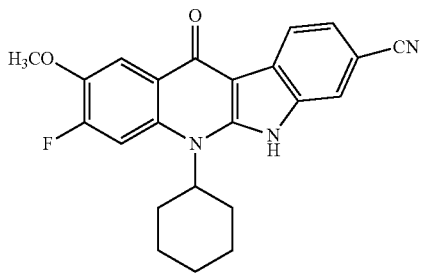 [SMILES: COc1cc2c(=O)c3c4ccc(C#N)cc4[nH]c3n(C3CCCCC3)c2cc1F]

Step C: 5-Cyclohexyl-3-fluoro-2-methoxy-11-oxo-6,11-dihydro-5H-indolo[2,3-b]quinoline-8-carbonitrile Methyl 6-cyano-2-(cyclohexyl(3-fluoro-4-methoxyphenyl)amino)-1H-indole-3-carboxylate (240 mg, 0.57 mmol) was dissolved in Diphenyl ether (10 mL) and the solution was refluxed for 1 hr. The mixture was cooled to RT. Hexane (20 mL) was added and the precipitate was collected by filtration. The precipitate was purified by silica gel chromatography (Hex:EA=2:1) to afford 5-Cyclohexyl-3-fluoro-2-methoxy-11-oxo-6,11-dihydro-5H-indolo[2,3-b]quinoline-8-carbonitrile (160 mg, 72% yield). MS m/z=390 [M+H].

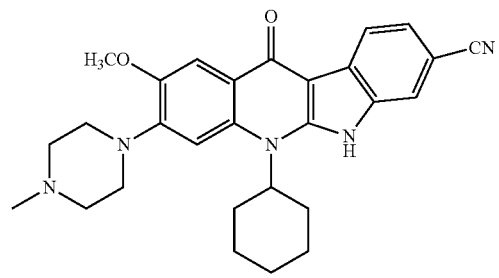 [SMILES: COc1cc2c(=O)c3c4ccc(C#N)cc4[nH]c3n(C3CCCCC3)c2cc1N1CCN(C)CC1]

Step D: 5-Cyclohexyl-2-methoxy-3-(4-methylpiperazin-1-yl)-11-oxo-6,11-dihydro-5H-indolo[2,3-b]quinoline-8-carbonitrile 1-Methylpiperazine (0.5 mL) and DIPEA (0.5 ml) were added to a solution of 5-Cyclohexyl-3-fluoro-2-methoxy-11-oxo-6,11-dihydro-5H-indolo[2,3-b]quinoline-8-carbonitrile (160 mg, 0.41 mmol) in DMSO (2 ml) and the mixture was heated to 120 to 140° C. for 3 days. The reaction mixture was cooled to RT and purified by preparative HPLC to afford 5-Cyclohexyl-2-methoxy-3-(4-methylpiperazin-1-yl)-11-oxo-6,11-dihydro-5H-indolo[2,3-b]quinoline-8-carbonitrile (53 mg, 27% yield). $^1$H NMR (300 MHz, CD$_3$OD) δ ppm 8.42 (d, J=8.1 Hz, 1H), 7.98 (s, 1H), 7.82 (d, J=1.4 Hz, 1H), 7.57 (dd, J=8.1, 1.4 Hz, 1H), 7.42 (s, 1H), 4.90-4.78 (m, 1H), 4.03 (s, 3H), 4.00-3.82 (m, 2H), 3.69-3.63 (m, 2H), 3.50-3.37 (m, 2H), 3.21-3.11 (m, 2H), 3.04 (s, 3H), 2.70-2.49 (m, 2H), 2.11-1.40 (m, 8H).

Example 11 (ALK-37)

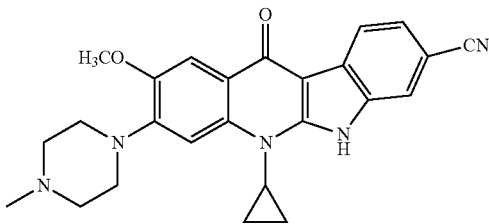 [SMILES: COc1cc2c(=O)c3c4ccc(C#N)cc4[nH]c3n(C3CC3)c2cc1N1CCN(C)CC1]

5-Cyclopropyl-2-methoxy-3-(4-methylpiperazin-1-yl)-11-oxo-6,11-dihydro-5H-indolo[2,3-b]quinoline-8-carbonitrile

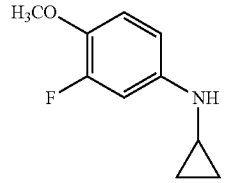

Step A: N-Cyclopropyl-3-fluoro-4-methoxyaniline

To a round bottom flask was sequentially added 3-Fluoro-4-methoxyaniline (1.0 g, 7.0 mmol), 1-Ethoxy-1-trimethylsiloxy-cyclopropane (1.50 g, 8.4 mmol), MeOH (7.5 ml) and Acetic acid (15 ml). After refluxing at 65° C. for 3 hr, the reaction mixture was concentrated in vacuo. The residue was dissolved in anhydrous THF (10 ml) (Solution A). A mixture of NaBH$_4$ (530 mg, 14 mmol), BF$_3$.Et$_2$O (2.2 ml, 14 mmol) in anhydrous THF (10 ml) was cooled in an ice bath and stirred for 1 hour. To this mixture was added Solution A slowly while maintaining the temperature at 0-5° C. The resulting mixture was stirred at room temperature for 16 hr and subsequently refluxed for 2 hr. The reaction mixture was cooled down, and EtOAc and water were added. The resulting mixture was extracted with EtOAc (3×150 ml). The EtOAc layers were combined, washed with brine, and dried over Na$_2$SO4. After filtration, the filtrate was concentrated in vacuum. The residue was purified on silica gel column with gradient petroleum ether/EtOAc as eluent to afford N-Cyclopropyl-3-fluoro-4-methoxyaniline as yellow oil (860 mg, 67% yield). $^1$H NMR (300 MHz, CDCl$_3$) δ ppm 6.84 (t, J=9.1 Hz, 1H), 6.61 (dd, J=13.4, 2.7 Hz, 1H), 6.45-6.43 (m, 1H), 4.02 (s, 1H), 3.82 (s, 3H), 2.37-2.35 (m, 1H), 0.76-0.66 (m, 2H), 0.54-0.45 (m, 2H).

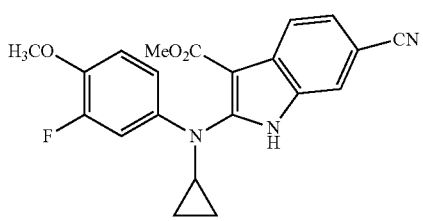 [SMILES: COC(=O)c1c(N(c2ccc(OC)c(F)c2)C2CC2)[nH]c2cc(C#N)ccc12]

Step B: Methyl 6-cyano-2-(cyclopropyl(3-fluoro-4-methoxyphenyl)amino)-1H-indole-3-carboxylate DABCO (62 mg, 0.55 mmol) was added to a solution of Methyl 6-cyano-1H-indole-3-carboxylate (200 mg, 1 mmol) in DCM (20 mL) and the mixture was cooled to 0° C. N-Chlorosuccinimide (147 mg, 1.1 mmol) was then added and the reaction was stirred at 0° C. for 2 hr. A solution of N-Cyclopropyl-3-fluoro-4-methoxyaniline (181 mg, 1 mmol) and Trichloroacetic acid (41 mg, 0.25 mmol) in DCM (5 mL) was added dropwise and the reaction was stirred for 2 hr at room temperature. The reaction was quenched by adding water and the mixture was extracted with DCM. Solvent was removed under vacuum and the residue was purified by silica gel chromatography (Hex:EA=4:1) to afford Methyl 6-cyano-2-(cyclopropyl(3-fluoro-4-methoxyphenyl)amino)-1H-indole-3-carboxylate (180 mg, 47% yield). $^1$H NMR (400 MHz, CDCl$_3$) δ ppm 8.94 (s, 1H), 8.17 (d, J=8.4 Hz, 1H), 7.57 (d, J=1.4 Hz, 1H), 7.48 (dd, J=8.4, 1.4 Hz, 1H), 6.94-6.82 (m, 2H), 6.77-6.69 (m, 1H), 3.85 (s, 3H), 3.74 (s, 3H), 3.17-2.99 (m, 1H), 1.00-0.93 (m, 2H), 0.81-0.74 (m, 2H).

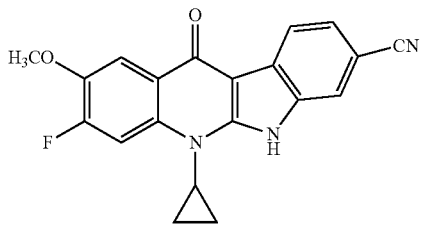 [SMILES: COc1cc2c(=O)c3c4ccc(C#N)cc4[nH]c3n(C3CC3)c2cc1F]

Step C: 5-Cyclopropyl-3-fluoro-2-methoxy-11-oxo-6,11-dihydro-5H-indolo[2,3-b]quinoline-8-carbonitrile Methyl 6-cyano-2-(cyclopropyl(3-fluoro-4-methoxyphenyl)amino)-1H-indole-3-carboxylate (180 mg, 0.47 mmol) was dissolved in Diphenyl ether (10 mL) and the solution was refluxed for 1 hr. The mixture was cooled to RT. Hexane (20 mL) was added and the precipitate was collected by filtration. The precipitate was purified by silica gel chromatography (Hex:EA=2:1) to afford 5-Cyclopropyl-3-fluoro-2-methoxy-11-oxo-6,11-dihydro-5H-indolo[2,3-b]quinoline-8-carbonitrile (102 mg, 62% yield). MS m/z=348 [M+H].

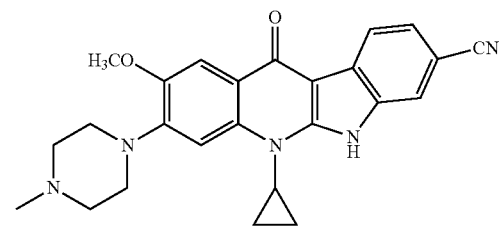 [SMILES: COc1cc2c(=O)c3c4ccc(C#N)cc4[nH]c3n(C3CC3)c2cc1N1CCN(C)CC1]

Step D: 5-Cyclopropyl-2-methoxy-3-(4-methylpiperazin-1-yl)-11-oxo-6,11-dihydro-5H-indolo[2,3-b]quinoline-8-carbonitrile 1-Methylpiperazine (0.5 mL) and DIPEA (0.5 ml) were added to a solution of 5-Cyclopropyl-3-fluoro-2-methoxy-11-oxo-6,11-dihydro-5H-indolo[2,3-b]quinoline-8-carbonitrile (160 mg, 0.41 mmol) in DMSO (2 ml) and the mixture was heated to 120 to 140° C. for 3 days. The reaction mixture was cooled to RT and purified by Preparative HPLC to afford 5-Cyclopropyl-2-methoxy-3-(4-methylpiperazin-1-yl)-11-oxo-6,11-dihydro-5H-indolo[2,3-b]quinoline-8-carbonitrile (36 mg, 18% yield). $^1$H NMR (300 MHz, CD$_3$OD) δ ppm 8.27 (d, J=7.8 Hz, 1H), 7.84 (s, 1H), 7.70 (s, 1H), 7.54 (s, 1H), 7.47 (d, J=7.8 Hz, 1H), 4.04 (s, 3H), 4.03-3.90 (m, 2H), 3.72-3.63 (m, 2H), 3.60-3.37 (m, 3H), 3.25-3.12 (m, 2H), 3.05 (s, 3H), 1.66-1.57 (m, 2H), 1.30-1.18 (m, 2H).

Example 12 (ALK-38)

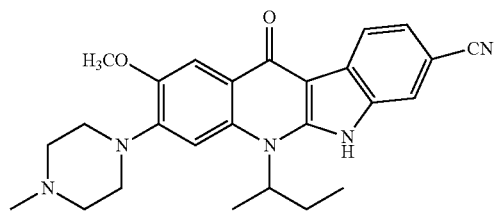 [SMILES: CCC(C)n1c2cc(N3CCN(C)CC3)c(OC)cc2c(=O)c2c3ccc(C#N)cc3[nH]c21]

5-(sec-Butyl)-2-methoxy-3-(4-methylpiperazin-1-yl)-11-oxo-6,11-dihydro-5H-indolo[2,3-b]quinoline-8-carbonitrile

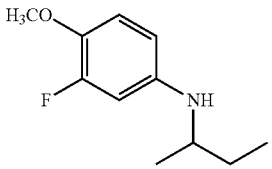

Step A: N-(sec-Butyl)-3-fluoro-4-methoxyaniline

2-Butanone (14.40 g, 200 mmol), Acetic acid (1.8 g, 30 mmol), and Sodium triacetoxyborohydride (6.36 g, 30 mmol) were added to a solution of 3-Fluoro-4-methoxyaniline (2.82 g, 20 mmol) in DCM (120 mL) and the mixture was stirred at RT for 12 hr. Water was added to quench the reaction and the mixture was extracted with DCM. The solvent was removed under and the residue was purified by silica gel chromatography to afford N-(sec-Butyl)-3-fluoro-4-methoxyaniline (2.6 g, 66% yield). MS m/z=198 [M+H].

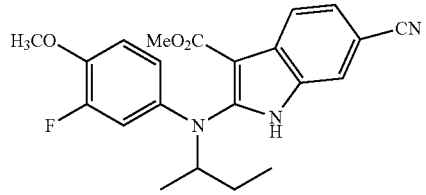 [SMILES: CCC(C)N(c1ccc(OC)c(F)c1)c1[nH]c2cc(C#N)ccc2c1C(=O)OC]

Step B: Methyl 2-(sec-butyl(3-fluoro-4-methoxyphenyl)amino)-6-cyano-1H-indole-3-carboxylate DABCO (62 mg, 0.55 mmol) was added to a solution of methyl 6-cyano-1H-indole-3-carboxylate (200 mg, 1 mmol) in DCM (20 mL) and the mixture was cooled to 0° C. N-Chlorosuccinimide (147 mg, 1.1 mmol) was then added and the reaction was stirred at 0° C. for 2 hr. A solution of N-(sec-Butyl)-3-fluoro-4-methoxyaniline (197 mg, 1 mmol) and Trichloroacetic acid (41 mg, 0.25 mmol) in DCM (5 mL) was added dropwise and the reaction was stirred for 2 hr at room temperature. The reaction was quenched by adding water and the mixture was extracted with DCM. Solvent was removed under vacuum and the residue was purified by silica gel chromatography (Hex:EA=4:1) to afford Methyl 2-(sec-butyl(3-fluoro-4-methoxyphenyl)amino)-6-cyano-1H-indole-3-carboxylate (210 mg, 53% yield). $^1$H NMR (400 MHz, CDCl$_3$) δ ppm 8.05 (d, J=8.3 Hz, 1H), 7.93 (s, 1H), 7.41 (d, J=8.3, 1.4 Hz, 1H), 7.37 (d, J=1.4 Hz, 1H), 7.07-6.85 (m, 3H), 4.60-4.54 (m, 1H), 3.93 (s, 3H), 3.88 (s, 3H), 1.79-1.75 (m, 1H), 1.54-1.51 (m, 1H), 1.26 (d, J=6.7 Hz, 3H), 0.98 (t, J=7.4 Hz, 3H).

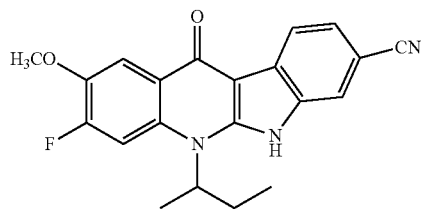 [SMILES: CCC(C)n1c2cc(F)c(OC)cc2c(=O)c2c3ccc(C#N)cc3[nH]c21]

Step C: 5-(sec-Butyl)-3-fluoro-2-methoxy-11-oxo-6,11-dihydro-5H-indolo[2,3-b]quinoline-8-carbonitrile Methyl 2-(sec-butyl(3-fluoro-4-methoxyphenyl)amino)-6-cyano-1H-indole-3-carboxylate (210 mg, 0.53 mmol) was dissolved in Diphenyl ether (10 mL) and the solution was refluxed for 1 hr. The mixture was cooled to RT. Hexane (20 mL) was added and the precipitate was collected by filtration. The precipitate was purified by silica gel chromatography (Hex:EA=2:1) to afford 5-(sec-Butyl)-3-fluoro-2-methoxy-11-oxo-6,11-dihydro-5H-indolo[2,3-b]quinoline-8-carbonitrile (150 mg, 78% yield). MS m/z=364 [M+H].

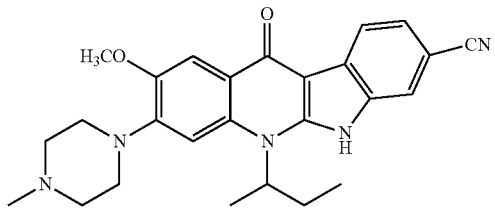 [SMILES: CCC(C)n1c2cc(N3CCN(C)CC3)c(OC)cc2c(=O)c2c3ccc(C#N)cc3[nH]c21]

Step D: 5-(sec-Butyl)-2-methoxy-3-(4-methylpiperazin-1-yl)-11-oxo-6,11-dihydro-5H-indolo[2,3-b]quinoline-8-carbonitrile 1-Methylpiperazine (0.5 mL) and DIPEA (0.5 ml) were added to a solution of 5-(sec-Butyl)-3-fluoro-2-methoxy-11-oxo-6,11-dihydro-5H-indolo[2,3-b]quinoline-8-carbonitrile (150 mg, 0.41 mmol) in DMSO (2 ml) and the mixture was heated to 120 to 140° C. for 3 days. The reaction mixture was cooled to RT and purified by Preparative HPLC to afford 5-(sec-Butyl)-2-methoxy-3-(4-methylpiperazin-1-yl)-11-oxo-6,11-dihydro-5H-indolo[2,3-b]quinoline-8-carbonitrile (35 mg, 19% yield). $^1$H NMR (300 MHz, CD$_3$OD) δ ppm 8.46 (d, J=8.1 Hz, 1H), 8.02 (s, 1H), 7.8 (s, 1H), 7.59 (d, J=8.1 Hz, 1H), 7.36 (s, 1H), 5.05-4.80 (m, 1H), 4.05 (s, 3H), 4.02-3.79 (m, 2H), 3.77-3.61 (m, 2H), 3.51-3.32 (m, 2H), 3.28-3.12 (m, 2H), 3.03 (s, 3H), 2.48-2.40 (m, 1H), 2.25-2.18 (m, 1H), 1.88 (d, J=6.8 Hz, 3H), 0.90 (t, J=7.3 Hz, 3H).

Example 13 (ALK-39)

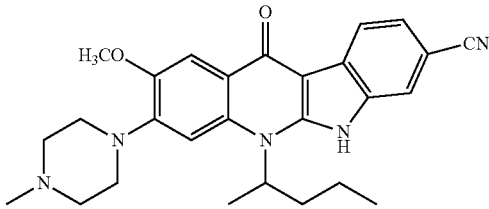 [SMILES: CCCC(C)n1c2cc(N3CCN(C)CC3)c(OC)cc2c(=O)c2c3ccc(C#N)cc3[nH]c21]

2-Methoxy-3-(4-methylpiperazin-1-yl)-11-oxo-5-(pentan-2-yl)-6,11-dihydro-5H-indolo[2,3-b]quinoline-8-carbonitrile

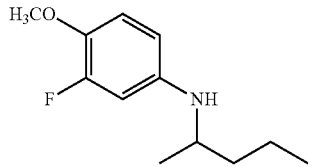

Step A: 3-Fluoro-4-methoxy-N-(pentan-2-yl)aniline 2-pentanone (17.2 g, 200 mmol), Acetic acid (1.8 g, 30 mmol), and Sodium triacetoxyborohydride (6.36 g, 30 mmol) were added to a solution of 3-Fluoro-4-methoxyaniline (2.82 g, 20 mmol) in DCM (120 mL) and the mixture was stirred at RT for 12 hr. Water was added to quench the reaction and the mixture was extracted with DCM. The solvent was removed under and the residue was purified by silica gel chromatography to afford 3-Fluoro-4-methoxy-N-(pentan-2-yl)aniline (2.1 g, 50% yield). MS m/z=212 [M+H].

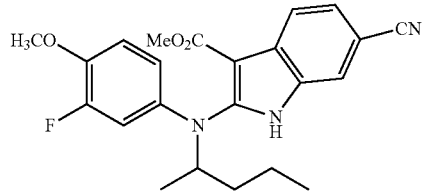 [SMILES: CCCC(C)N(c1ccc(OC)c(F)c1)c1[nH]c2cc(C#N)ccc2c1C(=O)OC]

Step B: Methyl 6-cyano-2-((3-fluoro-4-methoxyphenyl)(pentan-2-yl)amino)-1H-indole-3-carboxylate DABCO (62 mg, 0.55 mmol) was added to a solution of Methyl 6-cyano-1H-indole-3-carboxylate (200 mg, 1 mmol) in DCM (20 mL) and the mixture was cooled to 0° C. N-Chlorosuccinimide (147 mg, 1.1 mmol) was then added and the reaction was stirred at 0° C. for 2 hr. A solution of 3-Fluoro-4-methoxy-N-(pentan-2-yl)aniline (211 mg, 1 mmol) and Trichloroacetic acid (41 mg, 0.25 mmol) in DCM (5 mL) was added dropwise and the reaction was stirred for 2 hr at room temperature. The reaction was quenched by adding water and the mixture was extracted with DCM. Solvent was removed under vacuum and the residue was purified by silica gel chromatography (Hex:EA=4:1) to afford Methyl 6-cyano-2-((3-fluoro-4-methoxyphenyl)(pentan-2-yl)amino)-1H-indole-3-carboxylate (196 mg, 48% yield). $^1$H NMR (400 MHz, CDCl$_3$) δ ppm 8.05 (d, J=8.3 Hz, 1H), 7.77 (br s, 1H), 7.41 (dd, J=8.3, 1.5 Hz, 1H), 7.36 (d, J=1.5 Hz, 1H), 7.07-6.90 (m, 3H), 4.78-4.61 (m, 1H), 3.95 (s, 3H), 3.89 (s, 3H), 1.72-1.65 (m, 1H), 1.49-1.41 (m, 3H), 1.26 (d, J=6.8 Hz, 3H), 0.92 (t, J=7.2 Hz, 3H).

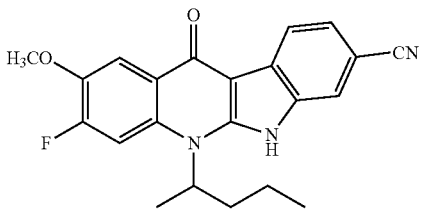 [SMILES: CCCC(C)n1c2cc(F)c(OC)cc2c(=O)c2c3ccc(C#N)cc3[nH]c21]

Step C: 3-Fluoro-2-methoxy-11-oxo-5-(pentan-2-yl)-6,11-dihydro-5H-indolo[2,3-b]quinoline-8-carbonitrile Methyl 6-cyano-2-((3-fluoro-4-methoxyphenyl)(pentan-2-yl)amino)-1H-indole-3-carboxylate (196 mg, 0.48 mmol) was dissolved in Diphenyl ether (10 mL) and the solution was refluxed for 1 hr. The mixture was cooled to RT. Hexane (20 mL) was added and the precipitate was collected by filtration. The precipitate was purified by silica gel chromatography (Hex:EA=2:1) to afford 3-Fluoro-2-methoxy-11-oxo-5-(pentan-2-yl)-6,11-dihydro-5H-indolo[2,3-b]quinoline-8-carbonitrile (148 mg, 82% yield). MS m/z=378 [M+H]. $^1$H NMR (300 MHz, CD$_3$OD) δ ppm 8.43 (d, J=8.0 Hz, 1H), 8.00 (s, 1H), 7.82 (s, 1H), 7.58 (d, J=8.0 Hz, 1H), 7.36 (s, 1H), 5.05-4.85 (m, 1H), 4.05 (s, 3H), 4.00-3.82 (m, 2H), 3.75-3.60 (m, 2H), 3.50-3.10 (m, 4H), 3.05 (s, 3H), 2.50-2.10 (m, 2H), 1.95-1.75 (m, 3H), 1.50-1.15 (m, 2H), 0.91 (t, J=7.3 Hz, 3H).

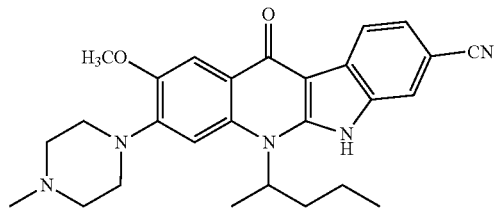 [SMILES: CCCC(C)n1c2cc(N3CCN(C)CC3)c(OC)cc2c(=O)c2c3ccc(C#N)cc3[nH]c21]

Step D: 2-Methoxy-3-(4-methylpiperazin-1-yl)-11-oxo-5-(pentan-2-yl)-6,11-dihydro-5H-indolo[2,3-b]quinoline-8-carbonitrile 1-Methylpiperazine (0.5 mL) and DIPEA (0.5 ml) were added to a solution of 3-Fluoro-2-methoxy-11-oxo-5-(pentan-2-yl)-6,11-dihydro-5H-indolo[2,3-b]quinoline-8-carbonitrile (148 mg, 0.39 mmol) in DMSO (2 ml) and the mixture was heated to 120 to 140° C. for 3 days. The reaction was cooled to RT and purified by Preparative HPLC to afford 2-Methoxy-3-(4-methylpiperazin-1-yl)-11-oxo-5-(pentan-2-yl)-6,11-dihydro-5H-indolo[2,3-b]quinoline-8-carbonitrile (45 mg, 23% yield). MS m/z=458[M+H].

Example 14 (ALK-40)

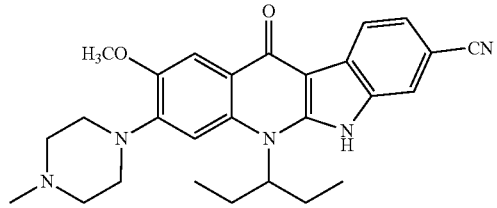 [SMILES: CCC(CC)n1c2cc(N3CCN(C)CC3)c(OC)cc2c(=O)c2c3ccc(C#N)cc3[nH]c21]

2-Methoxy-3-(4-methylpiperazin-1-yl)-11-oxo-5-(pentan-3-yl)-6,11-dihydro-5H-indolo[2,3-b]quinoline-8-carbonitrile The title compound was prepared in a method similar to that used in the preparation of 2-Methoxy-3-(4-methylpiperazin-1-yl)-11-oxo-5-(pentan-2-yl)-6,11-dihydro-5H-indolo[2,3-b]quinoline-8-carbonitrile. $^1$H NMR (300 MHz, CD$_3$OD) δ ppm 8.43 (d, J=8.1 Hz, 1H), 8.01 (s, 1H), 7.82 (s, 1H), 7.58 (dd, J=8.1, 1.4 Hz, 1H), 7.36 (d, J=1.4 Hz, 1H), 4.77-4.66 (m, 1H), 4.03 (s, 3H), 3.94-3.85 (m, 2H), 3.70-3.64 (m, 2H), 3.42-3.38 (m, 2H), 3.25-3.12 (m, 2H), 3.03 (s, 3H), 2.56-2.33 (m, 2H), 2.29-2.21 (m, 2H), 0.95-0.87 (m, 6H).

Example 15 (ALK-42)

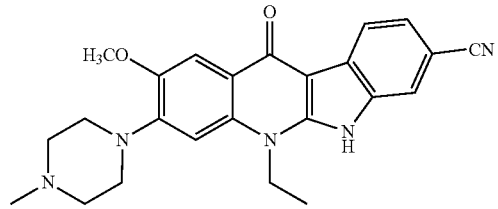 [SMILES: CCn1c2cc(N3CCN(C)CC3)c(OC)cc2c(=O)c2c3ccc(C#N)cc3[nH]c21]

5-Ethyl-2-methoxy-3-(4-methylpiperazin-1-yl)-11-oxo-6,11-dihydro-5H-indolo[2,3-b]quinoline-8-carbonitrile

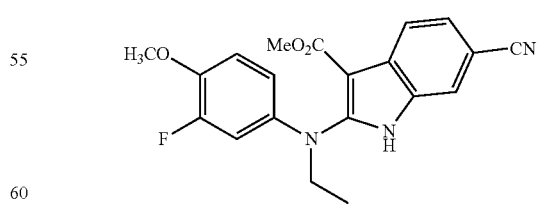

Step A: Methyl 6-cyano-2-(ethyl(3-fluoro-4-methoxyphenyl)amino)-1H-indole-3-carboxylate DABCO (62 mg, 0.55 mmol) was added to a solution of Methyl 6-cyano-1H-indole-3-carboxylate (200 mg, 1 mmol)

in DCM (20 mL) and the mixture was cooled to 0° C. N-Chlorosuccinimide (147 mg, 1.1 mmol) was then added and the reaction was stirred at 0° C. for 2 hr. A solution of N-Ethyl-3-fluoro-4-methoxyaniline (169 mg, 1 mmol) and Trichloroacetic acid (41 mg, 0.25 mmol) in DCM (5 mL) was added dropwise and the reaction was stirred for 2 hr at room temperature. The reaction was quenched by adding water and the mixture was extracted with DCM. Solvent was removed under vacuum and the residue was purified by silica gel chromatography (Hex:EA=4:1) to afford Methyl 6-cyano-2-(ethyl(3-fluoro-4-methoxyphenyl)amino)-1H-indole-3-carboxylate (160 mg, 44% yield). $^1$H NMR (400 MHz, CDCl$_3$) δ ppm 8.31 (s, 1H), 8.09 (d, J=8.7 Hz, 1H), 7.47-7.39 (m, 2H), 7.02-6.84 (m, 3H), 4.01 (q, J=7.1 Hz, 2H), 3.89 (s, 3H), 3.87 (s, 3H), 1.30 (t, J=7.1 Hz, 3H).

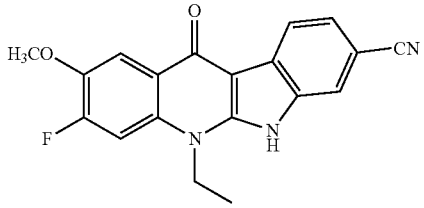 [SMILES: CCn1c2cc(F)c(OC)cc2c(=O)c2c3ccc(C#N)cc3[nH]c21]

Step B: 5-Ethyl-3-fluoro-2-methoxy-11-oxo-6,11-dihydro-5H-indolo[2,3-b]quinoline-8-carbonitrile Methyl 6-cyano-2-(ethyl(3-fluoro-4-methoxyphenyl) amino)-1H-indole-3-carboxylate (160 mg, 0.44 mmol) was dissolved in Diphenyl ether (10 mL) and the solution was refluxed for 1 hr. The mixture was cooled to RT. Hexane (20 mL) was added and the precipitate was collected by filtration. The precipitate was purified by silica gel chromatography (Hex:EA=2:1) to afford 5-Ethyl-3-fluoro-2-methoxy-11-oxo-6,11-dihydro-5H-indolo[2,3-b]quinoline-8-carbonitrile (98 mg, 67% yield). $^1$H NMR (400 MHz, DMSO-d$_6$) δ ppm 12.58 (s, 1H), 8.29 (d, J=8.1 Hz, 1H), 7.98 (d, J=9.7 Hz, 1H), 7.94-7.84 (m, 2H), 7.62 (dd, J=8.1, 1.5 Hz, 1H), 4.52 (d, J=7.4 Hz, 2H), 3.97 (s, 3H), 1.38 (t, J=7.4 Hz, 3H).

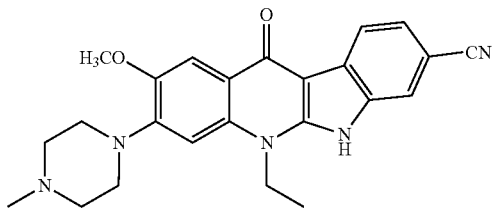 [SMILES: CCn1c2cc(N3CCN(C)CC3)c(OC)cc2c(=O)c2c3ccc(C#N)cc3[nH]c21]

Step C: 5-Ethyl-2-methoxy-3-(4-methylpiperazin-1-yl)-11-oxo-6,11-dihydro-5H-indolo[2,3-b]quinoline-8-carbonitrile 1-Methylpiperazine (0.5 mL) and DIPEA (0.5 ml) were added to a solution of 5-Ethyl-3-fluoro-2-methoxy-11-oxo-6,11-dihydro-5H-indolo[2,3-b]quinoline-8-carbonitrile (98 mg, 0.29 ml) in DMSO (2 ml) and the mixture was heated to 120 to 140° C. for 3 days. The reaction mixture was cooled to RT and purified by Preparative HPLC to afford 5-Ethyl-2-methoxy-3-(4-methylpiperazin-1-yl)-11-oxo-6,11-dihydro-5H-indolo[2,3-b]quinoline-8-carbonitrile (25 mg, 21% yield). $^1$H NMR (300 MHz, CD$_3$OD) δ ppm 8.31 (d, J=7.6 Hz, 1H), 7.91 (s, 1H), 7.59 (d, J=0.7 Hz, 1H), 7.50 (dd, J=7.6, 0.7 Hz, 1H), 7.06 (s, 1H), 4.50 (q, J=7.3 Hz, 2H), 4.06 (s, 3H), 4.04-3.86 (m, 2H), 3.75-3.63 (m, 2H), 3.50-3.37 (m, 2H), 3.26-3.17 (m, 2H), 3.05 (s, 3H), 1.53 (t, J=7.3 Hz, 3H).

Example 16 (ALK-43)

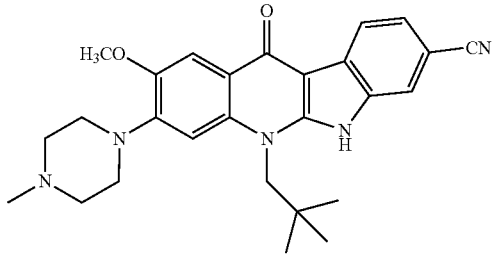 [SMILES: COc1cc2c(=O)c3c4ccc(C#N)cc4[nH]c3n(CC(C)(C)C)c2cc1N1CCN(C)CC1]

2-Methoxy-3-(4-methylpiperazin-1-yl)-5-neopentyl-11-oxo-6,11-dihydro-5H-indolo[2,3-b]quinoline-8-carbonitrile The title compound was prepared in a method similar to that used in the preparation of 2-Methoxy-3-(4-methylpiperazin-1-yl)-11-oxo-5-(pentan-2-yl)-6,11-dihydro-5H-indolo[2,3-b]quinoline-8-carbonitrile. $^1$H NMR (300 MHz, CD$_3$OD) δ ppm 8.38 (d, J=8.1 Hz, 1H), 7.95 (s, 1H), 7.67 (s, 1H), 7.55-7.50 (m, 1H), 7.32 (s, 1H), 4.72 (d, J=16.0 Hz, 1H), 4.21 (d, J=16.0 Hz, 1H), 4.04 (s, 3H), 4.01-3.96 (m, 2H), 3.86-3.68 (m, 2H), 3.15-3.10 (m, 4H), 3.02 (s, 3H), 1.04 (s, 9H).

Example 17 (ALK-44)

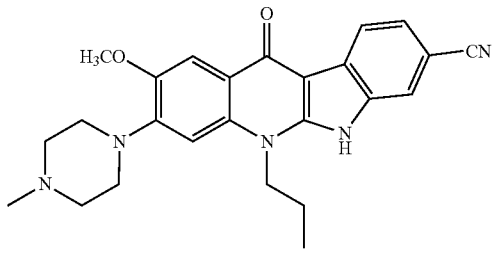 [SMILES: CCCn1c2cc(N3CCN(C)CC3)c(OC)cc2c(=O)c2c3ccc(C#N)cc3[nH]c21]

2-Methoxy-3-(4-methylpiperazin-1-yl)-11-oxo-5-propyl-6,11-dihydro-5H-indolo[2,3-b]quinoline-8-carbonitrile The title compound was prepared in a method similar to that used in the preparation of 2-Methoxy-3-(4-methylpiperazin-1-yl)-11-oxo-5-(pentan-2-yl)-6,11-dihydro-5H-indolo[2,3-b]quinoline-8-carbonitrile. $^1$H NMR (300 MHz, CD$_3$OD) δ ppm 8.24 (d, J=8.1 Hz, 1H), 7.83 (s, 1H), 7.47 (d, J=1.4 Hz, 1H), 7.42 (dd, J=8.1, 1.4 Hz, 1H), 6.94 (s, 1H), 4.32 (t, J=7.9 Hz, 2H), 4.03 (s, 3H), 3.99-3.90 (m, 2H), 3.71-3.68 (m, 2H), 3.41-3.38 (m, 2H), 3.20-3.17 (m, 2H), 3.04 (s, 3H), 2.00-1.80 (m, 2H), 1.09 (t, J=7.6 Hz, 3H).

Example 18 (ALK-45)

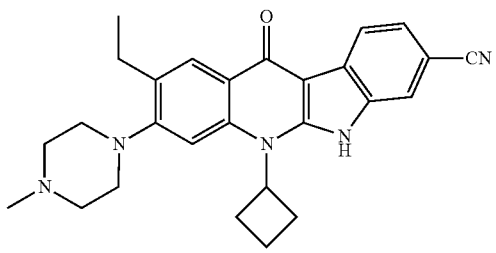 [SMILES: CCc1cc2c(=O)c3c4ccc(C#N)cc4[nH]c3n(C3CCC3)c2cc1N1CCN(C)CC1]

5-cyclobutyl-2-ethyl-3-(4-methylpiperazin-1-yl)-11-oxo-6,11-dihydro-5H-indolo[2,3-b]quinoline-8-carbonitrile

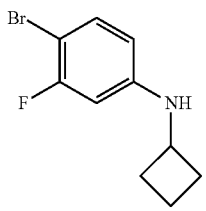

Step A: 4-Bromo-N-cyclobutyl-3-fluoroaniline

2-Cyclobutanone (14.0 g, 200 mmol), Acetic acid (1.8 g, 30 mmol), and Sodium triacetoxyborohydride (6.36 g, 30 mmol) were added to a solution of 4-Bromo-3-fluoroaniline (3.8 g, 20 mmol) in DCM (120 mL) and the mixture was stirred at RT for 12 hr. Water was added to quench the reaction and the mixture was extracted with DCM. The solvent was removed under and the residue was purified by silica gel chromatography to afford 4-Bromo-N-cyclobutyl-3-fluoroaniline (3.6 g, 74% yield). MS m/e=244 [M+H].

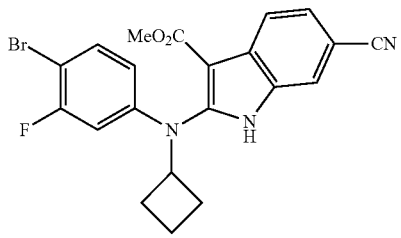 [SMILES: COC(=O)c1c(N(c2ccc(Br)c(F)c2)C2CCC2)[nH]c2cc(C#N)ccc12]

Step B: Methyl 2-((4-bromo-3-fluorophenyl)(cyclobutyl)amino)-6-cyano-1H-indole-3-carboxylate DABCO (62 mg, 0.55 mmol) was added to a solution of Methyl 6-cyano-1H-indole-3-carboxylate (200 mg, 1 mmol) in DCM (20 mL) and the mixture was cooled to 0° C. N-Chlorosuccinimide (147 mg, 1.1 mmol) was then added and the reaction was stirred at 0° C. for 2 hr. A solution of 4-Bromo-N-cyclobutyl-3-fluoroaniline (243 mg, 1 mmol) and Trichloroacetic acid (41 mg, 0.25 mmol) in DCM (5 mL) was added dropwise and the reaction was stirred for 2 hr at room temperature. The reaction was quenched by adding water and the mixture was extracted with DCM. Solvent was removed under vacuum and the residue was purified by silica gel chromatography (Hex:EA=4:1) to afford Methyl 2-((4-bromo-3-fluorophenyl)(cyclobutyl)amino)-6-cyano-1H-indole-3-carboxylate (230 mg, 52% yield). $^1$H NMR (400 MHz, CDCl$_3$) δ ppm 8.62 (s, 1H), 8.29 (d, J=8.4 Hz, 1H), 7.75-7.69 (m, 1H), 7.56 (dd, J=8.4, 1.4 Hz, 1H), 7.35-7.29 (m, 1H), 6.46-6.40 (m, 1H), 6.32-6.24 (m, 1H), 4.47-4.34 (m, 1H), 3.82 (s, 3H), 2.38-2.32 (m, 2H), 1.95-1.90 (m, 2H), 1.85-1.65 (m, 2H).

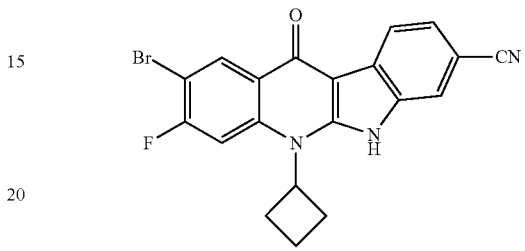

Step C: 2-Bromo-5-cyclobutyl-3-fluoro-11-oxo-6,11-dihydro-5H-indolo[2,3-b]quinoline-8-carbonitrile Methyl 2-((4-bromo-3-fluorophenyl)(cyclobutyl)amino)-6-cyano-1H-indole-3-carboxylate (230 mg, 0.52 mmol) was dissolved in Diphenyl ether (10 mL) and the solution was refluxed for 1 hr. The mixture was cooled to RT. Hexane (20 mL) was added and the precipitate was collected by filtration. The precipitate was purified by silica gel chromatography (Hex:EA=2:1) to afford 2-Bromo-5-cyclobutyl-3-fluoro-11-oxo-6,11-dihydro-5H-indolo[2,3-b]quinoline-8-carbonitrile (130 mg, 61% yield). MS m/z=410 [M+H].

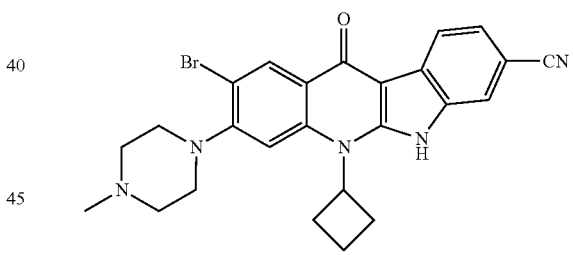

Step D: 2-Bromo-5-cyclobutyl-3-(4-methylpiperazin-1-yl)-11-oxo-6,11-dihydro-5H-indolo[2,3-b]quinoline-8-carbonitrile 1-Methylpiperazine (0.5 mL) and DIPEA (0.5 ml) were added to a solution of 2-Bromo-5-cyclobutyl-3-fluoro-11-oxo-6,11-dihydro-5H-indolo[2,3-b]quinoline-8-carbonitrile (130 mg, 0.32 mmol) in DMSO (2 ml) and the mixture was heated to 120 to 140° C. for 3 days. The reaction mixture was cooled to RT and purified by Preparative HPLC to afford 2-Bromo-5-cyclobutyl-3-(4-methylpiperazin-1-yl)-11-oxo-6,11-dihydro-5H-indolo[2,3-b]quinoline-8-carbonitrile (34 mg, 22% yield). $^1$H NMR (400 MHz, DMSO-d$_6$) δ ppm 11.94 (s, 1H), 10.16 (s, 1H), 8.43 (s, 1H), 8.26 (d, J=8.1 Hz, 1H), 7.94-7.88 (m, 1H), 7.61 (dd, J=8.1, 1.5 Hz, 1H), 7.25 (s, 1H), 5.33-5.20 (m, 1H), 3.68-3.63 (m, 4H), 3.18-3.14 (m, 4H), 2.95-2.92 (m, 5H), 2.50-2.37 (m, 2H), 1.96-1.79 (m, 2H).

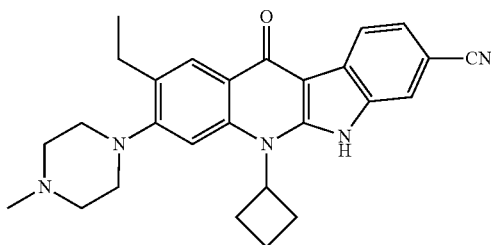

Step E: 5-Cyclobutyl-2-ethyl-3-(4-methylpiperazin-1-yl)-11-oxo-6,11-dihydro-5H-indolo[2,3-b]quinoline-8-carbonitrile A mixture of 2-Bromo-5-cyclobutyl-3-(4-methylpiperazin-1-yl)-11-oxo-6,11-dihydro-5H-indolo[2,3-b]quinoline-8-carbonitrile (30 mg, 0.061 mmol), $Na_2CO_3$ (25 mg, 0.183 mmol), $Pd(PPh_3)_2Cl_2$ (4.3 mg, 0.0061 mmol), and 4,4,5,5-Tetramethyl-2-vinyl-1,3,2-dioxaborolane (14 mg, 0.091 mmol) in $DME/H_2O$ (4.8 ml, V/V=5/1) was stirred under nitrogen at 80° C. overnight. After the reaction was complete as indicated by LC-MS, the reaction mixture was cooled down to RT. Water (50 ml) was added. The mixture was extracted with $CH_2Cl_2$ (2×150 ml). The combined $CH_2Cl_2$ layer was dried over $Na_2SO4$ and concentrated to give crude 5-Cyclobutyl-3-(4-methylpiperazin-1-yl)-11-oxo-2-vinyl-6,11-dihydro-5H-indolo[2,3-b]quinoline-8-carbonitrile (25 mg) which was used directly in the next step without further purification.

5-Cyclobutyl-3-(4-methylpiperazin-1-yl)-11-oxo-2-vinyl-6,11-dihydro-5H-indolo[2,3-b]quinoline-8-carbonitrile (crude, 25 mg) was dissolved in THF (5 ml). Pd/C (10%, 20 mg) was added to the THF solution. The mixture underwent hydrogenation at room temperature overnight until LC-MS indicated that the reaction was complete. The filtrate after filtration was concentrated and the residue was purified by preparative HPLC to afford 5-Cyclobutyl-2-ethyl-3-(4-methylpiperazin-1-yl)-11-oxo-6,11-dihydro-5H-indolo[2,3-b]quinoline-8-carbonitrile (8 mg, 30% yield). $^1$H NMR (300 MHz, $CD_3OD$) δ ppm 8.45-8.40 (m, 2H), 7.81 (d, J=0.8 Hz, 1H), 7.57 (dd, J=8.1, 0.8 Hz, 1H), 7.31 (s, 1H), 5.40-5.25 (m, 1H), 3.70-3.60 (m, 2H), 3.55-3.35 (m, 4H), 3.30-3.15 (m, 2H), 3.10-3.00 (m, 2H), 3.06 (s, 3H), 2.88 (q, J=7.5 Hz, 2H), 2.70-2.53 (m, 2H), 2.20-1.96 (m, 2H), 1.41 (t, J=7.5 Hz, 3H).

Example 19 (ALK-47)

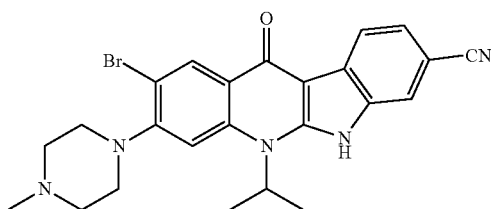

2-Bromo-5-isopropyl-3-(4-methylpiperazin-1-yl)-11-oxo-6,11-dihydro-5H-indolo[2,3-b]quinoline-8-carbonitrile

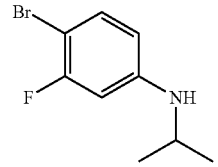

Step A: 4-Bromo-3-fluoro-N-isopropylaniline

Acetone (11.6 g, 200 mmol), Acetic acid (1.8 g, 30 mmol), and Sodium triacetoxyborohydride (6.36 g, 30 mmol) were added to a solution of 4-Bromo-3-fluoroaniline (3.8 g, 20 mmol) in DCM (120 mL) and the mixture was stirred at RT for 12 hr. Water was added to quench the reaction and the mixture was extracted with DCM. The solvent was removed under and the residue was purified by silica gel chromatography to afford 4-Bromo-3-fluoro-N-isopropylaniline (3.4 g, 73% yield). $^1$H NMR (400 MHz, $CDCl_3$) δ ppm 7.25 (dd, J=8.7, 8.0 Hz, 1H), 6.36 (dd, J=11.3, 2.7 Hz, 1H), 6.27-6.23 (m, 1H), 3.65 (s, 1H), 3.59-3.53 (m, 1H), 1.22 (d, J=6.2 Hz, 6H).

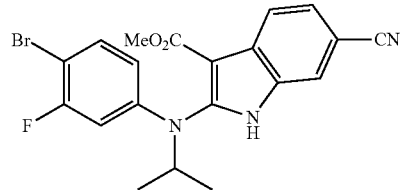 [SMILES: COC(=O)c1c(N(c2ccc(Br)c(F)c2)C(C)C)[nH]c2cc(C#N)ccc12]

Step B: Methyl 2-((4-bromo-3-fluorophenyl)(isopropyl)amino)-6-cyano-1H-indole-3-carboxylate DABCO (62 mg, 0.55 mmol) was added to a solution of Methyl 6-cyano-1H-indole-3-carboxylate (200 mg, 1 mmol) in DCM (20 mL) and the mixture was cooled to 0° C. N-Chlorosuccinimide (147 mg, 1.1 mmol) was then added and the reaction was stirred at 0° C. for 2 hr. A solution of 4-Bromo-3-fluoro-N-isopropylaniline (232 mg, 1 mmol) and Trichloroacetic acid (41 mg, 0.25 mmol) in DCM (5 mL) was added dropwise and the reaction was stirred for 2 hr at room temperature. The reaction was quenched by adding water and the mixture was extracted with DCM. Solvent was removed under vacuum and the residue was purified by silica gel chromatography (Hex:EA=4:1) to afford Methyl 2-((4-bromo-3-fluorophenyl)(isopropyl)amino)-6-cyano-1H-indole-3-carboxylate (245 mg, 57% yield). $^1$H NMR (400 MHz, $CDCl_3$) δ ppm 8.44 (s, 1H), 8.27 (d, J=8.3 Hz, 1H), 7.73-7.64 (m, 1H), 7.54 (dd, J=8.3, 1.4 Hz, 1H), 7.34 (dd, J=9.0, 7.9 Hz, 1H), 6.56 (dd, J=11.3, 2.7 Hz, 1H), 6.41 (dd, J=9.0, 2.7 Hz, 1H), 4.45-4.41 (m, 1H), 3.81 (s, 3H), 1.31 (d, J=6.6 Hz, 6H).

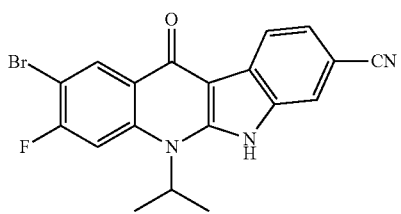 [SMILES: CC(C)n1c2cc(F)c(Br)cc2c(=O)c2c3ccc(C#N)cc3[nH]c21]

Step C: 2-Bromo-3-fluoro-5-isopropyl-11-oxo-6,11-dihydro-5H-indolo[2,3-b]quinoline-8-carbonitrile Methyl 2-((4-bromo-3-fluorophenyl)(isopropyl)amino)-6-cyano-1H-indole-3-carboxylate (245 mg, 0.57 mmol) was dissolved in Diphenyl ether (10 mL) and the solution was refluxed for 1 hr. The mixture was cooled to RT. Hexane (20 mL) was added and the precipitate was collected by filtration. The precipitate was purified by silica gel chromatography (Hex:EA=2:1) to afford 2-Bromo-3-fluoro-5-isopropyl-11-oxo-6,11-dihydro-5H-indolo[2,3-b]quinoline-8-carbonitrile (110 mg, 49% yield). $^1$H NMR (400 MHz, DMSO-$d_6$) δ 12.30 (s, 1H), 8.54 (d, J=8.3 Hz, 1H), 8.28 (d, J=8.0 Hz, 1H), 8.08 (d, J=11.9 Hz, 1H), 7.92 (d, J=1.4 Hz, 1H), 7.63 (dd, J=8.0, 1.4 Hz, 1H), 5.37-5.28 (m, 1H), 1.74 (d, J=7.0 Hz, 6H).

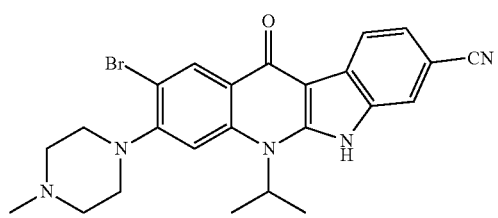 [SMILES: CC(C)n1c2cc(N3CCN(C)CC3)c(Br)cc2c(=O)c2c3ccc(C#N)cc3[nH]c21]

Step D: 2-Bromo-5-isopropyl-3-(4-methylpiperazin-1-yl)-11-oxo-6,11-dihydro-5H-indolo[2,3-b]quinoline-8-carbonitrile 1-Methylpiperazine (0.5 mL) and DIPEA (0.5 ml) were added to a solution of 2-Bromo-3-fluoro-5-isopropyl-11-oxo-6,11-dihydro-5H-indolo[2,3-b]quinoline-8-carbonitrile (110 mg, 0.28 mmol) in DMSO (2 ml) and the mixture was heated to 120 to 140° C. for 3 days. The reaction mixture was cooled to RT and purified by preparative HPLC to afford 2-Bromo-5-isopropyl-3-(4-methylpiperazin-1-yl)-11-oxo-6,11-dihydro-5H-indolo[2,3-b]quinoline-8-carbonitrile (29 mg, 22% yield). $^1$H NMR (300 MHz, CD$_3$OD) δ ppm 8.58 (s, 1H), 8.29 (d, J=7.9 Hz, 1H), 7.77 (s, 1H), 7.52 (d, J=7.9 Hz, 1H), 7.49 (s, 1H), 5.44-5.30 (m, 1H), 3.90-3.70 (m, 4H), 3.60-3.30 (m, 4H), 3.08 (s, 3H), 1.89 (d, J=7.1 Hz, 6H Example 20 (ALK-46)

5-isoPropyl-3-(4-methylpiperazin-1-yl)-11-oxo-2-vinyl-6,11-dihydro-5H-indolo[2,3-b]quinoline-8-carbonitrile A mixture of 2-Bromo-5-isopropyl-3-(4-methylpiperazin-1-yl)-11-oxo-6,11-dihydro-5H-indolo[2,3-b]quinoline-8-carbonitrile (30 mg, 0.061 mmol), Na$_2$CO$_3$ (25 mg, 0.183 mmol), Pd(PPh$_3$)$_2$Cl$_2$ (4.3 mg, 0.0061 mmol), and 4,4,5,5-Tetramethyl-2-vinyl-1,3,2-dioxaborolane (14 mg, 0.091 mmol) in DME/H$_2$O (4.8 ml, V/V=5/1) was stirred under nitrogen at 80 C for overnight. After the reaction was complete as indicated by LC-MS, the mixture was purified by preparative HPLC to afford 5-isoPropyl-3-(4-methylpiperazin-1-yl)-11-oxo-2-vinyl-6,11-dihydro-5H-indolo[2,3-b]quinoline-8-carbonitrile (10 mg, 37% yield). MS m/z=426 [M+H].

Example 21 (ALK-56)

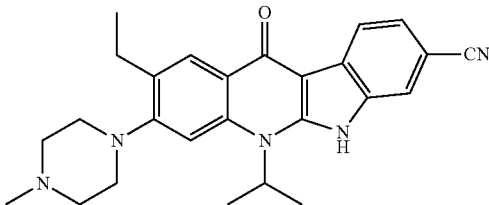 [SMILES: CCc1cc2c(=O)c3c4ccc(C#N)cc4[nH]c3n(C(C)C)c2cc1N1CCN(C)CC1]

2-Ethyl-5-isopropyl-3-(4-methylpiperazin-1-yl)-11-oxo-6,11-dihydro-5H-indolo[2,3-b]quinoline-8-carbonitrile 5-isoPropyl-3-(4-methylpiperazin-1-yl)-11-oxo-2-vinyl-6,11-dihydro-5H-indolo[2,3-b]quinoline-8-carbonitrile (50 mg, 0.12 mmol) was dissolved in THF (5 ml). Pd/C (10%, 20 mg) was added to the THF solution. The mixture underwent hydrogenation at room temperature overnight until LC-MS indicated that the reaction was complete. The filtrate after filtration was concentrated and the residue was purified by preparative HPLC to afford 2-Ethyl-5-isopropyl-3-(4-methylpiperazin-1-yl)-11-oxo-6,11-dihydro-5H-indolo[2,3-b]quinoline-8-carbonitrile (26 mg, 52% yield). $^1$H NMR (300 MHz, CD$_3$OD) δ ppm 8.38 (s, 1H), 8.29 (d, J=8.0 Hz, 1H), 7.70 (s, 1H), 7.50 (s, 1H), 7.44 (d, J=8.0 Hz, 1H), 5.40-5.30 (m, 1H), 3.75-3.65 (m, 2H), 3.63-3.25 (m, 6H), 3.06 (s, 3H), 2.90 (q, J=7.4 Hz, 2H), 1.88 (d, J=7.1 Hz, 6H), 1.40 (t, J=7.4 Hz, 3H).

Example 22 (ALK-48)

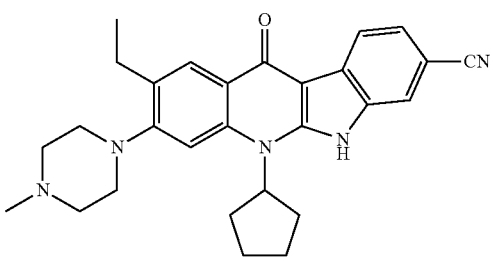 [SMILES: CCc1cc2c(=O)c3c4ccc(C#N)cc4[nH]c3n(C3CCCC3)c2cc1N1CCN(C)CC1]

5-Cyclopentyl-2-ethyl-3-(4-methylpiperazin-1-yl)-11-oxo-6,11-dihydro-5H-indolo[2,3-b]quinoline-8-carbonitrile

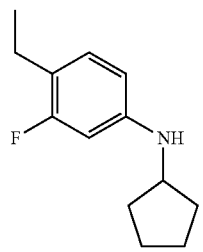

Step A: N-Cyclopentyl-4-ethyl-3-fluoroaniline

Cyclopentanone (16.8 g, 200 mmol), Acetic acid (1.8 g, 30 mmol), and Sodium triacetoxyborohydride (6.36 g, 30 mmol) were added to a solution of 4-Ethyl-3-fluoroaniline (2.78 g, 20 mmol) in DCM (120 mL) and the mixture was stirred at RT for 12 hr. Water was added to quench the reaction and the mixture was extracted with DCM. The solvent was removed under and the residue was purified by silica gel chromatography to afford N-Cyclopentyl-4-ethyl-3-fluoroaniline (3.1 g, 75% yield). MS m/z=208 [M+H].

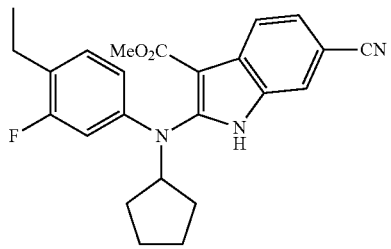 [SMILES: CCc1ccc(N(c2[nH]c3cc(C#N)ccc3c2C(=O)OC)C2CCCC2)cc1F]

Step B: Methyl 6-cyano-2-(cyclopentyl(4-ethyl-3-fluorophenyl)amino)-1H-indole-3-carboxylate DABCO (62 mg, 0.55 mmol) was added to a solution of Methyl 6-cyano-1H-indole-3-carboxylate (200 mg, 1 mmol) in DCM (20 mL) and the mixture was cooled to 0° C. N-Chlorosuccinimide (147 mg, 1.1 mmol) was then added and the reaction was stirred at 0° C. for 2 hr. A solution of N-Cyclopentyl-4-ethyl-3-fluoroaniline (207 mg, 1 mmol) and Trichloroacetic acid (41 mg, 0.25 mmol) in DCM (5 mL) was added dropwise and the reaction was stirred for 2 hr at room temperature. The reaction was quenched by adding water and the mixture was extracted with DCM. Solvent was removed under vacuum and the residue was purified by silica gel chromatography (Hex:EA=4:1) to afford Methyl 6-cyano-2-(cyclopentyl(4-ethyl-3-fluorophenyl)amino)-1H-indole-3-carboxylate (260 mg, 64% yield). $^1$H NMR (400 MHz, CDCl$_3$) δ ppm 8.44 (s, 1H), 8.22 (d, J=8.4 Hz, 1H), 7.64-7.61 (m, 1H), 7.55-7.41 (m, 1H), 7.06 (t, J=8.4 Hz, 1H), 6.59-6.39 (m, 2H), 4.48-4.45 (m, 1H), 3.81 (s, 3H), 3.75-3.47 (m, 2H), 2.61 (q, J=7.6 Hz, 2H), 2.17-1.92 (m, 2H), 1.74-1.62 (m, 2H), 1.34-1.26 (m, 2H), 1.21 (t, J=7.6 Hz, 3H).

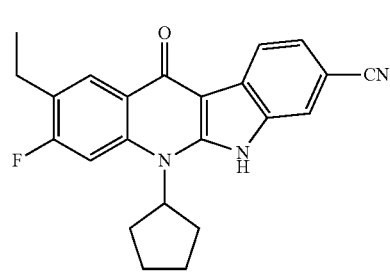 [SMILES: CCc1cc2c(=O)c3c4ccc(C#N)cc4[nH]c3n(C3CCCC3)c2cc1F]

Step C: 5-Cyclopentyl-2-ethyl-3-fluoro-11-oxo-6,11-dihydro-5H-indolo[2,3-b]quinoline-8-carbonitrile Methyl 6-cyano-2-(cyclopentyl(4-ethyl-3-fluorophenyl)amino)-1H-indole-3-carboxylate (260 mg, 0.64 mmol) was dissolved in Diphenyl ether (10 mL) and the solution was refluxed for 1 hr. The mixture was cooled to RT. Hexane (20 mL) was added and the precipitate was collected by filtration. The precipitate was purified by silica gel chromatography (Hex:EA=2:1) to afford 5-Cyclopentyl-2-ethyl-3-fluoro-11-oxo-6,11-dihydro-5H-indolo[2,3-b]quinoline-8-carbonitrile (140 mg, 59% yield). MS m/z=374 [M+H].

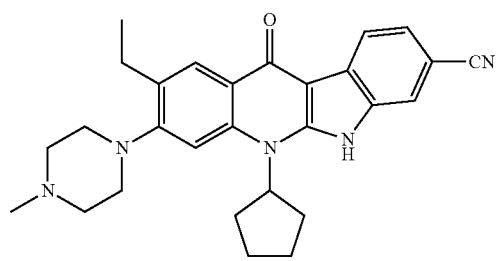 [SMILES: CCc1cc2c(=O)c3c4ccc(C#N)cc4[nH]c3n(C3CCCC3)c2cc1N1CCN(C)CC1]

Step D: 5-Cyclopentyl-2-ethyl-3-(4-methylpiperazin-1-yl)-11-oxo-6,11-dihydro-5H-indolo[2,3-b]quinoline-8-carbonitrile 1-Methylpiperazine (0.5 mL) and DIPEA (0.5 ml) were added to a solution of 5-Cyclopentyl-2-ethyl-3-fluoro-11-oxo-6,11-dihydro-5H-indolo[2,3-b]quinoline-8-carbonitrile (140 mg, 0.38 mmol) in DMSO (2 ml) and the mixture was heated to 120 to 140° C. for 3 days. The reaction mixture was cooled to RT and purified by preparative HPLC to afford 5-Cyclopentyl-2-ethyl-3-(4-methylpiperazin-1-yl)-11-oxo-6,11-dihydro-5H-indolo[2,3-b]quinoline-8-carbonitrile (39 mg, 23% yield). $^1$H NMR (300 MHz, CD$_3$OD) δ ppm 8.48 (s, 1H), 8.39 (d, J=8.0 Hz, 1H), 7.77 (s, 1H), 7.56 (d, J=8.0 Hz, 1H), 7.31 (s, 1H), 5.45-5.35 (m, 1H), 3.70-3.60 (m, 2H), 3.55-3.30 (m, 4H), 3.25-3.15 (m, 2H), 3.06 (s, 3H), 2.89 (q, J=7.5 Hz, 2H), 2.60-2.00 (m, 8H), 1.42 (t, J=7.5 Hz, 3H).

Example 23 (ALK-49)

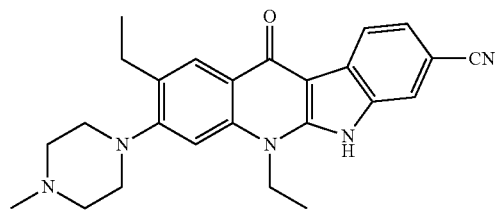 [SMILES: CCc1cc2c(=O)c3c4ccc(C#N)cc4[nH]c3n(CC)c2cc1N1CCN(C)CC1]

2,5-Diethyl-3-(4-methylpiperazin-1-yl)-11-oxo-6,11-dihydro-5H-indolo[2,3-b]quinoline-8-carbonitrile

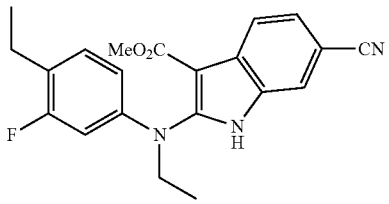 [SMILES: CCc1ccc(N(CC)c2[nH]c3cc(C#N)ccc3c2C(=O)OC)cc1F]

Step A: Methyl 6-cyano-2-(ethyl(4-ethyl-3-fluorophenyl)amino)-1H-indole-3-carboxylate DABCO (62 mg, 0.55 mmol) was added to a solution of Methyl 6-cyano-1H-indole-3-carboxylate (200 mg, 1 mmol) in DCM (20 mL) and the mixture was cooled to 0° C. N-Chlorosuccinimide (147 mg, 1.1 mmol) was then added and the reaction was stirred at 0° C. for 2 hr. A solution of N,4-Diethyl-3-fluoroaniline (167 mg, 1 mmol) and Trichloroacetic acid (41 mg, 0.25 mmol) in DCM (5 mL) was added dropwise and the reaction was stirred for 2 hr at room temperature. The reaction was quenched by adding water and the mixture was extracted with DCM. Solvent was removed under vacuum and the residue was purified by silica gel chromatography (Hex:EA=4:1) to afford Methyl 6-cyano-2-(ethyl(4-ethyl-3-fluorophenyl)amino)-1H-indole-3-carboxylate (197 mg, 54% yield). $^1$H NMR (400 MHz, CDCl$_3$) δ ppm 8.50 (s, 1H), 8.14 (d, J=8.4 Hz, 1H), 7.52-7.48 (m, 1H), 7.45 (dd, J=8.4, 1.4 Hz, 1H), 7.15-7.13 (t, J=8.6 Hz, 1H), 6.78-6.62 (m, 2H), 3.99 (q, J=7.1 Hz, 2H), 3.85 (s, 3H), 2.64 (q, J=7.6 Hz, 2H), 1.30 (t, J=7.1 Hz, 3H), 1.23 (t, J=7.6 Hz, 3H).

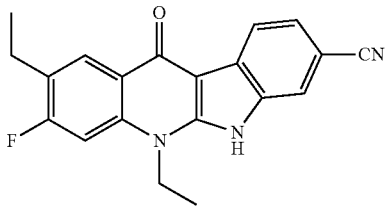 [SMILES: CCc1cc2c(=O)c3c4ccc(C#N)cc4[nH]c3n(CC)c2cc1F]

Step B: 2,5-Diethyl-3-fluoro-11-oxo-6,11-dihydro-5H-indolo[2,3-b]quinoline-8-carbonitrile Methyl 6-cyano-2-(ethyl(4-ethyl-3-fluorophenyl)amino)-1H-indole-3-carboxylate (197 mg, 0.54 mmol) was dissolved in Diphenyl ether (10 mL) and the solution was refluxed for 1 hr. The mixture was cooled to RT. Hexane (20 mL) was added and the precipitate was collected by filtration. The precipitate was purified by silica gel chromatography (Hex:EA=2:1) to afford 2,5-Diethyl-3-fluoro-11-oxo-6,11-dihydro-5H-indolo[2,3-b]quinoline-8-carbonitrile (122 mg, 68% yield). MS m/z=334 [M+H].

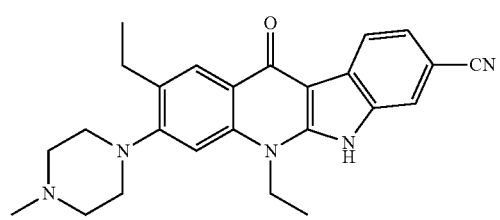 [SMILES: CCc1cc2c(=O)c3c4ccc(C#N)cc4[nH]c3n(CC)c2cc1N1CCN(C)CC1]

Step C: 2,5-Diethyl-3-(4-methylpiperazin-1-yl)-11-oxo-6,11-dihydro-5H-indolo[2,3-b]quinoline-8-carbonitrile 1-Methylpiperazine (0.5 mL) and DIPEA (0.5 ml) were added to a solution of 2,5-Diethyl-3-fluoro-11-oxo-6,11-dihydro-5H-indolo[2,3-b]quinoline-8-carbonitrile (122 mg, 0.37 mmol) in DMSO (2 ml) and the mixture was heated to 120 to 140° C. for 3 days. The reaction mixture was cooled to RT and purified by preparative HPLC to afford 2,5-Diethyl-3-(4-methylpiperazin-1-yl)-11-oxo-6,11-dihydro-5H-indolo[2,3-b]quinoline-8-carbonitrile (27 mg, 18% yield). $^1$H NMR (300 MHz, CD$_3$OD) δ ppm 8.43 (s, 1H), 8.38 (d, J=8.0 Hz, 1H), 7.75-7.68 (m, 1H), 7.60-7.49 (m, 1H), 7.32 (s, 1H), 4.58 (q, J=7.1 Hz, 2H), 3.71-3.67 (m, 2H), 3.61-3.37 (m, 4H), 3.35-3.23 (m, 2H), 3.05 (s, 3H), 2.93-2.83 (m, 2H), 1.56 (t, J=7.1 Hz, 3H), 1.41 (t, J=7.5 Hz, 3H).

Example 24 (ALK-51)

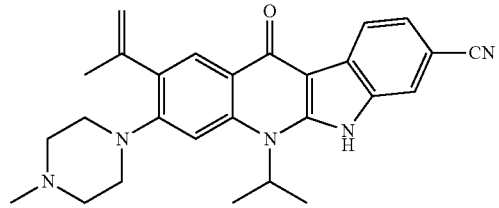 [SMILES: C=C(C)c1cc2c(=O)c3c4ccc(C#N)cc4[nH]c3n(C(C)C)c2cc1N1CCN(C)CC1]

5-isoPropyl-3-(4-methylpiperazin-1-yl)-11-oxo-2-(prop-1-en-2-yl)-6,11-dihydro-5H-indolo[2,3-b]quinoline-8-carbonitrile A mixture of 2-Bromo-5-isopropyl-3-(4-methylpiperazin-1-yl)-11-oxo-6,11-dihydro-5H-indolo[2,3-b]quinoline-8-carbonitrile (30 mg, 0.061 mmol), Na$_2$CO$_3$ (25 mg, 0.183 mmol), Pd(PPh$_3$)$_2$Cl$_2$ (4.3 mg, 0.0061 mmol), and 4,4,5,5-Tetramethyl-2-(prop-1-en-2-yl)-1,3,2-dioxaborolane (16 mg, 0.091 mmol) in DME/H$_2$O (4.8 ml, V/V=5/1) was stirred under nitrogen at 80° C. overnight. After the reaction was complete as indicated by LC-MS, the mixture was purified by preparative HPLC to afford 5-isoPropyl-3-(4-methylpiperazin-1-yl)-11-oxo-2-(prop-1-en-2-yl)-6,11-dihydro-5H-indolo[2,3-b]quinoline-8-carbonitrile (10 mg, 36% yield). $^1$H NMR (300 MHz, CD$_3$OD) δ ppm 8.41-8.34 (m, 1H), 8.30 (s, 1H), 7.82-7.72 (m, 1H), 7.53 (dd, J=8.1, 1.4 Hz, 1H), 7.37 (s, 1H), 5.46-5.25 (m, 3H), 3.88-3.84 (m, 2H), 3.69-3.66 (m, 2H), 3.41-3.35 (m, 2H), 3.30-3.10 (m, 2H), 3.03 (s, 3H), 2.27 (s, 3H), 1.88 (d, J=7.0 Hz, 6H).

Example 25 (ALK-52)

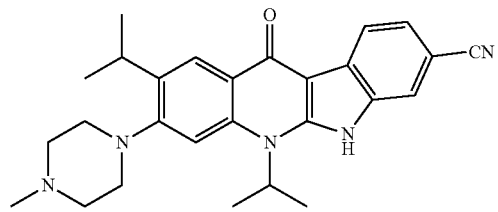 [SMILES: CC(C)c1cc2c(=O)c3c4ccc(C#N)cc4[nH]c3n(C(C)C)c2cc1N1CCN(C)CC1]

2,5-Diisopropyl-3-(4-methylpiperazin-1-yl)-11-oxo-6,11-dihydro-5H-indolo[2,3-b]quinoline-8-carbonitrile 5-isoPropyl-3-(4-methylpiperazin-1-yl)-11-oxo-2-(prop-1-en-2-yl)-6,11-dihydro-5H-indolo[2,3-b]quinoline-8-carbonitrile (50 mg, 0.12 mmol) was dissolved in THF (5 ml). Pd/C (10%, 20 mg) was added to the THF solution. The resulting mixture underwent hydrogenation at room temperature for overnight until LC-MS indicated that the reaction was complete. The filtrate after filtration was concentrated and the residue was purified by preparative HPLC to afford 2,5-Diisopropyl-3-(4-methylpiperazin-1-yl)-11-oxo-6,11-dihydro-5H-indolo[2,3-b]quinoline-8-carbonitrile (22 mg, 44% yield). $^1$H NMR (300 MHz, CD$_3$OD) δ ppm 8.53 (s, 1H), 8.42 (d, J=8.0 Hz, 1H), 7.82 (m, 1H), 7.60-7.52 (m, 2H), 5.45-5.27 (m, 1H), 3.92-3.25 (m, 9H), 3.07 (s, 3H), 1.89 (d, J=6.1 Hz, 6H), 1.38 (d, J=6.8 Hz, 6H).

Example 26 (ALK-54)

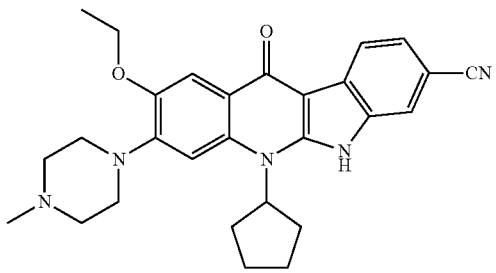 [SMILES: CCOc1cc2c(=O)c3c4ccc(C#N)cc4[nH]c3n(C3CCCC3)c2cc1N1CCN(C)CC1]

5-Cyclopentyl-2-ethoxy-3-(4-methylpiperazin-1-yl)-11-oxo-6,11-dihydro-5H-indolo[2,3-b]quinoline-8-carbonitrile

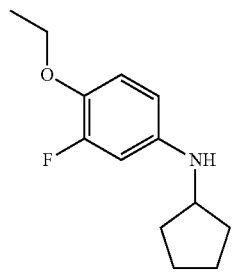 [SMILES: CCOc1ccc(NC2CCCC2)cc1F]

Step A: N-Cyclopentyl-4-ethoxy-3-fluoroaniline

Cyclopentanone (16.8 g, 200 mmol), Acetic acid (1.8 g, 30 mmol), and Sodium triacetoxyborohydride (6.36 g, 30 mmol) were added to a solution of 4-Ethoxy-3-fluoroaniline (3.10 g, 20 mmol) in DCM (120 mL) and the mixture was stirred at RT for 12 hr. Water was added to quench the reaction and the mixture was extracted with DCM. The solvent was removed under and the residue was purified by silica gel chromatography to afford N-Cyclopentyl-4-ethoxy-3-fluoroaniline (3.1 g, 70% yield). MS m/z=224 [M+H]. $^1$H NMR (300 MHz, CDCl$_3$) δ ppm 6.82 (t, J=9.1 Hz, 1H), 6.44-6.21 (m, 2H), 4.01 (q, J=7.0 Hz, 2H), 3.76- 3.61 (m, 1H), 3.48 (s, 1H), 2.00-1.98 (m, 2H), 1.80-1.54 (m, 4H), 1.54-1.23 (m, 2H), 1.38 (t, J=7.0 Hz, 3H).

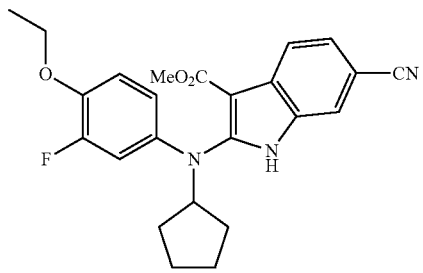 [SMILES: CCOc1ccc(N(c2[nH]c3cc(C#N)ccc3c2C(=O)OC)C2CCCC2)cc1F]

Step B: Methyl 6-cyano-2-(cyclopentyl(4-ethoxy-3-fluorophenyl)amino)-1H-indole-3-carboxylate DABCO (62 mg, 0.55 mmol) was added to a solution of Methyl 6-cyano-1H-indole-3-carboxylate (200 mg, 1 mmol) in DCM (20 mL) and the mixture was cooled to 0° C. N-Chlorosuccinimide (147 mg, 1.1 mmol) was then added and the reaction was stirred at 0° C. for 2 hr. A solution of N-Cyclopentyl-4-ethoxy-3-fluoroaniline (223 mg, 1 mmol) and Trichloroacetic acid (41 mg, 0.25 mmol) in DCM (5 mL) was added dropwise and the reaction was stirred for 2 hr at room temperature. The reaction was quenched by adding water and the mixture was extracted with DCM. Solvent was removed under vacuum and the residue was purified by silica gel chromatography (Hex:EA=4:1) to afford Methyl 6-cyano-2-(cyclopentyl(4-ethoxy-3-fluorophenyl)amino)-1H-indole-3-carboxylate (240 mg, 57% yield). $^1$H NMR (400 MHz, CDCl$_3$) δ ppm 8.17 (s, 1H), 8.13 (d, J=8.3 Hz, 1H), 7.49 (d, J=1.4 Hz, 1H), 7.46 (dd, J=8.3, 1.4 Hz, 1H), 6.93 (t, J=9.0 Hz, 1H), 6.81 (dd, J=12.7, 2.7 Hz, 1H), 6.73-6.70 (m, 1H), 4.65-4.56 (m, 1H), 4.11 (q, J=7.0 Hz, 2H), 3.85 (s, 3H), 2.11-1.94 (m, 2H), 1.73-1.60 (m, 4H), 1.61-1.49 (m, 2H), 1.46 (t, J=7.0 Hz, 3H).

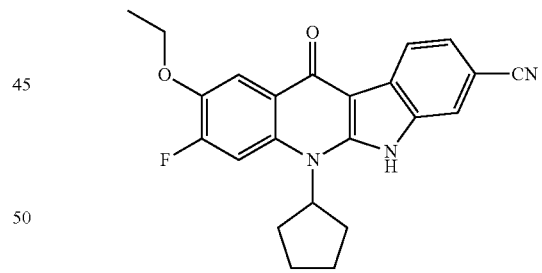

Step C: 5-Cyclopentyl-2-ethoxy-3-fluoro-11-oxo-6,11-dihydro-5H-indolo[2,3-b]quinoline-8-carbonitrile Methyl 6-cyano-2-(cyclopentyl(4-ethoxy-3-fluorophenyl)amino)-1H-indole-3-carboxylate (240 mg, 0.57 mmol) was dissolved in Diphenyl ether (10 mL) and the solution was refluxed for 1 hr. The mixture was cooled to RT. Hexane (20 mL) was added and the precipitate was collected by filtration. The precipitate was purified by silica gel chromatography (Hex:EA=2:1) to afford 5-Cyclopentyl-2-ethoxy-3-fluoro-11-oxo-6,11-dihydro-5H-indolo[2,3-b]quinoline-8-carbonitrile (170 mg, 77% yield). MS m/z=390 [M+H]. $^1$H NMR (400 MHz, DMSO-d$_6$) δ ppm 12.32 (s, 1H), 8.31

(d, J=8.1 Hz, 1H), 8.01 (d, J=9.8 Hz, 1H), 7.91 (d, J=1.4 Hz, 1H), 7.67-7.56 (m, 2H), 5.36-5.34 (m, 1H), 4.25 (q, J=6.9 Hz, 2H), 2.34-2.30 (m, 2H), 2.20-2.06 (m, 4H), 1.86-1.82 (m, 2H), 1.43 (t, J=6.9 Hz, 3H).

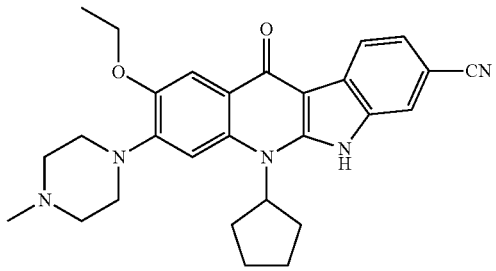 [SMILES: CCOc1cc2c(=O)c3c4ccc(C#N)cc4[nH]c3n(C3CCCC3)c2cc1N1CCN(C)CC1]

Step D: 5-Cyclopentyl-2-ethoxy-3-(4-methylpiperazin-1-yl)-11-oxo-6,11-dihydro-5H-indolo[2,3-b]quinoline-8-carbonitrile 1-Methylpiperazine (0.5 mL) and DIPEA (0.5 ml) were added to a solution of 5-Cyclopentyl-2-ethoxy-3-fluoro-11-oxo-6,11-dihydro-5H-indolo[2,3-b]quinoline-8-carbonitrile (170 mg, 0.44 mmol) in DMSO (2 ml) and the mixture was heated to 120 to 140° C. for 3 days. The reaction mixture was cooled to RT and purified by preparative HPLC to afford 5-Cyclopentyl-2-ethoxy-3-(4-methylpiperazin-1-yl)-11-oxo-6,11-dihydro-5H-indolo[2,3-b]quinoline-8-carbonitrile (45 mg, 22% yield). $^1$H NMR (300 MHz, CD$_3$OD) δ ppm 8.33 (d, J=8.0 Hz, 1H), 7.93 (s, 1H), 7.70 (s, 1H), 7.50 (d, J=8.0 Hz, 1H), 7.10 (s, 1H), 5.45-5.35 (m, 1H), 4.27 (q, J=6.8 Hz, 2H), 4.20-3.95 (m, 2H), 3.75-3.30 (m, 4H), 3.25-3.15 (m, 2H), 3.05 (s, 3H), 2.60-1.97 (m, 8H), 1.56 (t, J=6.8 Hz, 3H).

Example 27 (ALK-58)

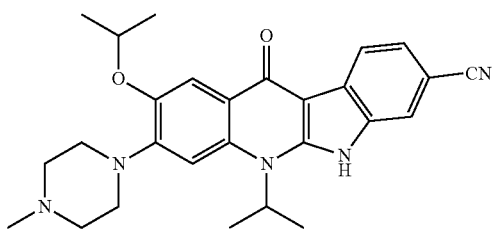 [SMILES: CC(C)Oc1cc2c(=O)c3c4ccc(C#N)cc4[nH]c3n(C(C)C)c2cc1N1CCN(C)CC1]

2-isopropoxy-5-isopropyl-3-(4-methylpiperazin-1-yl)-11-oxo-6,11-dihydro-5H-indolo[2,3-b]quinoline-8-carbonitrile

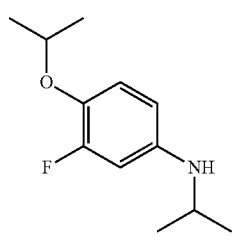

Step A: 3-Fluoro-4-isopropoxy-N-isopropylaniline

Acetone (11.6 g, 200 mmol), Acetic acid (1.8 g, 30 mmol), and Sodium triacetoxyborohydride (6.36 g, 30 mmol) were added to a solution of 3-Fluoro-4-isopropoxyaniline (3.38 g, 20 mmol) in DCM (120 mL) and the mixture was stirred at RT for 12 hr. Water was added to quench the reaction and the mixture was extracted with DCM. The solvent was removed under and the residue was purified by silica gel chromatography to afford 3-Fluoro-4-isopropoxy-N-isopropylaniline (3.1 g, 73% yield). $^1$H NMR (300 MHz, CDCl$_3$) δ ppm 6.83 (t, J=9.0 Hz, 1H), 6.50-6.33 (m, 2H), 4.28-4.26 (m, 1H), 3.52-3.50 (m, 1H), 3.27 (s, 1H), 1.30 (d, J=6.1 Hz, 6H), 1.19 (d, J=6.3 Hz, 6H).

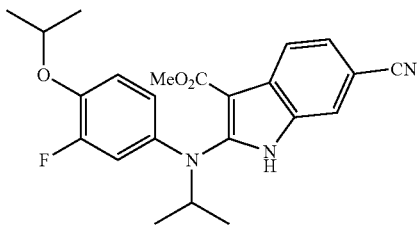 [SMILES: COC(=O)c1c(N(c2ccc(OC(C)C)c(F)c2)C(C)C)[nH]c2cc(C#N)ccc12]

Step B: Methyl 6-cyano-2-((3-fluoro-4-isopropoxyphenyl)(isopropyl)amino)-1H-indole-3-carboxylate DABCO (62 mg, 0.55 mmol) was added to a solution of Methyl 6-cyano-1H-indole-3-carboxylate (200 mg, 1 mmol) in DCM (20 mL) and the mixture was cooled to 0° C. N-Chlorosuccinimide (147 mg, 1.1 mmol) was then added and the reaction was stirred at 0° C. for 2 hr. A solution of 3-Fluoro-4-isopropoxy-N-isopropylaniline (211 mg, 1 mmol) and Trichloroacetic acid (41 mg, 0.25 mmol) in DCM (5 mL) was added dropwise and the reaction was stirred for 2 hr at room temperature. The reaction was quenched by adding water and the mixture was extracted with DCM. Solvent was removed under vacuum and the residue was purified by silica gel chromatography (Hex:EA=4:1) to afford Methyl 6-cyano-2-((3-fluoro-4-isopropoxyphenyl)(isopropyl)amino)-1H-indole-3-carboxylate (220 mg, 54% yield). $^1$H NMR (300 MHz, CDCl$_3$) δ ppm 8.05 (d, J=8.3 Hz, 1H), 7.85 (s, 1H), 7.45-7.33 (m, 1H), 6.99 (t, J=8.9 Hz, 1H), 6.91 (dd, J=12.1, 2.7 Hz, 1H), 6.82-6.80 (m, 1H), 4.81 (m, 1H), 4.54 (m, 1H), 3.86 (s, 3H), 1.39 (d, J=6.1 Hz, 6H), 1.31-1.21 (m, 6H).

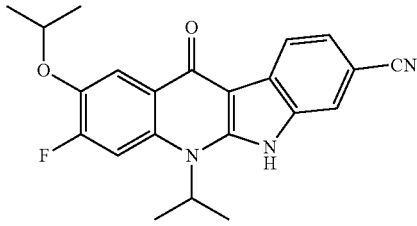 [SMILES: CC(C)Oc1cc2c(=O)c3c4ccc(C#N)cc4[nH]c3n(C(C)C)c2cc1F]

Step C: 3-Fluoro-2-isopropoxy-5-isopropyl-11-oxo-6,11-dihydro-5H-indolo[2,3-b]quinoline-8-carbonitrile Methyl 6-cyano-2-((3-fluoro-4-isopropoxyphenyl)(isopropyl)amino)-1H-indole-3-carboxylate (220 mg, 0.54 mmol) was dissolved in Diphenyl ether (10 mL) and the solution was refluxed for 1 hr. The mixture was cooled to RT. Hexane (20 mL) was added and the precipitate was collected by filtration. The precipitate was purified by silica gel chromatography (Hex:EA=2:1) to afford 3-Fluoro-2-isopropoxy-5-isopropyl-11-oxo-6,11-dihydro-5H-indolo[2,3-b]quinoline-8-carbonitrile (130 mg, 70% yield). MS m/z=378 [M+H].

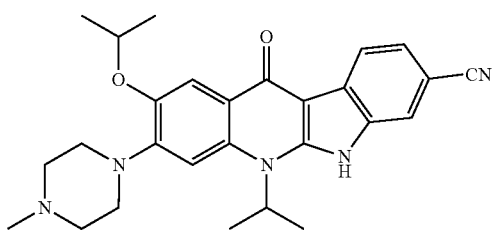 [SMILES: CC(C)Oc1cc2c(=O)c3c4ccc(C#N)cc4[nH]c3n(C(C)C)c2cc1N1CCN(C)CC1]

Step D: 2-isoPropoxy-5-isopropyl-3-(4-methylpiperazin-1-yl)-11-oxo-6,11-dihydro-5H-indolo[2,3-b]quinoline-8-carbonitrile 1-Methylpiperazine (0.5 mL) and DIPEA (0.5 ml) were added to a solution of 3-Fluoro-2-isopropoxy-5-isopropyl-11-oxo-6,11-dihydro-5H-indolo[2,3-b]quinoline-8-carbonitrile (130 mg, 0.34 mmol) in DMSO (2 ml) and the mixture was heated to 120 to 140° C. for 3 days. The reaction mixture was cooled to RT and purified by Preparative HPLC to afford 2-isoPropoxy-5-isopropyl-3-(4-methylpiperazin-1-yl)-11-oxo-6,11-dihydro-5H-indolo[2,3-b]quinoline-8-carbonitrile (35 mg, 22% yield). $^1$H NMR (300 MHz, CD$_3$OD) δ ppm 8.43 (d, J=8.6 Hz, 1H), 8.01 (s, 1H), 7.84 (s, 1H), 7.59 (d, J=8.6 Hz, 1H), 7.36 (s, 1H), 5.42-5.35 (m, 1H), 4.90-4.80 (m, 1H), 4.02-3.95 (m, 2H), 3.70-3.63 (m, 2H), 3.50-3.10 (m, 4H), 3.05 (s, 3H), 1.88 (d, J=7.1 Hz, 6H), 1.47 (d, J=6.0 Hz, 6H).

Example 28 (ALK-59)

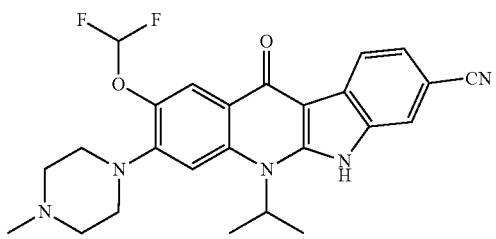 [SMILES: CC(C)n1c2cc(N3CCN(C)CC3)c(OC(F)F)cc2c(=O)c2c3ccc(C#N)cc3[nH]c21]

2-(Difluoromethoxy)-5-isopropyl-3-(4-methylpiperazin-1-yl)-11-oxo-6,11-dihydro-5H-indolo[2,3-b]quinoline-8-carbonitrile The title compound was prepared from 4-(Difluoromethoxy)-3-fluoroaniline using a method similar to that used in the preparation of 2-isoPropoxy-5-isopropyl-3-(4-methylpiperazin-1-yl)-11-oxo-6,11-dihydro-5H-indolo[2,3-b]quinoline-8-carbonitrile. $^1$H NMR (300 MHz, CD$_3$OD) δ ppm 8.35 (d, J=8.1 Hz, 1H), 8.20 (s, 1H), 7.79 (d, J=1.4 Hz, 1H), 7.54 (dd, J=8.1, 1.4 Hz, 1H), 7.44 (s, 1H), 6.93 (t, J=73.9 Hz, 1H), 5.51-5.24 (m, 1H), 3.98-3.90 (m, 2H), 3.72-3.62 (m, 2H), 3.50-3.35 (m, 4H), 3.04 (s, 3H), 1.87 (d, J=7.0 Hz, 6H).

Example 29 (ALK-60)

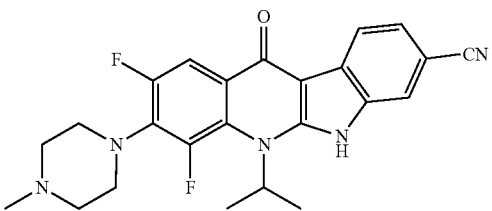 [SMILES: CC(C)n1c2[nH]c3cc(C#N)ccc3c2c(=O)c2cc(F)c(N3CCN(C)CC3)c(F)c21]

2,4-Difluoro-5-isopropyl-3-(4-methylpiperazin-1-yl)-11-oxo-6,11-dihydro-5H-indolo[2,3-b]quinoline-8-carbonitrile

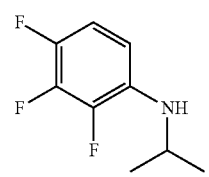

Step A: 2,3,4-Trifluoro-N-isopropylaniline

Acetone (11.6 g, 200 mmol), Acetic acid (1.8 g, 30 mmol), and Sodium triacetoxyborohydride (6.36 g, 30 mmol) were added to a solution of 2,3,4-Trifluoroaniline (2.94 g, 20 mmol) in DCM (120 mL) and the mixture was stirred at RT for 12 hr. Water was added to quench the reaction and the mixture was extracted with DCM. The solvent was removed under and the residue was purified by silica gel chromatography to afford 2,3,4-Trifluoro-N-isopropylaniline (3.1 g, 82% yield). $^1$H NMR (400 MHz, CDCl$_3$) δ ppm 6.88-6.77 (m, 1H), 6.40-6.34 (m, 1H), 3.65-3.57 (m, 2H), 1.25 (d, J=6.0 Hz, 6H).

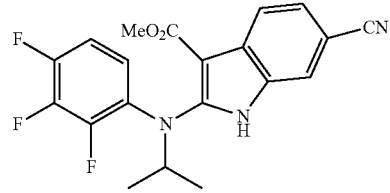 [SMILES: COC(=O)c1c(N(c2ccc(F)c(F)c2F)C(C)C)[nH]c2cc(C#N)ccc12]

Step B: Methyl 6-cyano-2-(isopropyl(2,3,4-trifluorophenyl)amino)-1H-indole-3-carboxylate DABCO (62 mg, 0.55 mmol) was added to a solution of Methyl 6-cyano-1H-indole-3-carboxylate (200 mg, 1 mmol) in DCM (20 mL) and the mixture was cooled to 0° C. N-Chlorosuccinimide (147 mg, 1.1 mmol) was then added and the reaction was stirred at 0° C. for 2 hr. A solution of 2,3,4-Trifluoro-N-isopropylaniline (189 mg, 1 mmol) and Trichloroacetic acid (41 mg, 0.25 mmol) in DCM (5 mL)

was added dropwise and the reaction was stirred for 2 hr at room temperature. The reaction was quenched by adding water and the mixture was extracted with DCM. Solvent was removed under vacuum and the residue was purified by silica gel chromatography (Hex:EA=4:1) to afford Methyl 6-cyano-2-(isopropyl(2,3,4-trifluorophenyl)amino)-1H-indole-3-carboxylate (210 mg, 54% yield). $^1$H NMR (400 MHz, CDCl$_3$) δ ppm 8.36 (s, 1H), 8.07 (d, J=8.3 Hz, 1H), 7.53 (d, J=1.4 Hz, 1H), 7.44 (dd, J=8.3, 1.4 Hz, 1H), 7.15-7.10 (m, 1H), 7.05-7.00 (m, 1H), 4.65-4.60 (m, 1H), 3.82 (s, 3H), 1.33 (dd, J=6.5, 0.9 Hz, 6H).

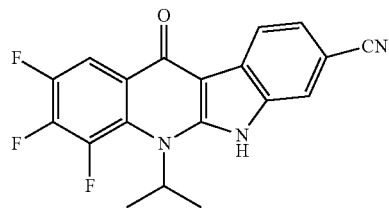 [SMILES: CC(C)n1c2[nH]c3cc(C#N)ccc3c2c(=O)c2cc(F)c(F)c(F)c21]

Step C: 2,3,4-Trifluoro-5-isopropyl-11-oxo-6,11-dihydro-5H-indolo[2,3-b]quinoline-8-carbonitrile Methyl 6-cyano-2-(isopropyl(2,3,4-trifluorophenyl) amino)-1H-indole-3-carboxylate (210 mg, 0.54 mmol) was dissolved in Diphenyl ether (10 mL) and the solution was refluxed for 1 hr. The mixture was cooled to RT. Hexane (20 mL) was added and the precipitate was collected by filtration. The precipitate was purified by silica gel chromatography (Hex:EA=2:1) to afford 2,3,4-Trifluoro-5-isopropyl-11-oxo-6,11-dihydro-5H-indolo[2,3-b]quinoline-8-carbonitrile (100 mg, 52% yield). MS m/z=356 [M+H].

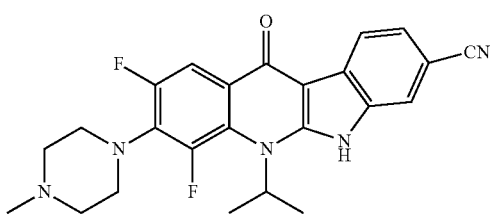 [SMILES: CC(C)n1c2[nH]c3cc(C#N)ccc3c2c(=O)c2cc(F)c(N3CCN(C)CC3)c(F)c21]

Step D: 2,4-Difluoro-5-isopropyl-3-(4-methylpiperazin-1-yl)-11-oxo-6,11-dihydro-5H-indolo[2,3-b] quinoline-8-carbonitrile 1-Methylpiperazine (0.5 mL) and DIPEA (0.5 ml) were added to a solution of 2,3,4-Trifluoro-5-isopropyl-11-oxo-6,11-dihydro-5H-indolo[2,3-b]quinoline-8-carbonitrile (100 mg, 0.28 mmol) in DMSO (2 ml) and the mixture was heated to 120 to 140° C. for 3 days. The reaction was cooled to RT and purified by Preparative HPLC to afford 2,4-Difluoro-5-isopropyl-3-(4-methylpiperazin-1-yl)-11-oxo-6,11-dihydro-5H-indolo[2,3-b]quinoline-8-carbonitrile (25 mg, 20% yield). MS m/z=436 [M+H].

Example 30 (ALK-62)

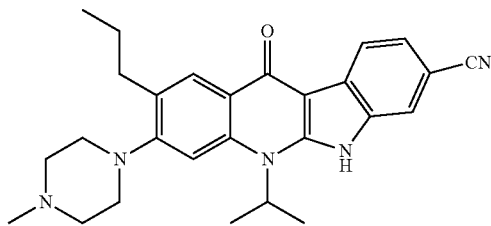 [SMILES: CCCc1cc2c(=O)c3c4ccc(C#N)cc4[nH]c3n(C(C)C)c2cc1N1CCN(C)CC1]

5-isoPropyl-3-(4-methylpiperazin-1-yl)-11-oxo-2-propyl-6,11-dihydro-5H-indolo[2,3-b]quinoline-8-carbonitrile A mixture of 2-Bromo-5-isopropyl-3-(4-methylpiperazin-1-yl)-11-oxo-6,11-dihydro-5H-indolo[2,3-b]quinoline-8-carbonitrile (30 mg, 0.061 mmol), Na$_2$CO$_3$ (25 mg, 0.183 mmol), Pd(PPh$_3$)$_2$Cl$_2$ (4.3 mg, 0.0061 mmol), and 4,4,5,5-tetramethyl-2-(prop-1-en-1-yl)-1,3,2-dioxaborolane (16 mg, 0.091 mmol) in DME/H$_2$O (4.8 ml, V/V=5/1) was stirred under nitrogen at 80° C. overnight. After the reaction was complete as indicated by LC-MS, the mixture was purified by preparative HPLC to afford 5-isoPropyl-3-(4-methylpiperazin-1-yl)-11-oxo-2-(prop-1-en-1-yl)-6,11-dihydro-5H-indolo[2,3-b]quinoline-8-carbonitrile. 5-isoPropyl-3-(4-methylpiperazin-1-yl)-11-oxo-2-(prop-1-en-1-yl)-6,11-dihydro-5H-indolo[2,3-b]quinoline-8-carbonitrile was dissolved in THF (5 ml). Pd/C (10%, 20 mg) was added to the THF solution. The mixture underwent hydrogenation at room temperature overnight until LC-MS indicated that the reaction was complete. The filtrate after filtration was concentrated and the residue was purified by preparative HPLC to afford 5-isoPropyl-3-(4-methylpiperazin-1-yl)-11-oxo-2-propyl-6,11-dihydro-5H-indolo[2,3-b]quinoline-8-carbonitrile (8 mg, 29% yield for two steps). $^1$H NMR (300 MHz, CD$_3$OD) δ ppm 8.37 (s, 1H), 8.32 (d, J=8.1 Hz, 1H), 7.74 (d, J=1.3 Hz, 1H), 7.56-7.39 (m, 2H), 5.39-5.32 (m, 1H), 3.71-3.68 (m, 2H), 3.55-3.37 (m, 4H), 3.29-3.22 (m, 2H), 3.05 (s, 3H), 2.90-2.70 (m, 2H), 1.87 (d, J=7.1 Hz, 6H), 1.85-1.73 (m, 2H), 1.04 (t, J=7.3 Hz, 3H).

Example 31 (ALK-63)

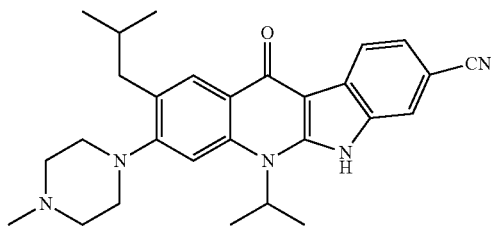 [SMILES: CC(C)Cc1cc2c(=O)c3c4ccc(C#N)cc4[nH]c3n(C(C)C)c2cc1N1CCN(C)CC1]

2-isoButyl-5-isopropyl-3-(4-methylpiperazin-1-yl)-11-oxo-6,11-dihydro-5H-indolo[2,3-b]quinoline-8-carbonitrile A mixture of 2-Bromo-5-isopropyl-3-(4-methylpiperazin-1-yl)-11-oxo-6,11-dihydro-5H-indolo[2,3-b]quinoline-8- carbonitrile (30 mg, 0.061 mmol), Na$_2$CO$_3$ (25 mg, 0.183 mmol), Pd(PPh$_3$)$_2$Cl$_2$ (4.3 mg, 0.0061 mmol), and 4,4,5,5-Tetramethyl-2-(2-methylprop-1-en-1-yl)-1,3,2-dioxaborolane (16 mg, 0.091 mmol) in DME/H$_2$O (4.8 ml, V/V=5/1) was stirred under nitrogen at 80° C. overnight. After the reaction was complete as indicated by LC-MS, the mixture was purified by preparative HPLC to afford 5-isoPropyl-3-(4-methylpiperazin-1-yl)-2-(2-methylprop-1-en-1-yl)-11-oxo-6,11-dihydro-5H-indolo[2,3-b]quinoline-8-carbonitrile. 5-isoPropyl-3-(4-methylpiperazin-1-yl)-2-(2-methylprop-1-en-1-yl)-11-oxo-6,11-dihydro-5H-indolo[2,3-b]quinoline-8-carbonitrile was dissolved in THF (5 ml). Pd/C (10%, 20 mg) was added to the THF solution. The mixture underwent hydrogenation at room temperature overnight until LC-MS indicated that the reaction was complete. The filtrate after filtration was concentrated and the resulting residue was purified by preparative HPLC to afford 5-isoPropyl-3-(4-methylpiperazin-1-yl)-11-oxo-2-propyl-6,11-dihydro-5H-indolo[2,3-b]quinoline-8-carbonitrile (10 mg, 35% yield for two steps). $^1$H NMR (300 MHz, CD$_3$OD) δ ppm 8.45 (s, 1H), 8.22 (d, J=8.0 Hz, 1H), 7.62 (s, 1H), 7.39 (s, 1H), 7.18 (d, J=8.0 Hz, 1H), 5.50-5.40 (m, 1H), 3.70-3.60 (m, 2H), 3.55-3.30 (m, 6H), 2.75 (d, J=7.1 Hz, 2H), 2.53 (s, 3H), 2.25-2.15 (m, 1H), 1.90 (d, J=7.1 Hz, 6H), 0.99 (d, J=6.6 Hz, 6H).

Example 32 (ALK-64)

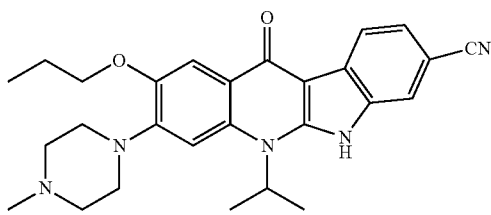 [SMILES: CCCOc1cc2c(=O)c3c4ccc(C#N)cc4[nH]c3n(C(C)C)c2cc1N1CCN(C)CC1]

5-isoPropyl-3-(4-methylpiperazin-1-yl)-11-oxo-2-propoxy-6,11-dihydro-5H-indolo[2,3-b]quinoline-8-carbonitrile

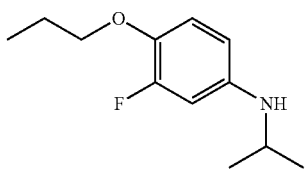

Step A: 3-Fluoro-N-isopropyl-4-propoxyaniline

Acetone (11.6 g, 200 mmol), Acetic acid (1.8 g, 30 mmol), and Sodium triacetoxyborohydride (6.36 g, 30 mmol) were added to a solution of 3-Fluoro-4-propoxyaniline (3.38 g, 20 mmol) in DCM (120 mL) and the mixture was stirred at RT for 12 hr. Water was added to quench the reaction and the mixture was extracted with DCM. The solvent was removed under and the residue was purified by silica gel chromatography to afford 3-Fluoro-N-isopropyl-4-propoxyaniline (3.2 g, 76% yield). MS m/z=212 [M+H].

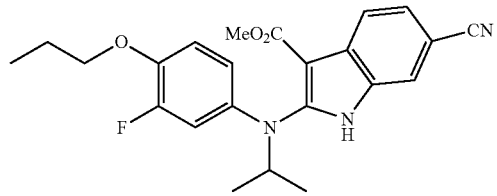 [SMILES: CCCOc1ccc(N(c2[nH]c3cc(C#N)ccc3c2C(=O)OC)C(C)C)cc1F]

Step B: Methyl 6-cyano-2-((3-fluoro-4-propoxyphenyl)(isopropyl)amino)-1H-indole-3-carboxylate DABCO (62 mg, 0.55 mmol) was added to a solution of Methyl 6-cyano-1H-indole-3-carboxylate (200 mg, 1 mmol) in DCM (20 mL) and the mixture was cooled to 0° C. N-Chlorosuccinimide (147 mg, 1.1 mmol) was then added and the reaction was stirred at 0° C. for 2 hr. A solution of 3-Fluoro-N-isopropyl-4-propoxyaniline (211 mg, 1 mmol) and Trichloroacetic acid (41 mg, 0.25 mmol) in DCM (5 mL) was added dropwise and the reaction was stirred for 2 hr at room temperature. The reaction was quenched by adding water and the mixture was extracted with DCM. Solvent was removed under vacuum and the residue was purified by silica gel chromatography (Hex:EA=4:1) to afford Methyl 6-cyano-2-((3-fluoro-4-propoxyphenyl)(isopropyl)amino)-1H-indole-3-carboxylate (235 mg, 57% yield). $^1$H NMR (400 MHz, CDCl$_3$) δ ppm 8.05 (d, J=8.3 Hz, 1H), 7.95 (s, 1H), 7.41 (dd, J=8.3, 1.4 Hz, 1H), 7.37 (d, J=1.4 Hz, 1H), 7.01 (t, J=8.9 Hz, 1H), 6.97 (dd, J=12.0, 2.6 Hz, 1H), 6.90-6.85 (m, 1H), 4.91-4.82 (m, 1H), 4.03 (t, J=6.6 Hz, 2H), 3.89 (s, 3H), 1.90-1.88 (m, 2H), 1.26 (d, J=6.6 Hz, 6H), 1.09 (t, J=7.4 Hz, 3H).

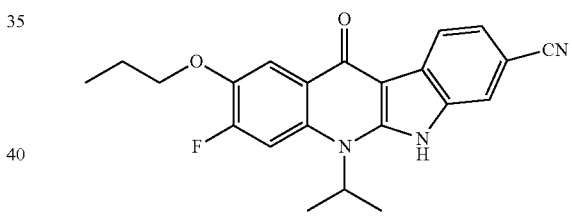

Step C: 3-Fluoro-5-isopropyl-11-oxo-2-propoxy-6,11-dihydro-5H-indolo[2,3-b]quinoline-8-carbonitrile Methyl 6-cyano-2-((3-fluoro-4-propoxyphenyl)(isopropyl)amino)-1H-indole-3-carboxylate (235 mg, 0.57 mmol) was dissolved in Diphenyl ether (10 mL) and the solution was refluxed for 1 hr. The mixture was cooled to RT. Hexane (20 mL) was added and the precipitate was collected by filtration. The precipitate was purified by silica gel chromatography (Hex:EA=2:1) to afford 3-Fluoro-5-isopropyl-11-oxo-2-propoxy-6,11-dihydro-5H-indolo[2,3-b]quinoline-8-carbonitrile (130 mg, 60% yield). MS m/z=378 [M+H].

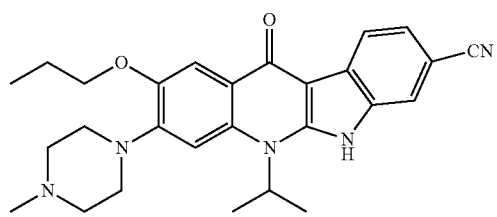 [SMILES: CCCOc1cc2c(=O)c3c4ccc(C#N)cc4[nH]c3n(C(C)C)c2cc1N1CCN(C)CC1]

Step D: 5-isoPropyl-3-(4-methylpiperazin-1-yl)-11-oxo-2-propoxy-6,11-dihydro-5H-indolo[2,3-b]quinoline-8-carbonitrile 1-Methylpiperazine (0.5 mL) and DIPEA (0.5 ml) were added to a solution of 3-Fluoro-5-isopropyl-11-oxo-2-propoxy-6,11-dihydro-5H-indolo[2,3-b]quinoline-8-carbonitrile (130 mg, 0.34 mmol) in DMSO (2 ml) and the mixture was heated to 120 to 140° C. for 3 days. The reaction mixture was cooled to RT and purified by Preparative HPLC to afford 5-isoPropyl-3-(4-methylpiperazin-1-yl)-11-oxo-2-propoxy-6,11-dihydro-5H-indolo[2,3-b]quinoline-8-carbonitrile (28 mg, 18% yield). $^1$H NMR (300 MHz, CD$_3$OD) δ ppm 8.37 (d, J=8.1 Hz, 1H), 7.93 (s, 1H), 7.78 (s, 1H), 7.54 (d, J=8.1 Hz, 1H), 7.33 (s, 1H), 5.46-5.25 (m, 1H), 4.18 (t, J=6.4 Hz, 2H), 4.10-3.97 (m, 2H), 3.75-3.65 (m, 2H), 3.50-3.20 (m, 4H), 3.06 (s, 3H), 2.03-1.94 (m, 2H), 1.88 (d, J=7.1 Hz, 6H), 1.17 (t, J=7.4 Hz, 3H).

Example 33 (ALK-66)

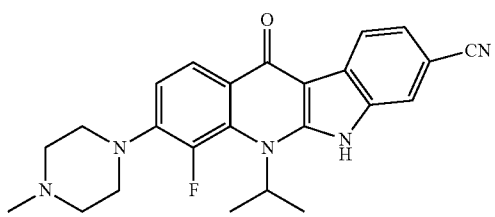 [SMILES: CC(C)n1c2[nH]c3cc(C#N)ccc3c2c(=O)c2ccc(N3CCN(C)CC3)c(F)c21]

4-Fluoro-5-isopropyl-3-(4-methylpiperazin-1-yl)-11-oxo-6,11-dihydro-5H-indolo[2,3-b]quinoline-8-carbonitrile

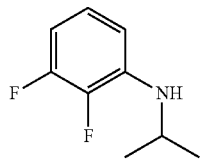

Step A: 2,3-Difluoro-N-isopropylaniline

Acetone (11.6 g, 200 mmol), Acetic acid (1.8 g, 30 mmol), and Sodium triacetoxyborohydride (6.36 g, 30 mmol) were added to a solution of 2,3-Difluoroaniline (2.58 g, 20 mmol) in DCM (120 mL) and the mixture was stirred at RT for 12 hr. Water was added to quench the reaction and the mixture was extracted with DCM. The solvent was removed under and the residue was purified by silica gel chromatography to afford 2,3-Difluoro-N-isopropylaniline (3.0 g, 88% yield). $^1$H NMR (400 MHz, CDCl$_3$) δ ppm 6.91-6.89 (m, 1H), 6.51-6.39 (m, 2H), 3.79 (br s, 1H), 3.70-3.68 (m, 1H), 1.26 (d, J=6.2 Hz, 6H).

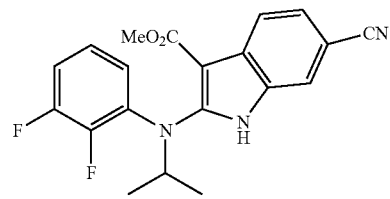 [SMILES: COC(=O)c1c(N(c2cccc(F)c2F)C(C)C)[nH]c2cc(C#N)ccc12]

Step B: Methyl 6-cyano-2-((2,3-difluorophenyl)(isopropyl)amino)-1H-indole-3-carboxylate DABCO (62 mg, 0.55 mmol) was added to a solution of Methyl 6-cyano-1H-indole-3-carboxylate (200 mg, 1 mmol) in DCM (20 mL) and the mixture was cooled to 0° C. N-Chlorosuccinimide (147 mg, 1.1 mmol) was then added and the reaction was stirred at 0° C. for 2 hr. A solution of 2,3-Difluoro-N-isopropylaniline (171 mg, 1 mmol) and Trichloroacetic acid (41 mg, 0.25 mmol) in DCM (5 mL) was added dropwise and the reaction was stirred for 2 hr at room temperature. The reaction was quenched by adding water and the mixture was extracted with DCM. Solvent was removed under vacuum and the residue was purified by silica gel chromatography (Hex:EA=4:1) to afford Methyl 6-cyano-2-((2,3-difluorophenyl)(isopropyl)amino)-1H-indole-3-carboxylate (200 mg, 54% yield). $^1$H NMR (400 MHz, CDCl$_3$) δ ppm 8.18 (s, 1H), 8.09 (d, J=8.4 Hz, 1H), 7.51 (d, J=1.4 Hz, 1H), 7.45 (dd, J=8.4, 1.4 Hz, 1H), 7.17-7.07 (m, 3H), 4.77-4.61 (m, 1H), 3.82 (s, 3H), 1.34 (d, J=6.6 Hz, 6H).

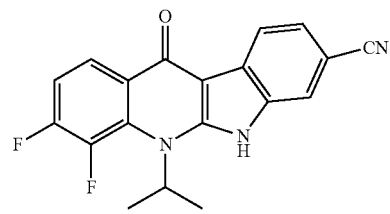 [SMILES: CC(C)n1c2[nH]c3cc(C#N)ccc3c2c(=O)c2ccc(F)c(F)c21]

Step C: 3,4-Difluoro-5-isopropyl-11-oxo-6,11-dihydro-5H-indolo[2,3-b]quinoline-8-carbonitrile Methyl 6-cyano-2-((2,3-difluorophenyl)(isopropyl)amino)-1H-indole-3-carboxylate (200 mg, 0.54 mmol) was dissolved in Diphenyl ether (10 mL) and the solution was refluxed for 1 hr. The mixture was cooled to RT. Hexane (20 mL) was added and the precipitate was collected by filtration. The precipitate was purified by silica gel chromatography (Hex:EA=2:1) to afford 3,4-Difluoro-5-isopropyl-11-oxo-6,11-dihydro-5H-indolo[2,3-b]quinoline-8-carbonitrile (112 mg, 61% yield). MS m/z=338 [M+H].

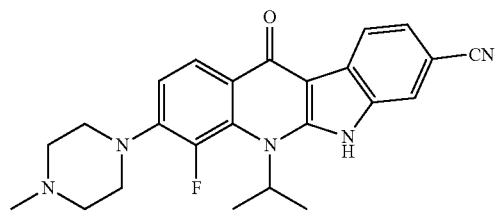 [SMILES: CC(C)n1c2[nH]c3cc(C#N)ccc3c2c(=O)c2ccc(N3CCN(C)CC3)c(F)c21]

Step D: 4-Fluoro-5-isopropyl-3-(4-methylpiperazin-1-yl)-11-oxo-6,11-dihydro-5H-indolo[2,3-b]quinoline-8-carbonitrile 1-Methylpiperazine (0.5 mL) and DIPEA (0.5 ml) were added to a solution of 3,4-Difluoro-5-isopropyl-11-oxo-6,11-dihydro-5H-indolo[2,3-b]quinoline-8-carbonitrile (112 mg, 0.33 mmol) in DMSO (2 ml) and the mixture was heated to 120 to 140° C. for 3 days. The reaction mixture was cooled to RT and purified by preparative HPLC to afford 4-Fluoro-5-isopropyl-3-(4-methylpiperazin-1-yl)-11-oxo-6,11-dihydro-5H-indolo[2,3-b]quinoline-8-carbonitrile (22 mg, 16% yield). MS m/z=418 [M+H].

Example 34 (ALK-67)

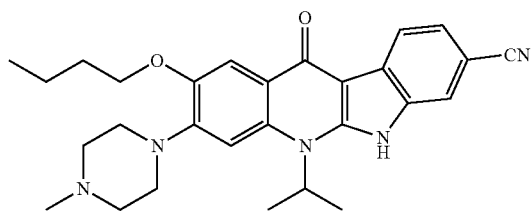 [SMILES: CCCCOc1cc2c(=O)c3c4ccc(C#N)cc4[nH]c3n(C(C)C)c2cc1N1CCN(C)CC1]

2-Butoxy-5-isopropyl-3-(4-methylpiperazin-1-yl)-11-oxo-6,11-dihydro-5H-indolo[2,3-b]quinoline-8-carbonitrile

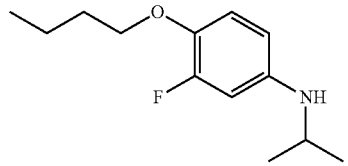 [SMILES: CCCCOc1ccc(NC(C)C)cc1F]

Step A: 4-Butoxy-3-fluoro-N-isopropylaniline

Acetone (11.6 g, 200 mmol), Acetic acid (1.8 g, 30 mmol), and Sodium triacetoxyborohydride (6.36 g, 30 mmol) were added to a solution of 4-Butoxy-3-fluoroaniline (3.66 g, 20 mmol) in DCM (120 mL) and the mixture was stirred at RT for 12 hr. Water was added to quench the reaction and the mixture was extracted with DCM. The solvent was removed under and the residue was purified by silica gel chromatography to afford 4-Butoxy-3-fluoro-N-isopropylaniline (3.2 g, 71% yield). $^1$H NMR (400 MHz, CDCl$_3$) δ ppm 6.84 (t, J=9.1 Hz, 1H), 6.39 (dd, J=13.5, 2.8 Hz, 1H), 6.30-6.25 (m, 1H), 3.96 (t, J=6.6 Hz, 2H), 3.56-3.49 (m, 1H), 3.27 (br s, 1H), 1.79-1.72 (m, 2H), 1.55-1.43 (m, 2H), 1.22 (d, J=6.2 Hz, 6H), 0.98 (t, J=7.4 Hz, 3H).

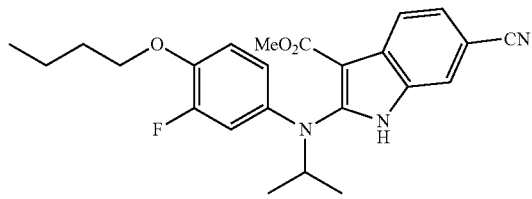 [SMILES: CCCCOc1ccc(N(c2[nH]c3cc(C#N)ccc3c2C(=O)OC)C(C)C)cc1F]

Step B: Methyl 2-((4-butoxy-3-fluorophenyl)(isopropyl)amino)-6-cyano-1H-indole-3-carboxylate DABCO (62 mg, 0.55 mmol) was added to a solution of Methyl 6-cyano-1H-indole-3-carboxylate (200 mg, 1 mmol) in DCM (20 mL) and the mixture was cooled to 0° C. N-Chlorosuccinimide (147 mg, 1.1 mmol) was then added and the reaction was stirred at 0° C. for 2 hr. A solution of 4-Butoxy-3-fluoro-N-isopropylaniline (225 mg, 1 mmol) and Trichloroacetic acid (41 mg, 0.25 mmol) in DCM (5 mL) was added dropwise and the reaction was stirred for 2 hr at room temperature. The reaction was quenched by adding water and the mixture was extracted with DCM. Solvent was removed under vacuum and the residue was purified by silica gel chromatography (Hex:EA=4:1) to afford Methyl 2-((4-butoxy-3-fluorophenyl)(isopropyl)amino)-6-cyano-1H-indole-3-carboxylate (245 mg, 58% yield). $^1$H NMR (400 MHz, CDCl$_3$) δ ppm 8.05 (d, J=8.3 Hz, 1H), 7.86 (s, 1H), 7.41 (dd, J=8.3, 1.4 Hz, 1H), 7.37 (d, J=1.4 Hz, 1H), 7.01 (t, J=8.9 Hz, 1H), 6.97 (dd, J=12.1, 2.6 Hz, 1H), 6.91-6.88 (m, 1H), 4.91-4.83 (m, 1H), 4.08 (t, J=6.5 Hz, 2H), 3.90 (s, 3H), 1.87-1.83 (m, 2H), 1.58-1.48 (m, 2H), 1.27 (d, J=6.7 Hz, 6H), 1.02 (t, J=7.4 Hz, 3H).

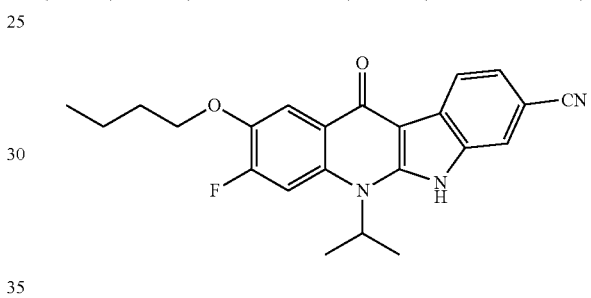

Step C: 2-Butoxy-3-fluoro-5-isopropyl-11-oxo-6,11-dihydro-5H-indolo[2,3-b]quinoline-8-carbonitrile Methyl 2-((4-butoxy-3-fluorophenyl)(isopropyl)amino)-6-cyano-1H-indole-3-carboxylate (245 mg, 0.58 mmol) was dissolved in Diphenyl ether (10 mL) and the solution was refluxed for 1 hr. The mixture was cooled to RT. Hexane (20 mL) was added and the precipitate was collected by filtration. The precipitate was purified by silica gel chromatography (Hex:EA=2:1) to afford 2-Butoxy-3-fluoro-5-isopropyl-11-oxo-6,11-dihydro-5H-indolo[2,3-b]quinoline-8-carbonitrile (165 mg, 73% yield). MS m/z=392 [M+H].

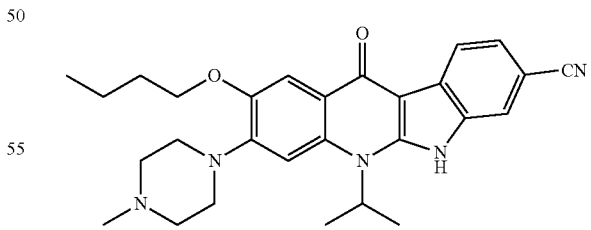

Step D: 2-Butoxy-5-isopropyl-3-(4-methylpiperazin-1-yl)-11-oxo-6,11-dihydro-5H-indolo[2,3-b]quinoline-8-carbonitrile 1-Methylpiperazine (0.5 mL) and DIPEA (0.5 ml) were added to a solution of 2-Butoxy-3-fluoro-5-isopropyl-11-oxo-6,11-dihydro-5H-indolo[2,3-b]quinoline-8-carbonitrile (165 mg, 0.42 mmol) in DMSO (2 ml) and the mixture was heated to 120 to 140° C. for 3 days. The reaction mixture was cooled to RT and purified by preparative HPLC to afford 2-Butoxy-5-isopropyl-3-(4-methylpiperazin-1-yl)-11-oxo-6,11-dihydro-5H-indolo[2,3-b]quinoline-8-carbonitrile (36 mg, 18% yield). $^1$H NMR (300 MHz, CD$_3$OD) δ ppm 8.39 (d, J=8.1 Hz, 1H), 7.95 (s, 1H), 7.79 (d, J=1.4 Hz, 1H), 7.55 (dd, J=8.1, 1.4 Hz, 1H), 7.32 (s, 1H), 5.40-5.32 (m, 1H), 4.21 (t, J=6.4 Hz, 2H), 3.99-3.95 (m, 2H), 3.71-3.69 (m, 2H), 3.43-3.40 (m, 2H), 3.28-3.12 (m, 2H), 3.04 (s, 3H), 1.96-1.89 (m, 2H), 1.87 (d, J=7.1 Hz, 6H), 1.68-1.54 (m, 2H), 1.06 (t, J=7.4 Hz, 3H).

Example 35 (ALK-68)

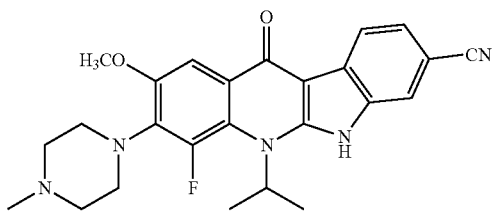

4-Fluoro-5-isopropyl-2-methoxy-3-(4-methylpiperazin-1-yl)-11-oxo-6,11-dihydro-5H-indolo[2,3-b]quinoline-8-carbonitrile

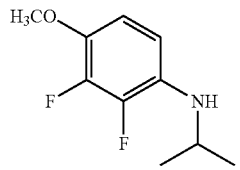

Step A: 2,3-Difluoro-N-isopropyl-4-methoxyaniline

Acetone (11.6 g, 200 mmol), Acetic acid (1.8 g, 30 mmol), and Sodium triacetoxyborohydride (6.36 g, 30 mmol) were added to a solution of 2,3-Difluoro-4-methoxyaniline (3.18 g, 20 mmol) in DCM (120 mL) and the mixture was stirred at RT for 12 hr. Water was added to quench the reaction and the mixture was extracted with DCM. The solvent was removed under and the residue was purified by silica gel chromatography to afford 2,3-Difluoro-N-isopropyl-4-methoxyaniline. (2.8 g, 70% yield). $^1$H NMR (400 MHz, CDCl$_3$) δ ppm 6.65 (td, J=8.7, 2.3 Hz, 1H), 6.39 (td, J=8.7, 2.3 Hz, 1H), 3.85 (s, 3H), 3.58-3.56 (m, 1H), 3.46 (s, 1H), 1.24 (d, J=6.2 Hz, 6H).

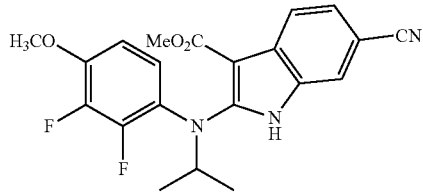 [SMILES: COC(=O)c1c(N(c2ccc(OC)c(F)c2F)C(C)C)[nH]c2cc(C#N)ccc12]

Step B: Methyl 6-cyano-2-((2,3-difluoro-4-methoxyphenyl)(isopropyl)amino)-1H-indole-3-carboxylate DABCO (62 mg, 0.55 mmol) was added to a solution of Methyl 6-cyano-1H-indole-3-carboxylate (200 mg, 1 mmol) in DCM (20 mL) and the mixture was cooled to 0° C. N-Chlorosuccinimide (147 mg, 1.1 mmol) was then added and the reaction was stirred at 0° C. for 2 hr. A solution of 2,3-Difluoro-N-isopropyl-4-methoxyaniline (201 mg, 1 mmol) and Trichloroacetic acid (41 mg, 0.25 mmol) in DCM (5 mL) was added dropwise and the reaction was stirred for 2 hr at room temperature. The reaction was quenched by adding water and the mixture was extracted with DCM. Solvent was removed under vacuum and the residue was purified by silica gel chromatography (Hex:EA=4:1) to afford Methyl 6-cyano-2-((2,3-difluoro-4-methoxyphenyl)(isopropyl)amino)-1H-indole-3-carboxylate (225 mg, 56% yield). $^1$H NMR (400 MHz, CDCl$_3$) δ ppm 8.25 (s, 1H), 8.02 (d, J=8.0 Hz, 1H), 7.45-7.36 (m, 2H), 7.13-7.06 (m, 1H), 6.846.80 (m, 1H), 4.85-4.79 (m, 1H), 3.95 (s, 3H), 3.85 (s, 3H), 1.27 (dd, J=6.5, 1.1 Hz, 6H).

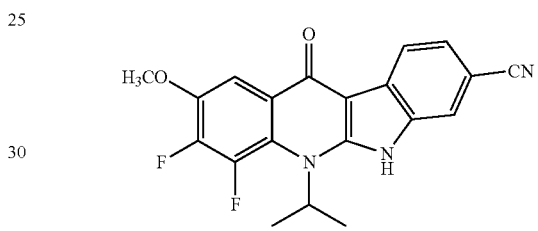

Step C: 3,4-Difluoro-5-isopropyl-2-methoxy-11-oxo-6,11-dihydro-5H-indolo[2,3-b]quinoline-8-carbonitrile Methyl 6-cyano-2-((2,3-difluoro-4-methoxyphenyl)(isopropyl)amino)-1H-indole-3-carboxylate (225 mg, 0.56 mmol) was dissolved in Diphenyl ether (10 mL) and the solution was refluxed for 1 hr. The mixture was cooled to RT. Hexane (20 mL) was added and the precipitate was collected by filtration. The precipitate was purified by silica gel chromatography (Hex:EA=2:1) to afford 3,4-Difluoro-5-isopropyl-2-methoxy-11-oxo-6,11-dihydro-5H-indolo[2,3-b]quinoline-8-carbonitrile. (135 mg, 65% yield). MS m/z=368 [M+H].

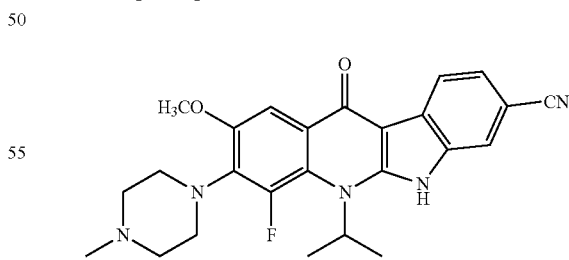

Step D: 4-Fluoro-5-isopropyl-2-methoxy-3-(4-methylpiperazin-1-yl)-11-oxo-6,11-dihydro-5H-indolo[2,3-b]quinoline-8-carbonitrile 1-Methylpiperazine (0.5 mL) and DIPEA (0.5 ml) were added to a solution of 3,4-Difluoro-5-isopropyl-2-methoxy- 11-oxo-6,11-dihydro-5H-indolo[2,3-b]quinoline-8-carbonitrile (135 mg, 0.37 mmol) in DMSO (2 ml) and the mixture was heated to 120 to 140° C. for 3 days. The reaction mixture was cooled to RT and purified by preparative HPLC to afford 4-Fluoro-5-isopropyl-2-methoxy-3-(4-methylpiperazin-1-yl)-11-oxo-6,11-dihydro-5H-indolo[2,3-b]quinoline-8-carbonitrile (24 mg, 15% yield). $^1$H NMR (300 MHz, CD$_3$OD+CDCl$_3$) δ ppm 8.33 (d, J=8.0 Hz, 1H), 7.77 (s, 1H), 7.72 (s, 1H), 7.48 (d, J=8.0 Hz, 1H), 5.20-5.00 (m, 1H), 4.04 (s, 3H), 3.80-3.50 (m, 6H), 3.40-3.25 (m, 2H), 3.00 (s, 3H), 1.74 (dd, J=5.6, 1.8 Hz, 6H).

Example 36 (ALK-71)

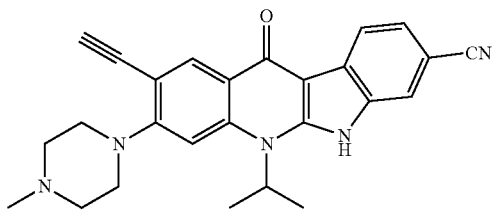 [SMILES: C#Cc1cc2c(=O)c3c4ccc(C#N)cc4[nH]c3n(C(C)C)c2cc1N1CCN(C)CC1]

2-Ethynyl-5-isopropyl-3-(4-methylpiperazin-1-yl)-11-oxo-6,11-dihydro-5H-indolo[2,3-b]quinoline-8-carbonitrile

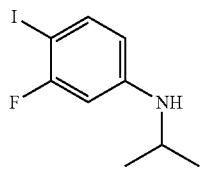

Step A: 3-Fluoro-4-iodo-N-isopropylaniline

Acetone (11.6 g, 200 mmol), Acetic acid (1.80 g, 30 mmol), and Sodium triacetoxyborohydride (6.36 g, 30 mmol) were added to a solution of 3-Fluoro-4-iodoaniline (4.74 g, 20 mmol) in DCM (120 mL) and the mixture was stirred at RT for 2 hr. Water was added to quench the reaction and the mixture was extracted with DCM. The solvent was removed under vacuum and the residue was purified by silica gel chromatography (Hex:EA=20:1) to afford 3-Fluoro-4-iodo-N-isopropylaniline (3.90 g, 70% yield). MS m/z=280 [M+H].

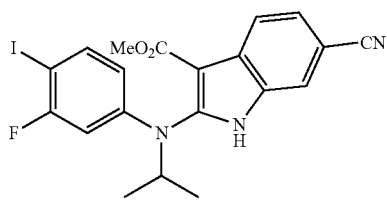 [SMILES: COC(=O)c1c(N(c2ccc(I)c(F)c2)C(C)C)[nH]c2cc(C#N)ccc12]

Step B: Methyl 6-cyano-2-((3-fluoro-4-iodophenyl)(isopropyl)amino)-1H-indole-3-carboxylate DABCO (62 mg, 0.55 mmol) was added to a solution of Methyl 6-cyano-1H-indole-3-carboxylate (200 mg, 1 mmol) in DCM (20 mL) and the mixture was cooled to 0° C. N-Chlorosuccinimide (147 mg, 1.1 mmol) was then added and the reaction was stirred at 0° C. for 2 hr. A solution of 3-Fluoro-4-iodo-N-isopropylaniline (417 mg, 1.5 mmol) and Trichloroacetic acid (41 mg, 0.25 mmol) in DCM (5 mL) was added dropwise and the reaction was stirred for 2 hr at room temperature. The reaction was quenched by adding water and the mixture was extracted with DCM. Solvent was removed under vacuum and the residue was purified by silica gel chromatography (Hex:EA=4:1) to afford Methyl 6-cyano-2-((3-fluoro-4-iodophenyl)(isopropyl)amino)-1H-indole-3-carboxylate (267 mg, 56% yield). MS m/z=478 [M+H].

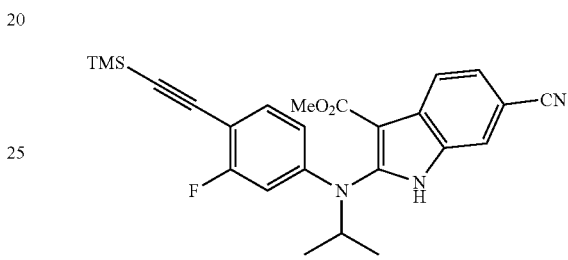

Step C: Methyl 6-cyano-2-((3-fluoro-4-(2-(trimethylsilyl)ethynyl)phenyl)(isopropyl)amino)-1H-indole-3-carboxylate Trimethylsilylacetylene (98 mg, 1 mmol), Methyl 6-cyano-2-((3-fluoro-4-iodophenyl)(isopropyl)amino)-1H-indole-3-carboxylate (238 g, 0.5 mmol), Copper iodide (28 mg, 0.15 mmol) and Pd(PPh$_3$)$_2$Cl$_2$ (34 mg, 0.05 mmol) in Diethyl amine (5 ml) is stirred under N$_2$ at 80° C. overnight. Water (20 ml) was added and the mixture was extracted with ethyl acetate (150 ml) for three times. The solvent was removed under vacuum and the residue was purified by silica gel chromatography to afford Methyl 6-cyano-2-((3-fluoro-4-(2-(trimethylsilyl)ethynyl)phenyl)(isopropyl)amino)-1H-indole-3-carboxylate (215 mg, 96% yield). MS m/z=448 [M+H].

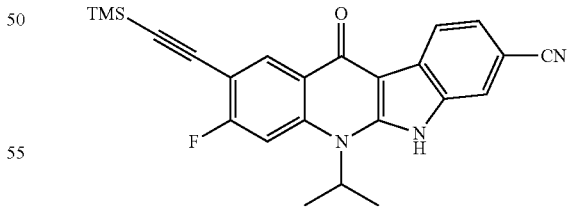

Step D: 2-(Trimethylsilyl)ethynyl-3-fluoro-5-isopropyl-11-oxo-6,11-dihydro-5H-indolo[2,3-b]quinoline-8-carbonitrile Methyl 6-cyano-2-((3-fluoro-4-(2-(trimethylsilyl)ethynyl)phenyl)(isopropyl)amino)-1H-indole-3-carboxylate (250 mg, 0.56 mmol) was dissolved in Diphenyl ether (10 mL) and the solution was refluxed for 3 hr. The mixture was cooled to RT. Hexane (20 mL) was added and the precipitate was collected by filtration. The precipitate was purified by silica gel chromatography (Hex:EA=2:1) to afford 2-(Trimethylsilyl)ethynyl-3-fluoro-5-isopropyl-11-oxo-6,11-dihydro-5H-indolo[2,3-b]quinoline-8-carbonitrile (115 mg, 60% yield). MS m/z=416 [M+H].

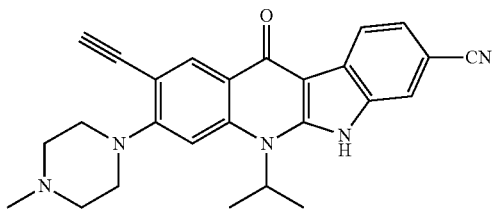 [SMILES: C#Cc1cc2c(=O)c3c4ccc(C#N)cc4[nH]c3n(C(C)C)c2cc1N1CCN(C)CC1]

Step E: 2-Ethynyl-5-isopropyl-3-(4-methylpiperazin-1-yl)-11-oxo-6,11-dihydro-5H-indolo[2,3-b]quinoline-8-carbonitrile 1-Methylpiperazine (0.5 mL) and DIPEA (0.5 ml) were added to a solution of 2-(Trimethylsilyl)ethynyl-3-fluoro-5-isopropyl-11-oxo-6,11-dihydro-5H-indolo[2,3-b]quinoline-8-carbonitrile (127 mg, 0.37 mmol) in DMSO (2 ml) and the mixture was heated to 120 to 140° C. for 2 days. The reaction mixture was cooled to RT and purified by preparative HPLC to afford 2-Ethynyl-5-isopropyl-3-(4-methylpiperazin-1-yl)-11-oxo-6,11-dihydro-5H-indolo[2,3-b]quinoline-8-carbonitrile (31 mg, 20% yield). $^1$H NMR (300 MHz, CD$_3$OD) δ ppm 8.52 (s, 1H), 8.34 (d, J=8.1 Hz, 1H), 7.80 (s, 1H), 7.56 (d, J=8.1 Hz, 1H), 7.31 (s, 1H), 5.43-5.30 (m, 1H), 4.20-4.09 (m, 2H), 4.02 (s, 1H), 3.80-3.70 (m, 2H), 3.50-3.23 (m, 4H), 3.07 (s, 3H), 1.89 (d, J=7.1 Hz, 6H).

Example 37 (ALK-72)

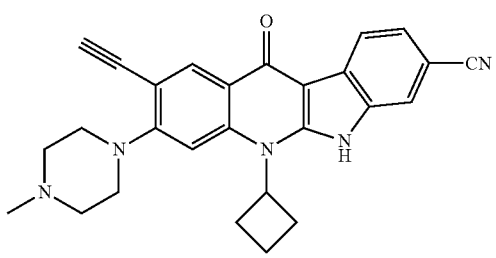 [SMILES: C#Cc1cc2c(=O)c3c4ccc(C#N)cc4[nH]c3n(C3CCC3)c2cc1N1CCN(C)CC1]

5-Cyclobutyl-2-ethynyl-3-(4-methylpiperazin-1-yl)-11-oxo-6,11-dihydro-5H-indolo[2,3-b]quinoline-8-carbonitrile

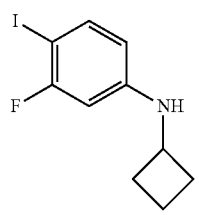 [SMILES: Fc1cc(NC2CCC2)ccc1I]

Step A: N-Cyclobutyl-3-fluoro-4-iodoaniline

Cyclobutanone (14.0 g, 200 mmol), Acetic acid (1.80 g, 30 mmol), and Sodium triacetoxyborohydride (6.36 g, 30 mmol) were added to a solution of 3-Fluoro-4-iodoaniline (4.74 g, 20 mmol) in DCM (120 mL) and the mixture was stirred at RT for 2 hr. Water was added to quench the reaction and the mixture was extracted with DCM. The solvent was removed under vacuum and the residue was purified by silica gel chromatography to afford N-Cyclobutyl-3-fluoro-4-iodoaniline (4.06 g, 70% yield). MS m/z=292 [M+H].

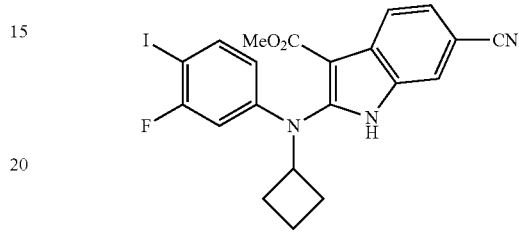

Step B: Methyl 6-cyano-2-(cyclobutyl(3-fluoro-4-iodophenyl)amino)-1H-indole-3-carboxylate DABCO (62 mg, 0.55 mmol) was added to a solution of Methyl 6-cyano-1H-indole-3-carboxylate (200 mg, 1 mmol) in DCM (20 mL) and the mixture was cooled to 0° C. N-Chlorosuccinimide (147 mg, 1.1 mmol) was then added and the reaction was stirred at 0° C. for 2 hr. A solution of N-Cyclobutyl-3-fluoro-4-iodoaniline (435 mg, 1.5 mmol) and Trichloroacetic acid (41 mg, 0.25 mmol) in DCM (5 mL) was added dropwise and the reaction was stirred for 2 hr at room temperature. The reaction was quenched by adding water and the mixture was extracted with DCM. Solvent was removed under vacuum and the residue was purified by silica gel chromatography (Hex:EA=4:1) to afford Methyl 6-cyano-2-(cyclobutyl(3-fluoro-4-iodophenyl)amino)-1H-indole-3-carboxylate (342 mg, 70% yield). MS m/z=490 [M+H].

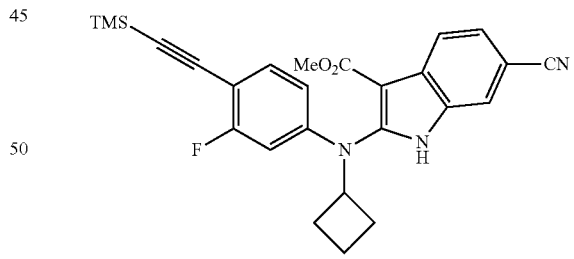

Step C: Methyl 6-cyano-2-(cyclobutyl(3-fluoro-4-((trimethylsilyl)ethynyl)phenyl)amino)-1H-indole-3-carboxylate Trimethylsilylacetylene (98 mg, 1 mmol), Methyl 6-cyano-2-((3-fluoro-4-iodophenyl)(cyclobutyl)amino)-1H-indole-3-carboxylate (245 g, 0.5 mmol), Copper iodide (28 mg, 0.15 mmol) and Pd(PPh3)2Cl2 (34 mg, 0.05 mmol) in Diethyl amine (5 ml) is stirred under N$_2$ at 80° C. overnight. Water (20 ml) was added and the mixture was extracted with ethyl acetate (150 ml) for three times. The solvent was removed under vacuum and the residue was purified by silica gel chromatography to afford Methyl 6-cyano-2-(cyclobutyl(3-fluoro-4-((trimethylsilyl)ethynyl)phenyl)amino)-1H-indole-3-carboxylate (206 mg, 90% yield). MS m/z=460 [M+H].

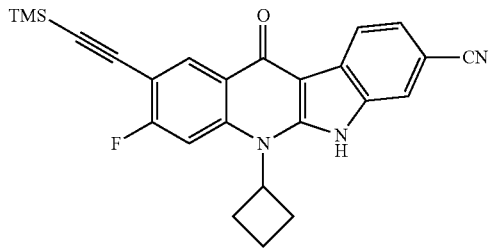 [SMILES: C[Si](C)(C)C#Cc1cc2c(=O)c3c4ccc(C#N)cc4[nH]c3n(C3CCC3)c2cc1F]

Step D: 5-Cyclobutyl-2-(Trimethylsilyl)ethynyl-3-fluoro-11-oxo-6,11-dihydro-5H-indolo[2,3-b]quinoline-8-carbonitrile Methyl 6-cyano-2-(cyclobutyl(3-fluoro-4-((trimethylsilyl)ethynyl)phenyl)amino)-1H-indole-3-carboxylate (257 mg, 0.56 mmol) was dissolved in Diphenyl ether (10 mL) and the solution was refluxed for 3 hr. The mixture was cooled to RT. Hexane (20 mL) was added and the precipitate was collected by filtration. The precipitate was purified by silica gel chromatography (Hex:EA=2:1) to afford 5-Cyclobutyl-2-(Trimethylsilyl)ethynyl-3-fluoro-11-oxo-6,11-dihydro-5H-indolo[2,3-b]quinoline-8-carbonitrile (213 mg, 60% yield). MS m/z=428 [M+H].

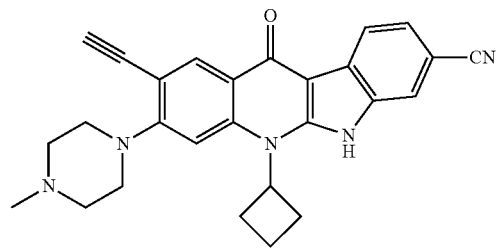 [SMILES: C#Cc1cc2c(=O)c3c4ccc(C#N)cc4[nH]c3n(C3CCC3)c2cc1N1CCN(C)CC1]

Step E: 5-Cyclobutyl-2-ethynyl-3-(4-methylpiperazin-1-yl)-11-oxo-6,11-dihydro-5H-indolo[2,3-b]quinoline-8-carbonitrile 1-Methylpiperazine (0.5 mL) and DIPEA (0.5 ml) were added to a solution of 5-Cyclobutyl-2-(Trimethylsilyl)ethynyl-3-fluoro-11-oxo-6,11-dihydro-5H-indolo[2,3-b]quinoline-8-carbonitrile (131 mg, 0.37 mmol) in DMSO (2 ml) and the mixture was heated to 120 to 140° C. for 2 days. The reaction mixture was cooled to RT and purified by preparative HPLC to afford 5-Cyclobutyl-2-ethynyl-3-(4-methylpiperazin-1-yl)-11-oxo-6,11-dihydro-5H-indolo[2,3-b]quinoline-8-carbonitrile (32 mg, 20% yield). $^1$H NMR (300 MHz, DMSO-$d_6$) δ ppm 11.88 (s, 1H), 8.33 (s, 1H), 8.26 (d, J=8.0 Hz, 1H), 7.91 (s, 1H), 7.61 (d, J=8.0 Hz, 1H), 7.04 (s, 1H), 5.40-5.20 (m, 1H), 4.57 (s, 1H), 4.00-3.95 (m, 2H), 3.92-3.05 (m, 8H), 2.94 (s, 3H), 2.60-2.35 (m, 2H), 2.00-1.90 (m, 2H).

Example 38 (ALK-73)

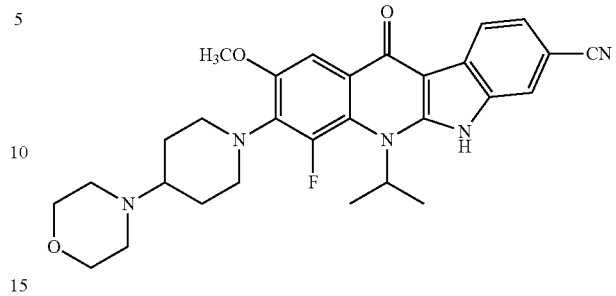

4-Fluoro-5-isopropyl-2-methoxy-3-(4-morpholinopiperidin-1-yl)-11-oxo-6,11-dihydro-5H-indolo[2,3-b]quinoline-8-carbonitrile 4-Morpholinopiperidine (0.5 g) and DIPEA (0.5 ml) were added to a solution of 3,4-Difluoro-5-isopropyl-2-methoxy-11-oxo-6,11-dihydro-5H-indolo[2,3-b]quinoline-8-carbonitrile (135 mg, 0.37 mmol) in DMSO (2 ml) and the mixture was heated to 120 to 140° C. for 3 days. The reaction mixture was cooled to RT and purified by preparative HPLC to afford 4-Fluoro-5-isopropyl-2-methoxy-3-(4-morpholinopiperidin-1-yl)-11-oxo-6,11-dihydro-5H-indolo[2,3-b]quinoline-8-carbonitrile (24 mg, 15% yield). $^1$H NMR (300 MHz, CD$_3$OD) δ ppm 8.21 (d, J=8.0 Hz, 1H), 7.64 (s, 1H), 7.60 (s, 1H), 7.39 (d, J=8.0 Hz, 1H), 5.10-4.90 (m, 1H), 4.20-4.10 (m, 2H), 4.00 (s, 3H), 3.90-3.70 (m, 2H), 3.65-3.50 (m, 4H), 3.45-3.20 (m, 5H), 2.33-2.20 (m, 2H), 2.10-1.85 (m, 2H), 1.70 (dd, J=6.9, 1.9 Hz, 6H).

Example 39 (ALK-74)

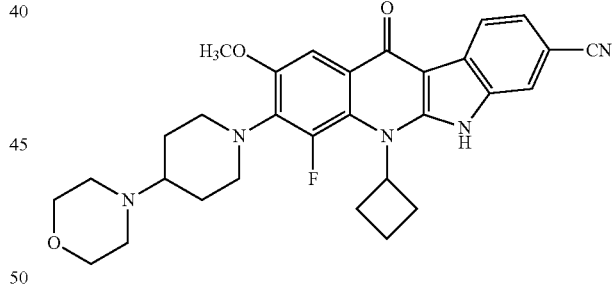

5-Cyclobutyl-4-fluoro-2-methoxy-3-(4-morpholinopiperidin-1-yl)-11-oxo-6,11-dihydro-5H-indolo[2,3-b]quinoline-8-carbonitrile

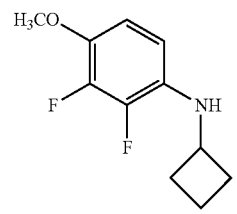 [SMILES: COc1ccc(NC2CCC2)c(F)c1F]

Step A: N-Cyclobutyl-2,3-difluoro-4-methoxyaniline

Cyclobutanone (14.0 g, 200 mmol), Acetic acid (1.8 g, 30 mmol), and Sodium triacetoxyborohydride (6.36 g, 30 mmol) were added to a solution of 2,3-Difluoro-4-methoxyaniline (3.18 g, 20 mmol) in DCM (120 mL) and the mixture was stirred at RT overnight. Water was added to quench the reaction and the mixture was extracted with DCM. The solvent was removed under and the residue was purified by silica gel chromatography to afford N-Cyclobutyl-2,3-difluoro-4-methoxyaniline (3.82 g, 90% yield). MS m/z=214 [M+H].

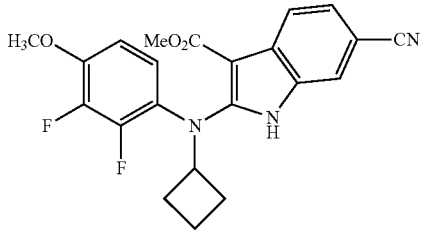 [SMILES: COC(=O)c1c(N(c2ccc(OC)c(F)c2F)C2CCC2)[nH]c2cc(C#N)ccc12]

Step B: Methyl 6-cyano-2-(cyclobutyl(2,3-difluoro-4-methoxyphenyl)amino)-1H-indole-3-carboxylate DABCO (62 mg, 0.55 mmol) was added to a solution of Methyl 6-cyano-1H-indole-3-carboxylate (200 mg, 1 mmol) in DCM (20 mL) and the mixture was cooled to 0° C. N-Chlorosuccinimide (147 mg, 1.1 mmol) was then added and the reaction was stirred at 0° C. for 2 hr. A solution of N-Cyclobutyl-2,3-difluoro-4-methoxyaniline (213 mg, 1 mmol) and Trichloroacetic acid (41 mg, 0.25 mmol) in DCM (5 mL) was added dropwise and the reaction was stirred for 2 hr at room temperature. The reaction was quenched by adding water and the mixture was extracted with DCM. Solvent was removed under vacuum and the residue was purified by silica gel chromatography (Hex:EA=5:1) to afford Methyl 6-cyano-2-(cyclobutyl(2,3-difluoro-4-methoxyphenyl)amino)-1H-indole-3-carboxylate (238 mg, 56% yield). MS m/z=412 [M+H].

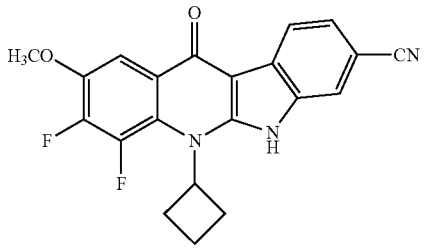 [SMILES: COc1cc2c(=O)c3c4ccc(C#N)cc4[nH]c3n(C3CCC3)c2c(F)c1F]

Step C: 5-Cyclobutyl-3,4-difluoro-2-methoxy-11-oxo-6,11-dihydro-5H-indolo[2,3-b]quinoline-8-carbonitrile Methyl 6-cyano-2-(cyclobutyl(2,3-difluoro-4-methoxyphenyl)amino)-1H-indole-3-carboxylate (230 mg, 0.56 mmol) was dissolved in Diphenyl ether (10 mL) and the solution was refluxed for 1 hr. The mixture was cooled to RT. Hexane (20 mL) was added and the precipitate was collected by filtration. The precipitate was purified by silica gel chromatography (Hex:EA=2:1) to afford 5-Cyclobutyl-3,4-difluoro-2-methoxy-11-oxo-6,11-dihydro-5H-indolo[2,3-b]quinoline-8-carbonitrile (137 mg, 65% yield). MS m/z=380 [M+H].

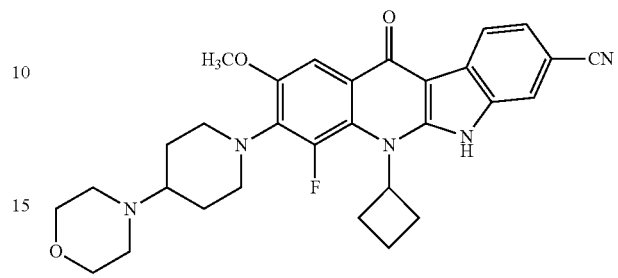

Step D: 5-Cyclobutyl-4-fluoro-2-methoxy-3-(4-morpholinopiperidin-1-yl)-11-oxo-6,11-dihydro-5H-indolo[2,3-b]quinoline-8-carbonitrile 4-Morpholinopiperidine (0.5 g) and DIPEA (0.5 ml) were added to a solution of 5-Cyclobutyl-3,4-difluoro-2-methoxy-11-oxo-6,11-dihydro-5H-indolo[2,3-b]quinoline-8-carbonitrile (140 mg, 0.37 mmol) in DMSO (2 ml) and the mixture was heated to 120 to 140° C. for 2 days. The reaction mixture was cooled to RT and purified by preparative HPLC to afford 5-Cyclobutyl-4-fluoro-2-methoxy-3-(4-morpholinopiperidin-1-yl)-11-oxo-6,11-dihydro-5H-indolo[2,3-b]quinoline-8-carbonitrile (29 mg, 15% yield). $^1$H NMR (300 MHz, CD$_3$OD) δ ppm 8.18 (d, J=8.0 Hz, 1H), 7.62 (s, 1H), 7.58 (s, 1H), 7.40 (d, J=8.0 Hz, 1H), 5.18-5.02 (m, 1H), 4.20-4.08 (m, 2H), 3.98 (s, 3H), 3.90-3.74 (m, 2H), 3.70-3.50 (m, 4H), 3.46-3.20 (m, 5H), 2.83-2.70 (m, 2H), 2.30-1.64 (m, 8H).

Example 40 (ALK-75)

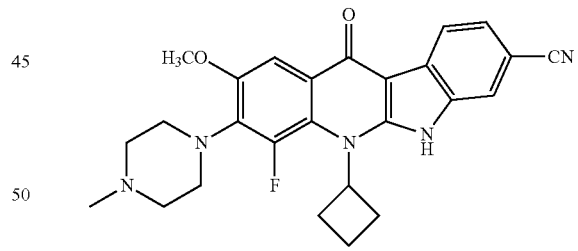

5-Cyclobutyl-4-fluoro-2-methoxy-3-(4-methylpiperazin-1-yl)-11-oxo-6,11-dihydro-5H-indolo[2,3-b]quinoline-8-carbonitrile 1-Methylpiperazine (0.5 ml) and DIPEA (0.5 ml) were added to a solution of 5-cyclobutyl-3,4-difluoro-2-methoxy-11-oxo-6,11-dihydro-5H-indolo[2,3-b]quinoline-8-carbonitrile (140 mg, 0.37 mmol) in DMSO (2 ml) and the mixture was heated to 120 to 140° C. for 2 days. The reaction mixture was cooled to RT and purified by preparative HPLC to afford 5-Cyclobutyl-4-fluoro-2-methoxy-3-(4-methylpiperazin-1-yl)-11-oxo-6,11-dihydro-5H-indolo[2,3-b]quinoline-8-carbonitrile (24 mg, 15% yield). $^1$H NMR (300 MHz, CD$_3$OD+CDCl$_3$) δ ppm 8.36 (d, J=8.1 Hz, 1H), 7.78-7.73 (m, 2H), 7.54 (d, J=8.1 Hz, 1H), 5.25-5.08 (m, 1H), 4.02 (s, 3H), 3.74-3.48 (m, 6H), 3.40-3.25 (m, 2H), 2.98 (s, 3H), 2.80-2.70 (m, 2H), 2.25-1.85 (m, 4H).

Example 41 (ALK-76)

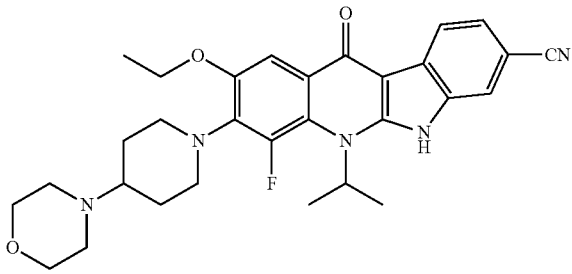 [SMILES: CCOc1cc2c(=O)c3c4ccc(C#N)cc4[nH]c3n(C(C)C)c2c(F)c1N1CCC(N2CCOCC2)CC1]

2-Ethoxy-4-fluoro-5-isopropyl-3-(4-morpholinopiperidin-1-yl)-11-oxo-6,11-dihydro-5H-indolo[2,3-b]quinoline-8-carbonitrile

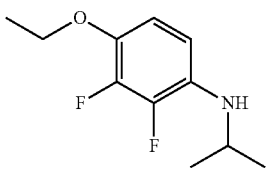

Step A: 4-Ethoxy-2,3-difluoro-N-isopropylaniline

Acetone (11.6 g, 200 mmol), Acetic acid (1.8 g, 30 mmol), and Sodium triacetoxyborohydride (6.36 g, 30 mmol) were added to a solution of 4-Ethoxy-2,3-difluoroaniline (3.46 g, 20 mmol) in DCM (120 mL) and the mixture was stirred at RT for 12 hr. Water was added to quench the reaction and the mixture was extracted with DCM. The solvent was removed under and the residue was purified by silica gel chromatography to afford 4-Ethoxy-2,3-difluoro-N-isopropylaniline (3.40 g, 80% yield). $^1$H NMR (400 MHz, CDCl$_3$) δ ppm 6.66-6.63 (m, 1H), 6.39-6.36 (m, 1H), 4.04 (q, J=7.0 Hz, 2H), 3.59-3.57 (m, 1H), 3.45 (s, 1H), 1.41 (t, J=7.0 Hz, 3H), 1.23 (d, J=6.2 Hz, 6H).

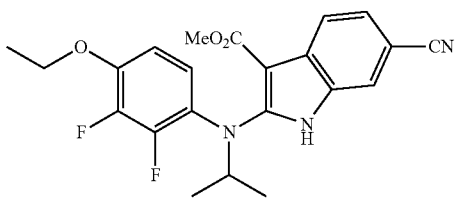 [SMILES: CCOc1ccc(N(c2[nH]c3cc(C#N)ccc3c2C(=O)OC)C(C)C)c(F)c1F]

Step B: Methyl 6-cyano-2-((4-ethoxy-2,3-difluorophenyl)(isopropyl)amino)-1H-indole-3-carboxylate DABCO (62 mg, 0.55 mmol) was added to a solution of Methyl 6-cyano-1H-indole-3-carboxylate (200 mg, 1 mmol) in DCM (20 mL) and the mixture was cooled to 0° C. N-Chlorosuccinimide (147 mg, 1.1 mmol) was then added and the reaction was stirred at 0° C. for 2 hr. A solution of 4-Ethoxy-2,3-difluoro-N-isopropylaniline (215 mg, 1 mmol) and Trichloroacetic acid (41 mg, 0.25 mmol) in DCM (5 mL) was added dropwise and the reaction was stirred for 2 hr at room temperature. The reaction was quenched by adding water and the mixture was extracted with DCM. Solvent was removed under vacuum and the residue was purified by silica gel chromatography (Hex:EA=4:1) to afford Methyl 6-cyano-2-((4-ethoxy-2,3-difluorophenyl)(isopropyl)amino)-1H-indole-3-carboxylate (247 mg, 60% yield). $^1$H NMR (400 MHz, CDCl$_3$) δ ppm 8.02 (d, J=8.3 Hz, 1H), 7.92 (s, 1H), 7.42-7.39 (m, 2H), 7.09-7.05 (m, 1H), 6.86-6.76 (m, 1H), 4.83 (m, 1H), 4.19 (q, J=7.0 Hz, 2H), 3.88 (s, 3H), 1.51 (t, J=7.0 Hz, 3H), 1.27 (dd, J=6.6, 1.2 Hz, 6H).

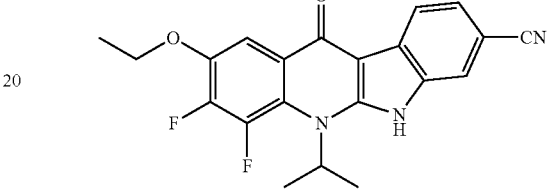

2-Ethoxy-3,4-difluoro-5-isopropyl-11-oxo-6,11-dihydro-5H-indolo[2,3-b]quinoline-8-carbonitrile Methyl 6-cyano-2-((4-ethoxy-2,3-difluorophenyl)(isopropyl)amino)-1H-indole-3-carboxylate (270 mg, 0.65 mmol) was dissolved in Diphenyl ether (10 mL) and the solution was refluxed for 1 hr. The mixture was cooled to RT. Hexane (20 mL) was added and the precipitate was collected by filtration. The precipitate was purified by silica gel chromatography (Hex:EA=2:1) to afford 2-Ethoxy-3,4-difluoro-5-isopropyl-11-oxo-6,11-dihydro-5H-indolo[2,3-b]quinoline-8-carbonitrile (155 mg, 41% yield). $^1$H NMR (400 MHz, DMSO-d$_6$) δ 12.11 (s, 1H), 8.26 (d, J=8.1 Hz, 1H), 7.89 (d, J=1.4 Hz, 1H), 7.78 (dd, J=9.0, 1.9 Hz, 1H), 7.63 (dd, J=8.1, 1.4 Hz, 1H), 5.06-5.04 (m, 1H), 4.27 (q, J=6.9 Hz, 2H), 1.67 (dd, J=7.0, 2.1 Hz, 6H), 1.43 (t, J=6.9 Hz, 3H).

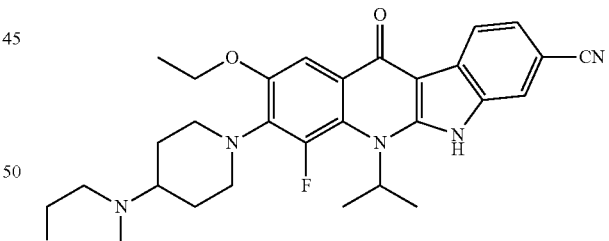

2-Ethoxy-4-fluoro-5-isopropyl-3-(4-morpholinopiperidin-1-yl)-11-oxo-6,11-dihydro-5H-indolo[2,3-b]quinoline-8-carbonitrile 4-Morpholinopiperidine (0.5 g) and DIPEA (0.5 ml) were added to a solution of 2-Ethoxy-3,4-difluoro-5-isopropyl-11-oxo-6,11-dihydro-5H-indolo[2,3-b]quinoline-8-carbonitrile (155 mg, 0.41 mmol) in DMSO (2 ml) and the mixture was heated to 120 to 140° C. for 3 days. The reaction mixture was cooled to RT and purified by preparative HPLC to afford 2-Ethoxy-4-fluoro-5-isopropyl-3-(4-morpholinopiperidin-1-yl)-11-oxo-6,11-dihydro-5H-indolo[2,3-b]quinoline-8-carbonitrile (48 mg, 22% yield). $^1$H NMR (300 MHz, CD$_3$OD) δ ppm 8.34 (d, J=8.1 Hz, 1H), 7.78 (s, 1H), 7.70 (s, 1H), 7.54 (d, J=8.1 Hz, 1H), 5.20-5.02 (m, 1H), 4.24 (q, J=6.9 Hz, 2H), 4.22-4.17 (m, 2H), 3.90-3.60 (m, 6H), 3.55-3.20 (m, 5H), 2.35-2.20 (m, 2H), 2.00-1.84 (m, 2H), 1.74 (dd, J=7.0, 2.0 Hz, 6H), 1.55 (t, J=6.9 Hz, 3H).

Example 42 (ALK-78)

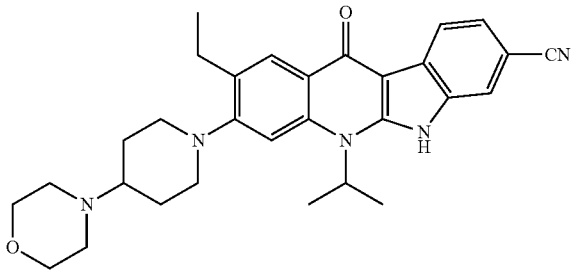 [SMILES: CCc1cc2c(=O)c3c4ccc(C#N)cc4[nH]c3n(C(C)C)c2cc1N1CCC(N2CCOCC2)CC1]

2-Ethyl-5-isopropyl-3-(4-morpholinopiperidin-1-yl)-11-oxo-6,11-dihydro-5H-indolo[2,3-b]quinoline-8-carbonitrile

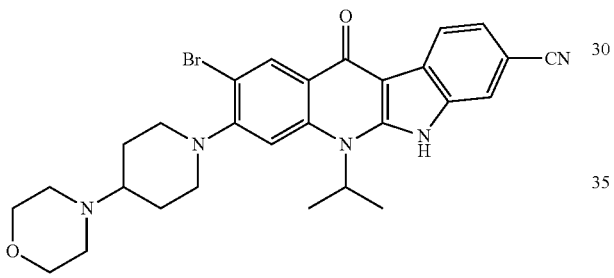

Step A: 2-Bromo-5-isopropyl-3-(4-morpholinopiperidin-1-yl)-11-oxo-6,11-dihydro-5H-indolo[2,3-b]quinoline-8-carbonitrile 4-Morpholinopiperidine (0.5 g) and DIPEA (0.5 ml) were added to a solution of 2-Bromo-3-fluoro-5-isopropyl-11-oxo-6,11-dihydro-5H-indolo[2,3-b]quinoline-8-carbonitrile (110 mg, 0.28 mmol) in DMSO (2 ml) and the mixture was heated to 120 to 140° C. for 3 days. The reaction mixture was cooled to RT and purified by preparative HPLC to afford 2-Bromo-5-isopropyl-3-(4-morpholinopiperidin-1-yl)-11-oxo-6,11-dihydro-5H-indolo[2,3-b]quinoline-8-carbonitrile (34 mg, 22% yield). MS m/z=548 [M+H].

Step B: 2-Ethyl-5-isopropyl-3-(4-morpholinopiperidin-1-yl)-11-oxo-6,11-dihydro-5H-indolo[2,3-b]quinoline-8-carbonitrile A mixture of 2-Bromo-5-isopropyl-3-(4-morpholinopiperidin-1-yl)-11-oxo-6,11-dihydro-5H-indolo[2,3-b]quinoline-8-carbonitrile (33 mg, 0.061 mmol), Na$_2$CO$_3$ (25 mg, 0.183 mmol), Pd(PPh$_3$)$_2$Cl$_2$ (4.3 mg, 0.0061 mmol), and 4,4,5,5-Tetramethyl-2-vinyl-1,3,2-dioxaborolane (14 mg, 0.091 mmol) in DME/H$_2$O (4.8 ml, V/V=5/1) was stirred under nitrogen at 80° C. overnight. After the reaction was complete as indicated by LC-MS, the solvent was removed under vacuum, and the residue was purified by silica gel chromatography to afford mixture of 5-isoPropyl-3-(4-morpholinopiperidin-1-yl)-11-oxo-2-vinyl-6,11-dihydro-5H-indolo[2,3-b]quinoline-8-carbonitrile and Triphenyl phosphine oxide. The mixture was dissolved in THF (5 ml). Pd/C (10%, 5 mg) was added to the THF solution. The mixture underwent hydrogenation at room temperature for overnight until LC-MS indicated that the reaction was complete. The filtrate after filtration was concentrated and the residue was purified by preparative HPLC to afford 2-Ethyl-5-isopropyl-3-(4-morpholinopiperidin-1-yl)-11-oxo-6,11-dihydro-5H-indolo[2,3-b]quinoline-8-carbonitrile (17 mg, 52% yield). MS m/z=498 [M+H].

Example 43 (ALK-77)

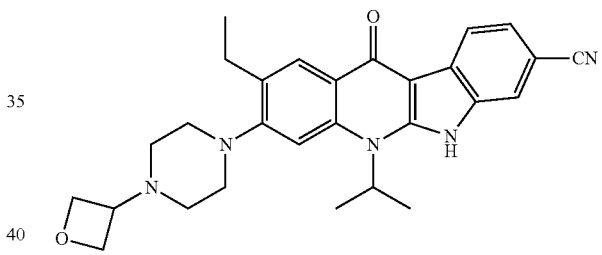

2-Ethyl-5-isopropyl-3-(4-(oxetan-3-yl)piperazin-1-yl)-11-oxo-6,11-dihydro-5H-indolo[2,3-b]quinoline-8-carbonitrile The title compound was prepared in a method similar to that used in the preparation of 2-Ethyl-5-isopropyl-3-(4-morpholinopiperidin-1-yl)-11-oxo-6,11-dihydro-5H-indolo[2,3-b]quinoline-8-carbonitrile. MS m/z=470 [M+H].

Example 44 (ALK-79)

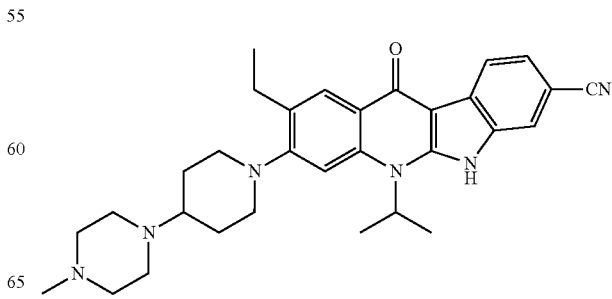

2-Ethyl-5-isopropyl-3-(4-(4-methylpiperazin-1-yl)
piperidin-1-yl)-11-oxo-6,11-dihydro-5H-indolo[2,3-
b]quinoline-8-carbonitrile

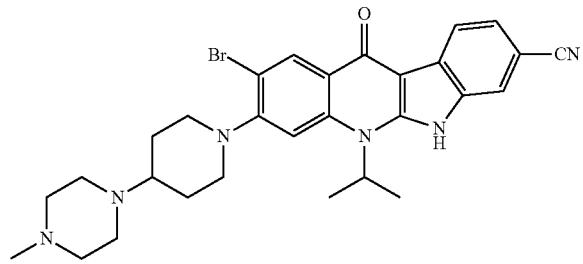 [SMILES: CC(C)n1c2cc(N3CCC(N4CCN(C)CC4)CC3)c(Br)cc2c(=O)c2c3ccc(C#N)cc3[nH]c21]

Step A: 2-Bromo-5-isopropyl-3-(4-(4-methylpiper-
azin-1-yl)piperidin-1-yl)-11-oxo-6,11-dihydro-5H-
indolo[2,3-b]quinoline-8-carbonitrile 4-Methylpiperazin-1-piperidine (1 g) and DIPEA (1 ml) were added to a solution of 2-Bromo-3-fluoro-5-isopropyl-11-oxo-6,11-dihydro-5H-indolo[2,3-b]quinoline-8-carbonitrile (330 mg, 0.84 mmol) in DMSO (2 ml) and the mixture was heated to 120 to 140° C. for 3 days. The reaction mixture was cooled to RT and purified by preparative HPLC to afford 2-Bromo-5-isopropyl-3-(4-(4-methylpiperazin-1-yl)piperidin-1-yl)-11-oxo-6,11-dihydro-5H-indolo[2,3-b]quinoline-8-carbonitrile (103 mg, 22% yield). MS m/z=561 [M+H].

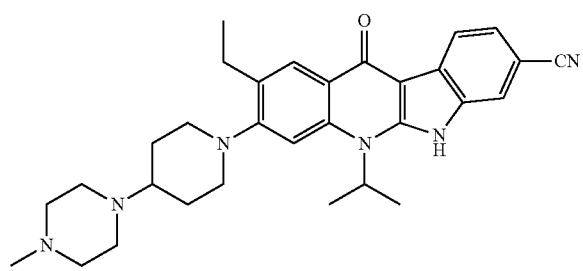 [SMILES: CCc1cc2c(=O)c3c4ccc(C#N)cc4[nH]c3n(C(C)C)c2cc1N1CCC(N2CCN(C)CC2)CC1]

Step B: 2-Ethyl-5-isopropyl-3-(4-(4-methylpiper-
azin-1-yl)piperidin-1-yl)-11-oxo-6,11-dihydro-5H-
indolo[2,3-b]quinoline-8-carbonitrile A mixture of 2-Bromo-5-isopropyl-3-(4-(4-methylpiperazin-1-yl)piperidin-1-yl)-11-oxo-6,11-dihydro-5H-indolo[2,3-b]quinoline-8-carbonitrile (340 mg, 0.61 mmol), Na$_2$CO$_3$ (250 mg, 1.83 mmol), Pd(PPh$_3$)$_2$Cl$_2$ (43 mg, 0.061 mmol), and 4,4,5,5-Tetramethyl-2-vinyl-1,3,2-dioxaborolane (14 0 mg, 0.91 mmol) in DME/H$_2$O (20 ml, V/V=4/1) was stirred under nitrogen at 80° C. overnight. After the reaction was complete as indicated by LC-MS, the solvent was removed under vacuum, and the residue was purified by silica gel chromatography to afford mixture of 5-isoPropyl-3-(4-(4-methylpiperazin-1-yl)piperidin-1-yl)-11-oxo-2-vinyl-6,11-dihydro-5H-indolo[2,3-b]quinoline-8-carbonitrile and Triphenyl phosphine oxide. The mixture was dissolved in THF (25 ml). Pd/C (10%, 5 mg) was added to the THF solution. The mixture underwent hydrogenation at room temperature for overnight until LC-MS indicated that the reaction was complete. The filtrate after filtration was concentrated and the residue was purified by preparative HPLC to afford 2-Ethyl-5-isopropyl-3-(4-(4-methylpiperazin-1-yl)piperidin-1-yl)-11-oxo-6,11-dihydro-5H-indolo[2,3-b]quinoline-8-carbonitrile (161 mg, 52% yield). MS m/z=511 [M+H].

Example 45 (ALK-80)

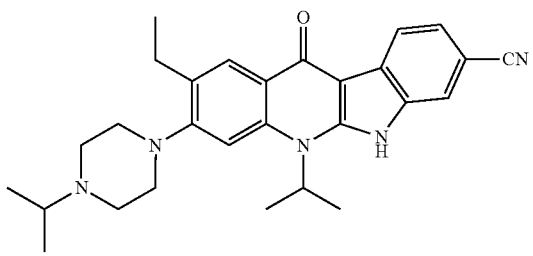 [SMILES: CCc1cc2c(=O)c3c4ccc(C#N)cc4[nH]c3n(C(C)C)c2cc1N1CCN(C(C)C)CC1]

2-Ethyl-5-isopropyl-3-(4-isopropylpiperazin-1-yl)-
11-oxo-6,11-dihydro-5H-indolo[2,3-b]quinoline-8-
carbonitrile

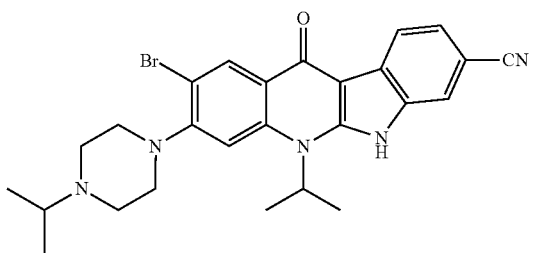 [SMILES: CC(C)N1CCN(c2cc3c(cc2Br)c(=O)c2c4ccc(C#N)cc4[nH]c2n3C(C)C)CC1]

Step A: 2-Bromo-5-isopropyl-3-(4-isopropylpiper-
azin-1-yl)-11-oxo-6,11-dihydro-5H-indolo[2,3-b]
quinoline-8-carbonitrile 4-isoPropylpiperazine (0.5 mL) and DIPEA (0.5 ml) were added to a solution of 2-Bromo-3-fluoro-5-isopropyl-11-oxo-6,11-dihydro-5H-indolo[2,3-b]quinoline-8-carbonitrile (110 mg, 0.28 mmol) in DMSO (2 ml) and the mixture was heated to 120 to 140° C. for 3 days. The reaction mixture was cooled to RT and purified by preparative HPLC to afford 2-Bromo-5-isopropyl-3-(4-isopropylpiperazin-1-yl)-11-oxo-6,11-dihydro-5H-indolo[2,3-b]quinoline-8-carbonitrile (31 mg, 22% yield). MS m/z=506 [M+H].

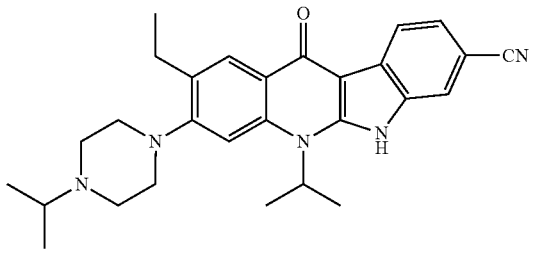 [SMILES: CCc1cc2c(=O)c3c4ccc(C#N)cc4[nH]c3n(C(C)C)c2cc1N1CCN(C(C)C)CC1]

Step B: 2-Ethyl-5-isopropyl-3-(4-isopropylpiperazin-1-yl)-11-oxo-6,11-dihydro-5H-indolo[2,3-b]quinoline-8-carbonitrile A mixture of 2-Bromo-5-isopropyl-3-(4-isopropylpiperazin-1-yl)-11-oxo-6,11-dihydro-5H-indolo[2,3-b]quinoline-8-carbonitrile (31 mg, 0.061 mmol), Na$_2$CO$_3$ (25 mg, 0.183 mmol), Pd(PPh$_3$)$_2$Cl$_2$ (4.3 mg, 0.0061 mmol), and 4,4,5,5-tetramethyl-2-vinyl-1,3,2-dioxaborolane (14 mg, 0.091 mmol) in DME/H2O (4.8 ml, V/V=5/1) was stirred under nitrogen at 80° C. overnight. After the reaction was complete as indicated by LC-MS, the solvent was removed under vacuum, and the residue was purified by silica gel chromatography to afford a mixture of 5-isoPropyl-3-(4-isopropylpiperazin-1-yl)-11-oxo-2-vinyl-6,11-dihydro-5H-indolo[2,3-b]quinoline-8-carbonitrile and Triphenyl phosphine oxide. The mixture was dissolved in THF (5 ml). Pd/C (10%, 5 mg) was added to the THF solution. The mixture underwent hydrogenation at room temperature overnight until LC-MS indicated that the reaction was complete. The filtrate after filtration was concentrated and the residue was purified by preparative HPLC to afford 2-Ethyl-5-isopropyl-3-(4-isopropylpiperazin-1-yl)-11-oxo-6,11-dihydro-5H-indolo[2,3-b]quinoline-8-carbonitrile (14 mg, 52% yield). MS m/z=456 [M+H].

Example 46 (ALK-81)

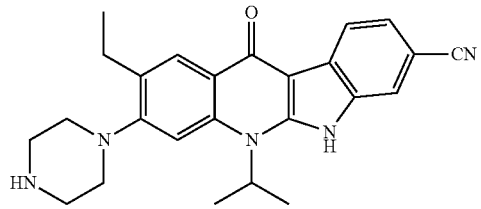 [SMILES: CCc1cc2c(=O)c3c4ccc(C#N)cc4[nH]c3n(C(C)C)c2cc1N1CCNCC1]

2-Ethyl-5-isopropyl-11-oxo-3-(piperazin-1-yl)-6,11-dihydro-5H-indolo[2,3-b]quinoline-8-carbonitrile

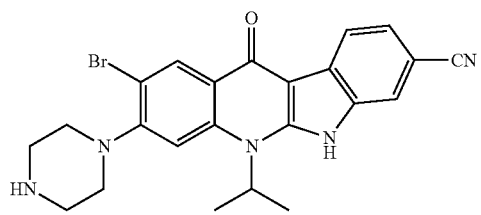 [SMILES: CC(C)n1c2cc(N3CCNCC3)c(Br)cc2c(=O)c2c3ccc(C#N)cc3[nH]c21]

Step A: 2-Bromo-5-isopropyl-11-oxo-3-(piperazin-1-yl)-6,11-dihydro-5H-indolo[2,3-b]quinoline-8-carbonitrile N-Boc-piperazine (0.5 g) and DIPEA (0.5 ml) were added to a solution of 2-Bromo-3-fluoro-5-isopropyl-11-oxo-6,11-dihydro-5H-indolo[2,3-b]quinoline-8-carbonitrile (110 mg, 0.28 mmol) in DMSO (2 ml) and the mixture was heated to 120 to 140° C. for 7 days. The reaction was cooled to RT and water (20 ml) was added. The mixture was extracted with dichloromethane (60 ml) for three times. The solvent was removed under vacuum and the residue was purified by silica gel chromatography (DCM/MeOH=10/1) to afford 2-Bromo-5-isopropyl-3-(N-Boc-piperazin-1-yl)-11-oxo-6,11-dihydro-5H-indolo[2,3-b]quinoline-8-carbonitrile. 2-Bromo-5-isopropyl-3-(N-Boc-piperazin-1-yl)-11-oxo-6,11-dihydro-5H-indolo[2,3-b]quinoline-8-carbonitrile was dissolved in DCM (1 ml) and Trichloroacetic acid (0.5 ml) was added and the mixture was stirred at RT overnight. The solvent was removed under vacuum to afford 2-Bromo-5-isopropyl-11-oxo-3-(piperazin-1-yl)-6,11-dihydro-5H-indolo[2,3-b]quinoline-8-carbonitrile (33 mg, 28%). MS m/z=464 [M+H].

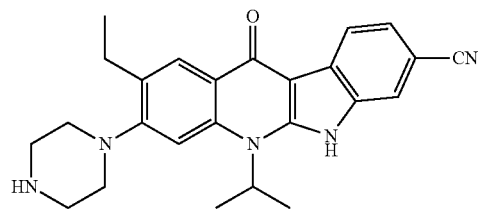 [SMILES: CCc1cc2c(=O)c3c4ccc(C#N)cc4[nH]c3n(C(C)C)c2cc1N1CCNCC1]

Step B: 2-Ethyl-5-isopropyl-11-oxo-3-(piperazin-1-yl)-6,11-dihydro-5H-indolo[2,3-b]quinoline-8-carbonitrile A mixture of 2-Bromo-5-isopropyl-3-(piperazin-1-yl)-11-oxo-6,11-dihydro-5H-indolo[2,3-b]quinoline-8-carbonitrile (28 mg, 0.061 mmol), Na$_2$CO$_3$ (25 mg, 0.183 mmol), Pd(PPh$_3$)$_2$Cl$_2$ (4.3 mg, 0.0061 mmol), and 4,4,5,5-Tetramethyl-2-vinyl-1,3,2-dioxaborolane (14 mg, 0.091 mmol) in DME/H$_2$O (4.8 ml, V/V=5/1) was stirred under nitrogen at 80° C. overnight. After the reaction was complete as indicated by LC-MS, the solvent was removed under vacuum, and the residue was purified by silica gel chromatography to afford a mixture of 5-isoPropyl-3-(piperazin-1-yl)-11-oxo-2-vinyl-6,11-dihydro-5H-indolo[2,3-b]quinoline-8-carbonitrile and Triphenyl phosphine oxide. The mixture was dissolved in THF (5 ml). Pd/C (10%, 5 mg) was added to the THF solution. The mixture underwent hydrogenation at room temperature overnight until LC-MS indicated that the reaction was complete. The filtrate after filtration was concentrated and the residue was purified by preparative HPLC to afford 2-Ethyl-5-isopropyl-11-oxo-3-(piperazin-1-yl)-6,11-dihydro-5H-indolo[2,3-b]quinoline-8-carbonitrile (13 mg, 52% yield). MS m/z=414 [M+H]. $^1$H NMR (300 MHz, CD$_3$OD) δ ppm 8.42 (s, 1H), 8.37 (d, J=8.0 Hz, 1H), 7.77 (s, 1H), 7.57-7.45 (m, 2H), 5.46-5.30 (m, 1H), 3.55-3.50 (m, 4H), 3.48-3.26 (m, 4H), 2.87 (q, J=7.4 Hz, 2H), 1.89 (d, J=7.1 Hz, 6H), 1.41 (t, J=7.4 Hz, 3H).

Example 47 (ALK-82)

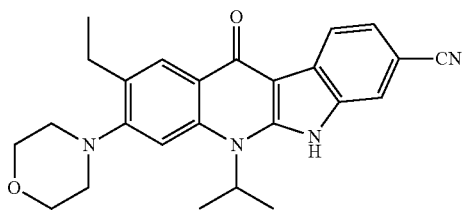 [SMILES: CCc1cc2c(=O)c3c4ccc(C#N)cc4[nH]c3n(C(C)C)c2cc1N1CCOCC1]

2-Ethyl-5-isopropyl-3-morpholino-11-oxo-6,11-dihydro-5H-indolo[2,3-b]quinoline-8-carbonitrile

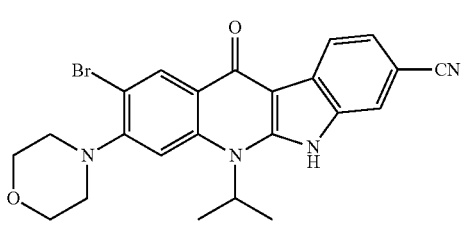 [SMILES: CC(C)n1c2cc(N3CCOCC3)c(Br)cc2c(=O)c2c3ccc(C#N)cc3[nH]c21]

Step A: 2-Bromo-5-isopropyl-3-morpholino-11-oxo-6,11-dihydro-5H-indolo[2,3-b]quinoline-8-carbonitrile Morpholine (0.5 mL) and DIPEA (0.5 ml) were added to a solution of 2-Bromo-3-fluoro-5-isopropyl-11-oxo-6,11-dihydro-5H-indolo[2,3-b]quinoline-8-carbonitrile (110 mg, 0.28 mmol) in DMSO (2 ml) and the mixture was heated to 120 to 140° C. for 3 days. The reaction mixture was cooled to RT and purified by preparative HPLC to afford 2-Bromo-5-isopropyl-3-morpholino-11-oxo-6,11-dihydro-5H-indolo[2,3-b]quinoline-8-carbonitrile (38 mg, 29% yield). MS m/z=465 [M+H].

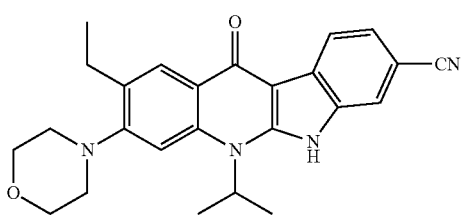 [SMILES: CCc1cc2c(=O)c3c4ccc(C#N)cc4[nH]c3n(C(C)C)c2cc1N1CCOCC1]

Step B: 2-Ethyl-5-isopropyl-3-morpholino-11-oxo-6,11-dihydro-5H-indolo[2,3-b]quinoline-8-carbonitrile A mixture of 2-Bromo-5-isopropyl-3-morpholino-11-oxo-6,11-dihydro-5H-indolo[2,3-b]quinoline-8-carbonitrile (25 mg, 0.061 mmol), Na$_2$CO$_3$ (25 mg, 0.183 mmol), Pd(PPh$_3$)$_2$Cl$_2$ (4.3 mg, 0.0061 mmol), and 4,4,5,5-Tetramethyl-2-vinyl-1,3,2-dioxaborolane (14 mg, 0.091 mmol) in DME/H$_2$O (4.8 ml, V/V=5/1) was stirred under nitrogen at 80° C. overnight. After the reaction was complete as indicated by LC-MS, the solvent was removed under vacuum, and the residue was purified by silica gel chromatography to afford a mixture of 5-isoPropyl-3-morpholino-11-oxo-2-vinyl-6,11-dihydro-5H-indolo[2,3-b]quinoline-8-carbonitrile and Triphenyl phosphine oxide. The mixture was dissolved in THF (5 ml). Pd/C (10%, 5 mg) was added to the THF solution. The mixture underwent hydrogenation at room temperature overnight until LC-MS indicated that the reaction was complete. The filtrate after filtration was concentrated and the residue was purified on HPLC to afford 2-Ethyl-5-isopropyl-3-morpholino-11-oxo-6,11-dihydro-5H-indolo[2,3-b]quinoline-8-carbonitrile (17 mg, 60% yield). MS m/z=415 [M+H].

Example 48 (ALK-83)

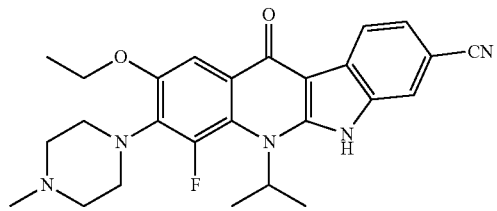 [SMILES: CCOc1cc2c(=O)c3c4ccc(C#N)cc4[nH]c3n(C(C)C)c2c(F)c1N1CCN(C)CC1]

2-Ethoxy-4-fluoro-5-isopropyl-3-(4-methylpiperazin-1-yl)-11-oxo-6,11-dihydro-5H-indolo[2,3-b]quinoline-8-carbonitrile 1-Methylpiperazine (0.5 mL) and DIPEA (0.5 ml) were added to a solution of 2-Ethoxy-3,4-difluoro-5-isopropyl-11-oxo-6,11-dihydro-5H-indolo[2,3-b]quinoline-8-carbonitrile (135 mg, 0.37 mmol) in DMSO (2 ml) and the mixture was heated to 120 to 140° C. for 3 days. The reaction mixture was cooled to RT and purified by preparative HPLC to afford 2-Ethoxy-4-fluoro-5-isopropyl-3-(4-methylpiperazin-1-yl)-11-oxo-6,11-dihydro-5H-indolo[2,3-b]quinoline-8-carbonitrile (26 mg, 15% yield). $^1$H NMR (300 MHz, CD$_3$OD) δ ppm 8.16 (d, J=8.0 Hz, 1H), 7.61 (s, 1H), 7.55 (s, 1H), 7.36 (d, J=8.0 Hz, 1H), 5.10-4.90 (m, 1H), 4.23 (q, J=6.9 Hz, 2H), 3.80-3.60 (m, 6H), 3.50-3.30 (m, 2H), 3.04 (s, 3H), 1.70 (dd, J=6.9, 1.9 Hz, 6H), 1.56 (t, J=6.9 Hz, 3H).

Example 49 (ALK-85)

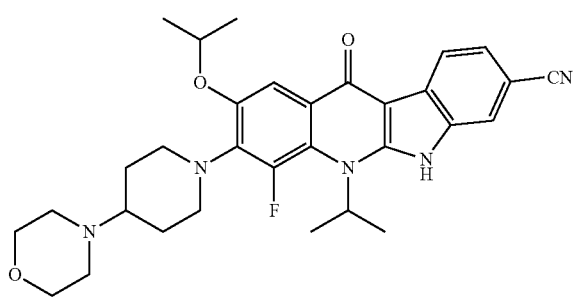 [SMILES: CC(C)Oc1cc2c(=O)c3c4ccc(C#N)cc4[nH]c3n(C(C)C)c2c(F)c1N1CCC(N2CCOCC2)CC1]

4-Fluoro-2-isopropoxy-5-isopropyl-3-(4-morpholinopiperidin-1-yl)-11-oxo-6,11-dihydro-5H-indolo[2,3-b]quinoline-8-carbonitrile

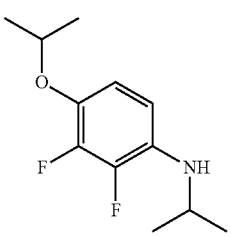 [SMILES: CC(C)Nc1ccc(OC(C)C)c(F)c1F]

Step A: 2,3-Difluoro-4-isopropoxy-N-isopropylaniline

Acetone (11.6 g, 200 mmol), Acetic acid (1.8 g, 30 mmol), and Sodium triacetoxyborohydride (6.36 g, 30 mmol) were added to a solution of 2,3-Difluoro-4-isopropoxyaniline (3.74 g, 20 mmol) in DCM (120 mL) and the mixture was stirred at RT for 12 hr. Water was added to quench the reaction and the mixture was extracted with DCM. The solvent was removed under and the residue was purified by silica gel chromatography to afford 2,3-Difluoro-4-isopropoxy-N-isopropylaniline. (3.80 g, 83% yield). $^1$H NMR (400 MHz, CDCl$_3$) δ ppm 6.70-6.65 (m, 1H), 6.36 (td, J=8.9, 2.4 Hz, 1H), 4.40-4.26 (m, 1H), 3.61-3.57 (m, 2H), 1.33 (d, J=6.1 Hz, 6H), 1.24 (d, J=6.3 Hz, 6H).

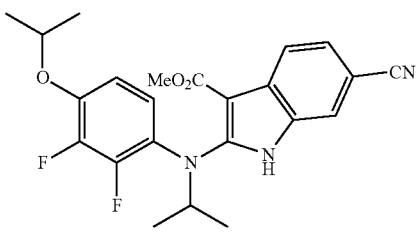 [SMILES: COC(=O)c1c(N(c2ccc(OC(C)C)c(F)c2F)C(C)C)[nH]c2cc(C#N)ccc12]

Step B: Methyl 6-cyano-2-((2,3-difluoro-4-isopropoxyphenyl)(isopropyl)amino)-1H-indole-3-carboxylate DABCO (62 mg, 0.55 mmol) was added to a solution of Methyl 6-cyano-1H-indole-3-carboxylate (200 mg, 1 mmol) in DCM (20 mL) and the mixture was cooled to 0° C. N-Chlorosuccinimide (147 mg, 1.1 mmol) was then added and the reaction was stirred at 0° C. for 2 hr. A solution of 2,3-Difluoro-4-isopropoxy-N-isopropylaniline (229 mg, 1 mmol) and Trichloroacetic acid (41 mg, 0.25 mmol) in DCM (5 mL) was added dropwise and the reaction was stirred for 2 hr at room temperature. The reaction was quenched by adding water and the mixture was extracted with DCM. Solvent was removed under vacuum and the residue was purified by silica gel chromatography (Hex:EA=4:1) to afford Methyl 6-cyano-2-((2,3-difluoro-4-isopropoxyphenyl)(isopropyl)amino)-1H-indole-3-carboxylate (230 mg, 54% yield). MS m/z=428 [M+H]. $^1$H NMR (300 MHz, CDCl$_3$) δ 8.05-7.95 (m, 2H), 7.43-7.33 (m, 2H), 7.02 (td, J=8.6, 2.3 Hz, 1H), 6.79-6.78 (m, 1H), 4.83-4.78 (m, 1H), 4.63-4.59 (m, 1H), 3.84 (s, 3H), 1.40 (d, J=6.1 Hz, 6H), 1.31-1.17 (m, 6H).

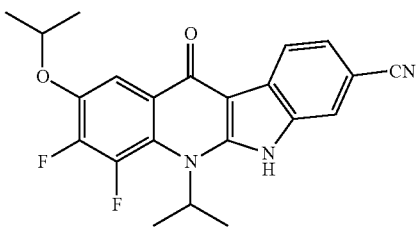 [SMILES: CC(C)Oc1cc2c(=O)c3c4ccc(C#N)cc4[nH]c3n(C(C)C)c2c(F)c1F]

Step C: 3,4-Difluoro-2-isopropoxy-5-isopropyl-11-oxo-6,11-dihydro-5H-indolo[2,3-b]quinoline-8-carbonitrile Methyl 6-cyano-2-((2,3-difluoro-4-isopropoxyphenyl)(isopropyl)amino)-1H-indole-3-carboxylate (230 mg, 0.54 mmol) was dissolved in Diphenyl ether (10 mL) and the solution was refluxed for 1 hr. The mixture was cooled to RT. Hexane (20 mL) was added and the precipitate was collected by filtration. The precipitate was purified by silica gel chromatography (Hex:EA=2:1) to afford 3,4-Difluoro-2-isopropoxy-5-isopropyl-11-oxo-6,11-dihydro-5H-indolo[2,3-b]quinoline-8-carbonitrile (125 mg, 59% yield). $^1$H NMR (400 MHz, DMSO-d$_6$) δ 12.13 (s, 1H), 8.28 (d, J=8.0 Hz, 1H), 7.91 (d, J=1.4 Hz, 1H), 7.82 (dd, J=9.0, 1.9 Hz, 1H), 7.64 (dd, J=8.0, 1.4 Hz, 1H), 5.08-5.06 (m, 1H), 4.83-4.81 (m, 1H), 1.68 (dd, J=7.1, 2.1 Hz, 6H), 1.38 (d, J=6.0 Hz, 6H).

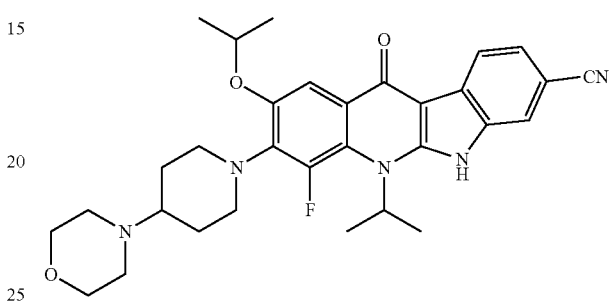

Step D: 4-Fluoro-2-isopropoxy-5-isopropyl-3-(4-morpholinopiperidin-1-yl)-11-oxo-6,11-dihydro-5H-indolo[2,3-b]quinoline-8-carbonitrile 4-Morpholinopiperidine (161 mg, 0.96 mmol) and DIPEA (0.5 ml) were added to a solution of 3,4-Difluoro-2-isopropoxy-5-isopropyl-11-oxo-6,11-dihydro-5H-indolo[2,3-b]quinoline-8-carbonitrile (125 mg, 0.32 mmol) in DMSO (2 ml) and the mixture was heated to 120 to 140° C. for 3 days. The reaction mixture was cooled to RT and purified by preparative HPLC to afford 4-Fluoro-2-isopropoxy-5-isopropyl-3-(4-morpholinopiperidin-1-yl)-11-oxo-6,11-dihydro-5H-indolo[2,3-b]quinoline-8-carbonitrile (35 mg, 20% yield). $^1$H NMR (300 MHz, CD$_3$OD) δ ppm 8.29 (d, J=8.0 Hz, 1H), 7.73-7.71 (m, 2H), 7.47 (d, J=8.0 Hz, 1H), 5.10-5.00 (m, 1H), 4.90-4.70 (m, 1H), 4.20-4.10 (m, 2H), 3.90-3.73 (m, 2H), 3.70-3.50 (m, 3H), 3.44-3.20 (m, 6H), 2.36-2.22 (m, 2H), 2.00-1.83 (m, 2H), 1.73 (dd, J=6.9, 1.8 Hz, 6H), 1.47 (d, J=6.0 Hz, 6H).

Example 50 (ALK-86)

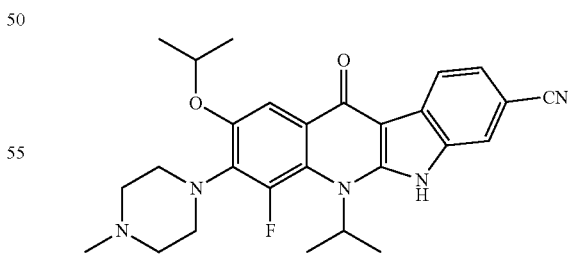

4-Fluoro-2-isopropoxy-5-isopropyl-3-(4-methylpiperazin-1-yl)-11-oxo-6,11-dihydro-5H-indolo[2,3-b]quinoline-8-carbonitrile 1-Methylpiperazine (0.5 mL) and DIPEA (0.5 ml) were added to a solution of 3,4-Difluoro-2-isopropoxy-5-isopropyl-11-oxo-6,11-dihydro-5H-indolo[2,3-b]quinoline-8-carbonitrile (125 mg, 0.32 mmol) in DMSO (2 ml) and the mixture was heated to 120 to 140° C. for 3 days. The reaction mixture was cooled to RT and purified by preparative HPLC to afford 4-Fluoro-2-isopropoxy-5-isopropyl-3-(4-morpholinopiperidin-1-yl)-11-oxo-6,11-dihydro-5H-indolo[2,3-b]quinoline-8-carbonitrile (52 mg, 35% yield). $^1$H NMR (300 MHz, CD$_3$OD) δ ppm 8.21 (d, J=8.0 Hz, 1H), 7.71 (s, 1H), 7.59 (s, 1H), 7.39 (d, J=8.0 Hz, 1H), 5.18-5.00 (m, 1H), 4.90-4.80 (m, 1H), 3.80-3.57 (m, 6H), 3.42-3.30 (m, 2H), 3.04 (s, 3H), 1.72 (dd, J=6.9, 1.8 Hz, 6H), 1.49 (d, J=6.0 Hz, 6H).

Example 51 (CJ-2204)

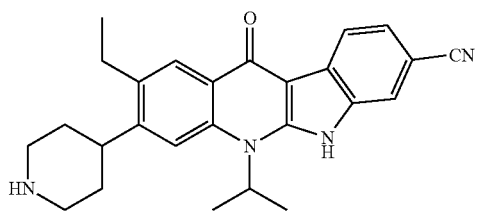 [SMILES: CCc1cc2c(=O)c3c4ccc(C#N)cc4[nH]c3n(C(C)C)c2cc1C1CCNCC1]

2-Ethyl-5-isopropyl-11-oxo-3-(piperidin-4-yl)-6,11-dihydro-5H-indolo[2,3-b]quinoline-8-carbonitrile

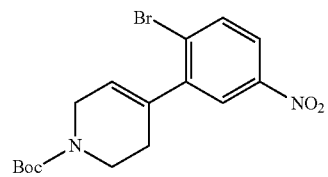 [SMILES: CC(C)(C)OC(=O)N1CC=C(c2cc([N+](=O)[O-])ccc2Br)CC1]

Step A: tert-Butyl 4-(2-bromo-5-nitrophenyl)-5,6-dihydropyridine-1(2H)-carboxylate tert-Butyl 4-(4,4,5,5-tetramethyl-1,3,2-dioxaborolan-2-yl)-5,6-dihydropyridine-1(2H)-carboxylate (471 mg, 1.52 mmol), Pd(dppf)Cl$_2$ (44 mg, 0.06 mmol), and K$_2$CO$_3$ (629 mg, 4.56 mmol) were added to a solution of 1-Bromo-2-iodo-4-nitrobenzene (500 mg, 1.52 mmol) in DME-H$_2$O (11 mL, 10:1 mixture). The mixture was stirred at 80° C. for 12 hr under nitrogen. The reaction was cooled to RT and the product was extracted with EtOAc. Solvent was removed under reduced pressure and the residue was purified by silica gel chromatography (Hex:EA=8:1) to afford tert-Butyl 4-(2-bromo-5-nitrophenyl)-5,6-dihydropyridine-1(2H)-carboxylate (470 mg, 80% yield). $^1$H NMR (300 MHz, CDCl$_3$) δ ppm 8.04 (d, J=2.7 Hz, 1H), 7.98 (dd, J=8.7, 2.7 Hz, 1H), 7.75 (d, J=8.7 Hz, 1H), 5.70-5.80 (m, 1H), 4.15-4.06 (m, 2H), 3.67 (t, J=5.6 Hz, 2H), 2.50-2.40 (m, 2H), 1.51 (s, 9H).

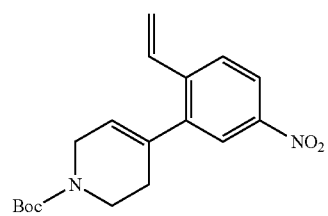 [SMILES: C=Cc1ccc([N+](=O)[O-])cc1C1=CCN(C(=O)OC(C)(C)C)CC1]

Step B: tert-Butyl 4-(5-nitro-2-vinylphenyl)-5,6-dihydropyridine-1(2H)-carboxylate 4,4,5,5-Tetramethyl-2-vinyl-1,3,2-dioxaborolane (80 mg, 0.52 mmol), Pd(dppf)Cl$_2$ (7.6 mg, 0.01 mmol), and K$_2$CO$_3$ (108 mg, 0.78 mmol) were added to a solution of tert-Butyl 4-(2-bromo-5-nitrophenyl)-5,6-dihydropyridine-1(2H)-carboxylate (100 mg, 0.26 mmol) in DME-H$_2$O (11 mL, 10:1 mixture). The mixture was stirred at 80° C. for 12 hr under nitrogen. The reaction was cooled to RT and the product was extracted with EtOAc. Solvent was removed under reduced pressure and the residue was purified by silica gel chromatography (Hex:EA=10:1) to afford tert-Butyl 4-(5-nitro-2-vinylphenyl)-5,6-dihydropyridine-1(2H)-carboxylate (68 mg, 79% yield). $^1$H NMR (300 MHz, CDCl$_3$) δ ppm 8.12 (dd, J=8.6, 2.4 Hz, 1H), 8.03 (d, J=2.4 Hz, 1H), 7.68 (d, J=8.6 Hz, 1H), 6.86 (dd, J=17.6, 11.1 Hz, 1H), 5.86 (d, J=17.6 Hz, 1H), 5.75-5.68 (m, 1H), 5.49 (d, J=11.1 Hz, 1H), 4.15-4.02 (m, 2H), 3.67 (t, J=5.6 Hz, 2H), 2.40-2.30 (m, 2H), 1.53 (s, 9H).

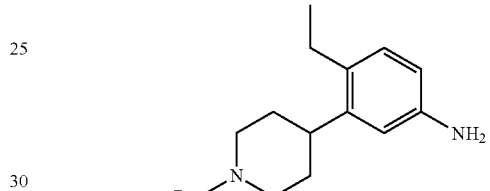

Step C: tert-Butyl 4-(5-amino-2-ethylphenyl)piperidine-1-carboxylate

10% Pd—C (140 mg) was added to a solution of tert-Butyl 4-(5-nitro-2-vinylphenyl)-5,6-dihydropyridine-1(2H)-carboxylate (1.4 g, 4.2 mmol) in Ethanol (20 mL) and the mixture underwent hydrogenation at RT overnight. The Pd—C was filtered off. Evaporation of Ethanol under reduced pressure afforded tert-Butyl 4-(5-amino-2-ethylphenyl)piperidine-1-carboxylate (1.2 g, 93% yield). $^1$H NMR (300 MHz, CDCl$_3$) δ ppm 6.97 (d, J=7.8 Hz, 1H), 6.58-6.40 (m, 2H), 4.38-4.18 (m, 2H), 2.90-2.70 (m, 3H), 2.57 (q, J=7.5 Hz, 2H), 1.75-1.50 (m, 4H), 1.49 (s, 9H), 1.16 (t, J=7.5 Hz, 3H).

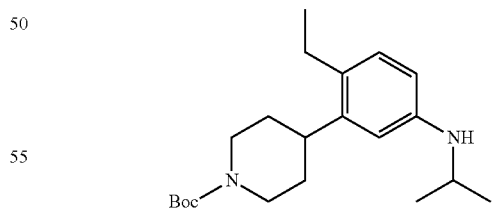

Step D: tert-Butyl 4-(2-ethyl-5-(isopropylamino)phenyl)piperidine-1-carboxylate

Acetone (2.28 g, 39.5 mmol), Acetic acid (0.356 g, 5.93 mmol), and Sodium triacetoxyborohydride (1.256 g, 5.93 mmol) were added to a solution of tert-Butyl 4-(5-amino-2-ethylphenyl)piperidine-1-carboxylate (1.2 g, 3.95 mmol) in DCM (120 mL) and the mixture was stirred at RT for 12 hr. Water was added to quench the reaction and the mixture was extracted with DCM. The solvent was removed under and the residue was purified by silica gel chromatography to afford tert-Butyl 4-(2-ethyl-5-(isopropylamino)phenyl)piperidine-1-carboxylate. (1.1 g, 81% yield). ¹H NMR (300 MHz, CDCl₃) δ ppm 6.98 (d, J=8.9 Hz, 1H), 6.45-6.40 (m, 2H), 4.30-4.20 (m, 2H), 3.65-3.50 (m, 1H), 2.82-2.70 (m, 3H), 2.56 (q, J=7.5 Hz, 2H), 1.75-1.51 (m, 4H), 1.49 (s, 9H), 1.25-1.13 (m, 9H).

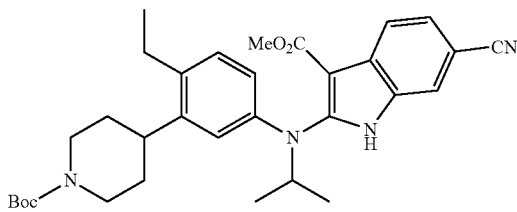 [SMILES: CCc1ccc(N(c2[nH]c3cc(C#N)ccc3c2C(=O)OC)C(C)C)cc1C1CCN(C(=O)OC(C)(C)C)CC1]

Step E: Methyl 2-((3-(1-(tert-butoxycarbonyl)piperidin-4-yl)-4-ethylphenyl)(isopropyl)amino)-6-cyano-1H-indole-3-carboxylate DABCO (123 mg, 1.1 mmol) was added to a solution of Methyl 6-cyano-1H-indole-3-carboxylate (400 mg, 2 mmol) in DCM (20 mL) and the mixture was cooled to 0° C. N-Chlorosuccinimide (293 mg, 2.2 mmol) was then added and the reaction was stirred at 0° C. for 2 hr. A solution of tert-Butyl 4-(2-ethyl-5-(isopropylamino)phenyl)piperidine-1-carboxylate (692 mg, 2 mmol) and Trichloroacetic acid (82 mg, 0.5 mmol) in DCM (5 mL) was added dropwise and the reaction was stirred for 2 hr at room temperature. The reaction was quenched by adding water and the mixture was extracted with DCM. Solvent was removed under vacuum and the residue was purified by silica gel chromatography (Hex:EA=4:1) to afford Methyl 2-((3-(1-(tert-butoxycarbonyl)piperidin-4-yl)-4-ethylphenyl)(isopropyl)amino)-6-cyano-1H-indole-3-carboxylate (470 mg, 43% yield). ¹H NMR (300 MHz, CDCl₃) δ ppm 8.27 (s, 1H), 8.02 (d, J=8.3 Hz, 1H), 7.40-7.35 (m, 2H), 7.21 (d, J=8.0 Hz, 1H), 7.00-6.85 (m, 2H), 4.98-4.78 (m, 1H), 4.36-4.20 (m, 2H), 3.84 (s, 3H), 3.00-2.72 (m, 3H), 2.70 (q, J=7.6 Hz, 2H), 1.75-1.50 (m, 4H), 1.46 (s, 9H), 1.25-1.20 (m, 9H).

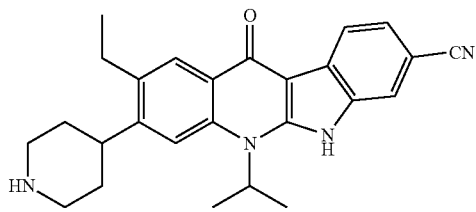 [SMILES: CCc1cc2c(=O)c3c4ccc(C#N)cc4[nH]c3n(C(C)C)c2cc1C1CCNCC1]

Step F: 2-Ethyl-5-isopropyl-11-oxo-3-(piperidin-4-yl)-6,11-dihydro-5H-indolo[2,3-b]quinoline-8-carbonitrile Methyl 2-((3-(1-(tert-butoxycarbonyl)piperidin-4-yl)-4-ethylphenyl)(isopropyl)amino)-6-cyano-1H-indole-3-carboxylate (200 mg, 0.54 mmol) was dissolved in Diphenyl ether (10 mL) and the solution was refluxed for 1 hr. The mixture was cooled to RT. Hexane (20 mL) was added and the precipitate was collected by filtration. The precipitate was purified by preparative-HPLC to afford 2-Ethyl-5-isopropyl-11-oxo-3-(piperidin-4-yl)-6,11-dihydro-5H-indolo[2,3-b]quinoline-8-carbonitrile (90 mg, 59% yield). ¹H NMR (300 MHz, DMSO-d6) δ ppm 12.42 (s, 1H), 8.30 (d, J=8.0 Hz, 1H), 8.21 (S, 1H), 7.89 (s, 1H), 7.66 (s, 1H), 7.61 (d, J=8.0 Hz, 1H), 5.35-5.25 (m, 1H), 3.50-3.05 (m, 5H), 2.84 (q, J=7.3 Hz, 2H), 2.15-1.93 (m, 4H), 1.79 (d, J=6.9 Hz, 6H), 1.26 (t, J=7.3 Hz, 3H).

Example 52 (CJ-2217)

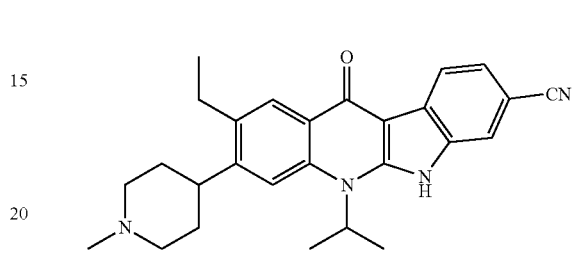

2-Ethyl-5-isopropyl-3-(1-methylpiperidin-4-yl)-11-oxo-6,11-dihydro-5H-indolo[2,3-b]quinoline-8-carbonitrile

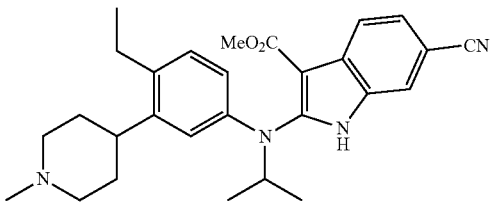 [SMILES: CCc1ccc(N(c2[nH]c3cc(C#N)ccc3c2C(=O)OC)C(C)C)cc1C1CCN(C)CC1]

Step A: Methyl 6-cyano-2-((4-ethyl-3-(1-methylpiperidin-4-yl)phenyl)(isopropyl)amino)-1H-indole-3-carboxylate TFA (1 mL) was added to a solution of Methyl 2-((3-(1-(tert-butoxycarbonyl)piperidin-4-yl)-4-ethylphenyl)(isopropyl)amino)-6-cyano-1H-indole-3-carboxylate (85 mg, 0.16 mmol) in DCM (5 mL) and the mixture was stirred at RT for 12 hr. Solvent was removed under reduced pressure and the residue was nutrilized with NaHCO₃ and extracted with EtOAc. EtOAc was removed under reduced pressure and the residue was dissolved in DCM (5 mL). 37% HCHO (38 mg, 0.47 mmol), Acetic acid (14 mg, 0.24 mmol), and NaBH(OAc)₃ (50 mg, 0.24 mmol) were then added and the reaction mixture was stirred at RT for 6 hr. Solvent was removed under reduced pressure and the product was extracted with EtOAc. EtOAc was evaporated under reduced pressure and the residue was purified by silica gel chromatography (EA:MeOH=80:20) to afford Methyl 6-cyano-2-((4-ethyl-3-(1-methylpiperidin-4-yl)phenyl)(isopropyl)amino)-1H-indole-3-carboxylate (70 mg, 98% yield). ¹H NMR (300 MHz, CDCl₃) δ ppm 8.30 (s, 1H), 8.02 (d, J=8.7 Hz, 1H), 7.40-7.30 (m, 2H), 7.18 (d, J=8.2 Hz, 1H), 7.06 (d, J=1.9 Hz, 1H), 6.88 (dd, J=8.2, 1.9 Hz, 1H), 4.90-4.75 (m, 1H), 3.82 (s, 3H), 3.15-3.00 (m, 2H), 2.85-2.75 (m, 1H), 2.20 (q, J=7.3 Hz, 2H), 2.37 (s, 3H), 2.25-2.10 (m, 2H), 1.90-1.65 (m, 4H), 1.25-1.12 (m, 9H).

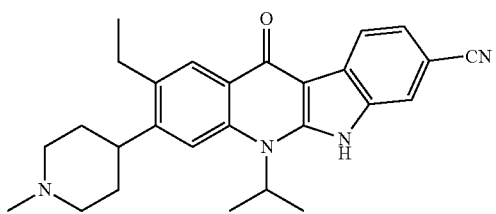 [SMILES: CCc1cc2c(=O)c3c4ccc(C#N)cc4[nH]c3n(C(C)C)c2cc1C1CCN(C)CC1]

Step B: 2-Ethyl-5-isopropyl-3-(1-methylpiperidin-4-yl)-11-oxo-6,11-dihydro-5H-indolo[2,3-b]quinoline-8-carbonitrile Methyl 6-cyano-2-((4-ethyl-3-(1-methylpiperidin-4-yl)phenyl)(isopropyl)amino)-1H-indole-3-carboxylate (70 mg, 0.15 mmol) was dissolved in Diphenyl ether (10 mL) and the solution was refluxed for 1 hr. The mixture was cooled to RT. Hexane (20 mL) was added and the precipitate was collected by filtration. The precipitate was purified by preparative-HPLC to afford 2-Ethyl-5-isopropyl-11-oxo-3-(piperidin-4-yl)-6,11-dihydro-5H-indolo[2,3-b]quinoline-8-carbonitrile (30 mg, 46% yield). $^1$H NMR (300 MHz, CD$_3$OD) δ ppm 8.22 (s, 1H), 8.19 (d, J=8.0 Hz, 1H), 7.74 (s, 1H), 7.61 (s, 1H), 7.32 (d, J=8.0 Hz, 1H), 5.30-5.20 (m, 1H), 3.64-3.59 (m, 2H), 3.32-3.13 (m, 3H), 2.99 (s, 3H), 2.92 (q, J=7.5 Hz, 2H), 2.20-2.02 (m, 4H), 1.88 (d, J=7.1 Hz, 6H), 1.35 (t, J=7.5 Hz, 3H).

Example 53 (CJ-2238)

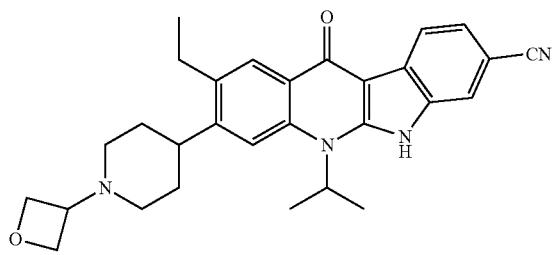 [SMILES: CCc1cc2c(=O)c3c4ccc(C#N)cc4[nH]c3n(C(C)C)c2cc1C1CCN(C2COC2)CC1]

2-Ethyl-5-isopropyl-3-(1-(oxetan-3-yl)piperidin-4-yl)-11-oxo-6,11-dihydro-5H-indolo[2,3-b]quinoline-8-carbonitrile

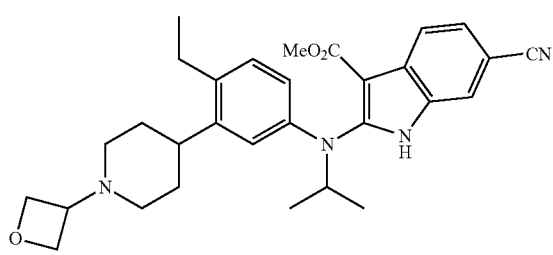 [SMILES: CCc1ccc(N(c2[nH]c3cc(C#N)ccc3c2C(=O)OC)C(C)C)cc1C1CCN(C2COC2)CC1]

Step A: Methyl 6-cyano-2-((4-ethyl-3-(1-(oxetan-3-yl)piperidin-4-yl)phenyl)(isopropyl)amino)-1H-indole-3-carboxylate TFA (1 mL) was added to a solution of Methyl 2-((3-(1-(tert-butoxycarbonyl)piperidin-4-yl)-4-ethylphenyl)(isopropyl)amino)-6-cyano-1H-indole-3-carboxylate (250 mg, 0.46 mmol) in DCM (5 mL) and the mixture was stirred at RT for 12 hr. Solvent was removed under reduced pressure and the residue was nutrilized with NaHCO$_3$ and extracted with EtOAc. EtOAc was removed under reduced pressure and the residue was dissolved in DCM (5 mL). Oxetan-3-one (99 mg, 1.38 mmol), Acetic acid (41 mg, 0.69 mmol), and NaBH(OAc)$_3$ (146 mg, 0.69 mmol) were then added and the reaction mixture was stirred at RT for 6 hr. Solvent was removed under reduced pressure and the product was extracted with EtOAc. EtOAc was evaporated under reduced pressure and the residue was purified by silica gel chromatography (EA:Hex=80:20) to afford Methyl 6-cyano-2-((4-ethyl-3-(1-(oxetan-3-yl)piperidin-4-yl)phenyl)(isopropyl)amino)-1H-indole-3-carboxylate (210 mg, 91% yield). $^1$H NMR (300 MHz, CDCl$_3$) δ ppm 8.02 (d, J=8.2 Hz, 1H), 7.89 (s, 1H), 7.37 (dd, J=8.2, 1.4 Hz, 1H), 7.31 (d, J=1.4 Hz, 1H), 7.23 (d, J=8.2 Hz, 1H), 7.08 (d, J=2.2 Hz, 1H), 6.95 (dd, J=8.2, 2.2 Hz, 1H), 4.95-4.80 (m, 1H), 4.75-4.55 (m, 4H), 3.86 (s, 3H), 3.60-3.40 (m, 1H), 2.95-2.60 (m, 5H), 2.00-1.70 (m, 6H), 1.27-1.15 (m, 9H).

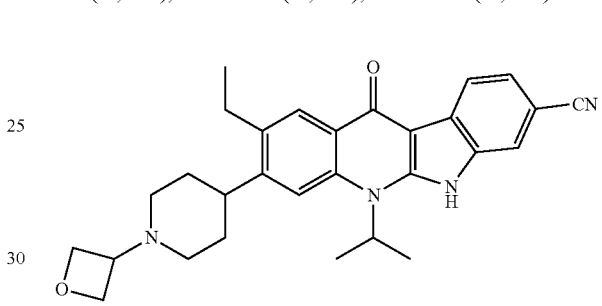

Step B: 2-Ethyl-5-isopropyl-3-(1-(oxetan-3-yl)piperidin-4-yl)-11-oxo-6,11-dihydro-5H-indolo[2,3-b]quinoline-8-carbonitrile Methyl 6-cyano-2-((4-ethyl-3-(1-(oxetan-3-yl)piperidin-4-yl)phenyl)(isopropyl)amino)-1H-indole-3-carboxylate (210 mg, 0.42 mmol) was dissolved in Diphenyl ether (10 mL) and the solution was refluxed for 1 hr. The mixture was cooled to RT. Hexane (20 mL) was added and the precipitate was collected by filtration. The precipitate was purified by preparative-HPLC to afford 2-Ethyl-5-isopropyl-3-(1-(oxetan-3-yl)piperidin-4-yl)-11-oxo-6,11-dihydro-5H-indolo[2,3-b]quinoline-8-carbonitrile (140 mg, 71% yield). $^1$H NMR (300 MHz, CD$_3$OD) δ ppm 8.27 (s, 1H), 8.21 (d, J=8.0 Hz, 1H), 7.75 (s, 1H), 7.63 (s, 1H), 7.35 (d, J=8.0 Hz, 1H), 5.40-5.30 (m, 1H), 5.25-4.85 (m, 4H), 4.60-4.40 (m, 1H), 3.75-3.60 (m, 2H), 3.50-3.10 (m, 3H), 2.90 (q, J=7.4 Hz, 2H), 2.45-2.20 (m, 4H), 1.89 (d, J=7.1 Hz, 6H), 1.35 (t, J=7.4 Hz, 3H).

Example 54 (CJ-2239)

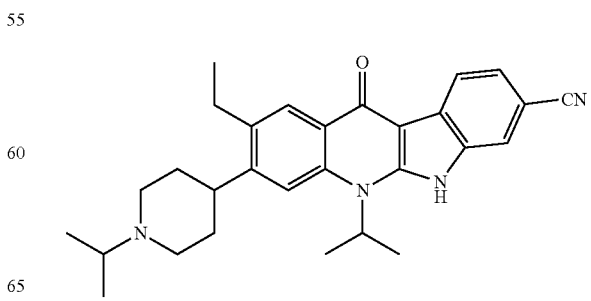

2-Ethyl-5-isopropyl-3-(1-isopropylpiperidin-4-yl)-11-oxo-6,11-dihydro-5H-indolo[2,3-b]quinoline-8-carbonitrile

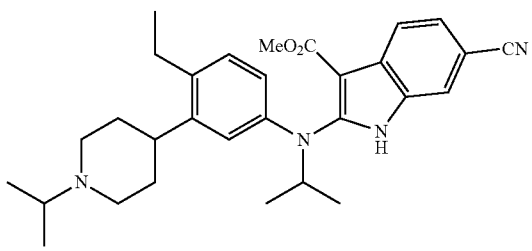 [SMILES: CCc1ccc(N(c2[nH]c3cc(C#N)ccc3c2C(=O)OC)C(C)C)cc1C1CCN(C(C)C)CC1]

Step A: Methyl 6-cyano-2-((4-ethyl-3-(1-isopropylpiperidin-4-yl)phenyl)(isopropyl)amino)-1H-indole-3-carboxylate TFA (1 mL) was added to a solution of Methyl 2-((3-(1-(tert-butoxycarbonyl)piperidin-4-yl)-4-ethylphenyl)(isopropyl)amino)-6-cyano-1H-indole-3-carboxylate (250 mg, 0.46 mmol) in DCM (5 mL) and the mixture was stirred at RT for 12 hr. Solvent was removed under reduced pressure and the residue was nutrilized with NaHCO₃ and extracted with EtOAc. EtOAc was removed under reduced pressure and the residue was dissolved in DCM (5 mL). Acetone (80 mg, 1.38 mmol), Acetic acid (41 mg, 0.69 mmol), and NaBH(OAc)₃ (146 mg, 0.69 mmol) were then added and the reaction mixture was stirred at RT for 12 hr. Solvent was removed under reduced pressure and the product was extracted with EtOAc. EtOAc was evaporated under reduced pressure and the residue was purified by silica gel chromatography (EA:MeOH=80:20) to afford Methyl 6-cyano-2-((4-ethyl-3-(1-isopropylpiperidin-4-yl)phenyl)(isopropyl)amino)-1H-indole-3-carboxylate (220 mg, 99% yield). ¹H NMR (300 MHz, CDCl₃) δ ppm 8.37 (s, 1H), 8.02 (d, J=8.6 Hz, 1H), 7.40-7.30 (m, 2H), 7.18 (d, J=8.2 Hz, 1H), 7.10 (d, J=2.2 Hz, 1H), 6.89 (dd, J=8.2, 2.2 Hz, 1H), 4.90-4.75 (m, 1H), 3.82 (s, 3H), 3.10-2.90 (m, 2H), 2.80-2.20 (m, 4H), 2.40-2.25 (m, 2H), 1.80-1.70 (m, 4H), 1.30-1.20 (m, 9H), 1.09 (d, J=6.5 Hz, 6H).

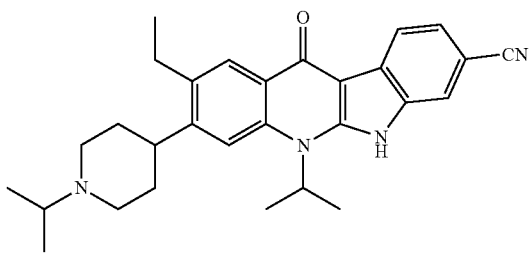 [SMILES: CCc1cc2c(=O)c3c4ccc(C#N)cc4[nH]c3n(C(C)C)c2cc1C1CCN(C(C)C)CC1]

Step B: 2-Ethyl-5-isopropyl-3-(1-isopropylpiperidin-4-yl)-11-oxo-6,11-dihydro-5H-indolo[2,3-b]quinoline-8-carbonitrile Methyl 6-cyano-2-((4-ethyl-3-(1-isopropylpiperidin-4-yl)phenyl)(isopropyl)amino)-1H-indole-3-carboxylate (220 mg, 0.45 mmol) was dissolved in Diphenyl ether (10 mL) and the solution was refluxed for 1 hr. The mixture was cooled to RT. Hexane (20 mL) was added and the precipitate was collected by filtration. The precipitate was purified by preparative-HPLC to 2-Ethyl-5-isopropyl-3-(1-isopropylpiperidin-4-yl)-11-oxo-6,11-dihydro-5H-indolo[2,3-b]quinoline-8-carbonitrile (100 mg, 49% yield). ¹H NMR (300 MHz, CD₃OD+CDCl₃) δ ppm 8.50-8.30 (m, 2H), 7.76 (s, 1H), 7.74 (s, 1H), 7.48 (dd, J=8.0, 1.3 Hz, 1H), 5.40-5.25 (m, 1H), 3.75-3.52 (m, 3H), 3.47-3.12 (m, 3H), 2.88 (q, J=7.5 Hz, 2H), 2.50-2.10 (m, 4H), 1.84 (d, J=7.1 Hz, 6H), 1.43 (d, J=6.7 Hz, 6H), 1.33 (t, J=7.5 Hz, 3H).

Example 55 (CJ-2240)

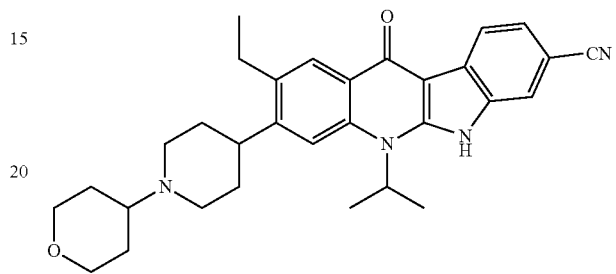

2-Ethyl-5-isopropyl-11-oxo-3-(1-(tetrahydro-2H-pyran-4-yl)piperidin-4-yl)-6,11-dihydro-5H-indolo[2,3-b]quinoline-8-carbonitrile

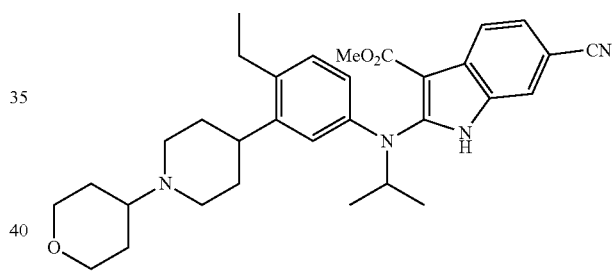

Step A: Methyl 6-cyano-2-((4-ethyl-3-(1-(tetrahydro-2H-pyran-4-yl)piperidin-4-yl)phenyl)(isopropyl)amino)-1H-indole-3-carboxylate TFA (1 mL) was added to a solution of Methyl 2-((3-(1-(tert-butoxycarbonyl)piperidin-4-yl)-4-ethylphenyl)(isopropyl)amino)-6-cyano-1H-indole-3-carboxylate (250 mg, 0.46 mmol) in DCM (5 mL) and the mixture was stirred at RT for 12 hr. Solvent was removed under reduced pressure and the residue was nutrilized with NaHCO₃ and extracted with EtOAc. EtOAc was removed under reduced pressure and the residue was dissolved in DCM (5 mL). Dihydro-2H-pyran-4(3H)-one (138 mg, 1.38 mmol), Acetic acid (41 mg, 0.69 mmol), and NaBH(OAc)₃ (146 mg, 0.69 mmol) were then added and the reaction mixture was stirred at RT for 12 hr. Solvent was removed under reduced pressure and the product was extracted with EtOAc. EtOAc was evaporated under reduced pressure and the residue was purified by silica gel chromatography (EA:MeOH=80:20) to afford Methyl 6-cyano-2-((4-ethyl-3-(1-(tetrahydro-2H-pyran-4-yl)piperidin-4-yl)phenyl)(isopropyl)amino)-1H-indole-3-carboxylate (240 mg, 99% yield). ¹H NMR (300 MHz, CDCl₃) δ ppm 8.17 (s, 1H), 8.02 (d, J=8.3 Hz, 1H), 7.35 (dd, J=8.3, 1.4 Hz, 1H), 7.34 (d, J=1.4 Hz, 1H), 7.20 (d, J=8.2 Hz, 1H), 7.08 (d, J=2.2 Hz, 1H), 6.92 (dd, J=8.2, 2.2 Hz, 1H), 4.90-4.78 (m, 1H), 4.10-3.95 (m, 2H), 3.84 (s, 3H), 3.45-3.25 (m, 2H), 3.20-3.00 (m, 2H), 2.80-2.50 (m, 4H), 2.40-2.25 (m, 2H), 1.80-1.55 (m, 8H), 1.25-1.15 (m, 9H).

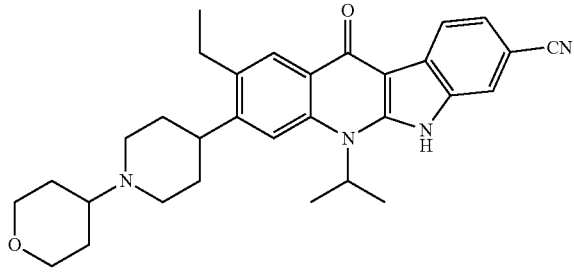 [SMILES: CCc1cc2c(=O)c3c4ccc(C#N)cc4[nH]c3n(C(C)C)c2cc1C1CCN(C2CCOCC2)CC1]

Step B: 2-Ethyl-5-isopropyl-11-oxo-3-(1-(tetrahydro-2H-pyran-4-yl)piperidin-4-yl)-6,11-dihydro-5H-indolo[2,3-b]quinoline-8-carbonitrile Methyl 6-cyano-2-((4-ethyl-3-(1-(tetrahydro-2H-pyran-4-yl)piperidin-4-yl)phenyl)(isopropyl)amino)-1H-indole-3-carboxylate (240 mg, 0.45 mmol) was dissolved in Diphenyl ether (10 mL) and the solution was refluxed for 1 hr. The mixture was cooled to RT. Hexane (20 mL) was added and the precipitate was collected by filtration. The precipitate was purified by preparative-HPLC to afford 2-Ethyl-5-isopropyl-11-oxo-3-(1-(tetrahydro-2H-pyran-4-yl)piperidin-4-yl)-6,11-dihydro-5H-indolo[2,3-b]quinoline-8-carbonitrile (80 mg, 36% yield). $^1$H NMR (300 MHz, CD$_3$OD+CDCl$_3$) δ ppm 8.43 (d, J=8.0 Hz, 1H), 8.41 (s, 1H), 7.75-7.67 (m, 2H), 7.53 (d, J=8.0 Hz, 1H), 5.40-5.20 (m, 1H), 4.20-4.10 (m, 2H), 3.75-3.62 (m, 2H), 3.55-3.40 (m, 3H), 3.35-3.02 (m, 3H), 2.88 (q, J=7.3 Hz, 2H), 2.60-2.30 (m, 2H), 2.20-1.90 (m, 6H), 1.83 (d, J=7.0 Hz, 6H), 1.34 (t, J=7.3 Hz, 3H).

Example 56 (CJ-2241)

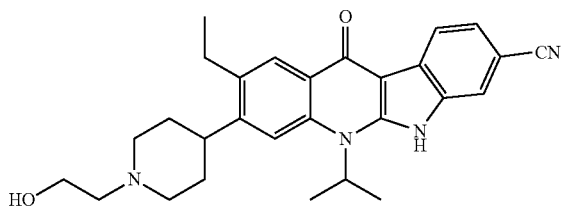 [SMILES: CCc1cc2c(=O)c3c4ccc(C#N)cc4[nH]c3n(C(C)C)c2cc1C1CCN(CCO)CC1]

2-Ethyl-3-(1-(2-hydroxyethyl)piperidin-4-yl)-5-isopropyl-11-oxo-6,11-dihydro-5H-indolo[2,3-b]quinoline-8-carbonitrile

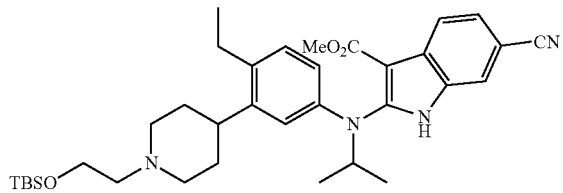 [SMILES: CCc1ccc(N(c2[nH]c3cc(C#N)ccc3c2C(=O)OC)C(C)C)cc1C1CCN(CCO[Si](C)(C)C(C)(C)C)CC1]

Step A: Methyl 2-((3-(1-(2-((tert-butyldimethylsilyl)oxy)ethyl)piperidin-4-yl)-4-ethylphenyl)(isopropyl)amino)-6-cyano-1H-indole-3-carboxylate TFA (1 mL) was added to a solution of Methyl 2-((3-(1-(tert-butoxycarbonyl)piperidin-4-yl)-4-ethylphenyl)(isopropyl)amino)-6-cyano-1H-indole-3-carboxylate (250 mg, 0.46 mmol) in DCM (5 mL) and the mixture was stirred at RT for 12 hr. Solvent was removed under reduced pressure and the residue was nutrilized with NaHCO$_3$ and extracted with EtOAc. EtOAc was removed under reduced pressure and the residue was dissolved in DCM (5 mL). 2-((tert-Butyldimethylsilyl)oxy)acetaldehyde (120 mg, 0.69 mmol), Acetic acid (41 mg, 0.69 mmol), and NaBH(OAc)$_3$ (146 mg, 0.69 mmol) were then added and the reaction mixture was stirred at RT for 6 hr. Solvent was removed under reduced pressure and the product was extracted with EtOAc. EtOAc was evaporated under reduced pressure and the residue was purified by silica gel chromatography (EtOAc) to afford Methyl 2-((3-(1-(2-((tert-butyldimethylsilyl)oxy)ethyl)piperidin-4-yl)-4-ethylphenyl)(isopropyl)amino)-6-cyano-1H-indole-3-carboxylate (250 mg, 90% yield). $^1$H NMR (300 MHz, CDCl$_3$) δ ppm 8.18 (s, 1H), 8.03 (d, J=8.3 Hz, 1H), 7.37 (dd, J=8.3, 1.4 Hz, 1H), 7.33 (d, J=1.4 Hz, 1H), 7.22 (d, J=8.2 Hz, 1H), 7.10 (d, J=2.2 Hz, 1H), 6.94 (dd, J=8.2, 2.2 Hz, 1H), 4.95-4.80 (m, 1H), 3.86 (s, 3H), 3.81 (t, J=6.5 Hz, 2H), 3.20-3.05 (m, 2H), 2.85-2.10 (m, 5H), 2.40-2.25 (m, 2H), 1.90-1.70 (m, 4H), 1.35-1.20 (m, 9H), 0.90 (s, 9H), 0.07 (s, 6H).

Example 56 (CJ-2241)

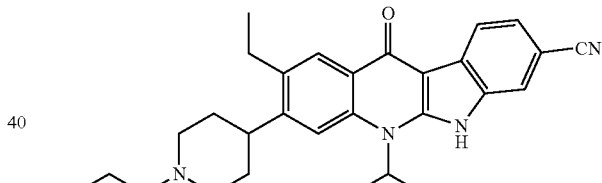

Step B: 2-Ethyl-3-(1-(2-hydroxyethyl)piperidin-4-yl)-5-isopropyl-11-oxo-6,11-dihydro-5H-indolo[2,3-b]quinoline-8-carbonitrile Methyl 2-((3-(1-(2-((tert-butyldimethylsilyl)oxy)ethyl)piperidin-4-yl)-4-ethylphenyl)(isopropyl)amino)-6-cyano-1H-indole-3-carboxylate (250 mg, 0.41 mmol) was dissolved in Diphenyl ether (10 mL) and the solution was refluxed for 1 hr. The mixture was cooled to RT. Hexane (20 mL) was added and the precipitate was collected by filtration. The precipitate was dissolved in MeOH (10 mL) and the solution was treated with KHSO$_4$ (278 mg, 2.05 mmol). The mixture was stirred at RT for 12 hr. Solvent was removed under reduced pressure and the residue was purified by preparative-HPLC to afford 2-Ethyl-3-(1-(2-hydroxyethyl)piperidin-4-yl)-5-isopropyl-11-oxo-6,11-dihydro-5H-indolo[2,3-b]quinoline-8-carbonitrile (70 mg, 37% yield). $^1$H NMR (300 MHz, CD$_3$OD+CDCl$_3$) δ ppm 8.44 (d, J=8.1 Hz, 1H), 8.42 (s, 1H), 7.79 (s, 1H), 7.77 (s, 1H), 7.56 (d, J=8.1 Hz, 1H), 5.40-5.25 (m, 1H), 4.00-3.75 (m, 4H), 3.45-3.20 (m, 5H), 2.91 (q, J=7.5 Hz, 2H), 2.50-2.10 (m, 4H), 1.88 (d, J=7.1 Hz, 6H), 1.36 (t, J=7.5 Hz, 3H).

Example 57 (CJ-2212)

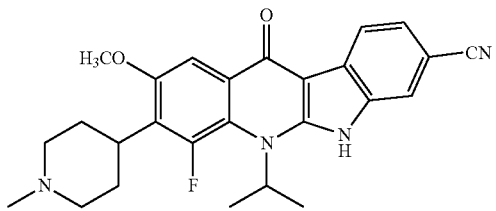 [SMILES: COc1cc2c(=O)c3c4ccc(C#N)cc4[nH]c3n(C(C)C)c2c(F)c1C1CCN(C)CC1]

4-Fluoro-5-isopropyl-2-methoxy-3-(1-methylpiperidin-4-yl)-11-oxo-6,11-dihydro-5H-indolo[2,3-b]quinoline-8-carbonitrile

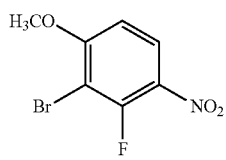 [SMILES: COc1ccc([N+](=O)[O-])c(F)c1Br]

Step A:
2-Bromo-3-fluoro-1-methoxy-4-nitrobenzene

25% Sodium methoxide (0.9 g, 4.2 mmol) was added dropwise to a solution of 2-Bromo-1,3-difluoro-4-nitrobenzene (1 g, 4.2 mmol) in MeOH (5 mL) and the mixture was stirred at 0° C. for 1 hr and RT for 4 hr. The reaction was quenched by addition of water and the product was extracted with EtOAc. Solvent was removed under reduced pressure and the residue was purified by silica gel chromatography (Hex:EA=10:1) to afford 2-Bromo-3-fluoro-1-methoxy-4-nitrobenzene (0.58 g, 55% yield). $^1$H NMR (300 MHz, CDCl$_3$) δ ppm 8.14 (dd, J=9.3, 8.3 Hz, 1H), 6.80 (dd, J=9.3, 1.7 Hz, 1H), 4.03 (s, 3H).

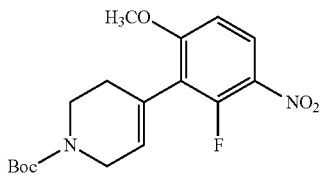 [SMILES: COc1ccc([N+](=O)[O-])c(F)c1C1=CCN(C(=O)OC(C)(C)C)CC1]

Step B: tert-Butyl 4-(2-fluoro-6-methoxy-3-nitrophenyl)-5,6-dihydropyridine-1(2H)-carboxylate tert-Butyl 4-(4,4,5,5-tetramethyl-1,3,2-dioxaborolan-2-yl)-5,6-dihydropyridine-1(2H)-carboxylate (1.854 g, 6 mmol), Pd(dppf)Cl$_2$ (117 mg, 0.16 mmol), and K$_2$CO$_3$ (1.656 g, 12 mmol) were added to a solution of 1-Bromo-2-iodo-4-nitrobenzene (1 g, 4 mmol) in DME-H$_2$O (22 mL, 10:1 mixture). The mixture was stirred at 80° C. for 12 hr under nitrogen. The reaction was cooled to RT and the product was extracted with EtOAc. Solvent was removed under reduced pressure and the residue was purified by silica gel chromatography (Hex:EA=3:1) to afford tert-Butyl 4-(2-fluoro-6-methoxy-3-nitrophenyl)-5,6-dihydropyridine-1(2H)-carboxylate (1.3 g, 92% yield). $^1$H NMR (300 MHz, CDCl$_3$) δ ppm 8.06 (m, 1H), 6.74 (d, J=9.3 Hz, 1H), 5.72 (s, 1H), 4.15-4.03 (m, 2H), 3.82 (s, 3H), 3.70-3.60 (m, 2H), 2.40-2.30 (m, 2H), 1.50 (s, 9H).

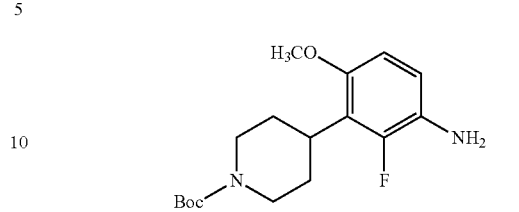

Step C: tert-Butyl 4-(3-amino-2-fluoro-6-methoxyphenyl)piperidine-1-carboxylate

10% Pd—C (140 mg) was added to a solution of tert-Butyl 4-(2-fluoro-6-methoxy-3-nitrophenyl)-5,6-dihydropyridine-1(2H)-carboxylate (1.3 g, 3.69 mmol) in Ethanol (20 mL) and the mixture underwent hydrogenation at RT overnight. The Pd—C was filtered off. Evaporation of Ethanol under reduced pressure afforded tert-Butyl 4-(3-amino-2-fluoro-6-methoxyphenyl)piperidine-1-carboxylate (1.1 g, 92% yield). $^1$H NMR (300 MHz, CDCl$_3$) δ ppm 6.65-6.45 (m, 2H), 4.30-4.10 (m, 2H), 3.74 (s, 3H), 3.43 (s, 2H), 3.30-3.20 (m, 1H), 2.80-2.70 (m, 2H), 2.20-2.00 (m, 2H), 1.70-1.55 (m, 2H), 1.49 (s, 9H).

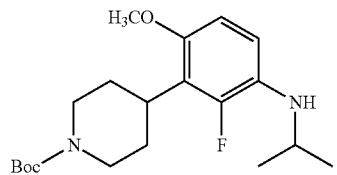 [SMILES: COc1ccc(NC(C)C)c(F)c1C1CCN(C(=O)OC(C)(C)C)CC1]

Step D: tert-Butyl 4-(2-fluoro-3-(isopropylamino)-6-methoxyphenyl)piperidine-1-carboxylate Acetone (1.74 g, 30 mmol), Acetic acid (0.27 g, 4.5 mmol), and Sodium triacetoxyborohydride (0.98 g, 4.5 mmol) were added to a solution of tert-Butyl 4-(3-amino-2-fluoro-6-methoxyphenyl)piperidine-1-carboxylate (1.0 g, 3 mmol) in DCM (20 mL) and the mixture was stirred at RT for 12 hr. Water was added to quench the reaction and the mixture was extracted with DCM. The solvent was removed under and the residue was purified by silica gel chromatography to afford tert-Butyl 4-(2-fluoro-3-(isopropylamino)-6-methoxyphenyl)piperidine-1-carboxylate. (1.06 g, 94% yield). $^1$H NMR (300 MHz, CDCl$_3$) δ ppm 6.58-6.44 (m, 2H), 4.30-4.10 (m, 2H), 3.74 (s, 3H), 3.60-3.50 (m, 1H), 3.74 (s, 1H), 3.30-3.17 (m, 1H), 2.83-2.70 (m, 2H), 2.40-2.00 (m, 2H), 1.63-1.55 (m, 2H), 1.49 (s, 9H), 1.21 (d, J=6.2 Hz, 6H).

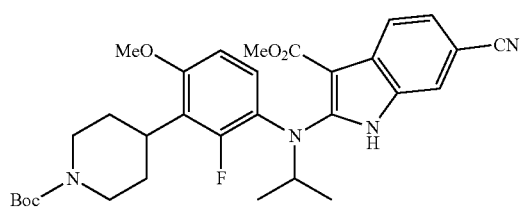 [SMILES: COC(=O)c1c(N(c2ccc(OC)c(C3CCN(C(=O)OC(C)(C)C)CC3)c2F)C(C)C)[nH]c2cc(C#N)ccc12]

Step E: Methyl 2-((3-(1-(tert-butoxycarbonyl)piperidin-4-yl)-2-fluoro-4-methoxyphenyl)(isopropyl)amino)-6-cyano-1H-indole-3-carboxylate DABCO (84 mg, 0.75 mmol) was added to a solution of Methyl 6-cyano-1H-indole-3-carboxylate (273 mg, 1.366 mmol) in DCM (20 mL) and the mixture was cool to 0° C. N-Chlorosuccinimide (200 mg, 1.5 mmol) was then added and the reaction was stirred at 0° C. for 2 hr. A solution of tert-Butyl 4-(2-fluoro-3-(isopropylamino)-6-methoxyphenyl)piperidine-1-carboxylate (500 mg, 1.366 mmol) and Trichloroacetic acid (56 mg, 0.342 mmol) in DCM (10 mL) was added dropwise and the reaction was stirred for 2 hr at room temperature. The reaction was quenched by adding water and the mixture was extracted with DCM. Solvent was removed under vacuum and the residue was purified by silica gel chromatography (Hex:EA=4:1) to afford Methyl 2-((3-(1-(tert-butoxycarbonyl)piperidin-4-yl)-2-fluoro-4-methoxyphenyl)(isopropyl)amino)-6-cyano-1H-indole-3-carboxylate (530 mg, 69% yield). $^1$H NMR (300 MHz, CDCl$_3$) δ ppm 8.34 (s, 1H), 7.96 (d, J=8.2 Hz, 1H), 7.40-7.30 (m, 2H), 7.18 (t, J=8.7 Hz, 1H), 6.72 (dd, J=8.7, 1.1 Hz, 1H), 4.90-4.75 (m, 1H), 4.25-4.10 (m, 2H), 3.86 (s, 3H), 3.84 (s, 3H), 3.30-3.20 (m, 1H), 2.80-2.65 (m, 2H), 2.20-2.00 (m, 2H), 1.65-1.50 (m, 2H), 1.46 (s, 9H), 1.20 (d, J=6.5 Hz, 6H).

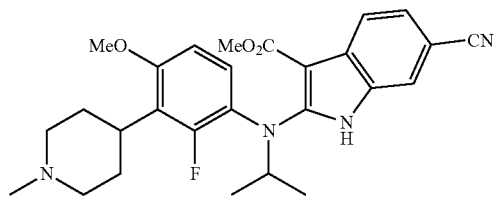 [SMILES: COC(=O)c1c(N(c2ccc(OC)c(C3CCN(C)CC3)c2F)C(C)C)[nH]c2cc(C#N)ccc12]

Step F: Methyl 6-cyano-2-((2-fluoro-4-methoxy-3-(1-methylpiperidin-4-yl)phenyl)(isopropyl)amino)-1H-indole-3-carboxylate TFA (1 mL) was added to a solution of Methyl 2-((3-(1-(tert-butoxycarbonyl)piperidin-4-yl)-2-fluoro-4-methoxyphenyl)(isopropyl)amino)-6-cyano-1H-indole-3-carboxylate (240 mg, 0.425 mmol) in DCM (5 mL) and the mixture was stirred at RT for 12 hr. Solvent was removed under reduced pressure and the residue was nutrilized with NaHCO$_3$ and extracted with EtOAc. EtOAc was removed under reduced pressure and the residue was dissolved in DCM (5 mL). 37% HCHO (100 mg, 1.28 mmol), Acetic acid (38 mg, 0.64 mmol), and NaBH(OAc)$_3$ (135 mg, 0.64 mmol) were then added and the reaction mixture was stirred at RT for 6 hr. Solvent was removed under reduced pressure and the product was extracted with EtOAc. EtOAc was evaporated under reduced pressure and the residue was purified by silica gel chromatography (EA:MeOH=80:20) to afford Methyl 6-cyano-2-((2-fluoro-4-methoxy-3-(1-methylpiperidin-4-yl)phenyl)(isopropyl)amino)-1H-indole-3-carboxylate (180 mg, 89% yield). $^1$H NMR (300 MHz, CDCl$_3$) δ ppm 8.85 (s, 1H), 7.94 (d, J=8.3 Hz, 1H), 7.38 (s, 1H), 7.32 (d, J=8.3 Hz, 1H), 7.15 (t, J=8.7 Hz, 1H), 6.69 (d, J=8.7 Hz, 1H), 4.95-4.80 (m, 1H), 3.83 (s, 3H), 3.81 (s, 3H), 3.20-3.00 (m, 3H), 2.45-2.25 (m, 2H), 2.35 (s, 3H), 2.20-2.02 (m, 2H), 1.73-1.60 (m, 2H), 1.19 (d, J=6.6 Hz, 6H).

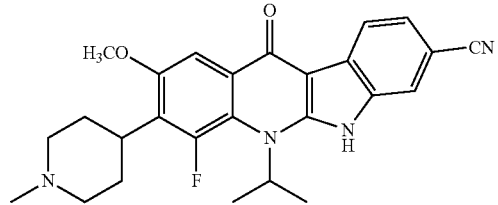 [SMILES: COc1cc2c(=O)c3c4ccc(C#N)cc4[nH]c3n(C(C)C)c2c(F)c1C1CCN(C)CC1]

Step G: 4-Fluoro-5-isopropyl-2-methoxy-3-(1-methylpiperidin-4-yl)-11-oxo-6,11-dihydro-5H-indolo[2,3-b]quinoline-8-carbonitrile Methyl 6-cyano-2-((2-fluoro-4-methoxy-3-(1-methylpiperidin-4-yl)phenyl)(isopropyl)amino)-1H-indole-3-carboxylate (180 mg, 0.38 mmol) was dissolved in Diphenyl ether (10 mL) and the solution was refluxed for 1 hr. The mixture was cooled to RT. Hexane (20 mL) was added and the precipitate was collected by filtration. The precipitate was purified by preparative-HPLC to afford 4-Fluoro-5-isopropyl-2-methoxy-3-(1-methylpiperidin-4-yl)-11-oxo-6,11-dihydro-5H-indolo[2,3-b]quinoline-8-carbonitrile (100 mg, 59% yield). $^1$H NMR (300 MHz, CD$_3$OD) δ ppm 8.25 (d, J=8.0 Hz, 1H), 7.76 (s, 1H), 7.67 (s, 1H), 7.44 (d, J=8.0 Hz, 1H), 5.10-5.00 (m, 1H), 4.03 (s, 3H), 3.80-3.62 (m, 3H), 3.30-3.12 (m, 2H), 2.96 (s, 3H), 2.80-2.60 (m, 2H), 2.18-2.00 (m, 2H), 1.73 (dd, J=7.0, 2.0 Hz, 6H).

Example 58 (CJ-2224)

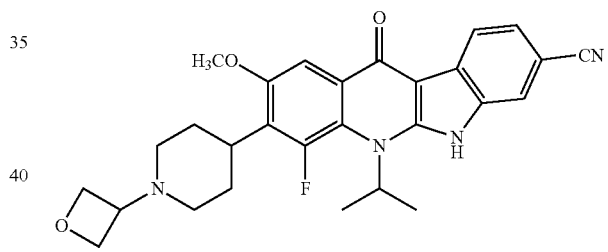

4-Fluoro-5-isopropyl-2-methoxy-3-(1-(oxetan-3-yl)piperidin-4-yl)-11-oxo-6,11-dihydro-5H-indolo[2,3-b]quinoline-8-carbonitrile

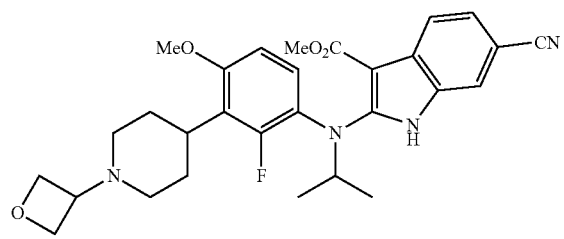 [SMILES: COC(=O)c1c(N(c2ccc(OC)c(C3CCN(C4COC4)CC3)c2F)C(C)C)[nH]c2cc(C#N)ccc12]

Step A: Methyl 6-cyano-2-((2-fluoro-4-methoxy-3-(1-(oxetan-3-yl)piperidin-4-yl)phenyl)(isopropyl)amino)-1H-indole-3-carboxylate TFA (1 mL) was added to a solution of Methyl 2-((3-(1-(tert-butoxycarbonyl)piperidin-4-yl)-2-fluoro-4-methoxyphenyl)(isopropyl)amino)-6-cyano-1H-indole-3-carboxylate (365 mg, 0.647 mmol) in DCM (5 mL) and the mixture was stirred at RT for 12 hr. Solvent was removed under reduced pressure and the residue was nutrilized with NaHCO₃ and extracted with EtOAc. EtOAc was removed under reduced pressure and the residue was dissolved in DCM (5 mL). Cyclobutanone (140 mg, 1.94 mmol), Acetic acid (58 mg, 0.97 mmol), and NaBH(OAc)₃ (206 mg, 0.97 mmol) were then added and the reaction mixture was stirred at RT for 6 hr. Solvent was removed under reduced pressure and the product was extracted with EtOAc. EtOAc was evaporated under reduced pressure and the residue was purified by silica gel chromatography (EA:MeOH=80:20) to afford Methyl 6-cyano-2-((2-fluoro-4-methoxy-3-(1-(oxetan-3-yl)piperidin-4-yl)phenyl)(isopropyl)amino)-1H-indole-3-carboxylate (190 mg, 58% yield). ¹H NMR (300 MHz, CDCl₃) δ ppm 8.20 (s, 1H), 7.96 (d, J=8.2 Hz, 1H), 7.48-7.30 (m, 2H), 7.17 (t, J=8.7 Hz, 1H), 6.73 (d, J=8.7 Hz, 1H), 4.95-4.80 (m, 1H), 4.64 (d, J=6.7 Hz, 4H), 3.88 (s, 3H), 3.85 (s, 3H), 3.51-3.49 (m, 1H), 3.25-3.05 (m, 1H), 2.95-2.75 (m, 2H), 2.45-2.25 (m, 2H), 2.00-1.80 (m, 2H), 1.73-1.60 (m, 2H), 1.20 (d, J=6.5 Hz, 6H).

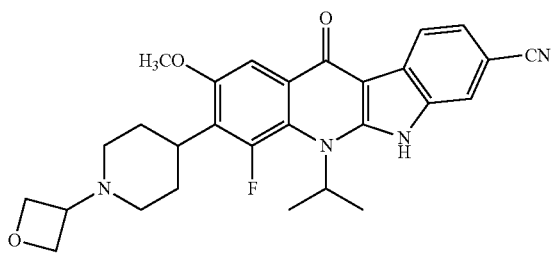 [SMILES: COc1cc2c(=O)c3c4ccc(C#N)cc4[nH]c3n(C(C)C)c2c(F)c1C1CCN(C2COC2)CC1]

Step B: 4-Fluoro-5-isopropyl-2-methoxy-3-(1-(oxetan-3-yl)piperidin-4-yl)-11-oxo-6,11-dihydro-5H-indolo[2,3-b]quinoline-8-carbonitrile Methyl 6-cyano-2-((2-fluoro-4-methoxy-3-(1-(oxetan-3-yl)piperidin-4-yl)phenyl)(isopropyl)amino)-1H-indole-3-carboxylate (190 mg, 0.37 mmol) was dissolved in Diphenyl ether (10 mL) and the solution was refluxed for 1 hr. The mixture was cooled to RT. Hexane (20 mL) was added and the precipitate was collected by filtration. The precipitate was purified by preparative-HPLC to afford 4-Fluoro-5-isopropyl-2-methoxy-3-(1-(oxetan-3-yl)piperidin-4-yl)-11-oxo-6,11-dihydro-5H-indolo[2,3-b]quinoline-8-carbonitrile (90 mg, 51% yield). ¹H NMR (300 MHz, CD₃OD) δ ppm 8.28 (d, J=8.0 Hz, 1H), 7.78 (d, J=1.1 Hz, 1H), 7.69 (d, J=0.7 Hz, 1H), 7.46 (dd, J=8.0, 1.1 Hz, 1H), 5.18-5.02 (m, 1H), 4.95-4.80 (m, 4H), 4.55-4.40 (m, 1H), 4.04 (s, 3H), 3.80-3.60 (m, 3H), 3.20-3.10 (m, 2H), 2.80-2.60 (m, 2H), 2.18-2.02 (m, 2H), 1.74 (dd, J=7.0, 2.1 Hz, 6H).

Example 59 (CJ-2225)

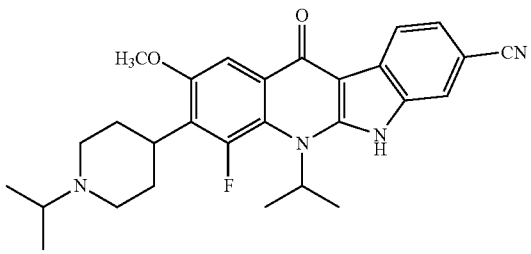 [SMILES: COc1cc2c(=O)c3c4ccc(C#N)cc4[nH]c3n(C(C)C)c2c(F)c1C1CCN(C(C)C)CC1]

4-Fluoro-5-isopropyl-3-(1-isopropylpiperidin-4-yl)-2-methoxy-11-oxo-6,11-dihydro-5H-indolo[2,3-b]quinoline-8-carbonitrile

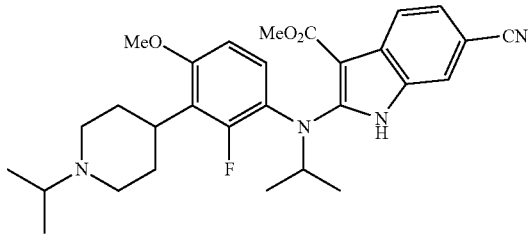 [SMILES: COC(=O)c1c(N(c2ccc(OC)c(C3CCN(C(C)C)CC3)c2F)C(C)C)[nH]c2cc(C#N)ccc12]

Step A: Methyl 6-cyano-2-((2-fluoro-3-(1-isopropylpiperidin-4-yl)-4-methoxyphenyl)(isopropyl)amino)-1H-indole-3-carboxylate TFA (1 mL) was added to a solution of Methyl 2-((3-(1-(tert-butoxycarbonyl)piperidin-4-yl)-2-fluoro-4-methoxyphenyl)(isopropyl)amino)-6-cyano-1H-indole-3-carboxylate (365 mg, 0.647 mmol) in DCM (5 mL) and the mixture was stirred at RT for 12 hr. Solvent was removed under reduced pressure and the residue was nutrilized with NaHCO₃ and extracted with EtOAc. EtOAc was removed under reduced pressure and the residue was dissolved in DCM (5 mL). Acetone (113 mg, 1.94 mmol), Acetic acid (58 mg, 0.97 mmol), and NaBH(OAc)₃ (206 mg, 0.97 mmol) were then added and the reaction mixture was stirred at RT for 12 hr. Solvent was removed under reduced pressure and the product was extracted with EtOAc. EtOAc was evaporated under reduced pressure and the residue was purified by silica gel chromatography (EA:MeOH=80:20) to afford Methyl 6-cyano-2-((2-fluoro-3-(1-isopropylpiperidin-4-yl)-4-methoxyphenyl)(isopropyl)amino)-1H-indole-3-carboxylate (150 mg, 46% yield). ¹H NMR (300 MHz, CDCl₃) δ ppm 7.98-7.90 (m, 2H), 7.35 (dd, J=8.3, 1.4 Hz, 1H), 7.31 (d, J=1.4 Hz, 1H), 7.16 (t, J=8.8 Hz, 1H), 6.72 (d, J=8.8 Hz, 1H), 4.95-4.80 (m, 1H), 3.87 (s, 6H), 3.20-2.75 (m, 4H), 2.40-2.20 (m, 4H), 1.75-1.55 (m, 2H), 1.19 (d, J=6.4 Hz, 6H), 1.08 (d, J=6.5 Hz, 6H).

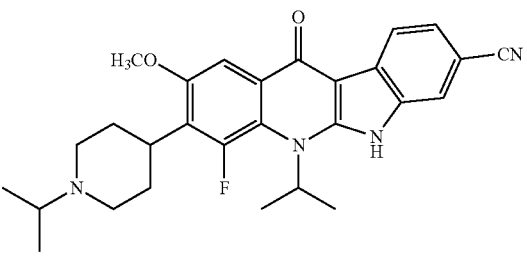 [SMILES: COc1cc2c(=O)c3c4ccc(C#N)cc4[nH]c3n(C(C)C)c2c(F)c1C1CCN(C(C)C)CC1]

Step B: 4-Fluoro-5-isopropyl-3-(1-isopropylpiperidin-4-yl)-2-methoxy-11-oxo-6,11-dihydro-5H-indolo[2,3-b]quinoline-8-carbonitrile Methyl 6-cyano-2-((2-fluoro-3-(1-isopropylpiperidin-4-yl)-4-methoxyphenyl)(isopropyl)amino)-1H-indole-3-carboxylate (150 mg, 0.296 mmol) was dissolved in Diphenyl ether (10 mL) and the solution was refluxed for 1 hr. The mixture was cooled to RT. Hexane (20 mL) was added and the precipitate was collected by filtration. The precipitate was purified by preparative-HPLC to afford 4-Fluoro-5-isopropyl-3-(1-isopropylpiperidin-4-yl)-2-methoxy-11-oxo-6,11-dihydro-5H-indolo[2,3-b]quinoline-8-carbonitrile (35 mg, 25% yield). $^1$H NMR (300 MHz, CD$_3$OD) δ ppm 8.26 (d, J=8.0 Hz, 1H), 7.76 (s, 1H), 7.68 (s, 1H), 7.44 (d, J=8.0 Hz, 1H), 5.10-5.00 (m, 1H), 4.03 (s, 3H), 3.80-3.50 (m, 4H), 3.30-3.20 (m, 2H), 2.80-2.60 (m, 2H), 2.15-2.03 (m, 2H), 1.73 (dd, J=7.0, 2.0 Hz, 6H), 1.45 (d, J=6.7 Hz, 6H).

Example 60 (CJ-2226)

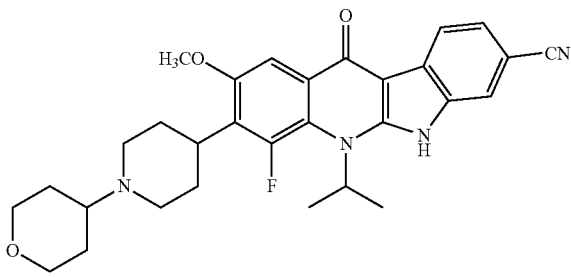 [SMILES: COc1cc2c(=O)c3c4ccc(C#N)cc4[nH]c3n(C(C)C)c2c(F)c1C1CCN(C2CCOCC2)CC1]

4-Fluoro-5-isopropyl-2-methoxy-11-oxo-3-(1-(tetrahydro-2H-pyran-4-yl)piperidin-4-yl)-6,11-dihydro-5H-indolo[2,3-b]quinoline-8-carbonitrile

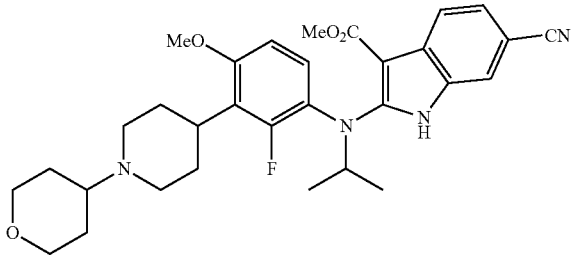 [SMILES: COC(=O)c1c(N(c2ccc(OC)c(C3CCN(C4CCOCC4)CC3)c2F)C(C)C)[nH]c2cc(C#N)ccc12]

Step A: Methyl 6-cyano-2-((2-fluoro-4-methoxy-3-(1-(tetrahydro-2H-pyran-4-yl)piperidin-4-yl)phenyl)(isopropyl)amino)-1H-indole-3-carboxylate TFA (1 mL) was added to a solution of Methyl 2-((3-(1-(tert-butoxycarbonyl)piperidin-4-yl)-2-fluoro-4-methoxyphenyl)(isopropyl)amino)-6-cyano-1H-indole-3-carboxylate (365 mg, 0.647 mmol) in DCM (5 mL) and the mixture was stirred at RT for 12 hr. Solvent was removed under reduced pressure and the residue was nutrilized with NaHCO$_3$ and extracted with EtOAc. EtOAc was removed under reduced pressure and the residue was dissolved in DCM (5 mL). Dihydro-2H-pyran-4(3H)-one (194 mg, 1.94 mmol), Acetic acid (58 mg, 0.97 mmol), and NaBH(OAc)$_3$ (206 mg, 0.97 mmol) were then added and the reaction mixture was stirred at RT for 12 hr. Solvent was removed under reduced pressure and the product was extracted with EtOAc. EtOAc was evaporated under reduced pressure and the residue was purified by silica gel chromatography (EA:MeOH=80:20) to afford Methyl 6-cyano-2-((2-fluoro-4-methoxy-3-(1-(tetrahydro-2H-pyran-4-yl)piperidin-4-yl)phenyl)(isopropyl)amino)-1H-indole-3-carboxylate (140 mg, 39% yield). $^1$H NMR (300 MHz, CDCl$_3$) δ ppm 8.55 (s, 1H), 7.95 (d, J=8.3 Hz, 1H), 7.40-7.27 (m, 2H), 7.16 (t, J=8.7 Hz, 1H), 6.70 (d, J=8.7 Hz, 1H), 4.95-4.75 (m, 1H), 4.12-4.00 (m, 2H), 3.84 (s, 3H), 3.82 (s, 3H), 3.45-3.25 (m, 2H), 3.15-3.02 (m, 3H), 2.75-2.27 (m, 5H), 1.80-1.60 (m, 6H), 1.20 (d, J=6.5 Hz, 6H).

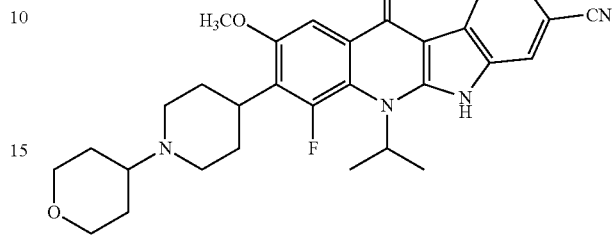

Step B: 4-Fluoro-5-isopropyl-2-methoxy-11-oxo-3-(1-(tetrahydro-2H-pyran-4-yl)piperidin-4-yl)-6,11-dihydro-5H-indolo[2,3-b]quinoline-8-carbonitrile Methyl 6-cyano-2-((2-fluoro-4-methoxy-3-(1-(tetrahydro-2H-pyran-4-yl)piperidin-4-yl)phenyl)(isopropyl)amino)-1H-indole-3-carboxylate (140 mg, 0.255 mmol) was dissolved in Diphenyl ether (10 mL) and the solution was refluxed for 1 hr. The mixture was cooled to RT. Hexane (20 mL) was added and the precipitate was collected by filtration. The precipitate was purified by preparative-HPLC to afford 4-Fluoro-5-isopropyl-2-methoxy-11-oxo-3-(1-(tetrahydro-2H-pyran-4-yl)piperidin-4-yl)-6,11-dihydro-5H-indolo[2,3-b]quinoline-8-carbonitrile (70 mg, 53% yield). $^1$H NMR (300 MHz, CD$_3$OD) δ ppm 8.25 (d, J=8.0 Hz, 1H), 7.75 (s, 1H), 7.66 (s, 1H), 7.43 (d, J=8.0 Hz, 1H), 5.15-4.95 (m, 1H), 4.20-4.07 (m, 2H), 4.03 (s, 3H), 3.82-3.70 (m, 3H), 3.60-3.40 (m, 3H), 3.30-3.20 (m, 2H), 2.80-2.60 (m, 2H), 2.20-1.80 (m, 6H), 1.73 (dd, J=6.9, 1.8 Hz, 6H).

Example 61 (CJ-2227)

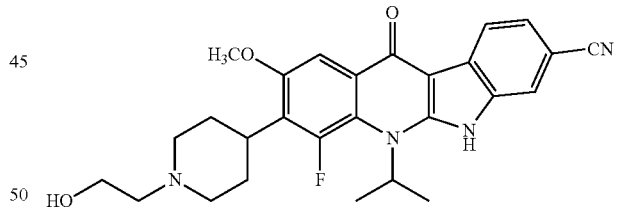

4-Fluoro-3-(1-(2-hydroxyethyl)piperidin-4-yl)-5-isopropyl-2-methoxy-11-oxo-6,11-dihydro-5H-indolo[2,3-b]quinoline-8-carbonitrile

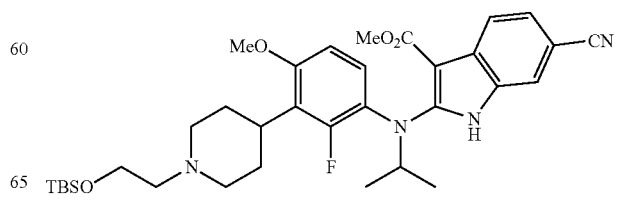

Step A: Methyl 2-((3-(1-(2-((tert-butyldimethylsilyl)oxy)ethyl)piperidin-4-yl)-2-fluoro-4-methoxyphenyl)(isopropyl)amino)-6-cyano-1H-indole-3-carboxylate TFA (1 mL) was added to a solution of Methyl 2-((3-(1-(tert-butoxycarbonyl)piperidin-4-yl)-2-fluoro-4-methoxyphenyl)(isopropyl)amino)-6-cyano-1H-indole-3-carboxylate (365 mg, 0.647 mmol) in DCM (5 mL) and the mixture was stirred at RT for 12 hr. Solvent was removed under reduced pressure and the residue was nutrilized with NaHCO$_3$ and extracted with EtOAc. EtOAc was removed under reduced pressure and the residue was dissolved in DCM (5 mL). 2-((tert-Butyldimethylsilyl)oxy)acetaldehyde (164 mg, 0.97 mmol), Acetic acid (58 mg, 0.97 mmol), and NaBH(OAc)$_3$ (206 mg, 0.97 mmol) were then added and the reaction mixture was stirred at RT for 6 hr. Solvent was removed under reduced pressure and the product was extracted with EtOAc. EtOAc was evaporated under reduced pressure and the residue was purified by silica gel chromatography (EtOAc) to afford Methyl 2-((3-(1-(2-((tert-butyldimethylsilyl)oxy)ethyl)piperidin-4-yl)-2-fluoro-4-methoxyphenyl)(isopropyl)amino)-6-cyano-1H-indole-3-carboxylate (180 mg, 45% yield). $^1$H NMR (300 MHz, CDCl$_3$) δ ppm 8.61 (s, 1H), 7.95 (d, J=8.3 Hz, 1H), 7.40-7.30 (m, 2H), 7.15 (t, J=8.7 Hz, 1H), 6.69 (d, J=8.7 Hz, 1H), 4.95-4.78 (m, 1H), 3.90-3.75 (m, 8H), 3.20-3.05 (m, 3H), 2.62 (t, J=6.3 Hz, 2H), 2.45-2.20 (m, 4H), 1.70-1.55 (m, 2H), 1.20 (d, J=6.5 Hz, 6H), 0.89 (s, 9H), 0.06 (s, 6H).

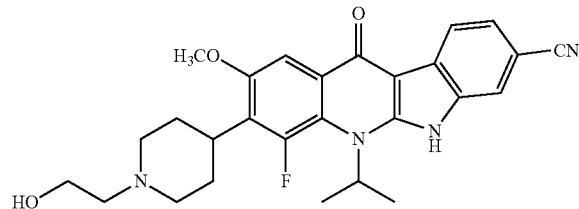 [SMILES: COc1cc2c(=O)c3c4ccc(C#N)cc4[nH]c3n(C(C)C)c2c(F)c1C1CCN(CCO)CC1]

Step B: 4-Fluoro-3-(1-(2-hydroxyethyl)piperidin-4-yl)-5-isopropyl-2-methoxy-11-oxo-6,11-dihydro-5H-indolo[2,3-b]quinoline-8-carbonitrile Methyl 2-((3-(1-(2-((tert-butyldimethylsilyl)oxy)ethyl)piperidin-4-yl)-2-fluoro-4-methoxyphenyl)(isopropyl)amino)-6-cyano-1H-indole-3-carboxylate (180 mg, 0.29 mmol) was dissolved in Diphenyl ether (10 mL) and the solution was refluxed for 1 hr. The mixture was cooled to RT. Hexane (20 mL) was added and the precipitate was collected by filtration. The precipitate was dissolved in MeOH (10 mL) and the solution was treated with KHSO$_4$ (197 mg, 1.45 mmol). The mixture was stirred at RT for 12 hr. Solvent was removed under reduced pressure and the residue was purified by preparative-HPLC to afford 4-Fluoro-3-(1-(2-hydroxyethyl)piperidin-4-yl)-5-isopropyl-2-methoxy-11-oxo-6,11-dihydro-5H-indolo[2,3-b]quinoline-8-carbonitrile (80 mg, 58% yield). $^1$H NMR (300 MHz, CD$_3$OD) δ ppm 8.26 (d, J=8.0 Hz, 1H), 7.75 (s, 1H), 7.68 (s, 1H), 7.44 (d, J=8.0 Hz, 1H), 5.20-5.02 (m, 1H), 4.03 (s, 3H), 4.00-3.84 (m, 2H), 3.80-3.60 (m, 3H), 3.35-3.20 (m, 4H), 2.80-2.60 (m, 2H), 2.15-2.00 (m, 2H), 1.73 (dd, J=6.9, 1.6 Hz, 6H).

Inhibitory Activity Against Wild-Type and Mutated ALK Enzymes

The cytoplasmic domain (amino acid 1058-1620) of wild-type human ALK protein expressed as N-terminal GST-fusion protein was purchased from Carna Biosciences, Inc (Japan). Mutated ALK proteins were expressed in SF9 insect cells with N-terminal tags cleaved after purification. Kinase activities of all enzymes were assessed using a Lance TR-FRET assay kit from Perkin Elmer Life Sciences (Waltham, Mass.). 2.5 μL of compound solution and 5 μL of protein solution were added into a black low volume 384 well microtiter plate which was incubated for 15 minutes with gentle shaking at room temperature, followed by adding 2.5 μL of fluorescently labeled peptide substrate (Ulight-CKKSRGDYMTMQIG) and ATP mixture solution. The kinase reaction was performed in 50 mM HEPES (pH 7.5) with 1 mM EGTA, 1 mM MgCl$_2$, and 2 mM DTT, 0.01% Tween-20 added right before the assay. Final concentrations of ATP, substrates, and DMSO were 100 μM, 20 nM, and 0.5%, respectively. Concentrations of different ALK proteins were adjusted accordingly to achieve comparable enzymatic activities for both wild-type and all mutated ALK proteins. Final ALK concentrations were 1 nM, 1 nM, 1 nM, 128 nM, and 2 nM for wild-type, F1174L, L1196M, S1206Y, and G1269A, respectively. The reaction was allowed to perform for 90 minutes in dark with gentle shaking at room temperature after which 10 μL of 20 mM EDTA and 2 nM Eu-W1024 anti-phosphotyrosine antibody (PT66) mixture solution in the detection buffer from the manufacturer was added to terminate the reaction and detect the phosphorylation of the peptide substrate. Final mixture was incubated in the dark for 1 hour before the plate was read on a Tecan Infinite M-1000 multi-mode plate reader (Tecan, Durham N.C.) with an excitation wavelength of 320 nm. Emission intensities were measured at both 620 and 665 nm with the intensity ratio between 665 and 620 nm corresponding to the peptide substrate phosphorylation. IC50 values of inhibitors were obtained by fitting the ratio of 665/620 nm vs inhibitor concentrations in a sigmoidal dose-response curve (variable slope) with a non-linear regression.

The following table (Table 1) includes ALK IC$_{50}$ values against wild-type ALK obtained using the procedure set forth above.

TABLE 1

Inhibitory activity against wild-type ALK

| Compound | ALK IC$_{50}$ (nM) | Compound | ALK IC$_{50}$ (nM) |
|---|---|---|---|
| ALK-18 | 1510 | CJ-2096 | >50,000 |
| ALK-20 | 33.1 | CJ-2113 | 1510 |
| ALK-21 | 23.6 | CJ-2172-2 | 2.0 |
| ALK-22 | 661 | CJ-2173-2 | 0.71, 1.5 |
| ALK-23 | 309 | CJ-2200 | Not tested |
| ALK-24 | 5.3 | CJ-2204 | 0.26 |
| ALK-25 | 17.8 | CJ-2212 | 0.49 |
| ALK-30 | >10000 | CJ-2217 | 0.52 |
| ALK-31 | >10000 | CJ-2224 | 5.5 |
| ALK-32 | >10000 | CJ-2225 | 2.5 |
| ALK-33 | >10000 | CJ-2226 | 1.3 |
| ALK-34 | 12.1 | CJ-2227 | 0.62 |
| ALK-35 | 4.5 | CJ-2238 | 2.6 |
| ALK-36 | 5.4 | CJ-2239 | 0.77 |
| ALK-37 | 16.5 | CJ-2240 | 0.78 |
| ALK-38 | 7.7 | CJ-2241 | 0.32 |
| ALK-39 | 6.1 | ALK-62 | 0.26, 0.34 |
| ALK-40 | 29.7 | ALK-63 | 1.1 |
| ALK-41 | 13.0 | ALK-64 | 0.79, 1.1 |
| ALK-42 | 24.7 | ALK-66 | 5.8 |
| ALK-43 | 28.5 | ALK-67 | 1.4 |
| ALK-44 | 16.4 | ALK-68 | 2.6 |
| ALK-45 | 1.8, 5.1 | ALK-69 | 0.87 |
| ALK-46 | 1.8, 1.5 | ALK-70 | 1.6 |
| ALK-47 | 1.4, 1.1 | ALK-71 | 0.31 |
| ALK-48 | 15.1 | ALK-72 | 0.67 |
| ALK-49 | 1.9, 2.8 | ALK-73 | 4.0 |
| ALK-50 | 18.2 | ALK-74 | 8.4 |

TABLE 1-continued

Inhibitory activity against wild-type ALK

| Compound | ALK IC$_{50}$ (nM) | Compound | ALK IC$_{50}$ (nM) |
|---|---|---|---|
| ALK-51 | 20.5 | ALK-75 | 3.6 |
| ALK-52 | 51.0, 60.9 | ALK-76 | 2.5 |
| ALK-53 | 4.4, 7.2 | ALK-77 | 1.1 |
| ALK-54 | 24.7 | ALK-78 | 0.7 |
| ALK-55 | 3.3, 6.0 | ALK-79 | 0.11 |
| ALK-56 | 2.9, 3.5 | ALK-80 | 0.22 |
| ALK-57 | 50.4 | ALK-81 | 0.10 |
| ALK-58 | 3.4 | ALK-82 | 2.3 |
| ALK-59 | 1.6 | ALK-83 | 2.0 |
| ALK-60 | 6.6 | ALK-85 | 22.9 |
| ALK-61 | 1.4 | ALK-86 | 5.8 |

The following table (Table 2) includes IC$_{50}$ values for representative inhibitors against mutated ALK proteins obtained using the procedure set forth above.

TABLE 2

Inhibitory activity (IC50) against wild-type and mutated ALK proteins

| | | Compound | | | | | | | |
|---|---|---|---|---|---|---|---|---|---|
| | | ALK-62 | ALK-64 | ALK-69 | ALK-70 | ALK-71 | ALK-72 | AP-26113 | CH5424802 | Crizotinib |
| IC50 (nM) | ALK Wild-type | 0.26, 0.34 | 0.79, 1.1 | 0.87 | 1.6 | 0.31 | 0.67 | 1.5 ± 0.3 | 3.1 ± 0.9 | 34.5 ± 5.0 |
| | ALK mutant (L1196M) | 1.5, 0.93 | 4.4, 3.2 | | 5.3, 4.8 | 0.95, 0.66 | 2.2, 2.2 | 3.5, 1.9 | 7.2, 6.1 | 529, 427 |
| | ALK mutant (F1174L) | 0.63 | 1.4 | | 5.2 | 1.3 | 1.9 | 2.4 | 6.0 | 66.0 |
| | ALK mutant (G1269A) | 2.0 | 1.7 | | 2.9 | 0.47, 0.55 | 2.4 | 1.6 | 8.5, 6.5 | 821, 580 |
| | ALK mutant (S1206Y) | 2.2 | 2.1 | | 3.2 | 1.3 | 2.8 | 5.4 | 8.1 | 200 |

Cell Viability Assay

The effect of compounds on cell viability was determined in a 4-day proliferation assay. Cells were maintained in RPMI1640 culture medium with 10% FBS at 37° C. and an atmosphere of 5% CO$_2$. Kappas-299 and H3122 were used within three months of thawing fresh vials. Cells were seeded in 96-well plates at a density of 3,000-10,000 cells/well in 75 µl of culture medium. Compounds were serially diluted in the appropriate medium, and 75 µl of the diluted compounds were added to the appropriate wells of the cell plate. After the addition of compounds, the cells were incubated at 37° C. in an atmosphere of 5% CO$_2$ for 4 days. Cell viability was determined using the CellTiter-Glo® Luminescent Cell Viability Assay Kit (Promega, Madison, Wis.) (for KARPAS-299 cells) or WST (2-(2-methoxy-4-nitrophenyl)-3-(4-nitrophenyl)-5-(2,4-disulfophenyl)-2H-tetrazolium, monosodium salt) Cell Counting-8 Kit (Dojindo Molecular Technologies, Inc., Rockville, Md.) (for H3122 cells) according to the manufacturers' instructions.

For WST assay, WST-8 reagent was added to each well at a final concentration of 10% (v/v), and then the plates were incubated at 37° C. for 1-2 hours for color development. The absorbance was measured at 450 nm using a SPECTRAmax PLUS plate reader (Molecular Devices, Sunnyvale, Calif.). The readings were normalized to the DMSO-treated cells and the half maximal inhibitory concentration (IC$_{50}$) was calculated by nonlinear regression analysis using the GraphPad Prism 5 software (GraphPad Software, La Jolla, Calif.).

For CellTiter-Glo assay, 100 µl of CellTiter-Glo® Reagent was added to each well, and then the plates were incubated at room temperature for 10-20 minutes. The luminescent signal was measured using a Tecan Infinite M1000 multimode microplate reader (Tecan, Morrisville, N.C.). The readings were normalized to the DMSO-treated cells and the IC$_{50}$ was calculated by nonlinear regression analysis using the GraphPad Prism 5 software.

The following table (Table 3) includes the inhibition of cell growth in the Kappas-299 cell line. Cells were treated for four days and cell growth was determined using a CellTiter-Glo assay.

TABLE 3

Inhibition of cell growth in Kappas-299 cells containing NPM-ALK fusion protein.
Mutiple values were obtained from independent experiments.

| Compound | Kappas-299 IC$_{50}$ (nM) | Compound | Kappas-299 IC$_{50}$ (nM) |
|---|---|---|---|
| ALK-20 | 515 | CJ-2212 | 9.7 |
| ALK-21 | 982 | CJ-2217 | 14 |
| ALK-22 | 90.3 | CJ-2224 | 33 |
| ALK-24 | 207 | CJ-2225 | 17 |
| ALK-25 | 137 | CJ-2226 | 1030 |
| ALK-34 | 138 | CJ-2227 | 36 |
| ALK-35 | 130, 136 | CJ-2238 | 231 |
| ALK-36 | 88, 152 | CJ-2239 | 16 |
| ALK-37 | 9884 | CJ-2240 | 35 |
| ALK-38 | 272, 173 | CJ-2241 | 292 |
| ALK-39 | 148, 96 | ALK-62 | 24 |
| ALK-40 | 415 | ALK-63 | 24 |
| ALK-41 | 1772 | ALK-64 | 73 |
| ALK-42 | >1000 | ALK-66 | 48 |
| ALK-43 | 266, 261 | ALK-67 | 61 |
| ALK-44 | >1000 | ALK-68 | 20 |
| ALK-45 | 35, 62 | ALK-69 | 46 |
| ALK-46 | 60, 102 | ALK-70 | 66 |
| ALK-47 | 29, 604 | ALK-71 | 31 |
| ALK-48 | 70, 84 | ALK-72 | 52 |
| ALK-49 | 317, 546 | ALK-73 | 4018 |
| ALK-50 | 86, 103 | ALK-74 | 98 |

TABLE 3-continued

Inhibition of cell growth in Kappas-299 cells containing NPM-ALK fusion protein.
Mutiple values were obtained from independent experiments.

| Compound | Kappas-299 IC$_{50}$ (nM) | Compound | Kappas-299 IC$_{50}$ (nM) |
|---|---|---|---|
| ALK-51 | 70, 99 | ALK-75 | 22 |
| ALK-52 | 123 | ALK-76 | 35 |
| ALK-53 | 46 | ALK-77 | 31 |
| ALK-54 | 63 | ALK-78 | 25 |
| ALK-55 | 36 | ALK-79 | 9.6 |
| ALK-56 | 37 | ALK-80 | 7.6 |
| ALK-57 | 152 | ALK-81 | 440 |
| ALK-58 | 140 | ALK-82 | 46 |
| ALK-59 | 447 | ALK-83 | 21 |
| ALK-60 | 66 | ALK-85 | 66 |
| ALK-61 | >1000 | ALK-86 | 31 |
| CJ-2204 | 768 | | |

The following table (Table 4) includes the inhibition of cell growth in the H3122 non-small-cell lung cell line containing the EML4-ALK fusion gene. Cells were treated for four days and cell growth was determined using a WST assay.

TABLE 4

Inhibition of cell growth in H3122 non-small cell lung cancer cell line harboring the EML4-ALK fusion gene.
Cells were treated by different concentrations of the inhibitors for 4 days.

| Compound | IC$_{50}$ (nM) in Inhibition of Tumor Cell Growth H3122 Cell line | Compound | IC$_{50}$ (nM) in Inhibition of Tumor Cell Growth H3122 Cell line |
|---|---|---|---|
| ALK-68 | 63 ± 34 | CJ-2212 | 19 ± 6 |
| ALK-73 | 86 ± 37 | CJ-2217 | 17 ± 8 |
| ALK-74 | 84 | CJ-2224 | 241 |
| ALK-75 | 35.93 | CJ-2225 | 30 ± 13 |
| ALK-76 | 85 ± 11 | CJ-2226 | 61 ± 14 |
| ALK-77 | 25.92 | CJ-2227 | 64 |
| ALK-78 | 13.08 | CJ-2238 | 1038 |
| ALK-79 | 2 ± 1 | CJ-2239 | 36 ± 13 |
| ALK-80 | 3 ± 1 | CJ-2240 | 33 ± 12 |
| ALK-83 | 8.8 | CJ-2241 | 154 |
| ALK-85 | 148 ± 26 | Critozinib | 43 ± 20 |
| ALK-86 | 161 | CH-5424802 | 71 ± 47 |

Summary of Pharmacokinetic Parameters

The pharmacokinetic (PK) parameters in SD rats for selected compounds with intravenous (IV) and oral (PO) administrations are provided in the following table (Table 5).

TABLE 5

Pharmacokinetic Profiles of Selected Inhibitors

| Compound | Tmax (h) IV | Tmax (h) PO | Cmax (ng/mL) IV | Cmax (ng/mL) PO | AUC0-t (ng·h/mL) IV | AUC0-t (ng·h/mL) PO | $t_{1/2}$ (h) IV | $t_{1/2}$ (h) PO | Oral Bioavailability (F) |
|---|---|---|---|---|---|---|---|---|---|
| ALK83 | 0.083 | 4.0 | 346 | 548 | 1102 | 4426 | 5.24 | 4.10 | 78.8% |
| ALK86 | 0.083 | 4.0 | 261 | 258 | 1079 | 2445 | 5.23 | 5.11 | 44.6% |
| CJ-2226 | 0.083 | 4.67 | 296 | 230 | 1002 | 2370 | 4.37 | 4.99 | 47.3% |
| CJ-2212 | 0.083 | 5.33 | 169 | 208 | 574 | 2064 | 4.78 | 4.08 | 70.6% |
| CJ-2224 | 0.083 | 0.67 | 959 | 1169 | 2344 | 9636 | 4.71 | 3.86 | 81.5% |
| CJ-2225 | 0.222 | 5.33 | 212 | 225 | 1108 | 2336 | 4.54 | 4.31 | 41.7% |

What is claimed is:

1. A compound of formula (I), and/or a pharmaceutically acceptable salt thereof:

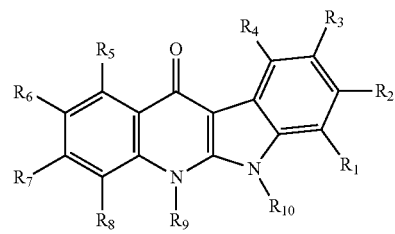

I wherein $R_1$, $R_4$, $R_5$, and $R_8$ are independently selected from hydrogen, alkyl, alkynyl, alkenyl, alkoxy, halo, hydroxyl, —CN, CONR$^b$R$^c$, —NR$^b$R$^c$, —NO$_2$, —O-cycloalkyl, —O-heterocyclyl, —O-aryl, —O-heteroayl, cycloalkyl, heterocyclyl, aryl, and heteroaryl, $R_2$ is CN, $R_3$ and $R_6$ are independently selected from hydrogen, alkyl, alkynyl, alkenyl, alkoxy, hydroxyl, —CN, —CONR$^b$R$^c$, —NR$^b$R$^c$, —NO$_2$, —O-cycloalkyl, —O-heterocyclyl, —O-aryl, —O-heteroayl, cycloalkyl, heterocyclyl, aryl, and heteroaryl, $R_7$ is selected from alkyl, alkynyl, alkenyl, alkoxy, hydroxyl, —CN, —CONR$^b$R$^c$, —NR$^b$R$^c$, —NO$_2$, —O-cycloalkyl, —O-heterocyclyl, —O-aryl, —O-heteroayl, cycloalkyl, heterocyclyl, aryl, and heteroaryl, $R_9$ is selected from alkyl, cycloalkyl, heterocyclyl, aryl, and heteroaryl, wherein the alkyl, alkynyl, alkenyl, alkoxy, cycloalkyl, heterocyclyl, aryl, and heteroaryl are each optionally substituted with at least one group independently selected from R$^a$, R$^a$ is selected from alkyl, alkoxy, hydroxyl, —CN, alkenyl, alkynyl, cycloalkyl, heterocyclyl, aryl, heteroaryl, —COOR$^b$, —CONR$^b$R$^c$, —NR$^b$R$^c$, and oxo, each of the alkyl, alkoxy, alkenyl, alkynyl, cycloalkyl, heterocyclyl, aryl, heteroaryl being optionally substituted with at least one group independently selected from alkyl, hydroxyl, alkoxy, halo, —COOR$^b$, —CONR$^b$R$^c$, and —NR$^b$R$^c$, and R$^b$ and R$^c$ are each independently selected from hydrogen, alkyl, alkenyl, cycloalkyl, heterocyclyl, aryl, and heteroaryl, and $R_{10}$ is H.

2. The compound of claim 1 and/or a pharmaceutically acceptable salt thereof, wherein $R_1$, $R_4$ and $R_5$ is hydrogen.

3. The compound of claim 1 and/or a pharmaceutically acceptable salt thereof, wherein $R_6$ is selected from alkyl, alkynyl, alkenyl, alkoxy, and cycloalkyl, the alkyl, alkynyl, alkenyl, alkoxy, and cycloalkyl being unsubstituted.

4. The compound of claim 1 and/or a pharmaceutically acceptable salt thereof, wherein $R_8$ is selected from hydrogen and fluoro.

5. The compound of claim 1 and/or a pharmaceutically acceptable salt thereof, wherein $R_7$ is selected from cycloalkly, heterocycyl, aryl and heteroaryl, the cycloalkly, heterocycyl, aryl and heteroaryl being each optionally substituted with at least one group independently selected from $R^a$, $R^a$ being the same as defined in claim 1.

6. The compound of claim 1 and/or a pharmaceutically acceptable salt thereof, wherein $R_7$ is heterocyclyl optionally substituted with at least one group independently selected from alkyl, cycloalkyl, and heterocyclyl, each of the alkyl, cycloalkyl and heterocyclyl being optionally substituted with at least one group independently selected from alkyl, hydroxyl, and alkoxy.

7. The compound of claim 1 and/or a pharmaceutically acceptable salt thereof, wherein $R_7$ is selected from piperidinyl, piperazinyl, and morpholinyl, each being optionally substituted with at least one group independently selected from alkyl, cycloalkyl and heterocyclyl, each of the alkyl, cycloalkly, and heterocyclyl is optionally substituted with hydroxyl.

8. The compound of claim 1 and/or a pharmaceutically acceptable salt thereof, wherein $R_9$ is selected from alkyl, and cycloalkyl, each of the alkyl and cycloalkyl being optionally substituted with at least one group independently selected from $R^a$, $R^a$ being the same as defined in claim 1.

9. The compound of claim 1 and/or a pharmaceutically acceptable salt thereof, wherein the compound of formula (I) is selected from compounds of formula (II):

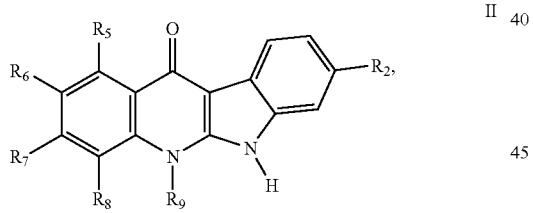

wherein $R_5$ is H or F,
$R_6$ is selected from hydrogen, alkyl, alkynyl, alkenyl, alkoxy, halo, hydroxyl, and —CN, the alkyl, alkynyl, alkenyl, alkoxy, and cycloalkyl being each optionally substituted with at least one group independently selected from $R^a$, $R^a$ being the same as defined in claim 1,
$R_7$ is heterocyclyl optionally substituted with at least one group independently selected from alkyl, cycloalkyl, and heterocyclyl, each of the alkyl, cycloalkyl and heterocyclyl being optionally substituted with at least one group independently selected from alkyl, hydroxyl, and alkoxy,
$R_8$ is H or F, and
$R_9$ is selected from alkyl, and cycloalkyl, each of the alkyl and cycloalkyl being optionally substituted with at least one group independently selected from $R^a$, $R^a$ being the same as defined in claim 1.

10. The compound of claim 1 and/or a pharmaceutically acceptable salt thereof, wherein the compound of formula (I) is selected from compounds of formula (III):

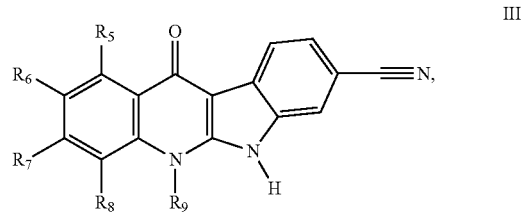

wherein $R_6$ is selected from alkyl, alkynyl, alkenyl, alkoxy, hydroxyl, and —CN, the alkyl, alkynyl, alkenyl, alkoxy, and cycloalkyl being each optionally substituted with at least one group independently selected from $R^a$, $R^a$ being the same as defined in claim 1,
wherein $R_7$ is heterocyclyl optionally substituted with at least one group independently selected from alkyl, cycloalkyl, and heterocyclyl, each of the alkyl, cycloalkyl and heterocyclyl being optionally substituted with at least one group independently selected from alkyl, hydroxyl, and alkoxy,
$R_8$ is H or F, and
$R_9$ is selected from hydrogen, alkyl, and cycloalkyl, each of the alkyl and cycloalkyl being optionally substituted with at least one group independently selected from $R^a$, $R^a$ being the same as defined in claim 1.

11. The compound of claim 1 and/or a pharmaceutically acceptable salt thereof, wherein the compound of formula (I) is selected from compounds of formula (IV):

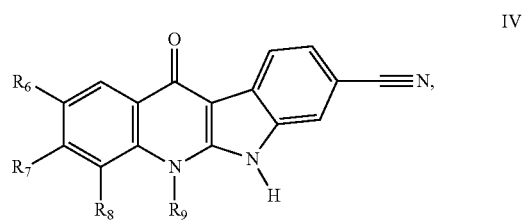

wherein $R_6$ is selected from hydrogen, alkyl, alkynyl, alkenyl, alkoxy, hydroxyl, and —CN, the alkyl, alkynyl, alkenyl, alkoxy, and cycloalkyl being each optionally substituted with at least one group independently selected from $R^a$, $R^a$ being the same as defined in claim 1,
$R_7$ is heterocyclyl optionally substituted with at least one group independently selected from alkyl, cycloalkyl, and heterocyclyl, each of the alkyl, cycloalkyl and heterocyclyl being optionally substituted with at least one group independently selected from alkyl, hydroxyl, and alkoxy, and
$R_9$ is selected from alkyl, and cycloalkyl, each of the alkyl and cycloalkyl being optionally substituted with at least one group independently selected from $R^a$, $R^a$ being the same as defined in claim 1.

12. The compound of claim 1 and/or a pharmaceutically acceptable salt thereof, wherein the compound is selected from the following compounds:

123
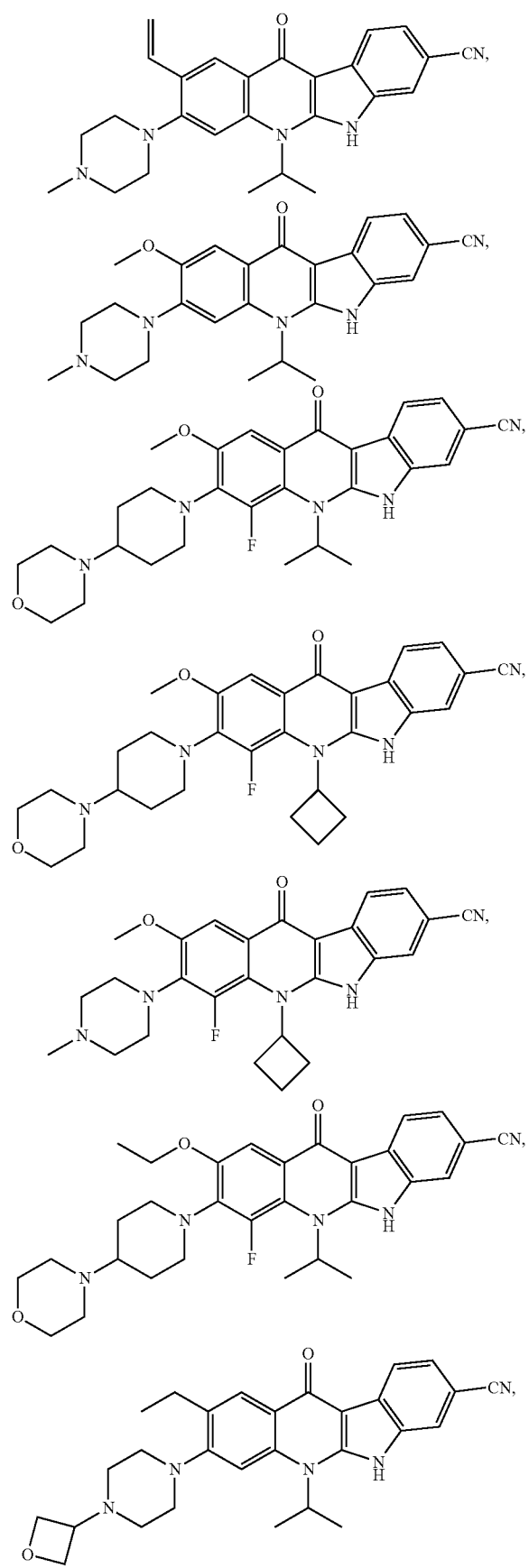
124
-continued
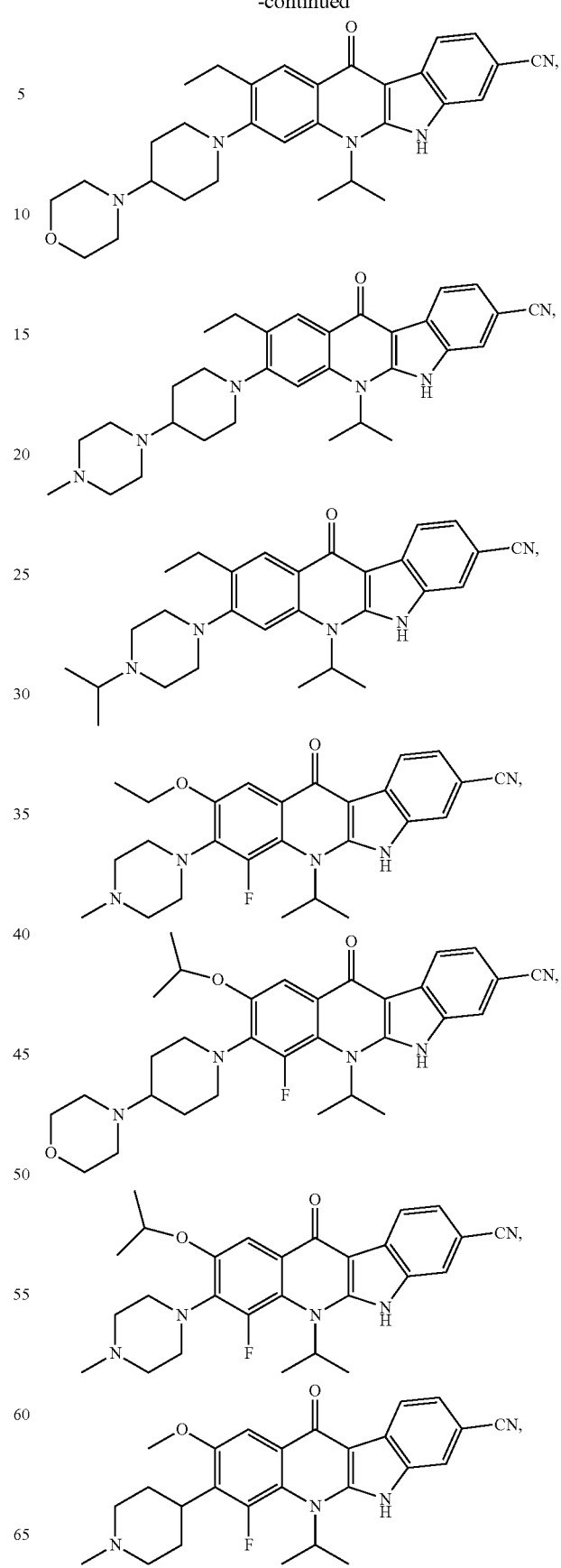

125
-continued
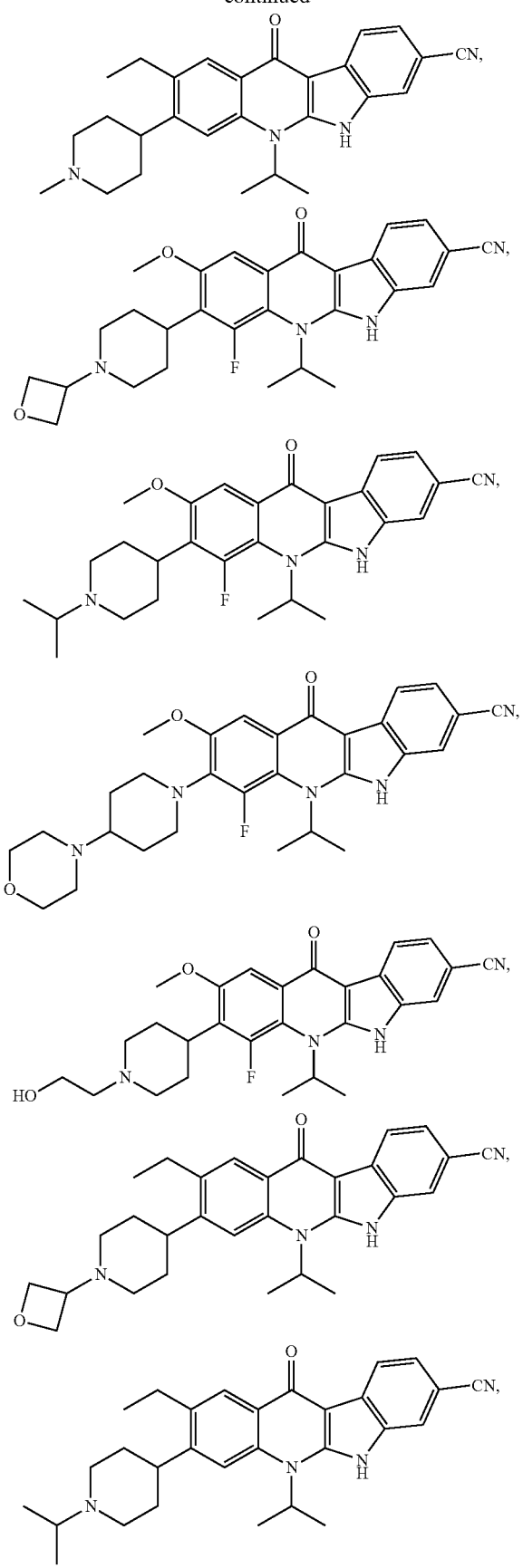
126
-continued
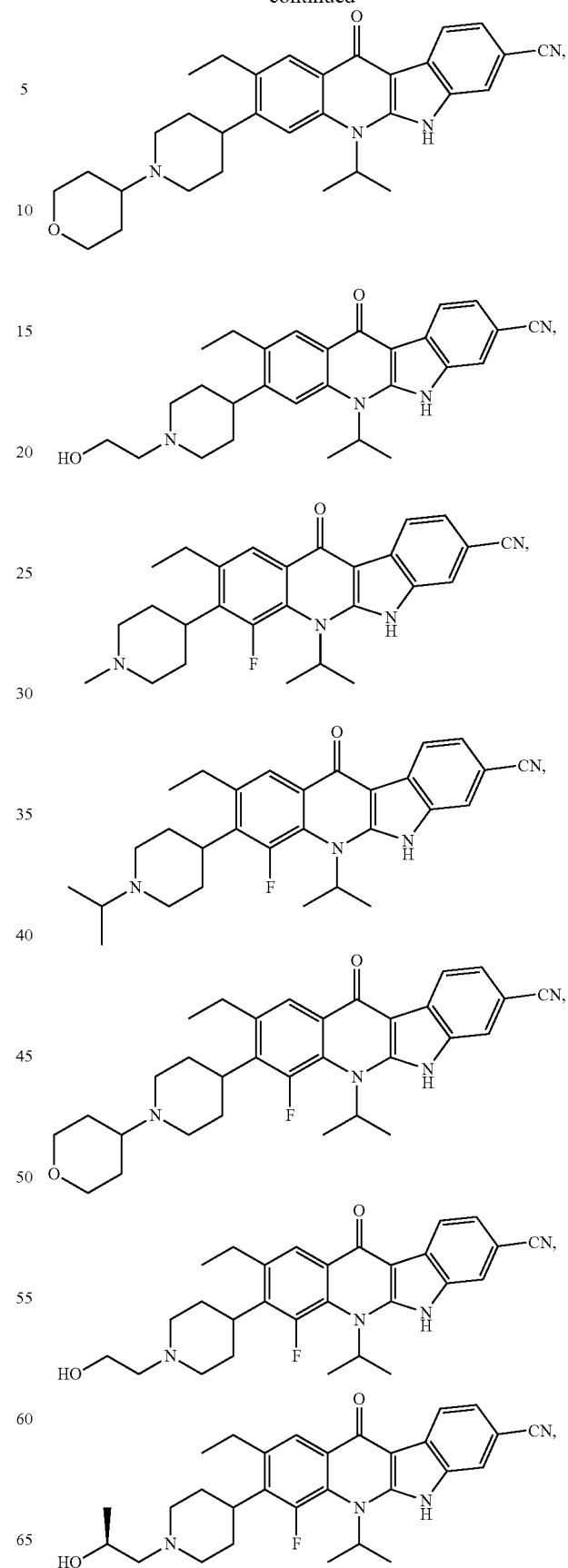

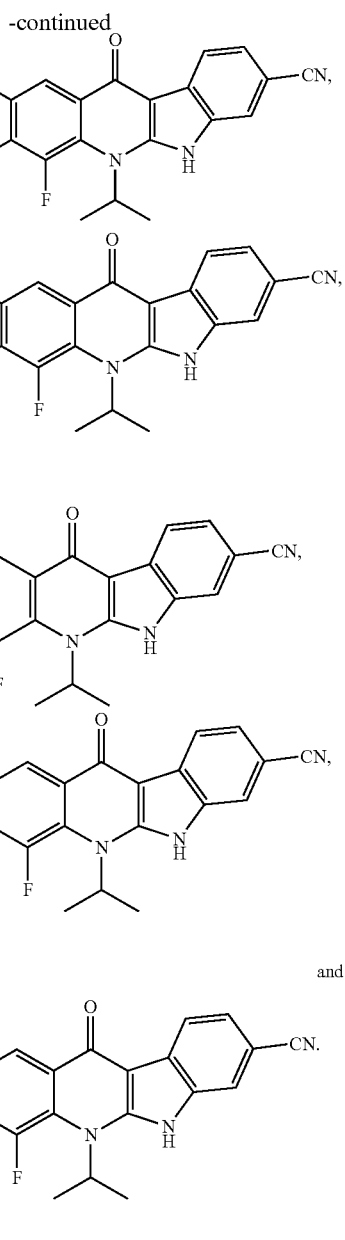

and

13. A pharmaceutical composition comprising at least one pharmaceutically acceptable carrier and as an active ingredient a therapeutically effective amount of the compound and/or a pharmaceutically acceptable salt thereof according to claim 1.

14. A method of treating a cancer responsive to inhibition of ALK comprising administering to a subject in need thereof an effective amount of the compound and/or a pharmaceutically acceptable salt thereof according to claim 1.

15. The method of claim 14, wherein the cancer contains an ALK fusion gene.

16. The method of claim 14, wherein the cancer is selected fromanaplastic large cell lymphomas, squamous cell carcinoma, diffuse large B-cell lymphoma, and non-small-cell lung cancer containing an ALK fusion gene.

17. A method of treating a disorder responsive to inhibition of ALK comprising administering to a subject in need thereof an effective amount of the compound and/or a pharmaceutically acceptable salt thereof according to claim 1.

18. A method of treating a cancer comprising administering to a subject in need thereof an effective amount of the compound and/or a pharmaceutically acceptable salt thereof according to claim 1, wherein the cancer is chosen from lung cancer, pancreatic cancer, skin cancer, bone cancer, head and neck cancer, uterine cancer, ovarian cancer, rectal cancer, breast cancer, colorectal cancer, stomach cancer, colon cancer, acute or chronic leukemia, adenocarcinoma, lymphoma, melanoma, prostate cancer, bladder cancer, kidney cancer, brain tumor, Hodgkin's Disease, neoplasms of the central nervous system (CNS), primary CNS lymphoma, mesothelioma, small intestine cancer, and esophagus cancer.

19. The method according to claim 18, wherein the cancer is chosen from lung cancer and brain cancer.

20. A method of treating a cancer comprising administering to a subject in need thereof an effective amount of the compound and/or a pharmaceutically acceptable salt thereof according to claim 1, wherein the cancer is chosen from lung adenocarcinoma, cholangiocarcinoma, ovarian cancer, gastric adenocarcinoma, colorectal cancer, inflammatory myofibroblastic tumor, angiosarcoma, and epithelioid hemangioendothelioma.

* * * * *

UNITED STATES PATENT AND TRADEMARK OFFICE
CERTIFICATE OF CORRECTION

PATENT NO. : 9,783,539 B2  
APPLICATION NO. : 15/121847  
DATED : October 10, 2017  
INVENTOR(S) : Jianyong Chen et al.

Page 1 of 1

It is certified that error appears in the above-identified patent and that said Letters Patent is hereby corrected as shown below:

In the Claims

Claim 12, Column 123, Lines 10-16, " 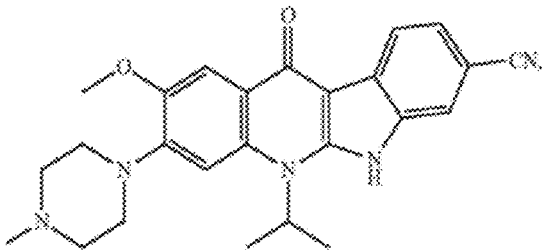 " should read

-- 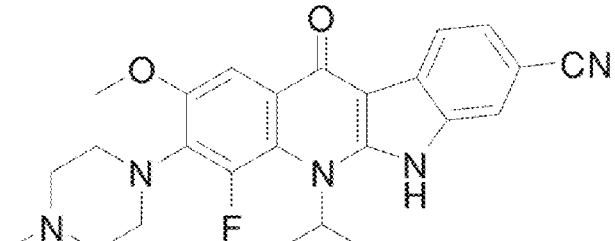 --.

Claim 16, Column 128, Line 16, "fromanaplastic" should read -- from anaplastic --.

Signed and Sealed this  
Twenty-sixth Day of December, 2017

Joseph Matal  
*Performing the Functions and Duties of the*  
*Under Secretary of Commerce for Intellectual Property and*  
*Director of the United States Patent and Trademark Office*